US012741944B2

(12) United States Patent
Lynch et al.

(10) Patent No.: US 12,741,944 B2
(45) Date of Patent: Sep. 22, 2026

(54) INHIBITORS OF SPINSTER HOMOLOG 2 (SPNS2) FOR USE IN THERAPY

(71) Applicants: University of Virginia Patent Foundation, Charlottesville, VA (US); Virginia Tech Intellectual Properties, Inc., Blacksburg, VA (US)

(72) Inventors: Kevin R. Lynch, Charlottesville, VA (US); Yugesh Kharel, Charlottesville, VA (US); Webster L. Santos, Blacksburg, VA (US); Russell G. Fritzemeier, Atlanta, GA (US); Ariel Louise Burgio, Christiansburg, VA (US); Christopher Shrader, Blacksburg, VA (US); Daniel Foster, Blacksburg, VA (US)

(73) Assignees: University of Virginia Patent Foundation, Charlottesville, VA (US); Virginia Tech Intellectual Properties, Inc., Blacksburg, VA (US)

( * ) Notice: Subject to any disclaimer, the term of this patent is extended or adjusted under 35 U.S.C. 154(b) by 463 days.

(21) Appl. No.: 18/044,686

(22) PCT Filed: Sep. 8, 2021

(86) PCT No.: PCT/US2021/049534

§ 371 (c)(1),
(2) Date: Mar. 9, 2023

(87) PCT Pub. No.: WO2022/056045

PCT Pub. Date: Mar. 17, 2022

(65) Prior Publication Data

US 2023/0331683 A1 Oct. 19, 2023

Related U.S. Application Data

(60) Provisional application No. 63/076,105, filed on Sep. 9, 2020.

(51) Int. Cl.

| | |
|---|---|
| ***C07D 241/04*** | (2006.01) |
| ***C07C 225/10*** | (2006.01) |
| ***C07D 207/12*** | (2006.01) |
| ***C07D 207/14*** | (2006.01) |
| ***C07D 207/16*** | (2006.01) |
| ***C07D 211/34*** | (2006.01) |
| ***C07D 211/56*** | (2006.01) |
| ***C07D 263/58*** | (2006.01) |
| ***C07D 277/82*** | (2006.01) |

(52) U.S. Cl.

CPC .......... *C07D 241/04* (2013.01); *C07C 225/10* (2013.01); *C07D 207/12* (2013.01); *C07D 207/14* (2013.01); *C07D 207/16* (2013.01); *C07D 211/34* (2013.01); *C07D 211/56* (2013.01); *C07D 263/58* (2013.01); *C07D 277/82* (2013.01)

(58) Field of Classification Search

CPC .................................................. C07D 241/04

See application file for complete search history.

(56) References Cited

U.S. PATENT DOCUMENTS

| | | | |
|---|---|---|---|
| 9,688,668 | B2 | 6/2017 | Santos et al. |
| 2009/0197897 | A1 | 8/2009 | Bugada et al. |
| 2012/0022108 | A1 | 1/2012 | Bessis et al. |
| 2014/0057895 | A1 | 2/2014 | Mizuno et al. |
| 2022/0089581 | A1 | 3/2022 | Lynch et al. |
| 2023/0373937 | A1 | 11/2023 | Lynch et al. |

FOREIGN PATENT DOCUMENTS

| | | |
|---|---|---|
| EP | 3275440 | 1/2018 |
| WO | 03062252 | 7/2003 |
| WO | 2005044797 | 5/2005 |
| WO | 2006123257 | 11/2006 |
| WO | 2007039781 | 4/2007 |
| WO | 2008064320 | 5/2008 |
| WO | 2013119946 | 8/2013 |
| WO | 2016054261 | 4/2016 |
| WO | 2019018795 | 1/2019 |
| WO | 2020154431 | 7/2020 |
| WO | 2020219792 | 10/2020 |
| WO | 2020227101 | 11/2020 |
| WO | 2022056042 | 3/2022 |
| WO | 2022056045 | 3/2022 |

OTHER PUBLICATIONS

Suzuki et al (2003): Bioorganic Med Chem Letters (2003), vol. 13, 4321-4326.*

"International Application Serial No. PCT US2020 014651, Invitation to Pay Additional Fees and Partial Search Report mailed Apr. 28, 2020", 19 pgs.

"International Application Serial No. PCT US2020 014651, International Search Report mailed Jun. 29, 2020", 6 pgs.

"International Application Serial No. PCT US2020 014651, Written Opinion mailed Jun. 29, 2020", 12 pgs.

"International Application Serial No. PCT US2020 014651, International Preliminary Report on Patentability mailed Aug. 5, 2021", 15 pgs.

"International Application Serial No. PCT US2021 049531, International Search Report mailed Jan. 4, 2022", 9 pgs.

"International Application Serial No. PCT US2021 049531, Written Opinion mailed Jan. 4, 2022", 10 pgs.

(Continued)

*Primary Examiner* — Golam M Shameem

(74) *Attorney, Agent, or Firm* — Schwegman Lundberg & Woessner, P.A.

(57) ABSTRACT

The present disclosure provides SPNS2 inhibitor compounds according to Formula (IA) and Formula (I), and their pharmaceutically acceptable salts, and/or tautomers as described in the disclosure, and the disclosure provides their pharmaceutical compositions and methods of use in therapy.

18 Claims, No Drawings

(56) References Cited

OTHER PUBLICATIONS

"International Application Serial No. PCT US2021 049534, International Search Report mailed Jan. 28, 2022", 8 pgs.
"International Application Serial No. PCT US2021 049534, Written Opinion mailed Jan. 28, 2022", 9 pgs.
"European Application Serial No. 20709362.6, Response to Communication Pursuant to Rules 161 and 162 EPC filed Feb. 15, 2022", 47 pgs.
Congdon, Molly D, "Structure-Activity Relationship Studies and Molecular Modeling of Naphthalene-Based Sphingosine Kinase 2 Inhibitors", ACS Medicinal Chemistry Letters, vol. 7, No. 3, XP055285993, (Mar. 10, 2016), 229-234.
Kharel, Yugesh, "Sphingosine kinase type 2 inhibition elevates circulating sphingosine 1-phosphate", Biochemical Journal, 447, (Oct. 1, 2012), 149-157.
Packiarajan, Mathivanan, "Azetidinyl oxadiazoles as potent mGluR5 positive allosteric modulators", Bioorganic and Medicinal Chemistry Letters, vol. 22, No. 20, (Aug. 25, 2012), 6469-6474.
"U.S. Appl. No. 18/044,688, Preliminary Amendment filed Mar. 9, 2023", 14 pgs.
"International Application Serial No. PCT US2021 049531, International Preliminary Report on Patentability mailed Mar. 23, 2023", 12 pgs.
"International Application Serial No. PCT US2021 049534, International Preliminary Report on Patentability mailed Mar. 23, 2023", 11 pgs.
"European Application Serial No. 21786692.0, Response filed Oct. 26, 2023 to Communication pursuant to Rules 161(1) and 162 EPC mailed Apr. 18, 2023", 10 pgs.
"U.S. Appl. No. 17/310,179, Restriction Requirement mailed Apr. 18, 2024", 10 pgs.
"U.S. Appl. No. 17/310,179, Response filed Jun. 12, 2024 to Restriction Requirement mailed Apr. 18, 2024", 20 pgs.
"U.S. Appl. No. 17/310,179, Non Final Office Action mailed Jul. 3, 2024", 13 pgs.
"U.S. Appl. No. 17/310,179, Response filed Jan. 2, 2025 to Non Final Office Action mailed Jul. 3, 2024", 23 pgs.
"U.S. Appl. No. 17/310,179, Final Office Action mailed Feb. 21, 2025", 12 pgs.
"U.S. Appl. No. 17/310,179, Response filed May 21, 2025 to Final Office Action mailed Feb. 21, 2025", 12 pgs.
"U.S. Appl. No. 17/310,179, Non Final Office Action mailed Jun. 4, 2025", 15 pgs.
"U.S. Appl. No. 18/044,688, Restriction Requirement mailed Jul. 23, 2025", 10 pgs.
"U.S. Appl. No. 17/310,179, Response filed Sep. 12, 2025 to Non Final Office Action mailed Jun. 4, 2025", 12 pgs.
"U.S. Appl. No. 18/044,688, Response filed Sep. 23, 2025 to Restriction Requirement mailed Jul. 23, 2025", 15 pgs.
"U.S. Appl. No. 18/044,688, Non Final Office Action mailed Oct. 17, 2025", 18 pgs.
"Chemical Abstract Registry No. 1906742-77-5, indexed in the Registry File on STN CAS", (May 9, 2016), 4 pgs.
Neeraj, N Patwardhan, "Structure-Activity Relationship Studies and in Vivo Activity of Guanidine-Based Sphingosine Kinase Inhibitors: Discovery of SphKI- and SphK2-Selective Inhibitor", Journal of Medicinal Chemistry, vol. 58, No. 4, (Feb. 26, 2015), 1879-1899.
Tsai, H C, "Sphingosine-1-Phosphate (S1P) and S1P Signaling Pathway: Therapeutic Targets in Autoimmunity and Inflammation", Drugs. 76(11), (Jul. 2016), 1067-79.
"European Application Serial No. 21786693.8, Communication Pursuant to Article 943 EPC mailed Apr. 29, 2026", 4 pgs.

* cited by examiner

INHIBITORS OF SPINSTER HOMOLOG 2 (SPNS2) FOR USE IN THERAPY

PRIORITY APPLICATION

This application is a U.S. National Stage filing under 35 U.S.C. § 371 of PCT Patent Application No. PCT/US2021/049534, filed on Sep. 8, 2021, which claims priority to U.S. Patent Application Ser. No. 63/076,105, filed Sep. 9, 2020, the disclosures of which are incorporated herein in their entirety by reference.

STATEMENT REGARDING FEDERALLY SPONSORED RESEARCH OR DEVELOPMENT

This invention was made with government support under R01GM121075 and R01AI144026 awarded by the National Institutes of Health. The government has certain rights in the invention.

BACKGROUND

Sphingosine 1-phosphate (S1P) is a simple lipid that is chemotactic when present extracellularly, but which is also a second messenger when intracellular. These roles require compartmentalization, which is provided in part by extrusion of S1P from cells. The S1P transporters, SPNS2 (endothelium) and MFSD2B (erythrocytes), release SIP from cells. When this release is coupled with S1P degradation in tissue parenchyma, a differential is generated between the extracellular (high) and intracellular (low) S1P concentrations. Mouse genetic studies indicate that endothelial cells use SPNS2 to provide most of the S1P in lymph as well as about one-third of plasma S1P, whereas erythrocytes provide the remainder of plasma S1P via MFSD2B. The S1P gradient in blood functions both to maintain endothelial barrier integrity and promote migration of lymphocytes from the thymus to the blood.

Investigations of S1P receptor modulators led to the realization that the lymph S1P gradient is particularly important for egress of lymphocytes from secondary lymphoid tissue into efferent lymph. However, on-target activity of S1P receptor modulators at endothelial and cardiac SIP receptors drives adverse events such as first dose bradycardia.

SUMMARY

The present disclosure provides, in various embodiments, compounds and their pharmaceutically acceptable salts conforming to Formula IA as SPNS2 inhibitors that avoid on-target adverse activity:

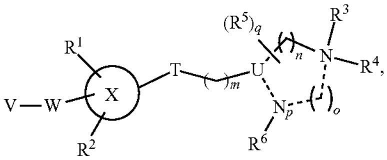

(IA)

X is a $C_6$-$C_{10}$-aryl or 5- to 10-membered heteroaryl (wherein 1 to 4 heteroaryl ring members are independently selected from N, O, and S).

$R^1$ and $R^2$ are independently selected from the group consisting of H, $C_1$-$C_6$-alkyl, $C_1$-$C_6$-alkoxy, $C_1$-$C_6$-haloalkoxy, $C_3$-$C_8$-cycloalkyl, $C_1$-$C_6$-haloalkyl, CN, and halo.

W is a bond, O, NH, —NHC(O)—, or —O—(N═)C(R)— (wherein R is H or $C_1$-$C_6$-alkyl).

V is selected from the group consisting of H, $C_1$-$C_{14}$-alkyl, $C_2$-$C_{12}$-alkenyl, ($C_6$-$C_{10}$)aryl, ($C_6$-$C_{10}$)heteroaryl, —$C_1$-$C_{10}$-alkyl-($C_6$-$C_{10}$)aryl, —$C_2$-$C_{12}$-alkenyl-($C_6$-$C_{10}$)aryl, —$C_1$-$C_{10}$-alkyl-($C_3$-$C_8$)cycloalkyl, -(3- to 14-membered heterocycloalkyl) (wherein 1-4 heterocycloalkyl members are independently selected from N, O, and S), —($C_1$-$C_{10}$)alkyl-(3- to 14-membered heterocycloalkyl) (wherein 1-4 heterocycloalkyl members are independently selected from N, O, and S).

T is selected from the group consisting of a bond, —C(O)—, —C(O)$NR^X$—, —C(S)$NR^x$—, —$NR^x$C(O)—, —$NR^x$—, —$NR^x$C(O)$NR^x$—, —$NR^x$C(O)O—, and —OC(O)$NR^x$—.

$R^x$ in each instance is independently selected from H and $C_1$-$C_6$-alkyl.

Subscript m is an integer selected from 0, 1, 2, 3, 4, 5, and 6.

Subscript n is an integer selected from 1 and 2, wherein the sum of n and o is greater than 0.

Each "---" is a single bond that is optionally present. It should be understood that all bonds "---" are either simultaneously present or absent. When "---" is present, then o is selected from 1, 2, and 3. Further, in one embodiment, p is 0, $(N)_pR^6$ represents a bond, and U is —CH— or N, or, in another embodiment, p is 1 and U is —CH—. When "---" is not present, per another embodiment, then o is 0 and U is —$CH_2$— or NH.

Subscript q is an integer selected from 1, 2, and 3.

$R^3$ is selected from the group consisting of, H, $C_1$-$C_6$-alkyl, and —C(NH)$NH_2$.

$R^4$ is absent when "---" is present. When "---" is absent, then $R^4$ is H or $C_1$-$C_6$-alkyl.

Each $R^5$ is independently selected from the group consisting of H, $C_1$-$C_6$-alkyl, $C_1$-$C_6$-alkoxy, $C_1$-$C_6$-haloalkoxy, $C_3$-$C_8$-cycloalkyl, $C_1$-$C_6$-haloalkyl, CN, $NH_2$, and halo.

$R^6$ is H or $C_1$-$C_6$-alkyl.

In Formula IA, each alkyl, alkoxy, alkenyl, alkynyl, aryl, cycloalkyl, heterocycloalkyl, and heteroaryl is optionally substituted with 1-5 substituents independently selected from the group consisting of hydroxy, halo, $C_1$-$C_6$-haloalkoxy, $C_1$-$C_6$-haloalkyl, —$NR'_2$, —NHC(O)($OC_1$-$C_6$-alkyl), —$NO_2$, —CN, oxo, —C(O)OH, —C(O)O($C_1$-$C_6$-alkyl), —$C_1$-$C_6$-alkyl($C_1$-$C_6$-alkoxy), —C(O)$NH_2$, $C_1$-$C_6$-alkyl, —C(O)$C_1$-$C_6$-alkyl, —$OC_1$-$C_6$-alkyl, —Si($C_1$-$C_6$-alkyl)$_3$, —S(O)$_{0-2}$—($C_1$-$C_6$-alkyl), $C_6$-$C_{10}$-aryl, —($C_1$-$C_6$-alkyl)($C_6$-$C_{10}$-aryl), 3- to 14-membered heterocycloalkyl, and —($C_1$-$C_6$-alkyl)-(3- to 14-membered heterocycle) (wherein 1-4 heterocycle members are independently selected from N, O, and S), and —O($C_6$-$C_{14}$-aryl).

Each R' is independently selected from the group consisting of $C_1$-$C_6$-alkyl, $C_2$-$C_6$-alkenyl, $C_2$-$C_6$-alkynyl, $C_6$-$C_{10}$-aryl, 3- to 14-membered heterocycloalkyl and —($C_1$-$C_6$-alkyl)-(3- to 14-membered heterocycloalkyl) (wherein 1-4 ring members are independently selected from N, O, and S), and 5- to 10-membered heteroaryl (wherein 1-4 heteroaryl members are independently selected from N, O, and S.

The present disclosure also provides, in various embodiments, compounds and their pharmaceutically acceptable salts conforming to Formula I as SPNS2 inhibitors that avoid on-target adverse activity:

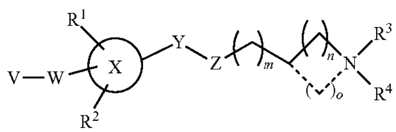

(I)

X is a $C_6$-$C_{10}$-aryl or 5- to 10-membered heteroaryl (wherein 1 to 4 heteroaryl ring members are independently selected from N, O, and S).

$R^1$ and $R^2$ are independently selected from the group consisting of H, $C_1$-$C_6$-alkyl, $C_1$-$C_6$-alkoxy, $C_1$-$C_6$-haloalkoxy, $C_3$-$C_8$-cycloalkyl, $C_1$-$C_6$-haloalkyl, CN, and halo.

W is a bond, O, NH, —NHC(O)—, or —O—(N═)C(R)— (wherein R is H or $C_1$-$C_6$-alkyl).

V is selected from the group consisting of H, $C_1$-$C_{14}$-alkyl, $C_2$-$C_{12}$-alkenyl, ($C_6$-$C_{10}$)aryl, ($C_6$-$C_{10}$)heteroaryl, —$C_1$-$C_{10}$-alkyl-($C_6$-$C_{10}$)aryl, —$C_2$-$C_{12}$-alkenyl-($C_6$-$C_{10}$) aryl, —$C_1$-$C_{10}$-alkyl-($C_3$-$C_8$)cycloalkyl, -(3- to 14-membered heterocycloalkyl) (wherein 1-4 heterocycloalkyl members are independently selected from N, O, and S), —($C_1$-$C_{10}$)alkyl-(3- to 14-membered heterocycloalkyl) (wherein 1-4 heterocycloalkyl members are independently selected from N, O, and S).

Y is —C(O)— and Z is —NH—, or Y is —NH— and Z is —C(O)—.

Each dashed line represented as "---" is a single bond that is optionally present.

$R^3$ is selected from the group consisting of, H, $C_1$-$C_6$-alkyl, and —C(NH)$NH_2$.

$R^4$ is absent when "---" is present, and when "---" is absent, then $R^4$ is H or $C_1$-$C_6$-alkyl.

Subscript m is an integer selected from 0, 1, 2, 3, 4, 5, and 6; n is an integer selected from 1 and 2; o is an integer selected from 0 and, when "---" is present, is selected from 2, and 3; and the sum of n and o is greater than 2.

Each alkyl, alkoxy, alkenyl, alkynyl, aryl, cycloalkyl, heterocycloalkyl, and heteroaryl in Formula I is optionally substituted with 1-5 substituents independently selected from the group consisting of hydroxy, halo, $C_1$-$C_6$-haloalkoxy, $C_1$-$C_6$-haloalkyl, —NR'$_2$, —NHC(O)(O$C_1$-$C_6$-alkyl), —$NO_2$, —CN, oxo, —C(O)OH, —C(O)O($C_1$-$C_6$-alkyl), —$C_1$-$C_6$-alkyl($C_1$-$C_6$-alkoxy), —C(O)$NH_2$, $C_1$-$C_6$-alkyl, —C(O)$C_1$-$C_6$-alkyl, —O$C_1$-$C_6$-alkyl, —Si($C_1$-$C_6$-alkyl)$_3$, —S(O)$_{0-2}$—($C_1$-$C_6$-alkyl), $C_6$-$C_{10}$-aryl, —($C_1$-$C_6$-alkyl)($C_6$-$C_{10}$-aryl), 3- to 14-membered heterocycloalkyl, and —($C_1$-$C_6$-alkyl)-(3- to 14-membered heterocycle) (wherein 1-4 heterocycle members are independently selected from N, O, and S), and —O($C_6$-$C_{14}$-aryl).

Each R' is independently selected from the group consisting of $C_1$-$C_6$-alkyl, $C_2$-$C_6$-alkenyl, $C_2$-$C_6$-alkynyl, $C_6$-$C_{10}$-aryl, 3- to 14-membered heterocycloalkyl and —($C_1$-$C_6$-alkyl)-(3- to 14-membered heterocycloalkyl) (wherein 1-4 ring members are independently selected from N, O, and S), and 5- to 10-membered heteroaryl (wherein 1-4 heteroaryl members are independently selected from N, O, and S.

Another embodiment of the disclosure is a pharmaceutical composition comprising a compound of Formula IA or Formula I or a pharmaceutically acceptable salt thereof.

The disclosure also provides, in an embodiment, a method of inhibiting spinster homolog 2 (SPNS2), comprising contacting SPNS2 with an effective amount of a compound of Formula IA or Formula I or a pharmaceutically acceptable salt thereof.

Still another embodiment is a method of treating a patient afflicted by a neoplastic disease, comprising administering to the patient a therapeutically effective amount of a compound of Formula IA or Formula I or a pharmaceutically acceptable salt thereof.

In an embodiment, the disclosure provides a method of treating a patient afflicted with an allergic disease, comprising administering to the patient a therapeutically effective amount of a compound of Formula IA or Formula I or a pharmaceutically acceptable salt thereof.

In another embodiment, the disclosure provides a method of treating a patient afflicted with an autoimmune disease, comprising administering to the patient a therapeutically effective amount of a compound of Formula IA or Formula I or a pharmaceutically acceptable salt thereof.

DETAILED DESCRIPTION

In a properly functioning immune system, the right cells get to the right places at the right times. Gradients of the chemotactic lipid, sphingosine 1-phosphate (S1P), enable correct positioning of immune cells. Lymphocyte egress from secondary lymphoid tissues is particularly dependent on S1P signaling. S1P's role in lymphocyte trafficking was discovered when the mechanism of action of the immunosuppressive drug fingolimod (FTY720) was investigated. Fingolimod's active metabolite, phospho-FTY720, desensitizes lymphocyte S1P1 receptors; thereby, rendering these cells unable to detect the S1P-rich environment of efferent lymph[1]. The resulting lymphopenia is now recognized as a general property of S1P1 receptor agonists. Although fingolimod and other S1P receptor modulators eventually became medicines for treating relapsing remitting multiple sclerosis[2], S1P1 receptor agonists have several on target liabilities including initial dose bradycardia and compromised endothelial barrier function[2]. Therefore, alternative strategies to achieve immunosuppression by modulating S1P signaling without undesirable on-target activity are needed.

S1P is synthesized ubiquitously, but its intracellular accumulation is limited by degradation and export. In lymph nodes (LN), brisk catabolic activity by S1P lyase keeps S1P[3] low while lymph endothelial cells extrude S1P into lymph via a transporter, SPNS2[4], resulting in a lymph—LN S1P gradient. Vascular (blood) S1P gradients are likewise maintained by prominent S1P catabolic activity in tissue parenchyma coupled with the extrusion of S1P into plasma. About ⅓ of plasma S1P is provided by vascular endothelial cells via SPNS2[4], with the remainder being released from red blood cells (RBCs) by a different S1P transporter. The RBC transporter is known now to be MFSD2B, which is an erythroid lineage-specific major facilitator superfamily member that is distantly related to SPNS2[5,6]. Germ line deletion of Mfsd2b results in a 50% decrease in plasma S1P but an astonishing 60-fold increase in RBC S1P; however, these animals are not lymphopenic[5]. RBCs lack S1P catabolic enzymes but express sphingosine kinase type 1 (SphK1), which accounts for the high levels of S1P in whole blood. Blood S1P gradients are necessary to maintain endothelial barrier integrity[7]. Indeed, Hla has proposed that vascular S1P gradients are a fundamental property of the closed circulatory systems of vertebrates[9].

The role of the catabolic enzyme S1P lyase in maintaining low LN S1P predicts that S1P lyase inhibitors will eliminate the S1P gradient, which will modulate the immune system by disrupting lymphocyte trafficking analogous to S1P1 agonists. Indeed, S1P lyase deficiency, whether accomplished through genetic manipulation of mice or S1P lyase inhibitor administration, raises S1P levels in tissues, including lymph nodes, with a resulting lymphopenia[3,10]. However, administering a selective S1P lyase inhibitor to rats and inducing global deletion of the gene (Sgpl1) in mice were both found to be nephrotoxic[10]. Furthermore, humans deficient in S1P lyase activity because of SGPL1 alleles encoding catalytically deficient S1P lyase exhibit multiple pathologies including steroid resistant nephrosis, adrenal insufficiency, and ichthyosis[11,12]. Such observations appear to eliminate S1P lyase as a therapeutic target.

Mice rendered deficient in Spns2 either through germ line or endothelium-specific deletion of Spns2, have a 10-fold decrease in S1P levels in thoracic duct lymph and are lymphopenic but the vascular S1P gradient is less affected (30% reduction in plasma S1P)[4]. These results validate the data disclosed herein that SPNS2 inhibitors of this disclosure, by preventing the formation of the lymph S1P gradient, recapitulate the therapeutic efficacy of S1P1 receptor agonists without their adverse events.

Application of an SPNS2 inhibitor in immuno-oncology comes from another mouse genetics study. In a screen of 810 mouse strains with different germ line gene deletions, $Spns2^{-/-}$ mice were found to have remarkably low metastatic colonization of the lungs when injected with B16-F10 melanoma cells[13]. This effect was observed with other lung metastatic colonization models and in similar models in liver. As expected, the total number of immune cells in the lung was reduced in the lymphopenic $Spns2^{-/-}$ mice, but the lung resident population was proportionally enriched in natural killer and $CD8^+$ effector cells[13].

Thus, results from the study of mice rendered deficient in Spns2 indicate that SPNS2 inhibitors are immunomodulatory. The SPNS2 inhibitors of the disclosure recapitulate the SPNS2 null phenotype, and they and enable S1P transport inhibition as a viable therapeutic strategy as well as providing heretofore unavailable chemical biology tools to explore S1P physiology in vivo.

Definitions

"Alkyl" refers to straight or branched chain hydrocarbyl including from 1 to about 20 carbon atoms. For instance, an alkyl can have from 1 to 10 carbon atoms or 1 to 6 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, $—CH(CH_3)_2$, $—CH(CH_3)(CH_2CH_3)$, $—CH(CH_2CH_3)_2$, $—C(CH_3)_3$, $—C(CH_2CH_3)_3$, $—CH_2CH(CH_3)_2$, $—CH_2CH(CH_3)(CH_2CH_3)$, $—CH_2CH(CH_2CH_3)_2$, $—CH_2C(CH_3)_3$, $—CH_2C(CH_2CH_3)_3$, $—CH(CH_3)CH(CH_3)(CH_2CH_3)$, $—CH_2CH_2CH(CH_3)_2$, $—CH_2CH_2C\ H(CH_3)(CH_2CH_3)$, $—CH_2CH_2CH(CH_2CH_3)_2$, $—CH_2CH_2C(CH_3)_3$, $—CH_2CH_2C(CH_2CH_3)_3$, $—CH(CH_3)CH_2CH(CH_3)_2$, $—CH(CH_3)CH(CH_3)CH(CH_3)_2$, and the like. Thus, alkyl groups include primary alkyl groups, secondary alkyl groups, and tertiary alkyl groups. An alkyl group can be unsubstituted or optionally substituted with one or more substituents as described herein below.

The phrase "substituted alkyl" refers to alkyl substituted at one or more positions, for example, 1, 2, 3, 4, 5, or even 6 positions, which substituents are attached at any available atom to produce a stable compound, with substitution as described herein. "Optionally substituted alkyl" refers to alkyl or substituted alkyl.

A "haloalkyl" is an alkyl, as defined herein, that is substituted with at least one, such as 1-8, halo substituents.

Each of the terms "halogen," "halide," and "halo" refers to —F, —Cl, —Br, or —I.

The term "alkenyl" refers to straight or branched chain hydrocarbyl groups including from 2 to about 20 carbon atoms having 1-3, 1-2, or at least one carbon to carbon double bond. An alkenyl group can be unsubstituted or optionally substituted with one or more substituents as described herein below.

"Substituted alkenyl" refers to alkenyl substituted at 1 or more, e.g., 1, 2, 3, 4, 5, or even 6 positions, which substituents are attached at any available atom to produce a stable compound, with substitution as described herein. "Optionally substituted alkenyl" refers to alkenyl or substituted alkenyl.

"Alkyne or "alkynyl" refers to a straight or branched chain unsaturated hydrocarbon having the indicated number of carbon atoms and at least one triple bond. Examples of a $(C_2-C_8)$alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

"Substituted alkynyl" refers to an alkynyl substituted at 1 or more, e.g., 1, 2, 3, 4, 5, or even 6 positions, which substituents are attached at any available atom to produce a stable compound, with substitution as described herein. "Optionally substituted alkynyl" refers to alkynyl or substituted alkynyl.

The term "alkoxy" refers to an —O-alkyl group having the indicated number of carbon atoms. For example, a $(C_1-C_6)$alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

A "haloalkoxy" is an alkoxy, as defined herein, that is substituted with at least one, such as 1-8, halo substituents.

The term "cycloalkyl" refers to a monocyclic, bicyclic, tricyclic, or polycyclic, 3- to 14-membered ring system, which is either saturated, such as "cycloalkyl," or unsaturated, such as "cycloalkenyl." The term "cycloalkenyl" refers specifically to cyclic alkenyl, such as $C_3-C_6$-cycloalkenyl. The cycloalkyl may be attached via any atom. Cycloalkyl, for instance, also contemplates fused rings wherein, for instance, a cycloalkyl is fused to an aryl or heteroaryl ring as defined herein. Representative examples of cycloalkyl include, but are not limited to cyclopropyl, cyclobutyl, cyclopentyl, cyclohexyl, cyclopropenyl, cyclobutenyl, cyclopentenyl, and cyclohexenyl. A cycloalkyl group can be unsubstituted or optionally substituted with one or more substituents as described herein.

"Substituted cycloalkyl" refers to cycloalkyl substituted at 1 or more, e.g., 1, 2, 3, 4, 5, or even 6 positions, which substituents are attached at any available atom to produce a stable compound, with substitution as described herein. "Optionally substituted cycloalkyl" refers to cycloalkyl or substituted cycloalkyl.

"Aryl" when used alone or as part of another term means a carbocyclic aromatic group whether or not fused having the number of carbon atoms designated or if no number is designated, up to 14 carbon atoms, such as a $C_6-C_{14}$-aryl. Particular aryl groups are phenyl, naphthyl, biphenyl, phenanthrenyl, naphthacenyl, and the like (see e.g. *Lang's Handbook of Chemistry* (Dean, J. A., ed) $13^{th}$ ed. Table 7-2 [1985]). A particular aryl is phenyl. "Aryl" also includes aromatic ring systems that are optionally fused with a cycloalkyl ring, as herein defined. An aryl group can be unsubstituted or optionally substituted with one or more substituents as described herein below.

A "substituted aryl" is an aryl that is independently substituted with one or more substituents attached at any available atom to produce a stable compound, wherein the substituents are as described herein. "Optionally substituted aryl" refers to aryl or substituted aryl.

The term "heteroatom" refers to N, O, and S. Disclosed compounds that contain N or S atoms can be optionally oxidized to the corresponding N-oxide, sulfoxide, or sulfone compounds.

"Heteroaryl," alone or in combination with any other moiety described herein, refers to a monocyclic aromatic ring structure containing 5 to 10, such as 5 or 6 ring atoms, or a bicyclic aromatic group having 8 to 10 atoms, containing one or more, such as 1-4, 1-3, or 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or heteroatom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, benzimidazolyl, benzisoimidazolyl, benzothiazolyl, benzoxazolyl, benzisoxazolyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. A heteroaryl group can be unsubstituted or optionally substituted with one or more substituents as described herein below.

A "substituted heteroaryl" is a heteroaryl that is independently substituted, unless indicated otherwise, with one or more, e.g., 1, 2, 3, 4 or 5, also 1, 2, or 3 substituents, also 1 substituent, attached at any available atom to produce a stable compound, wherein the substituents are as described herein. "Optionally substituted heteroaryl" refers to heteroaryl or substituted heteroaryl.

"Heterocycloalkyl" means a saturated or unsaturated non-aromatic monocyclic, bicyclic, tricyclic or polycyclic ring system that has from 3 to 14, such as 3 to 6, atoms in which from 1 to 3 carbon atoms in the ring are replaced by heteroatoms of O, S or N. A heterocycloalkyl is optionally fused with aryl or heteroaryl of 5-6 ring members, and includes oxidized S or N, such as sulfinyl, sulfonyl and N-oxide of a tertiary ring nitrogen. The point of attachment of the heterocycloalkyl ring is at a carbon or heteroatom such that a stable ring is retained. Examples of heterocycloalkyl groups include without limitation morpholino, tetrahydrofuranyl, dihydropyridinyl, piperidinyl, pyrrolidinyl, piperazinyl, dihydrobenzofuryl, and dihydroindolyl. A hetercycloalkyl group can be unsubstituted or optionally substituted with one or more substituents as described herein below.

"Optionally substituted heterocycloalkyl" denotes a heterocycloalkyl that is substituted with 1 to 3 substituents, e.g., 1, 2 or 3 substituents, attached at any available atom to produce a stable compound, wherein the substituents are as described herein.

The term "nitrile" or "cyano" can be used interchangeably and refer to a —CN group which is bound to a carbon atom of a heteroaryl ring, aryl ring and a heterocycloalkyl ring.

The term "oxo" refers to a ═O atom attached to a saturated or unsaturated moiety. The ═O atom can be attached to a carbon, sulfur, or nitrogen atom that is part of a cyclic or acyclic moiety.

A "hydroxyl" or "hydroxy" refers to an —OH group.

The substituent $—CO_2H$ may be replaced with bioisosteric replacements such as:

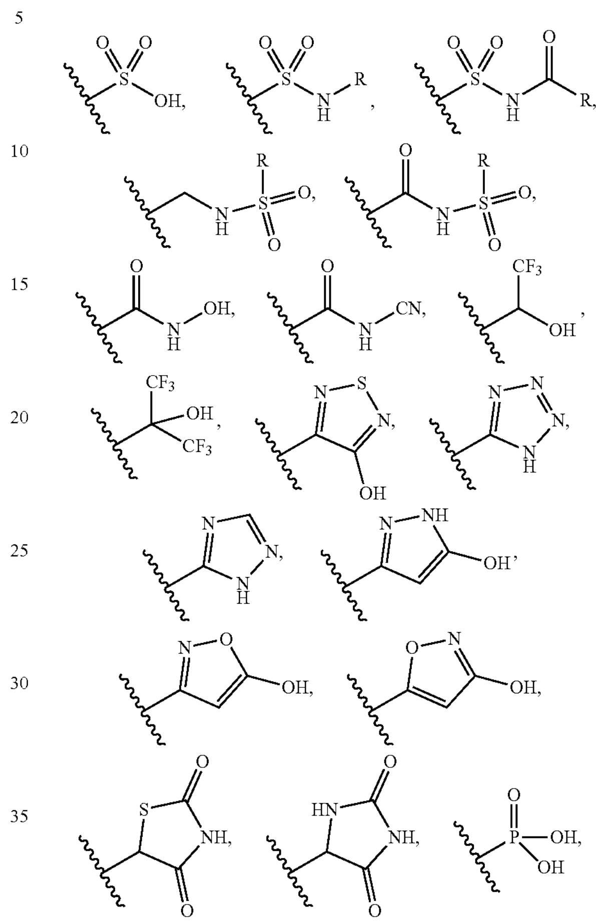

and the like, wherein R has the same definition as $R^A$ as defined herein. See, e.g., The Practice of Medicinal Chemistry (Academic Press: New York, 1996), at page 203.

Compounds described herein can exist in various isomeric forms, including configurational, geometric, and conformational isomers, including, for example, cis- or trans-conformations. The compounds may also exist in one or more tautomeric forms, including both single tautomers and mixtures of tautomers. The term "isomer" is intended to encompass all isomeric forms of a compound of this disclosure, including tautomeric forms of the compound. The compounds of the present disclosure may also exist in open-chain or cyclized forms. In some cases one or more of the cyclized forms may result from the loss of water. The specific composition of the open-chain and cyclized forms may be dependent on how the compound is isolated, stored or administered. For example, the compound may exist primarily in an open-chained form under acidic conditions but cyclize under neutral conditions. All forms are included in the disclosure.

Some compounds described herein can have asymmetric centers and therefore exist in different enantiomeric and diastereomeric forms. A compound as described herein can be in the form of an optical isomer or a diastereomer. Accordingly, the disclosure encompasses compounds and their uses as described herein in the form of their optical isomers, diastereoisomers and mixtures thereof, including a racemic mixture. Optical isomers of the compounds of the disclosure can be obtained by known techniques such as asymmetric synthesis, chiral chromatography, simulated moving bed technology or via chemical separation of stereoisomers through the employment of optically active resolving agents.

Unless otherwise indicated, the term "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound. The stereoisomer as described above can be viewed as composition comprising two stereoisomers that are present in their respective weight percentages described herein.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

As used herein, and unless otherwise specified to the contrary, the term "compound" is inclusive in that it encompasses a compound or a pharmaceutically acceptable salt, stereoisomer, and/or tautomer thereof. Thus, for instance, a compound of Formula I includes a pharmaceutically acceptable salt of the compound.

In this description, a "pharmaceutically acceptable salt" is a pharmaceutically acceptable, organic or inorganic acid or base salt of a compound described herein. Representative pharmaceutically acceptable salts include, e.g., alkali metal salts, alkali earth salts, ammonium salts, water-soluble and water-insoluble salts, such as the acetate, amsonate (4,4-diaminostilbene-2, 2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The terms "prevent," "preventing," and "prevention" refer to the prevention of the onset, recurrence, or spread of the disease in a patient resulting from the administration of a prophylactic or therapeutic agent.

The term "effective amount" refers to an amount of a compound as described herein or other active ingredient sufficient to provide a therapeutic or prophylactic benefit in the treatment or prevention of a disease or to delay or minimize symptoms associated with a disease. Further, a therapeutically effective amount with respect to a compound as described herein means that amount of therapeutic agent alone, or in combination with other therapies, that provides a therapeutic benefit in the treatment or prevention of a disease. Used in connection with a compound as described herein, the term can encompass an amount that improves overall therapy, reduces or avoids symptoms or causes of disease, or enhances the therapeutic efficacy of or synergies with another therapeutic agent.

A "patient" or subject" includes an animal, such as a human, cow, horse, sheep, lamb, pig, chicken, turkey, quail, cat, dog, mouse, rat, rabbit or guinea pig. In accordance with some embodiments, the animal is a mammal such as a non-primate and a primate (e.g., monkey and human). In one embodiment, a patient is a human, such as a human infant, child, adolescent or adult.

"Inhibitor" means a compound that induces dose dependent lymphopenia and a modest decrease in plasma S1P. In an embodiment, an inhibitor binds to SPNS2.

Compounds

As described generally above, the present disclosure provides compounds, pharmaceutically acceptable salts, and/or tautomers thereof, wherein the compounds conform to Formula IA:

(IA)

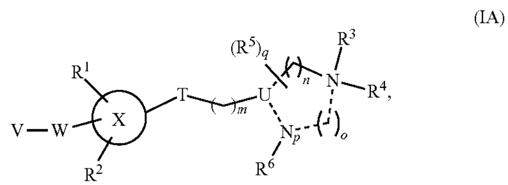

X is a $C_6$-$C_{10}$-aryl or 5- to 10-membered heteroaryl (wherein 1 to 4 heteroaryl ring members are independently selected from N, O, and S).

$R^1$ and $R^2$ are independently selected from the group consisting of H, $C_1$-$C_6$-alkyl, $C_1$-$C_6$-alkoxy, $C_1$-$C_6$-haloalkoxy, $C_3$-$C_8$-cycloalkyl, $C_1$-$C_6$-haloalkyl, CN, and halo.

W is a bond, O, NH, —NHC(O)—, or —O—(N═)C(R)— (wherein R is H or $C_1$-$C_6$-alkyl).

V is selected from the group consisting of H, $C_1$-$C_{14}$-alkyl, $C_2$-$C_{12}$-alkenyl, ($C_6$-$C_{10}$)aryl, ($C_6$-$C_{10}$)heteroaryl, —$C_1$-$C_{10}$-alkyl-($C_6$-$C_{10}$)aryl, —$C_2$-$C_{12}$-alkenyl-($C_6$-$C_{10}$) aryl, —$C_1$-$C_{10}$-alkyl-($C_3$-$C_8$)cycloalkyl, -(3- to 14-membered heterocycloalkyl) (wherein 1-4 heterocycloalkyl members are independently selected from N, O, and S), —($C_1$-$C_{10}$)alkyl-(3- to 14-membered heterocycloalkyl) (wherein 1-4 heterocycloalkyl members are independently selected from N, O, and S).

T is selected from the group consisting of a bond, —C(O)— —C(O)$NR^X$, —C(S)$NR^x$—, —$NR^x$C(O)—, —$NR^x$—, —$NR^x$C(O)$NR^x$—, and —$NR^x$C(O)O—.

$R^x$ in each instance is independently selected from H and $C_1$-$C_6$-alkyl.

Subscript m is an integer selected from 0, 1, 2, 3, 4, 5, and 6.

Subscript n is an integer selected from 1 and 2, wherein the sum of n and o is greater than 0.

Each "---" is a single bond that is optionally present. It should be understood that all bonds "---" are simultaneously present or absent. When "---" is present, then o is selected from 1, 2, and 3. Further, in one embodiment, p is 0, $(N)_pR^6$ represents a bond, and U is —CH— or N, or, in another embodiment, p is 1 and U is —CH—. When "---" is not present, per another embodiment, then o is 0 and U is —$CH_2$— or NH.

Subscript q is an integer selected from 1, 2, and 3.

$R^3$ is selected from the group consisting of, H, $C_1$-$C_6$-alkyl, and —C(NH)$NH_2$.

$R^4$ is absent when "---" is present. When "---" is absent, then $R^4$ is H or $C_1$-$C_6$-alkyl.

Each $R^5$ is independently selected from the group consisting of H, $C_1$-$C_6$-alkyl, $C_1$-$C_6$-alkoxy, $C_1$-$C_6$-haloalkoxy, $C_3$-$C_8$-cycloalkyl, $C_1$-$C_6$-haloalkyl, CN, $NH_2$, and halo.

$R^6$ is H or $C_1$-$C_6$-alkyl.

In Formula IA, each alkyl, alkoxy, alkenyl, alkynyl, aryl, cycloalkyl, heterocycloalkyl, and heteroaryl is optionally substituted with 1-5 substituents independently selected from the group consisting of hydroxy, halo, $C_1$-$C_6$-haloalkoxy, $C_1$-$C_6$-haloalkyl, —$NR'_2$, —NHC(O)($OC_1$-$C_6$-alkyl), —$NO_2$, —CN, oxo, —C(O)OH, —C(O)O($C_1$-$C_6$-alkyl), —$C_1$-$C_6$-alkyl($C_1$-$C_6$-alkoxy), —C(O)$NH_2$, $C_1$-$C_6$-alkyl, —C(O)$C_1$-$C_6$-alkyl, —$OC_1$-$C_6$-alkyl, —Si($C_1$-$C_6$-alkyl)$_3$, —S(O)$_{0-2}$—($C_1$-$C_6$-alkyl), $C_6$-$C_{10}$-aryl, —($C_1$-$C_6$-alkyl)($C_6$-$C_{10}$-aryl), 3- to 14-membered heterocycloalkyl, and —($C_1$-$C_6$-alkyl)-(3- to 14-membered heterocycle) (wherein 1-4 heterocycle members are independently selected from N, O, and S), and —O($C_6$-$C_{14}$-aryl).

Each R' is independently selected from the group consisting of $C_1$-$C_6$-alkyl, $C_2$-$C_6$-alkenyl, $C_2$-$C_6$-alkynyl, $C_6$-$C_{10}$-aryl, 3- to 14-membered heterocycloalkyl and —($C_1$-$C_6$-alkyl)-(3- to 14-membered heterocycloalkyl) (wherein 1-4 ring members are independently selected from N, O, and S), and 5- to 10-membered heteroaryl (wherein 1-4 heteroaryl members are independently selected from N, O, and S.

In some embodiments, T is a bond; "---" is absent; U is —$CH_2$— or —NH; and m is an integer selected from 1, 2, 3, 4, 5, and 6.

In other embodiments, T is —$NR^x$—; "---" is absent; and U is —$CH_2$— or —NH. In some embodiments, $R^x$ is H.

In still additional embodiments, T is —$NR^x$C(O)$NR^x$—; "---" is absent; and U is —$CH_2$— or —NH. In various embodiments, each instance of $R^x$ is H.

In some embodiments, "---" is present; and m is 0, 1, 2, or 3. In illustrative embodiments, m is 0.

In further embodiments, optionally in combination with any other embodiment described herein, p is 0, $(N)_pR^6$ represents a bond, and U is —CH— or N. In other embodiments, p is 1 and U is —CH—.

In various embodiments, optionally in combination with any other embodiment described herein, T is selected from the group consisting of —C(O)$NR^x$, —$NR^x$C(O)—, —$NR^x$—, —$NR^x$C(O)$NR^x$—, and —$NR^x$C(O)O—. In other embodiments, T is a bond. In still further embodiments, T is —C(O)—.

Another embodiment of the present disclosure is a Formula IA compound or pharmaceutically acceptable salt thereof wherein X is $C_6$-$C_{10}$-aryl. Examples of X include phenyl and naphthyl.

In other embodiments, X is a 5- to 10-membered heteroaryl (wherein 1 to 4 heteroaryl ring members are independently selected from N, O, and S). In illustrative embodiments, X is benzoxazolyl, benzothiazolyl, and benzimidazolyl.

In various embodiments, the present disclosure provides Formula IA compounds wherein X is a 10-membered heteroaryl (wherein 2 heteroaryl ring members are independently selected from N and O), T is —$NR^x$—, m is 0; and "---" is present.

Various embodiments contemplate Formula IA compounds wherein the moiety:

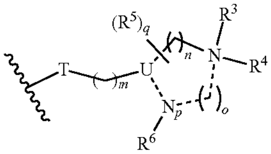

represents many combinations, as illustrated by the following non-limiting examples:

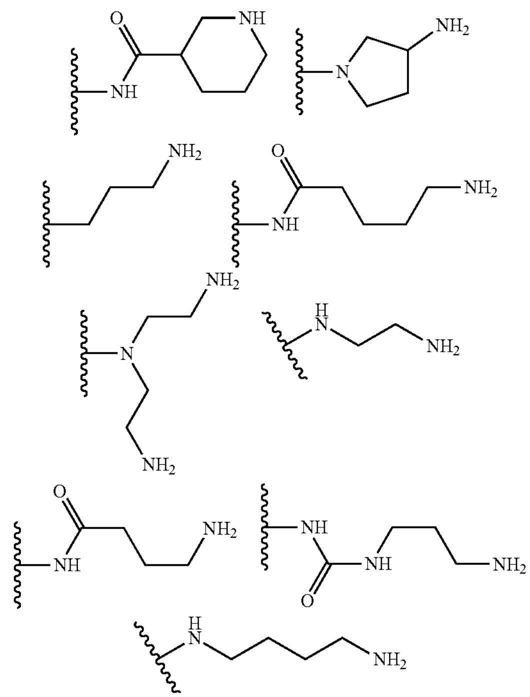

-continued

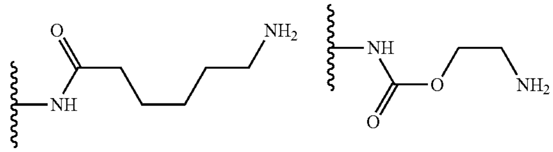

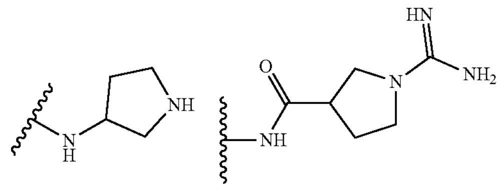

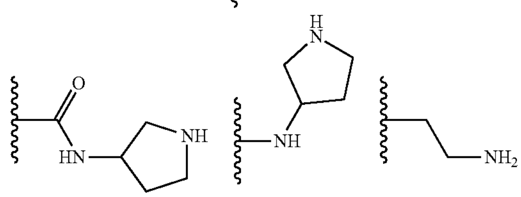

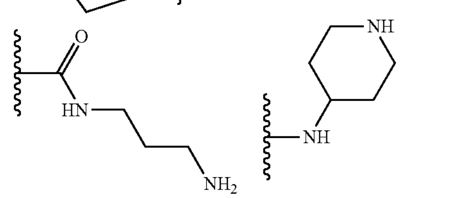

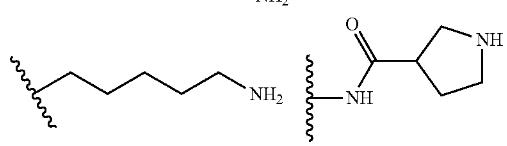

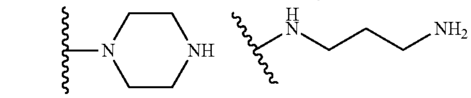

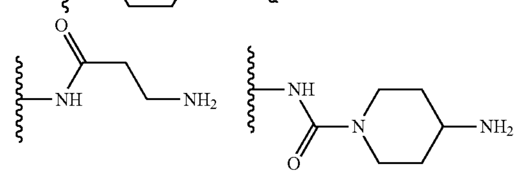

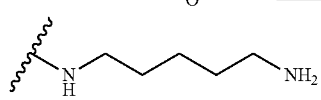

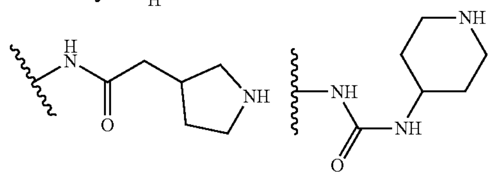

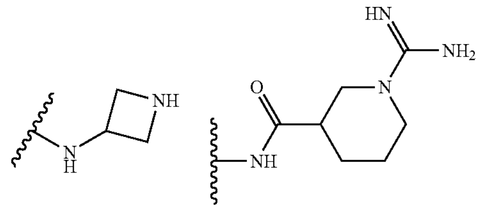

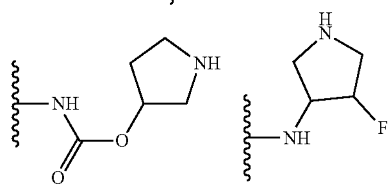

-continued

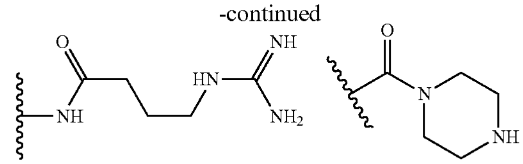

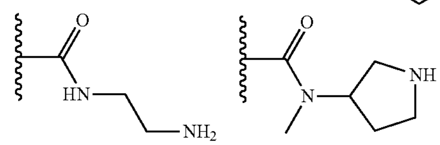

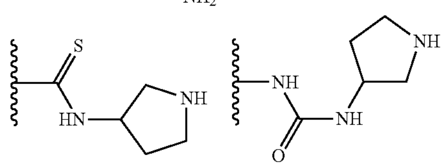

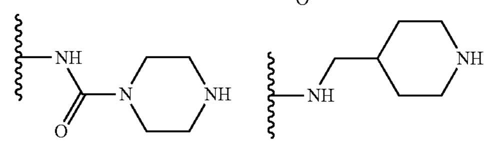

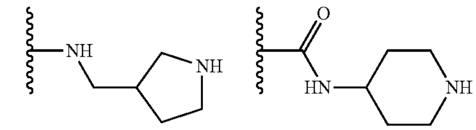

In various embodiments, the compound of Formula IA is a compound of Formula I, as described in summary above:

(I)

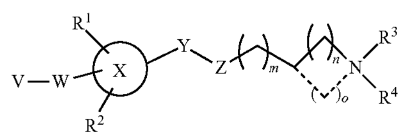

X is a $C_6$-$C_{10}$-aryl or 5- to 10-membered heteroaryl (wherein 1 to 4 heteroaryl ring members are independently selected from N, O, and S).

$R^1$ and $R^2$ are independently selected from the group consisting of H, $C_1$-$C_6$-alkyl, $C_1$-$C_6$-alkoxy, $C_1$-$C_6$-haloalkoxy, $C_3$-$C_8$-cycloalkyl, $C_1$-$C_6$-haloalkyl, CN, and halo.

W is a bond, 0, NH, —NHC(O)—, or —O—(N═)C(R)— (wherein R is H or $C_1$-$C_6$-alkyl).

V is selected from the group consisting of H, $C_1$-$C_{14}$-alkyl, $C_2$-$C_{12}$-alkenyl, ($C_6$-$C_{10}$)aryl, ($C_6$-$C_{10}$)heteroaryl, —$C_1$-$C_{10}$-alkyl-($C_6$-$C_{10}$)aryl, —$C_2$-$C_{12}$-alkenyl-($C_6$-$C_{10}$)aryl, —$C_1$-$C_{10}$-alkyl-($C_3$-$C_8$)cycloalkyl, -(3- to 14-membered heterocycloalkyl) (wherein 1-4 heterocycloalkyl members are independently selected from N, O, and S), —($C_1$-$C_{10}$)alkyl-(3- to 14-membered heterocycloalkyl) (wherein 1-4 heterocycloalkyl members are independently selected from N, O, and S).

Y is —C(O)— and Z is —NH—, or Y is —NH— and Z is —C(O)—.

Each dashed line represented as "---" is a single bond that is optionally present.

$R^3$ is selected from the group consisting of, H, $C_1$-$C_6$-alkyl, and —C(NH)$NH_2$.

In an embodiment, $R^4$ is absent when "---" is present. In another embodiment, $R^4$ is H or $C_1$-$C_6$-alkyl when "---" is absent.

Subscript m is an integer selected from 0, 1, 2, 3, 4, 5, and 6; n is an integer selected from 1 and 2; o is an integer selected from 0 and, when "---" is present, is selected from 2, and 3; and the sum of n and o is greater than 2.

Each alkyl, alkoxy, alkenyl, alkynyl, aryl, cycloalkyl, heterocycloalkyl, and heteroaryl in Formula I is optionally substituted with 1-5 substituents independently selected from the group consisting of hydroxy, halo, $C_1$-$C_6$-haloalkoxy, $C_1$-$C_6$-haloalkyl, —NR'$_2$, —NHC(O)(O$C_1$-$C_6$-alkyl), —$NO_2$, —CN, oxo, —C(O)OH, —C(O)O($C_1$-$C_6$-alkyl), —$C_1$-$C_6$-alkyl($C_1$-$C_6$-alkoxy), —C(O)$NH_2$, $C_1$-$C_6$-alkyl, —C(O)$C_1$-$C_6$-alkyl, —O$C_1$-$C_6$-alkyl, —Si($C_1$-$C_6$-alkyl)$_3$, —S(O)$_{0-2}$—($C_1$-$C_6$-alkyl), $C_6$-$C_{10}$-aryl, —($C_1$-$C_6$-alkyl)($C_6$-$C_{10}$-aryl), 3- to 14-membered heterocycloalkyl, and —($C_1$-$C_6$-alkyl)-(3- to 14-membered heterocycle) (wherein 1-4 heterocycle members are independently selected from N, O, and S), and —O($C_6$-$C_{14}$-aryl).

Each R' is independently selected from the group consisting of $C_1$-$C_6$-alkyl, $C_2$-$C_6$-alkenyl, $C_2$-$C_6$-alkynyl, $C_6$-$C_{10}$-aryl, 3- to 14-membered heterocycloalkyl and —($C_1$-$C_6$-alkyl)-(3- to 14-membered heterocycloalkyl) (wherein 1-4 ring members are independently selected from N, O, and S), and 5- to 10-membered heteroaryl (wherein 1-4 heteroaryl members are independently selected from N, O, and S.

Additional embodiments, optionally in combination with any other embodiment described herein, provide for Formula I compounds wherein "---" is present.

In various embodiments, o is 2. In further embodiments, o is 3, or o is 0.

In other embodiments, optionally in combination with any other embodiment described herein m is 0.

The present disclosure also provides Formula I compounds, or their pharmaceutically acceptable salts, wherein X is $C_6$-$C_{10}$-aryl. For example, in an embodiment X is phenyl.

Additional embodiments provide Formula I compounds wherein $R^3$ and $R^4$, if present, are independently selected from H and $C_1$-$C_6$-alkyl. In an illustrative embodiment, each of $R^3$ and $R^4$, if present, is H.

In other embodiments, $R^3$ is C(NH)$NH_2$.

The present disclosure also provides Formula I compounds, in embodiments, wherein W is a bond or O, and V is $C_1$-$C_{14}$-alkyl or —$C_1$-$C_{10}$-alkyl-($C_6$-$C_{10}$)aryl.

One embodiment, optionally in combination with any other embodiment described herein, provides for a Formula I compound or pharmaceutically acceptable salt thereof wherein each of $R^1$ and $R^2$ is H.

In various embodiments, X is phenyl; each of $R^1$ and $R^2$ is H; W is a bond or O; V is $C_1$-$C_{14}$-alkyl; o is O; $R^3$ is selected from the group consisting of, H, $C_1$-$C_6$-alkyl, and —C(NH)$NH_2$; and $R^4$ is H or $C_1$-$C_6$-alkyl.

The present disclosure provides specific examples of Formula I and Formula IA compounds, and their pharmaceutically acceptable salts, and/or tautomers thereof as set forth in Table 1 below.

TABLE 1

Examples of Formula I and Formula IA Compounds

| Compound | Structure |
|---|---|
| 2a | 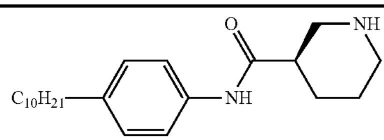 |

TABLE 1-continued

Examples of Formula I and Formula IA Compounds

| Compound | Structure |
|---|---|
| 2b | 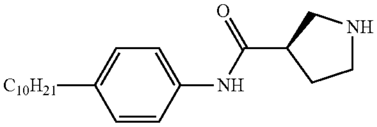 |
| 2c | 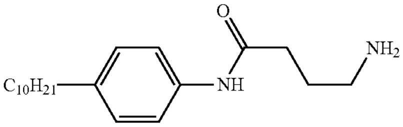 |
| 2d | 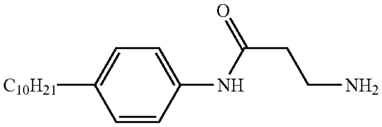 |
| 2e | 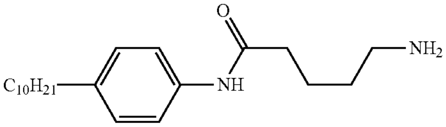 |
| 2f | 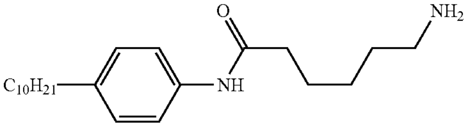 |
| 2g | 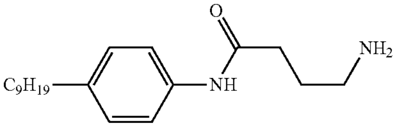 |
| 2h | 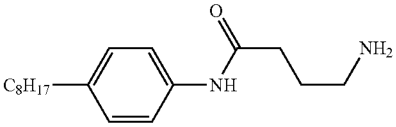 |
| 2i | 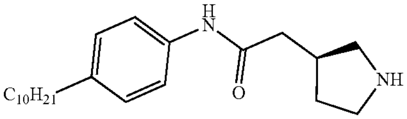 |
| 2j | 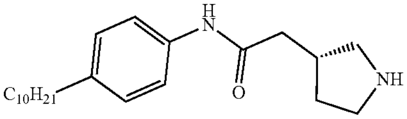 |
| 2k | 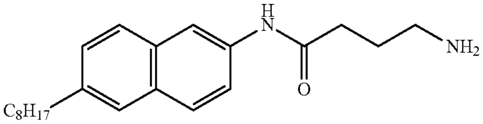 |

TABLE 1-continued
Examples of Formula I and Formula IA Compounds
| Compound | Structure |
|---|---|
| 2l | 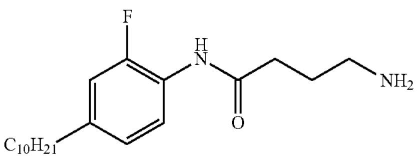 |
| 2m | 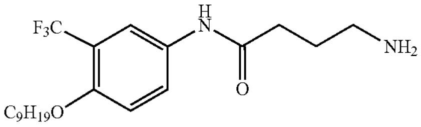 |
| 2n | 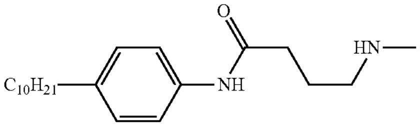 |
| 2o | 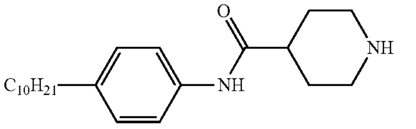 |
| 2p | 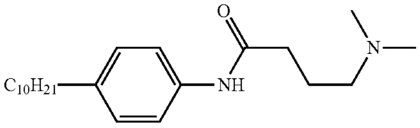 |
| 4a | 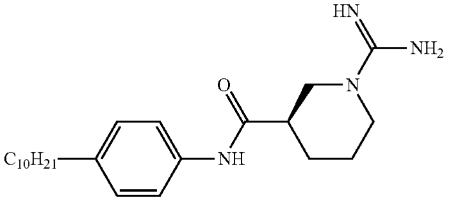 |
| 4b | 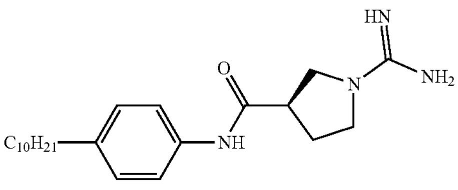 |
| 4c | 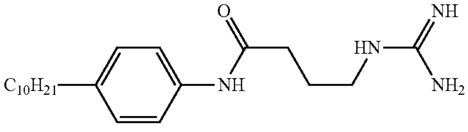 |
| 8a | 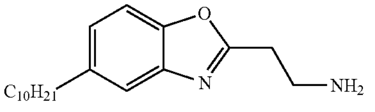 |
| 8b | 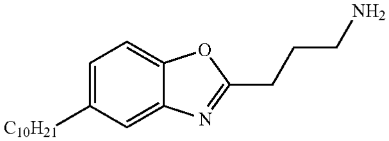 |
TABLE 1-continued
Examples of Formula I and Formula IA Compounds
| Compound | Structure |
|---|---|
| 8c | 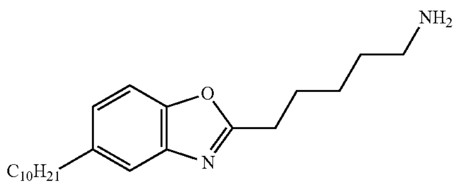 |
| 8d | 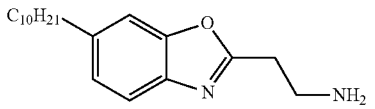 |
| 8e | 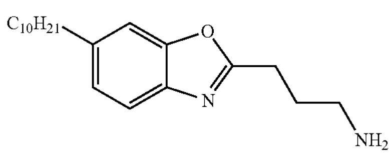 |
| 13a | 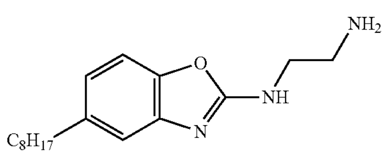 |
| 13b | 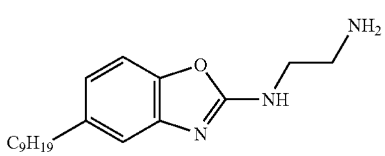 |
| 13c | 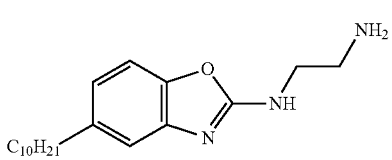 |
| 13d | 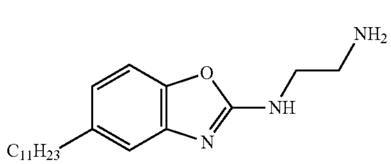 |
| 13e | 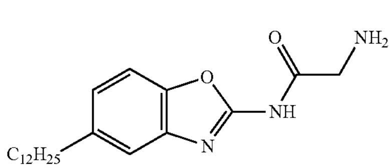 |
| 13f | 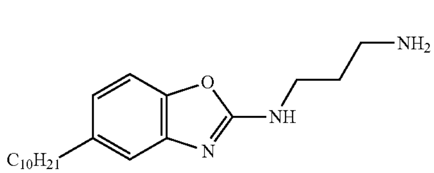 |

TABLE 1-continued
| Examples of Formula I and Formula IA Compounds | |
|---|---|
| Compound | Structure |
| 13g | 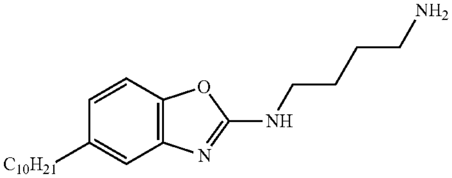 |
| 13h | 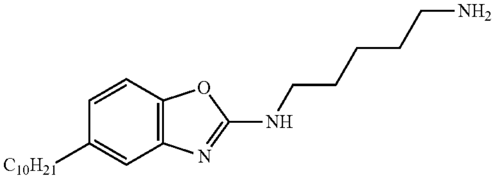 |
| 13i | 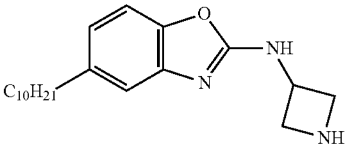 |
| 13j | 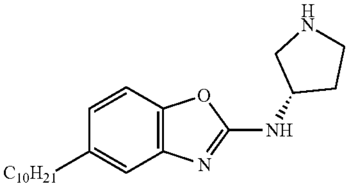 |
| 13k | 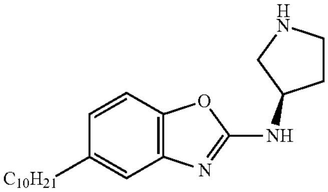 |
| 13l | 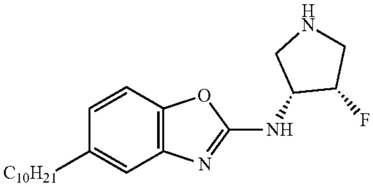 |
| 13m | 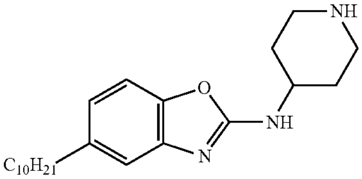 |
| 13n | 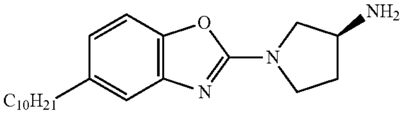 |
TABLE 1-continued
| Examples of Formula I and Formula IA Compounds | |
|---|---|
| Compound | Structure |
| 13o | 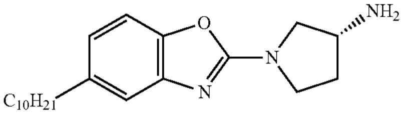 |
| 13p | 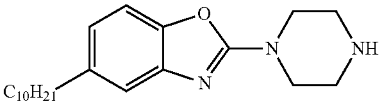 |
| 13q | 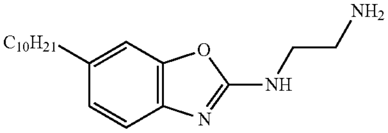 |
| 13r | 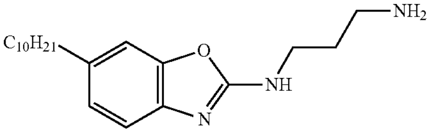 |
| 13s | 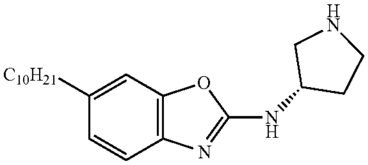 |
| 13t | 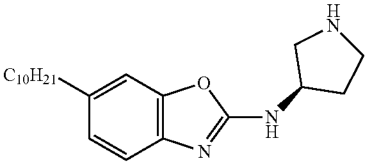 |
| 13u | 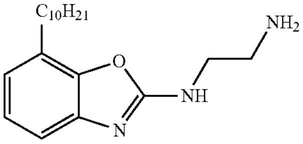 |
| 13v | 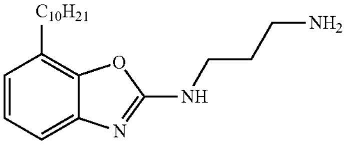 |
| 13w | 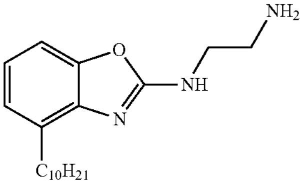 |

TABLE 1-continued
| Examples of Formula I and Formula IA Compounds | |
|---|---|
| Compound | Structure |
| 13x | 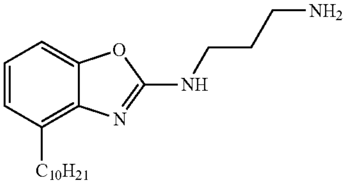 |
| 13y | 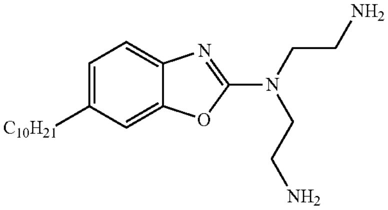 |
| 13z | 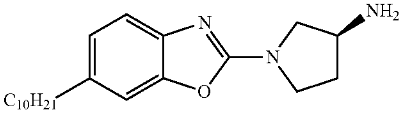 |
| 13aa | 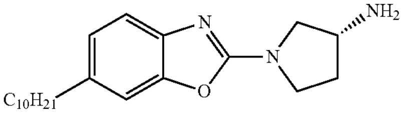 |
| 13ab | 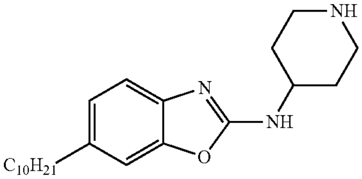 |
| 17a | 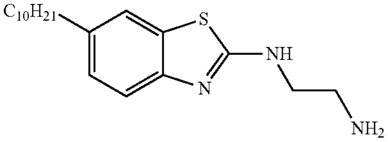 |
| 17b | 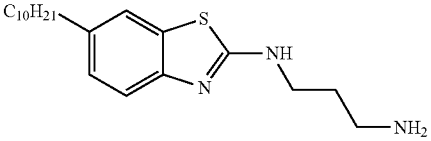 |
| 20a | 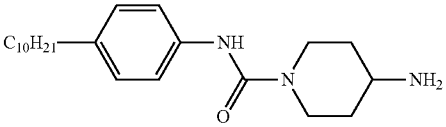 |
| 20b | 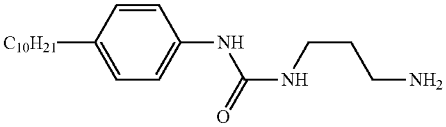 |
TABLE 1-continued
| Examples of Formula I and Formula IA Compounds | |
|---|---|
| Compound | Structure |
| 20c | 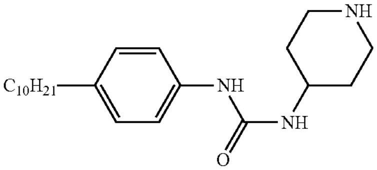 |
| 23a | 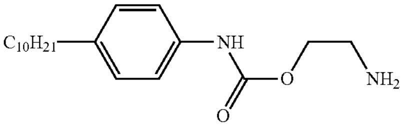 |
| 23b | 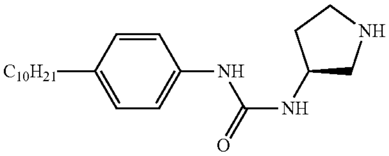 |
| 23c | 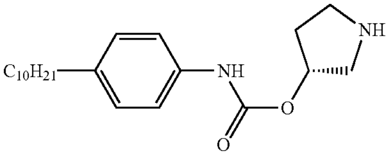 |
| 26a | 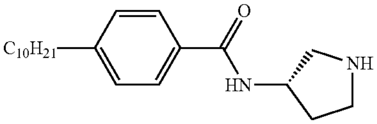 |
| 26b | 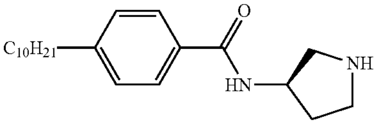 |
| 26c | 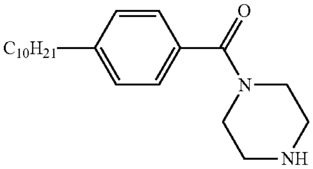 |
| 26d | 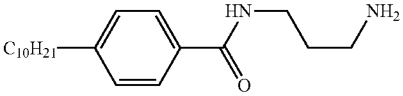 |
| 26e | 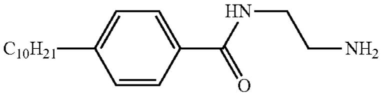 |
| 31 | 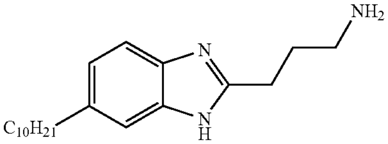 |

TABLE 1-continued

| Compound | Structure |
| --- | --- |
| | Examples of Formula I and Formula IA Compounds |
| 32 | 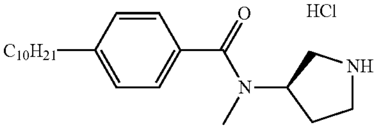 HCl |
| 33 | 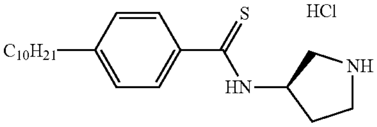 HCl |
| 34 | 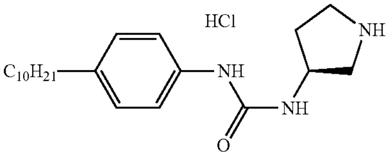 HCl |
| 35 | 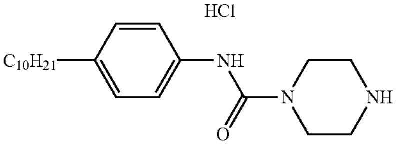 HCl |
| 36 | 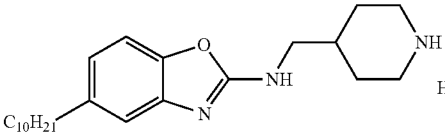 HCl |
| 37 | 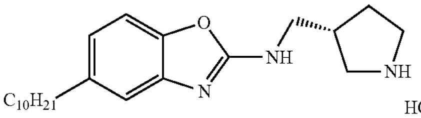 HCl |
| 38 | 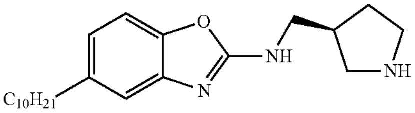 HCl |
| 39 | 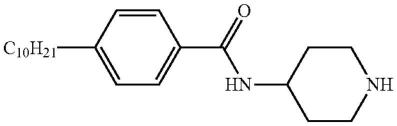 |

Pharmaceutical Composition

The disclosure also provides a pharmaceutical composition comprising a therapeutically effective amount of one or more compounds disclosed herein or a pharmaceutically acceptable salt, stereoisomer, and/or tautomer thereof in admixture with a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, flavor imparting agents.

In one embodiment, the pharmaceutical composition comprises a compound selected from those illustrated in Table 1 or a pharmaceutically acceptable salt, stereoisomer, and/or tautomer thereof, and a pharmaceutically acceptable carrier.

The pharmaceutical composition of the present disclosure is formulated, dosed, and administered in a fashion consistent with good medical practice. Factors for consideration in this context include the particular disorder being treated, the particular subject being treated, the clinical condition of the subject, the cause of the disorder, the site of delivery of the agent, the method of administration, the scheduling of administration, and other factors known to medical practitioners.

The "therapeutically effective amount" of a compound (or a pharmaceutically acceptable salt, stereoisomer, and/or tautomer thereof that is administered is governed by such considerations, and is the minimum amount necessary to induce dose dependent lymphopenia and a modest decrease in plasma S1P, or to inhibit SPNS2 activity, or both. Such amount may be below the amount that is toxic to normal cells, or the subject as a whole. Generally, the initial therapeutically effective amount of a compound (or a pharmaceutically acceptable salt, stereoisomer, or tautomer thereof) of the present disclosure that is administered is in the range of about 0.01 to about 200 mg/kg or about 0.1 to about 20 mg/kg of patient body weight per day, with the typical initial range being about 0.3 to about 15 mg/kg/day. Oral unit dosage forms, such as tablets and capsules, may contain from about 1 mg to about 1000 mg of a compound (or a pharmaceutically acceptable salt, stereoisomer, or tautomer thereof) of the present disclosure. In another embodiment, such dosage forms contain from about 50 mg to about 500 mg of a compound (or a pharmaceutically acceptable salt, stereoisomer, or tautomer thereof) of the present disclosure. In yet another embodiment, such dosage forms contain from about 25 mg to about 200 mg of a compound (or a pharmaceutically acceptable salt, stereoisomer, or tautomer thereof) of the present disclosure. In still another embodiment, such dosage forms contain from about 10 mg to about 100 mg of a compound (or a pharmaceutically acceptable salt, stereoisomer, or tautomer thereof) of the present disclosure. In a further embodiment such dosage forms contain from about 5 mg to about 50 mg of a compound (or a pharmaceutically acceptable salt, stereoisomer, or tautomer thereof) of the present disclosure.

The disclosed compositions can be administered orally, topically, parenterally, by inhalation or spray or rectally in dosage unit formulations. The term parenteral as used herein includes subcutaneous injections, intravenous, intramuscular, intrasternal injection or infusion techniques.

Suitable oral compositions as described herein include without limitation tablets, troches, lozenges, aqueous or oily suspensions, dispersible powders or granules, emulsion, hard or soft capsules, syrups or elixirs.

Also encompassed by the present disclosure are pharmaceutical compositions suitable for single unit dosages that comprise a compound of the disclosure or its pharmaceutically acceptable stereoisomer, salt, or tautomer and a pharmaceutically acceptable carrier.

Compositions suitable for oral use may be prepared according to any method known to the art for the manufacture of pharmaceutical compositions. For instance, liquid formulations of the inventive compounds contain one or more agents selected from the group consisting of sweetening agents, flavoring agents, coloring agents and preserving agents in order to provide pharmaceutically palatable preparations of the SPNS2 inhibitor.

For tablet compositions, a compound of the present disclosure in admixture with non-toxic pharmaceutically acceptable excipients is used for the manufacture of tablets. Examples of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions, a compound of the present disclosure is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending a compound of the present disclosure in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide a compound of the present disclosure in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the present disclosure may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation reaction products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds disclosed herein may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compositions for parenteral administrations are administered in a sterile medium. Depending on the vehicle used and concentration the concentration of the drug in the formulation, the parenteral formulation can either be a suspension or a solution containing dissolved drug. Adjuvants such as local anesthetics, preservatives and buffering agents can also be added to parenteral compositions.

Methods of Use

S1P gradients are chemotactic, a property that enables correct positioning of immune cells, and they help to maintain endothelial barrier integrity. Accordingly, S1P gradients are manipulated for therapeutic benefit using Formula I compounds because they target the endothelial S1P exporter, SPNS2.

Thus, in one embodiment, the disclosure provides a method of inhibiting spinster homolog 2 (SPNS2). The method comprises contacting SPNS2 with an effective amount of a compound as described herein. In some embodiments, the contacting occurs in vitro. In other embodiments, the contacting occurs ex vivo or in vivo.

Another embodiment is a method of treating a patient afflicted by a neoplastic disease, comprising administering to the patient a therapeutically effective amount a compound as described herein. In some embodiments, the neoplastic disease is metastatic neoplasms.

An additional embodiment is a method of treating a patient afflicted with an allergic disease, comprising administering to the patient a therapeutically effective amount of a compound as described herein. An illustrative allergic disease is asthma.

The compounds disclosed herein also are useful in a method of treating a patient afflicted with an autoimmune disease, comprising administering to the patient a therapeutically effective amount of the compound. In various embodiments, the autoimmune disease is chosen from multiple sclerosis, type I diabetes, inflammatory bowel diseases, Crohn's disease, ulcerative colitis, Grave's disease, Addison's disease, dermatomyositis, myasthenia gravis, systemic lupus erythematosus, scleroderma, and psoriasis. An exemplary autoimmune disease is multiple sclerosis. In accordance with some embodiments, multiple sclerosis comprises one or more progressive forms of multiple sclerosis as well as the remitting relapsing form of the disease.

Additional embodiments include a method of treating a patient afflicted with atherosclerosis or pulmonary arterial hypertension. The method comprises administering to the patient a therapeutically effective amount of a compound as described herein.

LITERATURE CITED IN THE DISCLOSURE

1. Chun J, Brinkmann V. A mechanistically novel, first oral therapy for multiple sclerosis: the development of fingolimod (FTY720, Gilenya). *Discovery Medicine* 12, 213-228 (2011) PMC3694367.
2. Cusack K P, Stoffel R H. S1P(1) receptor agonists: Assessment of selectivity and current clinical activity. *Current Opinion Drug Discovery & Development* 13, 481-488 (2010).
3. Schwab S R, Pereira J P, Matloubian M, Y. Xu Y, Huang Y, Cyster J G. Lymphocyte sequestration through S1P lyase inhibition and disruption of S1P gradients. *Science* 309, 1735-1739 (2005).
4. Mendoza A, Breat B, Ramoz-Perez W D, Pitt L A, Gobert M, Sunkara M, Lafaille J J, Morris A J, Schwab S R. The transporter SPNS2 is required for secretion of lymph but not plasma sphingosine-1-phosphate. *Cell Reports* 2, 1104-1110 (2012) PMC3616496.
5. Vu T M, Ishizu A-N, Foo J C, Toh X R, Zhang F, Whee D M, Torta F, Cazenave-Gassiot A, Matsumura T, Kim S, To S-AES, Suda T, Silver D L, Wenk M R, Nguyen L N. MFSD2B is essential for the sphingosine-1-phosphate export in erythrocytes and platelets. *Nature* 550, 524-528 (2017).
6. Kobayashi N, Kawasaki-Nishi S, Otsuka M, Hisano Y, Yamaguchi A, Nishi T. MSFD2B is a sphingosine 1-phosphate transporter in erythroid cells. *Scientific Reports* 8, 4969 (2018).
7. Camerer E, Regard J B, Cornelisssen I, Srinivasan Y, Duong D N, Palmer D, Pham T H, Wong J S, Pappu R, Coughlin S R. Sphingosine-1-phosphate in the plasma compartment regulates basal and inflammation-induced vascular leak in mice. *J Clinical Investigation* 119, 1871-1879 (2009).
8. Xiong Y, Hla T. S1P control of endothelial integrity. *Current Topics in Microbiology & Immunology* 378, 85-105 (2014) PMC4240614.
9. Yanagida K, Hla T. Vascular and immunobiology of the circulatory sphingosine 1-phosphate gradient. *Annual Review Physiology* 79, 67-91 (2016) PMC5500220.
10. Schumann J, Grevot A, Ledieu D, Wolf A, Schubart A, Piaia A, Sutter E, Côté S, Beerli C, Pognan F, Billich A, Moulin P, Walker U J. Reduced activity of sphingosine-1-phosphate lyase induces podocyte-related glomerular proteinuria, skin irritation, and platelet activation. *Toxicologic Pathology* 43, 694-703 (2015).
11. Prasad R, Hadjidemetriou I, Maharaj A, Meimaridou E, Buonocore F, Saleem M, Hurcombe J, Bierzynska A, Barbagelata E, Bergadá I, Cassinelli H, Das U, Krone R, Hacihamdioglu B, Sari E, Yesilkaya E, Storr H L, Clemente M, Fernandez-Cancio M, Camats N, Ram N, Achermann J C, Van Veldhoven P P, Guasti L, Braslavsky D, Guran T, Metherell L A. Sphingosine 1-phosphate lyase mutations cause primary adrenal insufficiency and steroid-resistant nephrotic syndrome. *J Clinical Investigation* 127, 942-953 (2017) PMC5330744.
12. Lovric S, Goncalves S, Gee H Y, Oskouian B, Srinivas H, Choi W I, Shril S, Ashraf S, Tan W, Rao J, Airik M, Schapiro D, Braun D A, Sadowski C E, Widmeier E, Jobst-Schwan T, Schmidt J M, Girik V, Capitani G, Suh J H, Lachaussee N, Arrondel C, Patat J, Gribouval O, Furlano M, Boyer O, Schmitt A, Vuiblet V, Hashmi S, Wilcken R, Bernier F P, Innes A M, Parboosingh J S, Lamont R E, Midgley J P, Wright N, Majewski J, Zenker M, Schaefer F, Kuss N, Greil J, Giese T, Schwarz K, Catheline V, Schanze D, Franke I, Sznajer Y, Truant A S, Adams B, Desir J, Biemann R, Pei Y, Ars E, Lloberas N, Madrid A, Dharnidharka V R, Connolly A M, Willing M C, Cooper M A, Lifton R P, Simons M, Riezman H, Antignac C, Saba J D, Hildebrandt F. Mutations in sphingosine-1-phosphate lyase cause nephrosis with ichthyosis and adrenal insufficiency. *J Clinical Investigation* 127, 912-928 (2017) PMC5330730.
13. van der Weyden L, Arends M J, Campbell A D, Bald T, Wardle-Jones H, Griggs N, Velasco-Herrera M D, Tuting T, Sansom O J, Karp N A, Clare S, Gleeson D, Ryder E, Galli A, Tuck E, Cambridge E L, Voet T, Macaulay I C, Wong K, Sanger Mouse Genetics Project, Spiegel S, Speak A O, Adams D J. Genome-wide in vivo screen identifies novel new regulators for metastatic colonization. *Nature* 541, 233-236 (2017) PMC5603286.

EXAMPLES

The present disclosure will be more fully understood by reference to the following examples. The examples should not, however, be construed as limiting the scope of the present disclosure.

General Procedure 1: HCTU Coupling A

To a 6-dram vial containing N-boc-amino acid (1.1 equiv) was added DMF (0.2 M), DIEA (1.8 equiv) and HCTU (1.1 equiv). The resulting mixture was allowed to stir at rt for 5 minutes, followed by addition of aniline derivative (1 equiv). The resulting mixture was allowed to stir at rt until consumption of aniline as monitored by TLC (1-4 hours). The resulting reaction mixture was diluted in ethyl acetate and washed with a saturated lithium bromide solution. The organic layer was then dried over anhydrous sodium sulfate and concentrated in vacuo to afford an orange oil which was then subjected to flash chromatography with an appropriate ethyl acetate in dichloromethane solvent system to afford the pure product.

General Procedure 2: HCTU Coupling B

To a 6-dram vial containing 4-iodobenzoic acid derivative (1.1 equiv) was added DCM (0.2 M), DIEA (1.8 equiv) and HCTU (1.1 equiv). The resulting mixture was allowed to stir at room temperature for 5 minutes, followed by addition of a mono-N-Boc protected diamine derivative (1.0 equiv). The resulting mixture was allowed to stir at room temperature for 18 hours at which time starting material was completely consumed on TLC. The resulting reaction mixture concentrated in vacuo to afford a yellow oil which was then subjected to flash chromatography with an appropriate ethyl acetate in hexanes solvent system to afford the pure product.

General Procedure 3: HCl Boc Deprotection

To a 6-dram vial containing a Boc-protected amine (1.0 equiv) was added hydrogen chloride (30-100 equiv, 4M in dioxane). The resulting mixture was allowed to stir until consumption of starting material as monitored by TLC (0.5-6 hours). A thick white precipitate forms during the course of the reaction. This precipitate was either vacuum filtered over a filter frit and washed with diethyl ether or triturated with diethyl ether and/or ethyl acetate to afford the pure product as an HCl salt.

General Procedure 4: TFA Boc Deprotection

To a round bottom flask containing Boc-protected amine or diboc protected guanidine compounds (1 equiv) dissolved in dichloromethane was added TFA (30 equiv). The resulting solution was allowed to stir until consumption of starting material as monitored by TLC (1-6 hours). Concentration in vacuo and filtration of the resulting off-white solid, followed by washing with diethyl ether afforded the corresponding TFA salts.

General Procedure 5: Guanylation

TFA salt or HCl amine salt (1 equiv), DIEA (15 equiv), and (Z)-tert-butyl (((tert-butoxycarbonyl)imino)(1H-pyrazol-1-yl)methyl)carbamate (1 equiv) were added to a microwave vial containing MeCN at room temperature. The resulting solution was then placed in a CEM microwave synthesized and heated to 50° C. for 3 hours. After cooling down to room temperature, the solution was concentrated in vacuo to afford the crude mixture as a yellow oil, which was then purified by column chromatography using the appropriate ethyl acetate and hexanes solvent system to afford the diboc protected guanidino compounds.

General Procedure 6: Suzuki Cross-Coupling A

To a pressure-sealed tube purged with nitrogen was added 1-decene and 0.5 M 9-BBN in THE (2.2 equiv). The resulting mixture was allowed to stir at 70° C. for 1-2 hours. Upon completion of the hydroboration step, sequential addition of an aryl iodide or aryl bromide (1.0 equiv), Pd(dppf)$Cl_2$*$CH_2Cl_2$ (0.075 equiv), and 3M KOH (3.0 equiv) was performed. The resulting mixture was allowed to stir at 70° C. for 16 hours or until complete consumption of the starting material was observed on TLC. The resulting mixture was concentrated in vacuo to afford a brown oil which was then subjected to flash chromatography with an appropriate ethyl acetate and hexane solvent system to afford the purified product.

General Procedure 7: Suzuki Cross-Coupling B

To a pressure-sealed tube purged with nitrogen was added 1-decene (1.0 equiv) and 0.5 M 9-BBN in THE (1.5 equiv). The resulting mixture was allowed to stir at 70° C. for 2 hours. Upon completion of the hydroboration step, sequential addition of an aryl iodide (1.0 equiv), Pd(dppf)$Cl_2$*$CH_2Cl_2$ (0.05 equiv), and 3M KOH (3.0 equiv) was performed. The resulting mixture was allowed to stir at 70° C. for 4 hours until complete consumption of the starting material was observed on TLC. The resulting mixture was concentrated in vacuo to afford a brown oil which was then subjected to flash chromatography with an appropriate ethyl acetate and hexane solvent system to afford the purified product.

General Procedure 8: CDI Coupling

To a 6-dram vial containing an N-Boc-amino acid (1.3 equiv) was added DCM and CDI (1.3 equiv). The resulting mixture was allowed to stir at room temperature for 2 hours, followed by addition of phenol (1.0 equiv) and DIEA (1.6 equiv). The resulting mixture was allowed to stir at room temperature for an additional 16 hours at which point the starting material was determined to be completely consumed by TLC. The resulting mixture was concentrated in vacuo to afford a brown oil which was then subjected to flash chromatography with an appropriate ethyl acetate and hexane solvent system to afford the purified product.

General Procedure 9: Mitsunobu Coupling

To a pressure-sealed tube containing $PPh_3$ (2.0 equiv) was added THE and a Boc protected amine (1.0 equiv) under inert atmosphere. The resulting mixture was allowed to stir at 0° C. for 20 minutes, followed by the addition of DIAD (2.0 equiv). The resulting mixture was heated 70° C. for 4 hours, where starting material was determined to be completely consumed by TLC. The crude reaction mixture was diluted in ethyl acetate and washed with water. The organic layer was then dried over anhydrous sodium sulfate and concentrated in vacuo to afford an orange oil which was then subjected to flash chromatography with an appropriate ethyl acetate and hexanes solvent system to afford the purified product.

General Procedure 10: Mercaptobenzoxazole Ring Formation

To a pressure-sealed tube containing 2-amino-4-bromophenol (1.0 equiv) was added EtOH/$H_2O$ (5:1), $K_2CO_3$ (1.2 equiv), and $CS_2$ (1.2 equiv). The resulting mixture was allowed to stir at 80° C. for 3 hours, where starting material was determined to be completely consumed based of TLC. The resulting mixture was diluted in water, and acetic acid was added in dropwise until a white solid was precipitated. This solid was solubilized by ethyl acetate, which was then subjected to flash chromatography with an appropriate ethyl acetate in hexane solvent system to afford the pure product.

General Procedure 11: Chlorination A

To a round bottom flask containing 5-bromobenzo[d]oxazole-2-thiol (1.0 equiv) was sequentially added DCM, $SOCl_2$ (2.5 equiv), and DMF (0.04 equiv) under inert atmosphere. The resulting mixture was allowed to stir at rt for 1 hour, where starting material was determined to be completely consumed based of TLC. The result mixture was diluted in ethyl acetate and washed with water. The organic layer was then dried over anhydrous sodium sulfate and concentrated in vacuo to afford a light pink oil which was then subjected to flash chromatography with an appropriate ethyl acetate in hexanes solvent system to afford the pure product.

General Procedure 12: Chlorination B

To a seal-pressured tube containing 6-bromobenzo[d]thiazol-2(3H)-one (1.0 equiv) was sequentially added $POCl_3$ (30 equiv). The resulting mixture was allowed to stir at 98° C. for 16 hours, where starting material was determined to be completely consumed based of TLC. The resulting mixture was poured over ice. The solution was neutralized to pH 9 by addition of $NH_{40}H$, and the resulting solid collected by filtration.

General Procedure 13: Nucleophilic Aromatic Substitution

To a pressure-sealed tube containing benzoxazole (1.0 equiv) was added DMF, N-boc-amine (1.2 equiv), and $K_2CO_3$ (2.0 equiv). The resulting mixture was allowed to stir at 120° C. for 2 hours, where starting material was determined to be completely consumed based of TLC. The resulting reaction mixture was diluted in ethyl acetate and washed with a saturated lithium bromide solution. The organic layer was then dried over anhydrous sodium sulfate and concentrated in vacuo to afford a clear oil which was then subjected to flash chromatography with an appropriate ethyl acetate in hexanes solvent system to afford the pure product.

General Procedure 14: Urea Synthesis 1-iodo-4-isocyanatobenzene (1.0 equiv) was added to an oven dried 6-dram vial containing a stir bar and purged with nitrogen. Anhydrous DCM was added to the vial and the solution was cooled to 0° C. with an ice bath. A mono-N-Boc protected diamine (1.05 equiv) was dissolved in DCM and added dropwise to the 1-iodo-4-isocyanatobenzene solution. The reaction mixture was then allowed to warm to room temperature slowly over the course of 16 hours. After complete consumption of starting material was observed by TLC, the crude reaction mixture was concentrated under reduced pressure and subjected to flash chromatography with an appropriate ethyl acetate and hexanes mobile phase to yield purified product.

General Procedure 15: Carbamate Synthesis 1-iodo-4-isocyanatobenzene (1.0 equiv) was added to an oven dried 6-dram vial containing a stir bar and purged with nitrogen. Anhydrous DCM was added to the vial and the solution was cooled to 0° C. with an ice bath. An N-Boc protected amino-alcohol (1.05 equiv) was dissolved in DCM and added dropwise to the 1-iodo-4-isocyanatobenzene solution. The reaction mixture was then allowed to warm to room temperature slowly over the course of 16 hours. After complete consumption of starting material was observed by TLC, the crude reaction mixture was concentrated under reduced pressure and subjected to flash chromatography with an appropriate ethyl acetate and hexanes mobile phase to yield purified product.

General Procedure 16: Nitro-Aniline Reduction

To a dry pressure tube containing nitroaniline (1.0 equiv) dissolved in 200 proof ethanol was added tin (II) chloride (5.0 equiv). After, 12.1 M hydrochloric acid (10 equiv) was added. This was then refluxed for one hour, where starting material was determined to be completely consumed based off TLC. The resulting mixture was diluted with 3 M aq. NaOH. This was allowed to stir for five minutes and then extracted three times with ethyl acetate.

General Procedure 17: Benzimidazole Ring Closure

To a 6-dram vial containing aryl amide derivatives, 13.7 M acetic acid (70 equiv) was added and the reaction was allowed to stir at 65° C. for 3 hours. The resulting mixture was diluted with ethyl acetate and washed with brine in triplicate. The combined organic layer was then dried over anhydrous sodium sulfate, concentrated in vacuo, and subjected to flash chromatography with an appropriate ethyl acetate in hexanes solvent system to yield purified product.

Scheme 1—Example Synthesis for N-(4-decylphenyl)-4-guanidinobutanamide hydrochloride

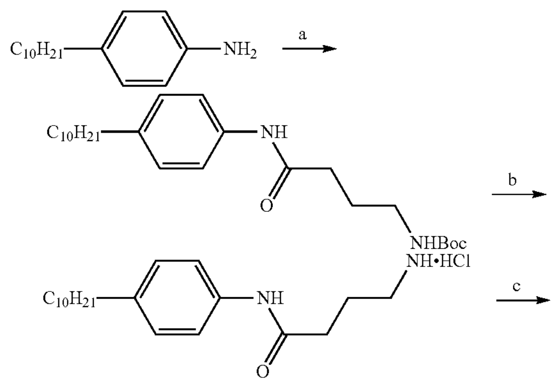

-continued

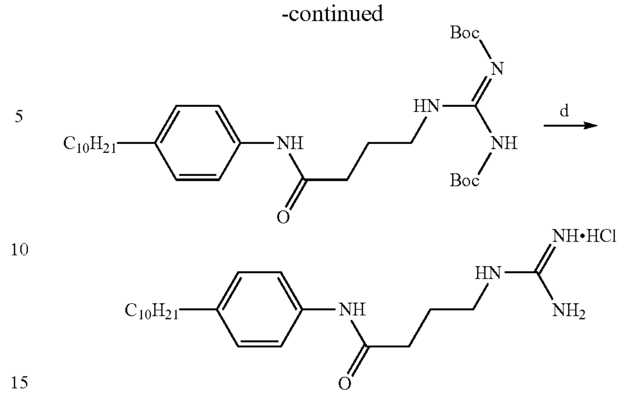

(a) N-boc-amino acid (1.1 equiv), HCTU (1.1 equiv), DIEA (1.8 equiv), DMF, rt; (b) HCl, dioxane, rt; (c) N,N'-Di-Boc-1H-pyrazole-1-carboxamidine (1 equiv), DIEA (15 equiv), MeCN, 50° C. µw; (d) HCl, dioxane, rt.

tert-butyl (R)-3-((4-decylphenyl)carbamoyl)piperidine-1-carboxylate (1a)

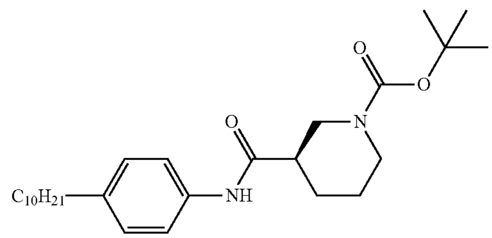

Synthesized according to General Procedure 1. White solid (92%, 298 mg). $^1H$ NMR (400 MHz, $CDCl_3$) δ 9.00 (brs, 1H), 7.47 (d, J=8.4 Hz, 2H), 7.06 (d, J=8.5 Hz, 2H), 4.07 (dd, J=13.5, 3.9 Hz, 1H), 3.85 (brs, 1H), 3.18 (t, J=11.7 Hz, 1H), 3.03-2.79 (m, 1H), 2.59-2.40 (m, 3H), 1.99-1.76 (m, 2H), 1.69-1.60 (m, 1H), 1.60-1.49 (m, 2H), 1.49-1.33 (m, 10H), 1.32-1.18 (m, 14H), 0.86 (t, J=6.8 Hz, 3H). $^{13}C$ NMR (101 MHz, $CDCl_3$) δ 171.7, 154.9, 138.6, 136.1, 128.6, 119.8, 79.9, 46, 44.7, 43.8, 35.3, 31.9, 31.5, 29.6, 29.6, 29.5, 29.3, 29.2, 28.4, 27.9, 24.3, 22.7, 14.1. HRMS: (ESI) [M+Na]+ calc. for $C_{27}H_{44}N_2O_3Na$, 467.3250, observed, 467.3233.

tert-butyl (R)-3-((4-decylphenyl)carbamoyl)pyrrolidine-1-carboxylate (1b)

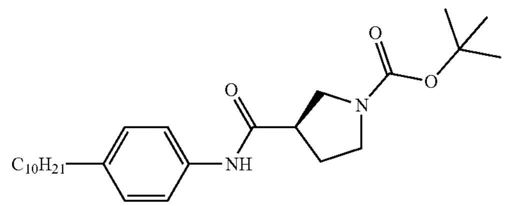

Synthesized according to General Procedure 1. White solid (95%, 316 mg). $^1H$ NMR (400 MHz, $CDCl_3$) δ 8.83 (s, 1H), 7.43 (d, J=8.2 Hz, 2H), 7.06 (d, J=8 Hz, 2H), 3.70-3.45

(m, 3H), 3.28 (dt, J=10.6, 7.8, 1H), 3.11-2.97 (m, 1H), 2.52 (t, J=7.7 Hz, 2H), 2.26-1.99 (m, 2H), 1.63-1.50 (m, 2H), 1.45 (s, 9H), 1.34-1.20 (m, 14H), 0.88 (t, J=6.8 Hz, 3H). $^{13}C$ NMR (101 MHz, $CDCl_3$) δ 171.1, 154.4, 139.0, 135.7, 128.6, 120.2, 79.5, 48.9, 45.7, 45.2, 45.2, 44.3, 35.3, 31.5, 29.6, 29.6, 29.5, 29.3, 29.3, 28.5, 22.7, 14.1. HRMS: (ESI) [M+Na]+ calc. for $C_{26}H_{42}N_2O_3Na$, 453.3093, observed, 453.3082.

tert-butyl (4-((4-decylphenyl)amino)-4-oxobutyl) carbamate (1c)

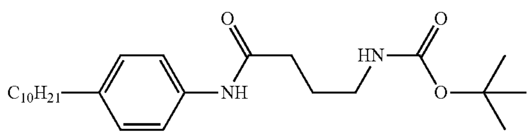

Synthesized according to General Procedure 1. White solid (90%, 252 mg). $^1H$ NMR (400 MHz, $CDCl_3$) δ 7.43 (d, J=8.4 Hz, 2H), 7.10 (d, J=8.5 Hz, 2H), 3.12 (t, J=6.8 hz, 2H), 2.56 (t, J=7.6 Hz, 2H), 2.37 (t, J=7.5 Hz, 2H), 1.83 (p, J=7.1 Hz, 2H), 1.58 (t, J=6.9 Hz, 2H), 1.42 (s, 9H), 1.37-1.19 (m, 14H), 0.89 (t, J=6.8 Hz, 3H). $^{13}C$ NMR (101 MHz, $CDCl_3$) δ 173.8, 158.6, 139.9, 137.5, 129.6, 121.3, 80.0, 40.9, 36.3, 35.2, 33.1, 32.8, 30.7, 30.7, 30.6, 30.5, 30.3, 28.8, 27.3, 23.7, 14.5. HRMS: (ESI) [M+H]+ calc. for $C_{25}H_{43}N_2O_3$, 419.3268, observed, 419.3257.

tert-butyl (3-((4-decylphenyl)amino)-3-oxopropyl) carbamate (1d)

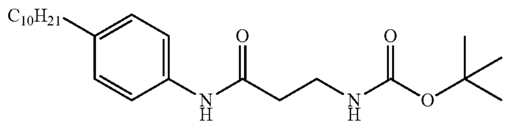

Synthesized according to General Procedure 1. White solid (100%, 360 mg). $^1H$ NMR (400 MHz, $CDCl_3$) δ 7.69 (s, 1H), 7.41 (d, J=8.4 Hz, 2H), 7.12 (d, J=8.4 Hz, 2H), 5.21 (s, 1H), 3.48 (q, J=6.1 Hz, 2H), 2.63-2.49 (m, 4H), 1.57 (p, J=7.4 Hz, 2H), 1.43 (s, 9H), 1.36-1.17 (m, 14H), 0.87 (d, J=6.8 Hz, 3H). $^{13}C$ NMR (101 MHz, $CDCl_3$) δ 169.7, 156.4, 139.3, 135.5, 129.0, 120.0, 79.7, 37.6, 36.6, 35.5, 32.0, 31.7, 29.8, 29.7, 29.6, 29.5, 29.4, 28.5, 22.8, 14.3. HRMS: (ESI) [M-boc+H]+ calc. for $C_{19}H_{33}N_2O$, 305.2587, observed, 305.2573.

tert-butyl (5-((4-decylphenyl)amino)-5-oxopentyl) carbamate (1e)

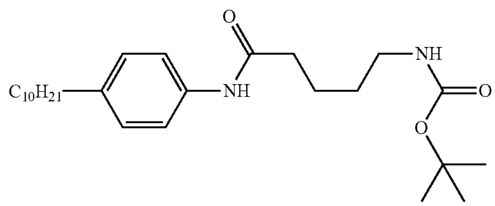

Synthesized according to General Procedure 1. White solid (95%, 258 mg). $^1H$ NMR (400 MHz, $CDCl_3$) δ 7.55 (s, 1H), 7.42 (d, J=8.4 Hz, 2H), 7.10 (d, J=8.4 Hz, 2H), 4.68 (s, 1H), 3.16 (q, J=6.6 Hz, 2H), 2.54 (dd, J=8.7, 6.7 Hz, 2H), 2.37 (t, J=7.5 Hz, 2H), 1.80-1.69 (m, 2H), 1.55 (p, J=6.9 Hz, 4H), 1.43 (s, 9H), 1.34-1.20 (m, 14H), 0.86 (t, J=7.0 Hz, 3H). $^{13}C$ NMR (101 MHz, $CDCl_3$) δ 171.3, 156.4, 139.0, 135.8, 128.9, 120.0, 79.4, 39.7, 37.0, 35.5, 32.0, 31.7, 29.8, 29.7, 29.6, 29.5, 29.4, 28.6, 22.8, 22.7, 14.3. HRMS: (ESI) [M+H]+ calc. for $C_{26}H_{45}N_2O_3$, 433.3425, observed, 433.3405.

tert-butyl (6-((4-decylphenyl)amino)-6-oxohexyl) carbamate (1f)

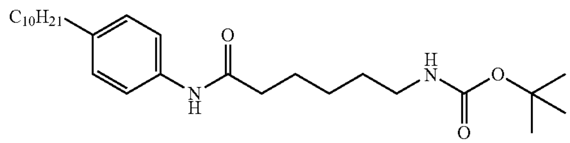

Synthesized according to General Procedure 1. Light brown solid (96%, 310 mg). $^1H$ NMR (400 MHz, $CDCl_3$) δ 7.41 (d, J=8.4 Hz, 2H), 7.10 (d, J=8.4 Hz, 2H), 4.60 (s, 1H), 3.11 (q, J=6.7 Hz, 2H), 2.55 (d, J=7.6 Hz, 2H), 2.33 (t, J=7.5 Hz, 2H), 1.73 (p, J=7.5 Hz, 2H), 1.60-1.34 (m, 15H), 1.35-1.20 (m, 14H), 0.88 (t, J=6.7 Hz, 3H). $^{13}C$ NMR (101 MHz, $CDCl_3$) δ 171.2, 156.2, 139.0, 135.7, 128.9, 120.0, 79.3, 40.4, 37.6, 35.5, 32.0, 31.7, 29.9, 29.8, 29.7, 29.6, 29.5, 29.4, 28.6, 26.4, 25.3, 22.8, 14.3. HRMS: (ESI) [M+H]+ calc. for $C_{27}H_{47}N_2O_3$, 447.3581, observed, 447.3573.

tert-butyl (4-((4-nonylphenyl)amino)-4-oxobutyl) carbamate (1g)

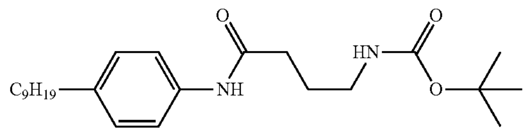

Synthesized according to General Procedure 1. White solid (71%, 178 mg). $^1H$ NMR (400 MHz, $CDCl_3$) δ 8.61 (s, 1H), 7.49 (d, J=8.0 Hz, 2H), 7.11 (d, J=8.4 Hz, 2H), 4.83 (t, J=5.1 Hz, 1H), 3.24 (q, J=6.3 Hz, 2H), 2.55 (d, J=7.8 Hz, 2H), 2.36 (d, J=7.8 Hz, 2H), 1.92-1.81 (m, 2H), 1.58 (q, J=8.0 Hz, 2H), 1.45 (s, 9H), 1.25 (s, 12H), 0.88 (t, J=6.6 Hz, 3H). $^{13}C$ NMR (101 MHz, $CDCl_3$) δ 171.2, 157.3, 138.8, 136.1, 128.9, 119.9, 79.9, 39.4, 35.5, 34.8, 32.0, 31.7, 29.7, 29.7, 29.5, 29.4, 28.5, 27.4, 22.8, 14.3. HRMS: (ESI) [M+H]+ calc. for $C_{24}H_{41}N_2O_3$, 405.3112, observed, 405.3110.

tert-butyl (4-((4-octylphenyl)amino)-4-oxobutyl) carbamate (1h)

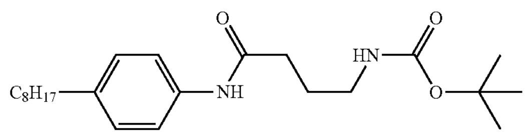

Synthesized according to General Procedure 1. Yellow solid (71%, 172 mg). $^{1}$H NMR (400 MHz, $CDCl_3$) δ 8.60 (s, 1H), 7.49 (d, J=8.0 Hz, 2H), 7.11 (d, J=8.4 Hz, 2H), 4.82 (t, J=6.9 Hz, 1H), 3.24 (q, J=6.3 Hz, 2H), 2.54 (d, J=7.8 Hz, 2H), 2.37 (d, J=6.6 Hz, 2H), 1.87 (tt, J=8.2, 5.7 Hz, 2H), 1.57 (p, J=7.6 Hz, 2H), 1.45 (s, 9H), 1.28 (s, 10H), 0.86 (t, J=7.1 Hz, 3H). $^{13}$C NMR (101 MHz, $CDCl_3$) δ 171.2, 157.3, 138.8, 136.1, 128.9, 119.9, 79.9, 39.4, 35.5, 34.8, 32.0, 31.7, 29.6, 29.4, 29.4, 28.5, 27.4, 22.8, 14.3. HRMS: (ESI) [M+H]+ calc. for $C_{23}H_{39}N_2O_3$, 391.2955, observed, 391.2932.

tert-butyl (S)-3-(2-((4-decylphenyl)amino)-2-oxo-ethyl)pyrrolidine-1-carboxylate (1i)

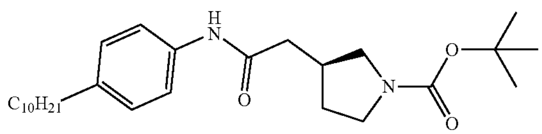

Synthesized according to General Procedure 1. White solid (68%, 240 mg). $^{1}$H NMR (400 MHz, $CDCl_3$) δ 7.48 (s, 1H), 7.40 (d, J=7.9 Hz, 2H), 7.11 (d, J=6.2 Hz, 2H), 3.61 (dd, J=10.8, 7.2 Hz, 1H), 3.51-3.39 (m, 1H), 3.37-3.21 (m, 1H), 3.06-2.95 (m, 1H), 2.76-2.64 (m, 1H), 2.55 (t, J=7.7 Hz, 2H), 2.50-2.29 (m, 3H), 2.18-2.04 (m, 1H), 1.57 (q, J=7.8 Hz, 3H), 1.45 (s, 9H), 1.36-1.18 (m, 14H), 0.87 (d, J=6.8 Hz, 3H). $^{13}$C NMR (101 MHz, $CDCl_3$) δ 169.6, 154.8, 139.3, 135.4, 129.0, 120.1, 79.4, 51.1, 45.3, 40.8, 35.8, 35.5, 32.0, 31.7, 31.0, 29.8, 29.7, 29.6, 29.5, 29.4, 28.7, 22.8, 14.3. HRMS: (ESI) [M+H]+ calc. for $C_{27}H_{45}N_2O_3$, 445.3425, observed, 445.3424.

tert-butyl (R)-3-(2-((4-decylphenyl)amino)-2-oxo-ethyl)pyrrolidine-1-carboxylate (1j)

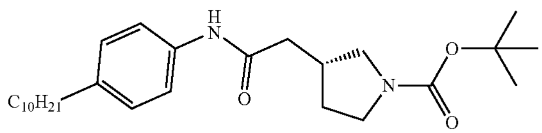

Synthesized according to General Procedure 1. Crude mixture dried in vacuo and carried forward to the next reaction without purification.

tert-butyl (4-((6-octylnaphthalen-2-yl)amino)-4-oxobutyl)carbamate (1k)

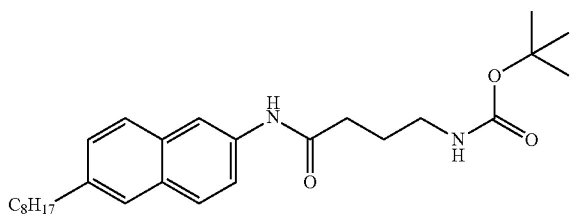

Synthesized according to General Procedure 1. White solid (71%, 280 mg). $^{1}$H NMR (400 MHz, $CDCl_3$) δ 8.93 (s, 1H), 8.26 (s, 1H), 7.70 (d, J=8.5 Hz, 2H), 7.55-7.48 (m, 2H), 7.29 (dd, J=8.4, 1.7 Hz, 1H), 4.87 (t, J=6.5 Hz, 1H), 3.27 (q, J=6.3 Hz, 2H), 2.73 (t, J=7.7 Hz, 2H), 2.43 (t, J=6.7 Hz, 2H), 1.94-1.86 (m, 2H), 1.68 (p, J=7.5 Hz, 2H), 1.47 (s, 9H), 1.41-1.22 (m, 10H), 0.87 (t, 3H). $^{13}$C NMR (101 MHz, $CDCl_3$) δ 171.5, 157.4, 139.5, 135.3, 132.4, 130.8, 128.1, 128.1, 127.6, 126.0, 120.1, 116.4, 79.9, 39.4, 36.2, 34.8, 32.0, 31.5, 29.6, 29.5, 29.4, 28.5, 27.4, 22.8, 14.3. HRMS: (ESI) [M+H]+ calc. for $C_{27}H_{41}N_2O_3$, 441.3112, observed, 441.3133.

tert-butyl (4-((4-decyl-2-fluorophenyl)amino)-4-oxobutyl)carbamate (1l)

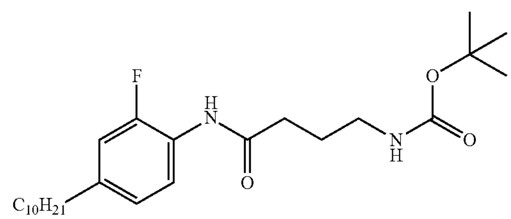

Synthesized according to General Procedure 1. Yellow solid (82%, 190 mg). $^{1}$H NMR (400 MHz, $CDCl_3$) δ 8.09 (t, J=8.4 Hz, 1H), 7.93 (s, 1H), 6.93-6.86 (m, 2H), 4.79 (s, 1H), 3.23 (q, J=6.4 Hz, 2H), 2.57-2.51 (m, 2H), 2.43 (t, J=7.0 Hz, 2H), 1.90 (p, J=6.9 Hz, 2H), 1.56 (p, J=7.2 Hz, 2H), 1.42 (s, 9H), 1.34-1.19 (m, 14H), 0.87 (t, J=6.8 Hz, 3H). $^{13}$C NMR (101 MHz, $CDCl_3$) δ 171.2, 156.7, 151.6, 140.1 (d, J=6.5 Hz), 123.8 (d, J=10.2 Hz), 123.3 (d, J=213.0 Hz), 114.8 (d, J=18.9 Hz), 79.6, 39.8, 35.4, 34.8, 32.0, 31.3, 29.7, 29.7, 29.6, 29.5, 29.3, 28.5, 26.6, 22.8, 14.3. HRMS: (ESI) [M+Na]+ calc. for $C_{25}H_{41}FN_2NaO_3$, 459.2993, observed, 459.3016.

tert-butyl (4-((4-(nonyloxy)-3-(trifluoromethyl)phenyl)amino)-4-oxobutyl)carbamate (1m)

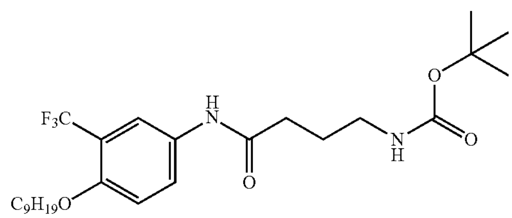

Synthesized according to General Procedure 1. Yellow solid (86%, 462 mg). $^{1}$H NMR (400 MHz, $CDCl_3$) δ 9.08 (s, 1H), 7.80 (d, J=8.8 Hz, 1H), 7.74 (s, 1H), 6.91 (d, J=8.9 Hz, 1H), 4.88 (t, 1H), 3.99 (t, J=6.4 Hz, 2H), 3.24 (q, J=6.3 Hz, 2H), 2.37 (t, 2H), 1.89-1.83 (m, 2H), 1.82-1.73 (m, 2H), 1.47-1.43 (m, 11H), 1.37-1.21 (m, 10H), 0.87 (t, J=6.9 Hz, 3H). $^{13}$C NMR (101 MHz, $CDCl_3$) δ 171.4, 157.5, 153.5, 131.2, 124.9, 123.8 (q, J=271.5 Hz), 119.2, 119.1 (q, J=30.9 Hz), 113.5, 80.1, 69.2, 39.4, 34.5, 32.0, 29.6, 29.4, 29.4, 29.2, 28.5, 27.4, 25.9, 22.8, 14.2. HRMS: (ESI) [M+H]+ calc. for $C_{25}H_{40}F_3N_2O_4$, 489.2935, observed, 489.2930.

tert-butyl (4-((4-decylphenyl)amino)-4-oxobutyl) (methyl)carbamate (1n)

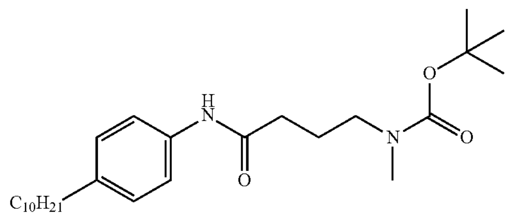

Synthesized according to General Procedure 1. Colorless oil (73%, 332 mg). $^1H$ NMR (500 MHz, $CDCl_3$) δ 9.2 (s, 1H), 7.5 (d, J=7.9 Hz, 1H), 7.4 (s, 1H), 7.1 (d, J=8.3 Hz, 2H), 3.4-3.3 (m, 2H), 2.9 (s, 3H), 2.5 (d, J=7.7 Hz, 3H), 2.4-2.2 (m, 2H), 2.0-1.9 (m, 2H), 1.6 (p, J=7.5 Hz, 2H), 1.5 (s, 9H), 1.3-1.2 (m, 14H), 0.9 (t, J=6.9 Hz, 3H). $^{13}C$ NMR (101 MHz, $CDCl_3$) δ 171.3, 157.3, 138.5, 136.5, 128.9, 119.8, 80.2, 47.0, 35.5, 34.5, 34.2, 32.0, 31.7, 29.7, 29.6, 29.5, 29.4, 28.6, 24.4, 22.8, 14.2. HRMS: (ESI) [M+H]+ calc. for $C_{26}H_{45}N_2O_3$, 433.3430, observed, 433.3418.

tert-butyl 4-((4-decylphenyl)carbamoyl)piperidine-1-carboxylate (1o)

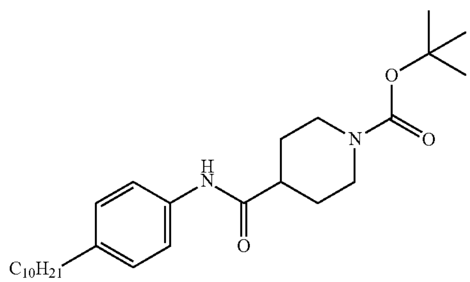

Synthesized according to General Procedure 1. Colorless oil (86%, 380 mg). $^1H$ NMR (500 MHz, $CDCl_3$) δ 7.4 (d, J=8.5 Hz, 2H), 7.4 (s, 1H), 7.1 (d, J=8.0 Hz, 2H), 4.2 (s, 1H), 2.8 (s, 2H), 2.5 (t, J=7.7 Hz, 2H), 2.4-2.3 (m, 1H), 1.9 (d, J=13.2 Hz, 2H), 1.8-1.7 (m, 3H), 1.6-1.5 (m, 2H), 1.5 (s, 9H), 1.3-1.2 (m, 14H), 0.9 (t, J=6.9 Hz, 3H). $^{13}C$ NMR (101 MHz, $CDCl_3$) δ 172.7, 154.8, 139.3, 135.5, 129.0, 120.1, 79.8, 44.4, 43.3, 35.5, 32.0, 31.6, 29.7, 29.7, 29.6, 29.5, 29.4, 28.8, 28.6, 22.8, 14.2. HRMS: (ESI) [M+H]+ calc. for $C_{27}H_{45}N_2O_3$, 445.3425, observed, 445.3420.

(R)—N-(4-decylphenyl)piperidine-3-carboxamide 2,2,2-trifluoroacetate (2a)

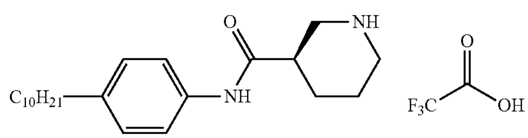

Synthesized according to General Procedure 4. White solid (28%, 83 mg). $^1H$ NMR (400 MHz, $CD_3OD$) δ 7.44 (d, J=8.4 Hz, 2H), 7.11 (d, J=8.4 Hz, 2H), 2.55 (t, J=7.6 Hz, 2H), 2.13-2.04 (m, 1H), 2.01-1.77 (m, 3H), 1.62-1.50 (m, 2H), 1.36-1.19 (m, 14H), 0.88 (t, J=6.7 Hz, 3H). $^{13}C$ NMR (101 MHz, $CD_3OD$) δ 172.8, 140.3, 137.1, 129.7, 121.4, 46.2, 45.1, 40.5, 36.3, 33.1, 32.7, 30.7, 30.7, 30.6, 30.5, 30.3, 27.4, 23.7, 22.0, 14.5. HRMS: (ESI) [M+H]+ calc. for $C_{22}H_{37}N_2O$, 345.2906, observed, 345.2906.

(R)—N-(4-decylphenyl)pyrrolidine-3-carboxamide 2,2,2-trifluoroacetate (2b)

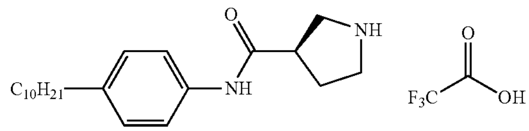

Synthesized according to General Procedure 4. White solid (77%, 250 mg). $^1H$ NMR (400 MHz, $CD_3OD$) δ 7.45 (d, J=8.4 Hz, 2H), 7.12 (d, J=8.5 Hz, 2H), 3.59 (dd, J=11.8, 5.5 Hz, 1H), 3.50-3.31 (m, 4H), 2.56 (t, J=7.6 Hz, 2H), 2.44-2.33 (m, 1H), 2.28-2.17 (m, 1H), 1.58 (p, J=6.8 Hz, 2H), 1.36-1.21 (m, 14H), 0.89 (t, J=6.7 Hz, 3H). $^{13}C$ NMR (101 MHz, $CD_3OD$) δ 172.2, 140.3, 137.2, 129.7, 121.3, 48.9, 46.5, 44.7, 36.3, 33.1, 32.7, 30.7, 30.7, 30.6, 30.5, 30.5, 30.3, 23.7, 14.5. HRMS: (ESI) [M+H]+ calc. for $C_{21}H_{35}N_2O$, 331.2744, observed, 331.2760.

4-amino-N-(4-decylphenyl)butanamide hydrochloride (2c)

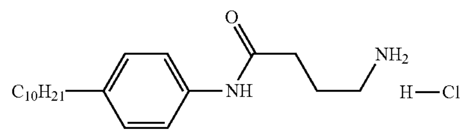

Synthesized according to General Procedure 3. White solid (64%, 125 mg). $^1H$ NMR (400 MHz, $CD_3OD$) δ 7.45 (d, J=8.5 Hz, 2H), 7.12 (d, J=8.7 Hz, 2H), 3.03 (t, J=7.5 Hz, 2H), 2.59-2.52 (m, 4H), 2.05-1.96 (m, 2H), 1.59 (p, J=7.0 Hz, 2H), 1.36-1.23 (m, 14H), 0.89 (t, J=6.7 Hz, 3H). $^{13}C$ NMR (101 MHz, $CD_3OD$) δ 172.6, 140.1, 137.3, 129.7, 121.3, 40.4, 36.3, 34.4, 33.1, 32.8, 30.7, 30.7, 30.6, 30.5, 30.3, 24.3, 23.7, 14.5. HRMS: (ESI) [M+H]+ calc. for $C_{20}H_{35}N_2O$, 319.2749, observed, 319.2733.

3-amino-N-(4-decylphenyl)propanamide hydrochloride (2d)

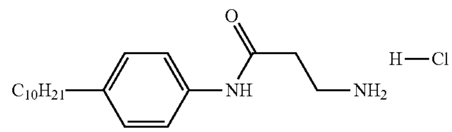

Synthesized according to General Procedure 3. White solid (79%, 226 mg). $^1H$ NMR (400 MHz, $CD_3OD$) δ 7.47 (d, J=8.5 Hz, 2H), 7.12 (d, J=8.5 Hz, 2H), 3.26 (t, J=6.4 Hz, 2H), 2.80 (t, J=6.3 Hz, 2H), 2.57 (t, J=7.6 Hz, 2H), 1.60 (p, J=7.1 Hz, 2H), 1.39-1.20 (m, 14H), 0.90 (t, J=6.6 Hz, 3H).

$^{13}C$ NMR (101 MHz, $CD_3OD$) δ 170.3, 140.2, 137.2, 129.7, 121.2, 37.0, 36.3, 33.6, 33.1, 32.8, 30.7, 30.7, 30.6, 30.5, 30.3, 23.7, 14.5. HRMS: (ESI) [M+H]+ calc. for $C_{19}H_{33}N_2O$, 305.2587, observed, 305.2599.

5-amino-N-(4-decylphenyl)pentanamide hydrochloride (2e)

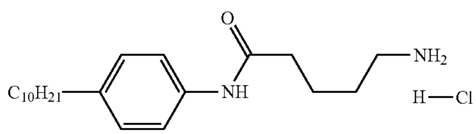

Synthesized according to General Procedure 3. White solid (90%, 54 mg). $^1H$ NMR (400 MHz, $CD_3OD$) δ 7.45 (d, J=8.5 Hz, 2H), 7.11 (d, J=8.4 Hz, 2H), 2.97 (t, J=7.1 Hz, 2H), 2.56 (t, J=7.6 Hz, 2H), 2.45 (t, J=6.7 Hz, 2H), 1.82-1.68 (m, 4H), 1.59 (p, J=7.3 Hz, 2H), 1.37-1.21 (m, 14H), 0.90 (t, J=6.8 Hz, 3H). $^{13}C$ NMR (101 MHz, $CD_3OD$) δ 173.6, 140.1, 137.4, 129.7, 121.3, 40.4, 36.8, 36.3, 33.1, 32.8, 30.7, 30.7, 30.6, 30.5, 30.3, 28.0, 23.7, 23.4, 14.5. HRMS: (ESI) [M+H]+ calc. for $C_{21}H_{40}N_3O$, 350.3166, observed, 350.3171.

6-amino-N-(4-decylphenyl)hexanamide hydrochloride (2f)

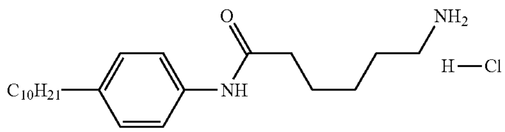

Synthesized according to General Procedure 3. White solid (81%, 209 mg). $^1H$ NMR (400 MHz, $CD_3OD$) δ 7.45 (d, J=8.5 Hz, 2H), 7.11 (d, J=8.8 Hz, 2H), 2.94 (t, J=7.6 Hz, 2H), 2.56 (t, J=7.7.6 Hz, 2H), 2.41 (t, J=7.3 Hz, 2H), 1.79-1.65 (m, 4H), 1.58 (p, J=7.0 Hz, 2H), 1.52-1.42 (m, 2H), 1.37-1.21 (m, 14H), 0.89 (t, J=6.8 Hz, 3H). $^{13}C$ NMR (101 MHz, $CD_3OD$) δ 174.1, 140.0, 137.4, 129.6, 121.3, 40.5, 37.4, 36.3, 33.1, 32.8, 30.7, 30.7, 30.7, 30.6, 30.5, 30.3, 28.3, 27.0, 26.2, 23.7, 14.5. HRMS: (ESI) [M+H]+ calc. for $C_{22}H_{39}N_2O$, 347.3057, observed, 347.3050.

4-amino-N-(4-nonylphenyl)butanamide hydrochloride (2g)

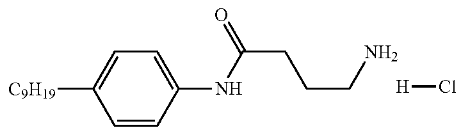

Synthesized according to General Procedure 3. White solid (62%, 84 mg). $^1H$ NMR (400 MHz, $CD_3OD$) δ 7.45 (d, J=8.4 Hz, 2H), 7.11 (d, J=8.4 Hz, 2H), 3.02 (t, J=7.5 Hz, 2H), 2.60-2.51 (m, 4H), 2.01 (p, J=7.0 Hz, 2H), 1.59 (p, J=7.2 Hz, 2H), 1.36-1.23 (m, 12H), 0.88 (t, J=6.8 Hz, 3H). $^{13}C$ NMR (101 MHz, $CD_3OD$) δ 172.7, 140.1, 137.3, 129.7, 121.3, 40.4, 36.3, 34.4, 33.1, 32.8, 30.7, 30.6, 30.4, 30.3, 24.3, 23.7, 14.5. HRMS: (ESI) [M+H]+ calc. for $C_{19}H_{33}N_2O$, 305.2587, observed, 305.2564.

4-amino-N-(4-octylphenyl)butanamide hydrochloride (2h)

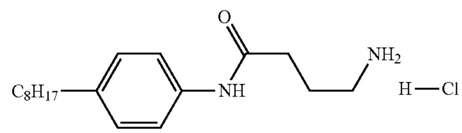

Synthesized according to General Procedure 3. White solid (67%, 90 mg). $^1H$ NMR (400 MHz, $CD_3OD$) δ 7.45 (d, J=8.5 Hz, 2H), 7.12 (d, J=8.5 Hz, 2H), 3.02 (t, J=7.6 Hz, 2H), 2.60-2.51 (m, 4H), 2.05-1.96 (m, 2H), 1.59 (p, J=7.3 Hz, 2H), 1.37-1.22 (m, 10H), 0.88 (t, J=6.8 Hz, 3H). $^{13}C$ NMR (101 MHz, $CD_3OD$) δ 172.7, 140.1, 137.3, 129.7, 121.3, 40.4, 36.3, 34.4, 33.0, 34.8, 30.6, 30.4, 30.3, 24.3, 23.7, 14.4. HRMS: (ESI) [M+H]+ calc. for $C_{18}H_{31}N_2O$, 291.2431, observed, 291.2421.

(S)—N-(4-decylphenyl)-2-(pyrrolidin-3-yl)acetamide hydrochloride (2i)

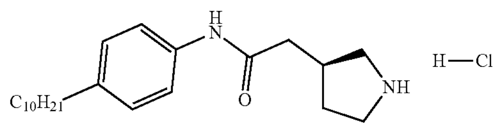

Synthesized according to General Procedure 3. White solid (100%, 213 mg). $^1H$ NMR (400 MHz, $CD_3OD$) δ 7.43 (d, J=8.5 Hz, 2H), 7.12 (d, J=8.8 Hz, 2H), 3.55 (dd, J=11.7, 7.7 Hz, 1H), 3.45-3.37 (m, 1H), 3.30-3.20 (m, 1H), 3.00 (dd, J=11.7, 9.0 Hz, 1H), 2.80-2.69 (m, 1H), 2.66-2.50 (m, 4H), 2.32-2.22 (m, 1H), 1.80-1.70 (m, 1H), 1.58 (p, J=7.5 Hz, 2H), 1.36-1.21 (m, 14H), 0.88 (t, J=6.8 Hz, 3H). $^{13}C$ NMR (101 MHz, $CD_3OD$) δ 170.2, 138.8, 135.8, 128.3, 119.9, 49.6, 44.8, 38.4, 34.9, 34.8, 31.6, 31.3, 29.6, 29.3, 29.3, 29.2, 29.0, 28.8, 22.3, 13.0. HRMS: (ESI) [M+H]+ calc. for $C_{22}H_{37}N_2O$, 345.2900, observed, 345.2872.

(R)—N-(4-decylphenyl)-2-(pyrrolidin-3-yl)acetamide hydrochloride (2j)

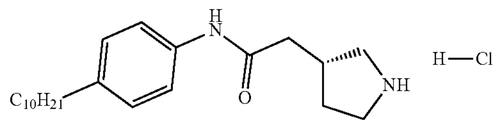

Synthesized according to General Procedure 3. White solid (91%, 167 mg). $^1H$ NMR (400 MHz, $CD_3OD$) δ 7.44 (d, J=8.5 Hz, 2H), 7.12 (d, J=8.5 Hz, 2H), 3.55 (dd, J=11.7, 7.7 Hz, 1H), 3.47-3.37 (m, 1H), 3.30-3.20 (m, 1H), 3.01 (dd, J=11.7, 9.0 Hz, 1H), 2.81-2.69 (m, 1H), 2.68-2.50 (m, 4H), 2.32-2.22 (m, 1H), 1.82-1.70 (m, 1H), 1.59 (p, J=7.2 Hz, 2H), 1.38-1.20 (m, 14H), 0.89 (t, J=6.8 Hz, 3H). $^{13}C$ NMR (101 MHz, $CD_3OD$) δ 171.7, 140.2, 137.2, 129.7, 121.3, 51.0, 46.2, 39.9, 36.3, 36.2, 33.1, 32.8, 31.1, 30.8, 30.7, 30.6, 30.5, 30.3, 23.7, 14.5. HRMS: (ESI) [M+H]+ calc. for $C_{22}H_{37}N_2O$, 345.2900, observed, 345.2878.

(4-amino-N-(6-octylnaphthalen-2-yl)butanamide hydrochloride (2k)

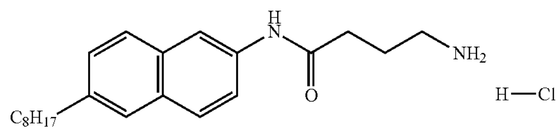

Synthesized according to General Procedure 3. White solid (83%, 185 mg). $^1H$ NMR (400 MHz, $CD_3OD$) δ 8.17 (d, J=2.2 Hz, 1H), 7.73 (d, J=8.8 Hz, 1H), 7.68 (d, J=8.4 Hz, 1H), 7.56-7.51 (m, 2H), 7.31 (dd, J=8.4, 1.7 Hz, 1H), 3.06 (t, J=7.6 Hz, 2H), 2.73 (t, J=7.6 Hz, 2H), 2.61 (t, J=7.0 Hz, 2H), 2.10-2.00 (m, 2H), 1.68 (p, J=7.5 Hz, 2H), 1.41-1.19 (m, 10H), 0.87 (t, J=6.8 Hz, 3H). $^{13}C$ NMR (101 MHz, $CD_3OD$) δ 172.9, 140.8, 136.5, 133.6, 132.3, 129.1, 129.0, 128.4, 127.1, 121.2, 117.7, 40.4, 37.0, 34.5, 33.0, 32.6, 30.6, 30.4, 30.4, 24.3, 23.7, 14.5. HRMS: (ESI) [M+H]+ calc. for $C_{22}H_{33}N_2O$, 341.2587, observed, 341.2603.

(4-amino-N-(4-decyl-2-fluorophenyl)butanamide hydrochloride (2l)

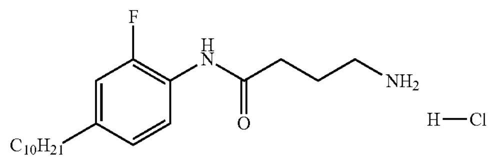

Synthesized according to General Procedure 3. White solid (66%, 101 mg). $^1H$ NMR (400 MHz, $CD_3OD$) δ 7.68 (t, J=8.3 Hz, 1H), 7.02-6.91 (m, 2H), 3.03 (t, J=7.8 Hz, 2H), 2.59 (t, J=7.3 Hz, 4H), 2.02 (p, J=7.2 Hz, 2H), 1.59 (p, J=7.1 Hz, 2H), 1.40-1.20 (m, 14H), 0.90 (t, J=6.7 Hz, 3H). $^{13}C$ NMR (101 MHz, $CD_3OD$) δ 173.2, 155.9 (d, J=246 Hz), 143.2, 125.9, 125.2, 124.1 (d J=12 Hz), 116.2 (d, J=19.5 Hz), 40.4, 36.2, 33.9, 33.1, 32.4, 30.7, 30.6, 30.5, 30.2, 24.3, 23.7, 14.5. HRMS: (ESI) [M+H]+ calc. for $C_{20}H_{34}FN_2O$, 337.2650, observed, 337.2649.

4-amino-N-(4-(nonyloxy)-3-(trifluoromethyl)phenyl) butanamide hydrochloride (2m)

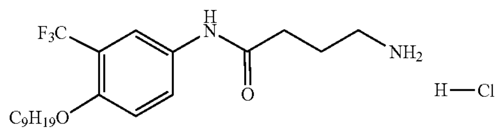

Synthesized according to General Procedure 3. Light yellow solid (46%, 140 mg). $^1H$ NMR (400 MHz, $CD_3OD$) δ 7.89 (d, J=2.6 Hz, 1H), 7.69 (dd, J=8.9, 2.7 Hz, 1H), 7.09 (d, J=8.9 Hz, 1H), 4.04 (t, J=6.2 Hz, 2H), 3.03 (t, J=7.5 Hz, 2H), 2.56 (t, J=7.1 Hz, 2H), 2.02 (p, J=7.1 Hz, 2H), 1.82-1.72 (m, 2H), 1.55 (p, J=7.7 Hz, 2H), 1.40-1.24 (m, 10H), 0.88 (t, J=6.8 Hz, 3H). $^{13}C$ NMR (101 MHz, $CD_3OD$) δ 172.7, 154.8, 132.3, 126.3, 124.9 (q, J=267 Hz), 120.1 (q, J=6 Hz), 119.5 (q, J=31 Hz), 114.6, 70.0, 40.4, 34.3, 33.0, 30.6, 30.3, 30.3, 30.2, 26.9, 24.2, 23.7, 14.4. HRMS: (ESI) [M+H]+ calc. for $C_{20}H_{32}F_3N_2O_2$, 389.2410, observed, 389.2415.

N-(4-decylphenyl)-4-(methylamino)butanamide hydrochloride (2n)

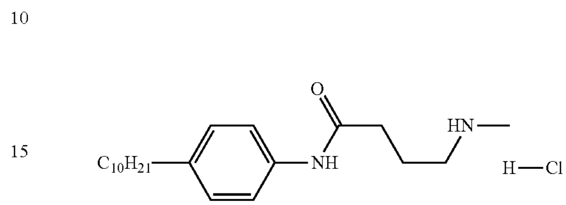

Synthesized according to General Procedure 3. White solid (53%, 148 mg). $^1H$ NMR (400 MHz, $CD_3OD$) δ 7.45 (d, J=8.4 Hz, 2H), 7.12 (d, J=8.4 Hz, 2H), 3.09 (t, J=7.4 Hz, 2H), 2.72 (s, 3H), 2.56 (t, J=7.5 Hz, 4H), 2.03 (p, J=7.0 Hz, 2H), 1.58 (p, J=7.4 Hz, 2H), 1.38-1.21 (m, 14H), 0.89 (t, J=6.8 Hz, 3H). $^{13}C$ NMR (101 MHz, $CD_3OD$) δ 172.6, 140.1, 137.3, 129.7, 121.3, 50.1, 36.3, 34.4, 33.6, 33.1, 32.7, 30.7, 30.7, 30.6, 30.5, 30.3, 23.7, 22.9, 14.5. HRMS: (ESI) [M+H]+ calc. for $C_{21}H_{37}N_2O$, 333.2900, observed, 333.2897.

N-(4-decylphenyl)piperidine-4-carboxamide hydrochloride (2o)

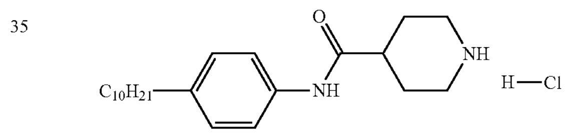

Synthesized according to General Procedure 3. White solid (84%, 260 mg). $^1H$ NMR (400 MHz, $CD_3OD$) δ 7.46 (d, J=8.5 Hz, 2H), 7.12 (d, J=8.5 Hz, 2H), 3.47 (dt, J=13.0, 3.8 Hz, 2H), 3.09 (td, J=12.6, 3.4 Hz, 2H), 2.80-2.70 (m, 1H), 2.56 (t, J=7.8 Hz, 2H), 2.14-2.05 (m, 2H), 2.04-1.91 (m, 2H), 1.59 (p, J=8.0 Hz, 2H), 1.36-1.20 (m, 14H), 0.88 (t, J=6.8 Hz, 3H). $^{13}C$ NMR (101 MHz, $CD_3OD$) δ 174.0, 140.2, 137.2, 129.7, 121.4, 44.3, 41.6, 36.3, 33.1, 32.7, 30.7, 30.7, 30.6, 30.5, 30.3, 26.7, 23.7, 14.5. HRMS: (ESI) [M+H]+ calc. for $C_{22}H_{37}N_2O$, 345.2900, observed, 345.2902.

4-(dimethylamino)-N-(4-decylphenyl)butanamide hydrochloride (2p)

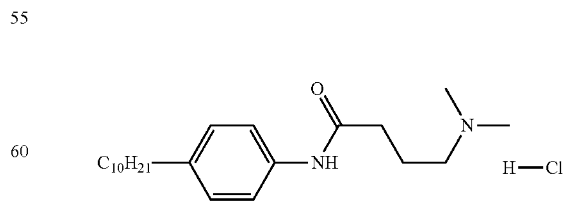

Amine free base of the title compound was synthesized according to General Procedure 11. The title compound was produced by dissolving the amine free base in methanolic HCl, followed by concentration in vacuo. White solid (30%, 123 mg). $^1$H NMR (400 MHz, $CD_3OD$) δ 7.44 (d, J=8.4 Hz, 2H), 7.12 (d, J=8.4 Hz, 2H), 3.24-3.17 (m, 2H), 2.91 (s, 6H), 2.60-2.51 (m, 4H), 2.06 (p, J=7.0 Hz, 2H), 1.59 (p, J=7.2 Hz, 2H), 1.38-1.21 (m, 14H), 0.89 (t, J=6.7 Hz, 3H). $^{13}$C NMR (101 MHz, $CD_3OD$) δ 172.6, 140.2, 137.2, 129.7, 121.4, 58.8, 43.5, 36.3, 34.1, 33.1, 32.7, 30.7, 30.7, 30.6, 30.4, 30.3, 23.7. HRMS: (ESI) [M+H]+ calc. for $C_{22}H_{39}N_2O$, 347.3057, observed, 347.3054.

tert-butyl (R)-(((tert-butoxycarbonyl)amino)(3-((4-decylphenyl)carbamoyl)piperidin-1-yl)methylene) carbamate (3a)

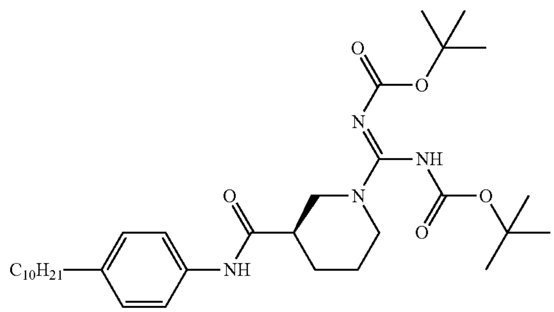

Synthesized according to General Procedure 5. Purified by silica chromatography (40% ethyl acetate in hexanes). White solid (53%, 58 mg). $^1$H NMR (400 MHz, $CDCl_3$) δ 10.23 (brs, 1H), 7.55 (d, J=8.0 Hz, 2H), 7.08 (d, J=8.2 Hz, 2H), 4.32 (brs, 1H), 3.78-3.42 (m, 1H), 3.41-3.13 (m, 1H), 2.76 (p, J=5.4 Hz, 1H), 2.54 (t, J=7.6 Hz, 2H), 2.41-2.12 (m, 1H), 1.91-1.78 (m, 1H), 1.70-1.39 (m, 24H), 1.36-1.60 (m, 14H), 0.87 (t, J=0.87, 3H). $^{13}$C NMR (101 MHz, $CDCl_3$) δ 170.7, 162.3, 156.0, 150.6, 138.9, 136.1, 128.7, 120.4, 82.4, 79.8, 48.6, 43.0, 35.5, 32.0, 31.7, 29.7, 29.6, 29.4, 29.3, 28.3, 28.1, 27.6, 23.9, 22.8, 14.1. HRMS: (ESI) [M+H]+ calc. for $C_{33}H_{55}N_4O_5$, 587.4172, observed, 587.4184.

tert-butyl (R)-(((tert-butoxycarbonyl)amino)(3-((4-decylphenyl)carbamoyl)pyrrolidin-1-yl)methylene) carbamate (3b)

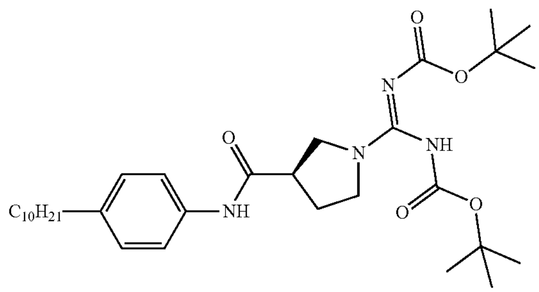

Synthesized according to General Procedure 5. Purified by silica chromatography (40% ethyl acetate in hexanes). Colorless residue (62%, 70 mg). $^1$H NMR (400 MHz, $CDCl_3$) δ $^{13}$C NMR (101 MHz, $CDCl_3$) δ HRMS: (ESI) [M+H]+ calc. for $C_{32}H_{53}N_4O_5$, 573.4010, observed, 573.4000.

tert-butyl (((tert-butoxycarbonyl)amino)(3-((4-decylphenyl)carbamoyl)prop-1-yl)methylene)carbamate (3c)

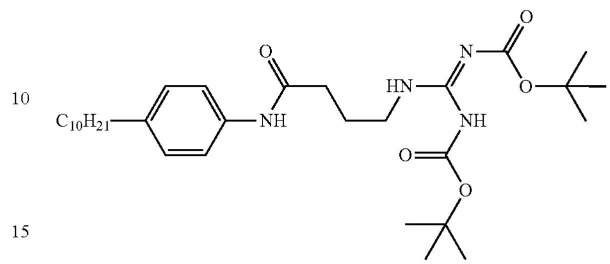

Synthesized according to General Procedure 5. Purified by silica chromatography (40% ethyl acetate in hexanes). White solid (70%, 218 mg). $^1$H NMR (400 MHz, $CDCl_3$) δ 11.54 (brs, 1H), 9.45 (brs, 1H), 8.60 (t, J=6.3 Hz, 2H), 7.47 (d, J=8.4 Hz, 2H), 7.08 (d, J=8.6 Hz, 2H), 3.52 (q, J=6.1 Hz, 2H), 2.54 (t, J=7.6 Hz, 2H), 2.47-2.37 (m, 2H), 1.98-1.88 (m, 2H), 1.59-1.51 (m, 2H), 1.50 (s, 9H), 1.33 (s, 9H), 1.37-1.17 (m, 14H), 0.87 (t, J=6.7 Hz, 3H). $^{13}$C NMR (101 MHz, $CDCl_3$) δ 171.3, 163.2, 157.2, 153.2, 138.7, 135.9, 128.4, 121.2, 83.5, 79.8, 39.3, 35.4, 34.4, 31.9, 31.6, 29.6, 29.5, 29.3, 29.2, 28.1, 28.0, 28.0, 27.6, 22.7, 14.1. HRMS: (ESI) [M+H]+ calc. for $C_{31}H_{53}N_4O_5$, 561.4010, observed, 561.4016.

(R)-1-carbamimidoyl-N-(4-decylphenyl)piperidine-3-carboxamide 2,2,2-trifluoroacetate (4a)

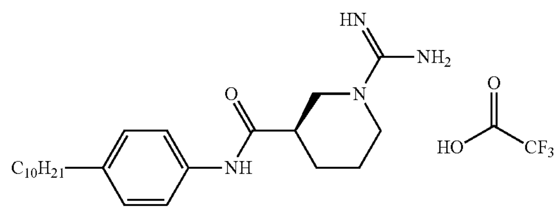

Synthesized according to General Procedure 4. White solid (70%, 35 mg). $^1$H NMR (400 MHz, $CD_3OD$) δ 7.42 (d, J=8.4 Hz, 2H), 7.12 (d, J=8.5 Hz, 2H), 3.95-3.85 (m, 1H), 3.84-3.73 (m, 1H), 3.39 (dd, J=13.9, 10.1 Hz, 1H), 3.24-3.15 (m, 1H), 2.71-2.61 (m, 1H), 2.57 (t, J=7.6 Hz, 2H), 2.18-2.08 (m, 1H), 1.94-1.82 (m, 2H), 1.77-1.53 (m, 3H), 1.38-1.20 (m, 14H), 0.90 (t, J=6.7 Hz, 3H). $^{13}$C NMR (101 MHz, $CD_3OD$) δ 173.3, 157.9, 140.3, 137.2, 48.9, 47.4, 44.0, 36.3, 33.1, 32.8, 30.7, 30.7, 30.6, 30.5, 30.3, 28.8, 25.0, 23.7, 14.5. HRMS: (ESI) [M+H]+ calc. for $C_{23}H_{39}N_4O$, 387.3124, observed, 387.3154.

(R)-1-carbamimidoyl-N-(4-decylphenyl)piperidine-3-carboxamide 2,2,2-trifluoroacetate (4b)

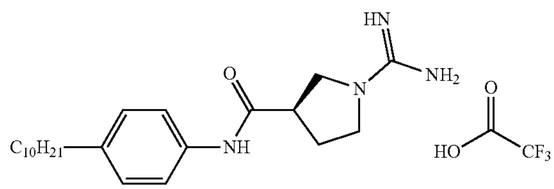

Synthesized according to General Procedure 4. White solid (70%, 35 mg). $^{1}$H NMR (400 MHz, $CD_3OD$) δ 7.42 (d, J=8.4 Hz, 2H), 7.12 (d, J=8.5 Hz, 2H), 3.95-3.85 (m, 1H), 3.84-3.73 (m, 1H), 3.39 (dd, J=13.9, 10.1 Hz, 1H), 3.24-3.15 (m, 1H), 2.71-2.61 (m, 1H), 2.57 (t, J=7.6 Hz, 2H), 2.18-2.08 (m, 1H), 1.94-1.82 (m, 2H), 1.77-1.53 (m, 3H), 1.38-1.20 (m, 14H), 0.90 (t, J=6.7 Hz, 3H). $^{13}$C NMR (101 MHz, $CD_3OD$) δ 173.3, 157.9, 140.3, 137.2, 48.9, 47.4, 44.0, 36.3, 33.1, 32.8, 30.7, 30.7, 30.6, 30.5, 30.3, 28.8, 25.0, 23.7, 14.5. HRMS: (ESI) [M+H]+ calc. for $C_{23}H_{39}N_4O$, 387.3124, observed, 387.3154.

N-(4-decylphenyl)-4-guanidinobutanamide hydrochloride (4c)

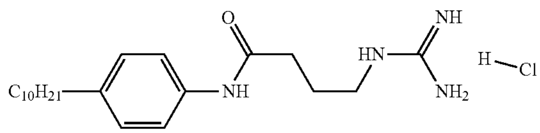

Synthesized according to General Procedure 3. White solid (56%, 59 mg). $^{1}$H NMR (400 MHz, $CDCl_3$) δ 7.45 (d, J=8.4 Hz, 2H), 7.12 (d, J=8.5 Hz, 2H), 3.26 (t, J=7.2 Hz, 2H), 2.57 (t, J=7.6 Hz, 2H), 2.48 (t, J=7.0 Hz, 2H), 2.00-1.89 (m, 2H), 1.59 (p, J=8 Hz, 2H), 1.37-1.22 (m, 14H), 0.89 (t, J=6.8 Hz, 3H). $^{13}$C NMR (101 MHz, $CDCl_3$) δ 173.3, 158.7, 140.1, 137.3, 129.7, 121.4, 41.9, 36.3, 34.0, 33.1, 32.8, 30.7, 30.7, 30.6, 30.5, 30.3, 25.8, 23.7, 14.5. HRMS: (ESI) [M+H]+ calc. for $C_{21}H_{37}N_4O$, 361.2962, observed, 361.2952.

Scheme 2—Example Synthesis for 2-(5-decylbenzo[d]oxazol-2-yl)ethan-1-amine hydrochloride

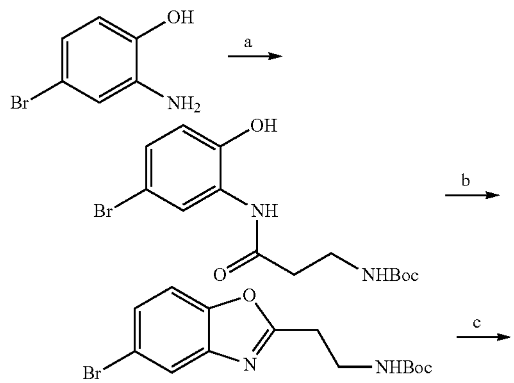

-continued

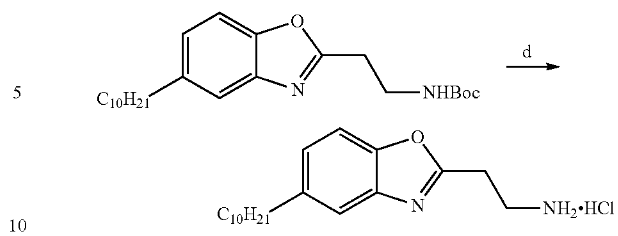

(a) N-boc-amino acid (1.3 equiv), CDI (1.3 equiv), DIEA (1.6 equiv), DCM, rt; (b) $PPh_3$ (2.0 equiv), DIAD (2.0 equiv), THF, 70° C.; (c) (i) 9-BBN (2.2 equiv), 1-decene (2.0 equiv), (ii) aryl bromide (1.0 equiv), $Pd(dppf)Cl_2*CH_2Cl_2$ (0.075 equiv), 3M KOH (3.0 equiv), THF, 70° C.; (d) 4M HCl/Dioxane, DCM, rt.

tert-butyl (3-((5-bromo-2-hydroxyphenyl)amino)-3-oxopropyl)carbamate (5a)

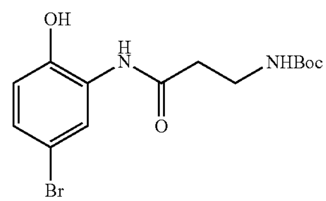 [SMILES: CC(C)(C)OC(=O)NCCC(=O)Nc1cc(Br)ccc1O]

Synthesized according to General Procedure 1. Orange solid (39%, 322 mg). $^{1}$H NMR (500 MHz, DMSO-$d_6$) δ 10.10 (s, 1H), 9.19 (s, 1H), 8.03 (d, J=2.5 Hz, 1H), 7.03 (dd, J=8.6, 2.5 Hz, 1H), 6.77 (d, J=8.5 Hz, 2H), 3.16 (q, J=6.6 Hz, 2H), 2.49 (t, J=7.0 Hz, 2H), 1.33 (s, 9H). $^{13}$C NMR (400, DMSO)$^{13}$C NMR (126 MHz, DMSO-$d_6$) δ 170.6, 156.0, 147.3, 128.4, 127.0, 124.5, 117.3, 110.0, 78.1, 37.1, 37.0, 28.7. HRMS ($ESI^+$) m/z calc'd. for $C_{14}H_{20}BrN_2O_4^+$ $(M+H)^+$ 359.0601, found 359.0596.

tert-butyl (4-((5-bromo-2-hydroxyphenyl)amino)-4-oxobutyl)carbamate (5b)

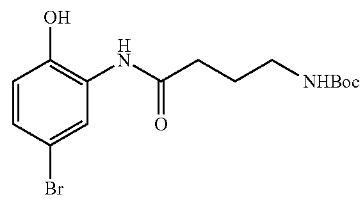 [SMILES: CC(C)(C)OC(=O)NCCCC(=O)Nc1cc(Br)ccc1O]

Synthesized according to General Procedure 1. Crude mixture dried in vacuo and carried forward to the next reaction without purification.

tert-butyl (6-((5-bromo-2-hydroxyphenyl)amino)-6-oxohexyl)carbamate (5c)

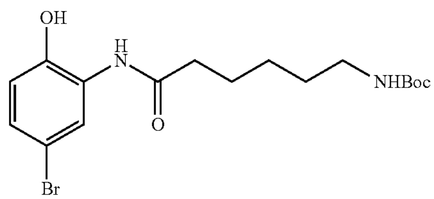 [SMILES: CC(C)(C)OC(=O)NCCCCCC(=O)Nc1cc(Br)ccc1O]

Synthesized according to General Procedure 1. Orange solid (50%, 320 mg). $^1$H NMR (400 MHz, DMSO-$d_6$) δ 10.12 (s, 1H), 9.15 (s, 1H), 8.05 (d, J=2.5 Hz, 1H), 7.04 (dd, J=8.6, 2.5 Hz, 1H), 6.78 (d, J=8.5 Hz, 1H), 6.75-6.71 (m, 1H), 2.87 (q, J=6.8 Hz, 2H), 2.36 (t, J=7.4 Hz, 2H), 1.52 (p, J=7.4 Hz, 2H), 1.34 (s, 9H), 1.23 (td, J=8.4, 4.1 Hz, 2H).

tert-butyl (3-((4-bromo-2-hydroxyphenyl)amino)-3-oxopropyl)carbamate

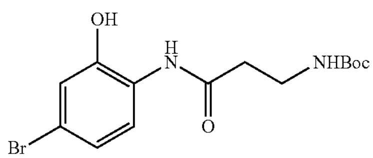 [SMILES: CC(C)(C)OC(=O)NCCC(=O)Nc1ccc(Br)cc1O]

Synthesized according to General Procedure 1. Yellow solid (38%, 228 mg). $^1$H NMR (500 MHz, DMSO-$d_6$) δ 10.26 (s, 1H), 9.17 (s, 1H), 7.69 (d, J=8.6 Hz, 1H), 6.95 (d, J=2.3 Hz, 1H), 6.88 (dd, J=8.6, 2.2 Hz, 1H), 6.76 (s, 1H), 3.14 (q, J=6.7 Hz, 2H), 2.47 (t, J=6.3 Hz, 2H), 1.31 (s, 9H).

tert-butyl (4-((4-bromo-2-hydroxyphenyl)amino)-4-oxobutyl)carbamate (5e)

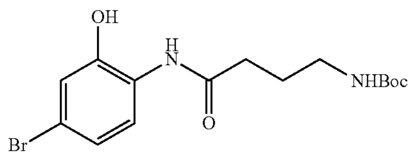 [SMILES: CC(C)(C)OC(=O)NCCCC(=O)Nc1ccc(Br)cc1O]

Synthesized according to General Procedure 1. Light yellow solid (38%, 228 mg). $^1$H NMR (400 MHz, DMSO-$d_6$) δ 10.24 (s, 1H), 9.11 (s, 1H), 7.67 (d, J=8.6 Hz, 1H), 6.93 (d, J=2.3 Hz, 1H), 6.85 (dd, J=8.6, 2.3 Hz, 1H), 6.75-6.70 (m, 1H), 2.87 (q, J=6.6 Hz, 2H), 2.29 (t, J=7.4 Hz, 2H), 1.64-1.53 (m, 2H), 1.29 (s, 9H). HRMS (ESI$^+$) m/z calc'd. for $C_{15}H_{22}BrN_2O_4^+$ (M+H)$^+$ 373.0757, found 373.0757.

tert-butyl (3-((5-bromo-2-hydroxyphenyl)amino)-3-oxopropyl)carbamate (6a)

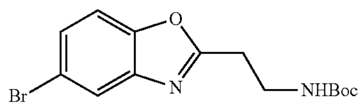 [SMILES: CC(C)(C)OC(=O)NCCc1nc2cc(Br)ccc2o1]

Synthesized according to General Procedure 9. Pink solid (69%, 230 mg). 6 $^1$H NMR (500 MHz, Chloroform-d) δ 7.81 (d, J=1.8 Hz, 1H), 7.43 (dd, J=8.6, 1.9 Hz, 1H), 7.37 (d, J=8.6 Hz, 1H), 5.21 (t, J=6.2 Hz, 1H), 3.68 (q, J=6.2 Hz, 2H), 3.12 (t, J=6.2 Hz, 2H), 1.42 (s, 9H). HRMS (ESI$^+$) m/z calc'd. for $C_{14}H_{18}BrN_2O_3^+$ (M+H)$^+$ 341.0495, found 341.0493.

tert-butyl (3-(5-bromobenzo[d]oxazol-2-yl)propyl) carbamate (6b)

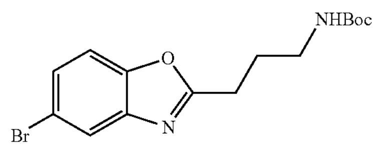 [SMILES: CC(C)(C)OC(=O)NCCCc1nc2cc(Br)ccc2o1]

Synthesized according to General Procedure 9. Pink solid (80%, 117 mg). $^1$H NMR (400 MHz, Chloroform-d) δ 7.84-7.75 (m, 1H), 7.42 (ddd, J=8.6, 1.9, 0.7 Hz, 1H), 7.35 (dt, J=8.6, 0.7 Hz, 1H), 4.72 (s, 1H), 3.27 (q, J=6.6 Hz, 2H), 3.02-2.94 (m, J=7.9, 7.5 Hz, 2H), 2.08 (p, J=7.1 Hz, 2H), 1.42 (s, 9H). HRMS (ESI$^+$) m/z calc'd. for $C_{15}H_{20}BrN_2O_3^+$ (M+H)$^+$ 355.0652, found 355.0653.

tert-butyl (5-(5-bromobenzo[d]oxazol-2-yl)pentyl) carbamate (6c)

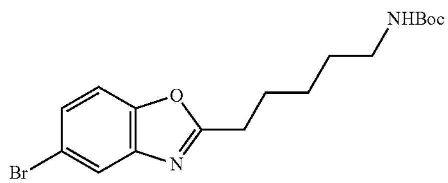 [SMILES: CC(C)(C)OC(=O)NCCCCCc1nc2cc(Br)ccc2o1]

Synthesized according to General Procedure 9. Amber oil (24%, 75 mg). $^1$H NMR (500 MHz, Chloroform-d) δ 7.80 (d, J=1.9 Hz, 1H), 7.45-7.33 (m, 2H), 4.65 (s, 1H), 3.14 (t, J=6.8 Hz, 2H), 2.94 (t, J=7.5 Hz, 2H), 1.90 (p, J=7.5 Hz, 2H), 1.55 (p, J=7.1 Hz, 2H), 1.44 (s, 9H), 1.27-1.23 (m, 2H). HRMS (ESI$^+$) m/z calc'd. for $C_{17}H_{24}BrN_2O_3^+$ (M+H)$^+$ 383.0965, found 383.1040.

tert-butyl (2-(6-bromobenzo[d]oxazol-2-yl)ethyl) carbamate (6d)

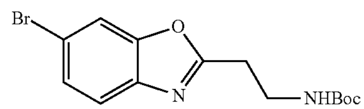 [SMILES: CC(C)(C)OC(=O)NCCc1nc2ccc(Br)cc2o1]

Synthesized according to General Procedure 9. Pink solid (33%, 70 mg). $^1$H NMR (500 MHz, Chloroform-d) δ 7.38 (s, 1H), 7.30-7.25 (m, 1H), 7.20 (d, J=8.3 Hz, 2H), 5.95 (s, 1H), 5.00 (s, 1H), 3.58 (t, J=5.4 Hz, 2H), 3.44 (q, J=5.9 Hz, 2H), 1.43 (s, 9H).

tert-butyl (3-(6-bromobenzo[d]oxazol-2-yl)propyl) carbamate (6e)

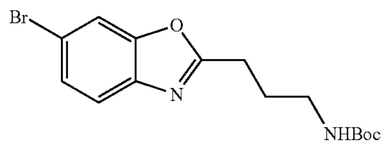 [SMILES: CC(C)(C)OC(=O)NCCCc1nc2ccc(Br)cc2o1]

Synthesized according to General Procedure 9. Light yellow solid (82%, 215 mg). $^1$H NMR (500 MHz, Chloroform-d) δ 7.37 (d, J=1.9 Hz, 1H), 7.28-7.25 (m, 1H), 7.19 (d, J=8.3 Hz, 1H), 6.07 (d, J=6.9 Hz, 1H), 4.89 (t, J=6.5 Hz, 1H), 3.52 (q, J=6.3 Hz, 2H), 3.26 (t, J=6.3 Hz, 2H), 1.84-1.77 (m, 2H), 1.46 (s, 9H).

tert-butyl (2-(5-decylbenzo[d]oxazol-2-yl)ethyl) carbamate (7a)

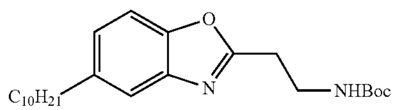

Synthesized according to General Procedure 6. Clear oil (53%, 62 mg). $^1$H NMR (400 MHz, Chloroform-d) δ 7.46 (d, J=1.7 Hz, 1H), 7.36 (dd, J=8.2, 1.4 Hz, 1H), 7.11 (dt, J=8.4, 1.6 Hz, 1H), 5.33 (s, 1H), 3.66 (t, J=6.3 Hz, 2H), 3.10 (t, J=6.2 Hz, 2H), 2.70 (t, J=7.7 Hz, 2H), 1.68-1.60 (m, 2H), 1.43 (d, J=1.3 Hz, 9H), 1.29 (d, J=22.9 Hz, 14H), 0.88 (t, J=6.8 Hz, 3H) HRMS (ESI$^+$) m/z calc'd. for $C_{24}H_{39}N_2O_3{}^+$ (M+H)$^+$ 403.2955, found 403.2933.

tert-butyl (3-(5-decylbenzo[d]oxazol-2-yl)propyl) carbamate (7b)

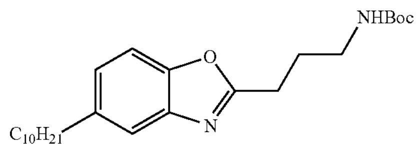

Synthesized according to General Procedure 6. White solid (28%, 99 mg). $^1$H NMR (500 MHz, Chloroform-d) δ 7.42 (s, 1H), 7.32 (d, J=8.3 Hz, 1H), 7.07 (d, J=8.4 Hz, 1H), 4.89 (s, 1H), 3.27-3.18 (m, 2H), 2.93 (t, J=7.3 Hz, 2H), 2.66 (t, J=7.6 Hz, 2H), 2.08-1.99 (m, 2H), 1.87-1.72 (m, 1H), 1.39 (s, 10H), 1.31-1.15 (m, 14H), 0.84 (t, J=6.9 Hz, 3H). HRMS (ESI$^+$) m/z calc'd. for $C_{15}H_{20}BrN_2O_3{}^+$ (M+H)$^+$ 417.3112, found 417.3106.

tert-butyl (5-(5-decylbenzo[d]oxazol-2-yl)pentyl) carbamate (7c)

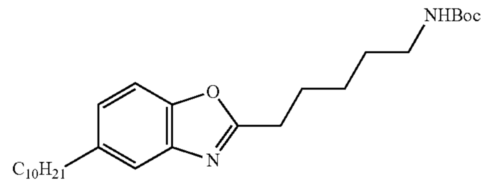

Synthesized according to General Procedure 6. Off-white solid (68%, 59 mg). $^1$H NMR (500 MHz, Chloroform-d) δ 7.45 (d, J=1.7 Hz, 1H), 7.35 (d, J=8.3 Hz, 1H), 7.10 (dd, J=8.3, 1.7 Hz, 1H), 4.63 (d, J=6.2 Hz, 1H), 3.13 (q, J=6.7 Hz, 2H), 2.91 (t, J=7.5 Hz, 2H), 2.69 (t, 2H), 1.89 (p, J=7.6 Hz, 2H), 1.63 (d, J=7.5 Hz, 2H), 1.54 (q, J=7.2 Hz, 2H), 1.43 (s, 11H), 1.35-1.22 (m, 14H), 0.88 (t, J=6.9 Hz, 3H). HRMS (ESI$^+$) m/z calc'd. for $C_{27}H_{45}N_2O_3{}^+$ (M+H)$^+$ 445.3425, found 445.3417.

tert-butyl (2-(6-decylbenzo[d]oxazol-2-yl)ethyl) carbamate (7d)

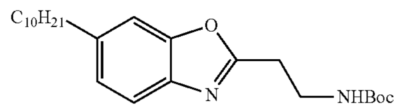

Synthesized according to General Procedure 6. Yellow oil (80%, 66 mg). $^1$H NMR (500 MHz, Chloroform-d) δ 7.56 (d, J=8.1 Hz, 1H), 7.30 (s, 1H), 7.14 (d, J=8.2 Hz, 1H), 5.29 (t, J=6.2 Hz, 1H), 3.69 (q, J=6.2 Hz, 2H), 3.11 (t, J=6.1 Hz, 2H), 2.72 (t, J=7.7 Hz, 2H), 1.65 (p, J=7.2 Hz, 2H), 1.44 (s, 8H), 1.36-1.23 (m, 14H), 0.89 (t, J=6.8 Hz, 3H). HRMS (ESI$^+$) m/z calc'd. for $C_{24}H_{39}N_2O_3{}^+$ (M+H)$^+$ 403.2955, found 403.2952.

tert-butyl (3-(6-decylbenzo[d]oxazol-2-yl)propyl) carbamate (7e)

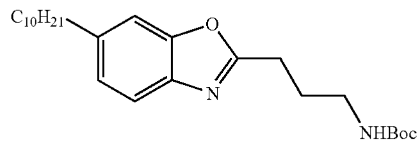

Synthesized according to General Procedure 6. Yellow oil (29%, 27 mg). $^1$H NMR (400 MHz, Chloroform-d) δ 7.51 (d, J=8.1 Hz, 1H), 7.26-7.23 (m, 1H), 7.09 (dd, J=8.1, 1.6 Hz, 1H), 4.75 (s, 1H), 3.24 (q, J=6.6 Hz, 2H), 2.93 (t, J=7.4 Hz, 2H), 2.68 (dd, J=8.6, 6.8 Hz, 2H), 2.04 (t, J=7.1 Hz, 2H), 1.67-1.52 (m, 2H), 1.39 (s, 9H), 1.32-1.18 (m, 14H), 0.89-0.80 (m, 3H). HRMS (ESI$^+$) m/z calc'd. for $C_{25}H_{41}N_2O_3{}^+$ (M+H)$^+$ 417.3112, found 417.3111.

2-(5-decylbenzo[d]oxazol-2-yl)ethan-1-amine hydrochloride (8a)

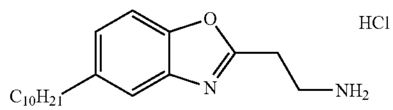

Synthesized according to General Procedure 3. White solid (73%, 38 mg). $^1$H NMR (500 MHz, Methanol-$d_4$) δ 7.50-7.47 (m, 2H), 7.22 (dd, J=8.4, 1.8 Hz, 1H), 3.50 (t, J=6.7 Hz, 2H), 3.34 (t, J=6.9, 1.5 Hz, 2H), 2.72 (t, J=7.6 Hz, 2H), 1.64 (p, J=7.5 Hz, 2H), 1.34-1.24 (m, 15H), 0.88 (t, J=6.9 Hz, 3H). $^{13}$C NMR (126 MHz, Methanol-$d_4$) δ 164.8, 150.7, 142.1, 141.1, 127.1, 119.8, 111.2, 37.6, 36.8, 33.2, 33.1, 30.7, 30.7, 30.6, 30.5, 30.2, 27.1, 23.7, 14.4. HRMS (ESI$^+$) m/z calc'd. for $C_{19}H_{31}N_2O^+$ (M+H)$^+$ 303.2431, found 303.2422.

3-(5-decylbenzo[d]oxazol-2-yl)propan-1-amine hydrochloride (8b)

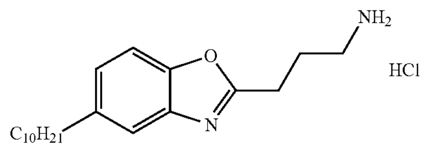

Synthesized according to General Procedure 3. White solid (92%, 70 mg). $^1$H NMR (500 MHz, Methanol-$d_4$) δ 7.48-7.42 (m, 2H), 7.21 (dd, J=8.4, 1.7 Hz, 1H), 3.12-3.07 (m, 4H), 2.74-2.70 (m, 2H), 2.41-2.18 (m, 2H), 1.65 (t, J=7.6 Hz, 2H), 1.34-1.24 (m, 14H), 0.89 (t, J=6.9 Hz, 3H). $^{13}$C NMR (126 MHz, Methanol-$d_4$) δ 167.6, 150.5, 142.0, 141.0, 126.9, 119.5, 111.0, 40.0, 36.8, 33.2, 33.1, 30.7, 30.7, 30.6, 30.4, 30.2, 26.3, 25.3, 23.7, 14.4. HRMS (ESI$^+$) m/z calc'd. for $C_{20}H_{33}N_2O^+$ (M+H)$^+$ 317.2587, found 317.2585.

5-(5-decylbenzo[d]oxazol-2-yl)pentan-1-amine hydrochloride (8c)

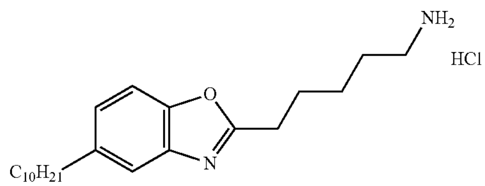

Synthesized according to General Procedure 3. Off-white solid (59%, 30 mg). $^1$H NMR (500 MHz, Methanol-$d_4$) δ 7.45 (d, J=8.4 Hz, 1H), 7.42 (d, J=1.6 Hz, 1H), 7.20 (dd, J=8.4, 1.7 Hz, 1H), 2.99 (t, J=7.4 Hz, 2H), 2.94 (t, J=7.6 Hz, 2H), 2.75-2.69 (m, 2H), 1.94 (p, J=7.5 Hz, 2H), 1.76-1.68 (m, 2H), 1.68-1.60 (m, 2H), 1.55-1.47 (m, 2H), 1.36-1.24 (m, 14H), 0.89 (t, J=6.9 Hz, 3H). $^{13}$C NMR (126 MHz, Methanol-$d_4$) δ 167.6, 149.0, 140.5, 139.6, 125.3, 117.9, 109.6, 39.1, 35.4, 31.8, 31.7, 29.3, 29.3, 29.2, 29.0, 28.8, 27.5, 26.8, 25.7, 25.4, 22.3, 13.0. HRMS (ESI$^+$) m/z calc'd. for $C_{22}H_{37}N_2O^+$ (M+H)$^+$ 345.2900, found 345.2879.

2-(6-decylbenzo[d]oxazol-2-yl)ethan-1-amine hydrochloride (8d)

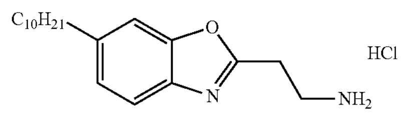

Synthesized according to General Procedure 3. White solid (54%, 30 mg). $^1$H NMR (500 MHz, Methanol-$d_4$) δ 7.57 (d, J=8.1 Hz, 1H), 7.42 (d, J=1.5 Hz, 1H), 7.22 (d, J=8.2, 1H), 3.50 (t, J=6.7 Hz, 2H), 3.33 (t, J=6.7 Hz, 2H), 2.75 (t, J=7.6 Hz, 2H), 1.66 (t, J=7.5 Hz, 2H), 1.35-1.23 (m, 14H), 0.89 (t, J=6.8 Hz, 3H). $^{13}$C NMR (126 MHz, Methanol-$d_4$) δ 164.2, 152.6, 142.5, 139.9, 126.5, 120.0, 111.3, 37.6, 37.0, 33.1, 30.7, 30.7, 30.6, 30.5, 30.2, 27.1, 23.7, 14.4. HRMS (ESI$^+$) m/z calc'd. for $C_{19}H_{31}N_2O^+$ (M+H)$^+$ 303.2431, found 303.2432.

3-(6-decylbenzo[d]oxazol-2-yl)propan-1-amine hydrochloride (8e)

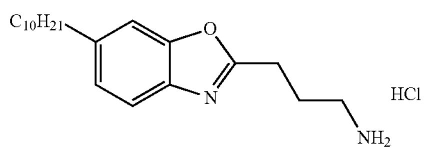

Synthesized according to General Procedure 3. White solid (79%, 18 mg). $^1$H NMR (400 MHz, Methanol-$d_4$) δ 7.55 (dd, J=8.1, 0.6 Hz, 1H), 7.41 (dd, J=1.5, 0.7 Hz, 1H), 7.22 (dd, J=8.2, 1.6 Hz, 1H), 3.15-3.06 (m, 4H), 2.79-2.72 (m, 2H), 2.28-2.19 (m, 2H), 1.68 (q, J=7.0 Hz, 2H), 1.40-1.22 (m, 15H), 0.93-0.86 (m, 3H). $^{13}$C NMR (126 MHz, Methanol-$d_4$) δ 167.0, 152.4, 142.2, 139.8, 126.4, 119.6, 111.1, 40.0, 37.0, 33.1, 30.7, 30.7, 30.6, 30.4, 30.2, 26.3, 25.3, 23.7, 14.4.

Scheme 3—Example Synthesis for N$^1$-(5-decylbenzo[d]oxazol-2-yl)ethane-1,2-diamine hydrochloride

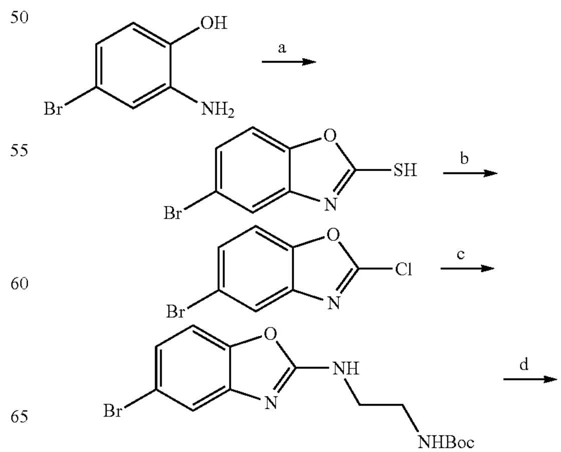

-continued

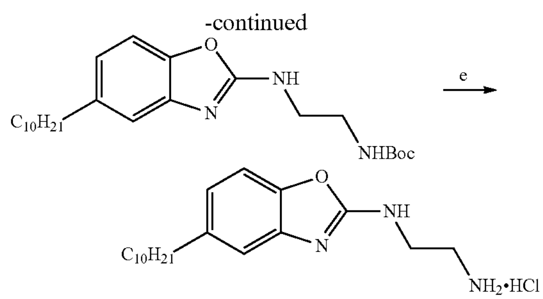

(a) $CS_2$ (1.2 equiv), $K_2CO_3$ (1.2 equiv), EtOH/$H_2O$, 80° C.; (b) $SOCl_2$ (2.5 equiv), DMF (0.04 equiv), DCM, rt; (c) N-boc-amine (1.2 equiv), $K_2CO_3$ (2.0 equiv), DMF, 120° C.; (d) (i) 9-BBN (2.2 equiv), 1-decene (2.0 equiv); (ii) aryl bromide (1.0 equiv), Pd(dppf)$Cl_2$*$CH_2Cl_2$ (0.15 equiv), 3M KOH (3.0 equiv), THF, 70° C.; (e) 4M HCl/Dioxane, DCM, rt.

5-bromobenzo[d]oxazole-2-thiol (9)

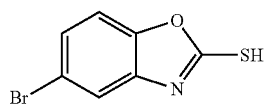

Synthesized according to General Procedure 10. Crude mixture dried in vacuo and carried forward to the next reaction without purification.

5-bromo-2-chlorobenzo[d]oxazole (10)

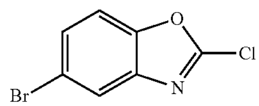 [SMILES: Clc1nc2cc(Br)ccc2o1]

Synthesized according to General Procedure 11. Crude mixture dried in vacuo and carried forward to the next reaction without purification.

tert-butyl (2-((5-bromobenzo[d]oxazol-2-yl)amino) ethyl)carbamate (11a)

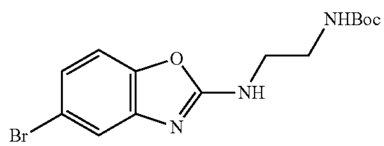 [SMILES: CC(C)(C)OC(=O)NCCNc1nc2cc(Br)ccc2o1]

Synthesized according to General Procedure 13. Light pink solid (67%, 92 mg). $^1$H NMR (500 MHz, Chloroform-d) δ 7.46 (d, J=1.9 Hz, 1H), 7.14 (dd, J=8.4, 1.9 Hz, 1H), 7.09 (d, J=8.4 Hz, 1H), 5.96 (s, 1H), 4.99 (s, 1H), 3.59 (q, J=5.3 Hz, 2H), 3.44 (q, J=5.8 Hz, 2H), 1.43 (s, 9H). HRMS ($ESI^+$) m/z calc'd. for $C_{14}H_{19}BrN_3O_3^+$ $(M+H)^+$ 356.0604, found 356.0617.

tert-butyl (3-((5-bromobenzo[d]oxazol-2-yl)amino) propyl)carbamate (11b)

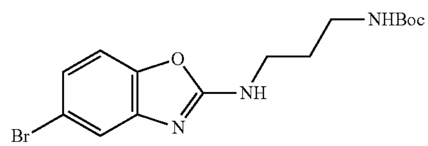 [SMILES: CC(C)(C)OC(=O)NCCCNc1nc2cc(Br)ccc2o1]

Synthesized according to General Procedure 13. White solid (91%, 90 mg). $^1$H NMR (500 MHz, Chloroform-d) δ 7.44 (d, J=1.9 Hz, 1H), 7.11 (dd, J=8.4, 1.9 Hz, 1H), 7.08-7.06 (m, 1H), 6.24 (s, 1H), 4.96 (s, 1H), 3.52 (q, J=6.1 Hz, 2H), 3.26 (q, J=6.3 Hz, 2H), 1.79 (p, J=6.2 Hz, 2H), 1.45 (s, 9H). HRMS ($ESI^+$) m/z calc'd. for $C_{15}H_{21}BrN_3O_3^+$ $(M+H)^+$ 370.0761, found 370.0754.

tert-butyl (4-((5-bromobenzo[d]oxazol-2-yl)amino) butyl)carbamate diamine (11c)

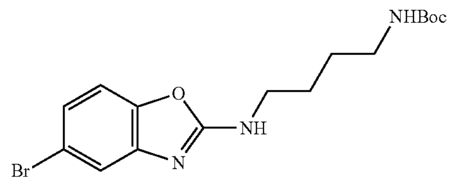 [SMILES: CC(C)(C)OC(=O)NCCCCNc1nc2cc(Br)ccc2o1]

Synthesized according to General Procedure 13. White solid (51%, 170 mg). $^1$H NMR (400 MHz, Chloroform-d) δ 7.47 (dd, J=1.9, 0.5 Hz, 1H), 7.14 (dd, J=8.4, 1.9 Hz, 1H), 7.09 (dd, J=8.4, 0.5 Hz, 1H), 5.23 (s, 1H), 4.68 (s, 1H), 3.53-3.47 (m, 2H), 3.19 (q, J=6.6 Hz, 2H), 1.76-1.67 (m, 3H), 1.66-1.57 (m, 2H), 1.45 (s, 9H). HRMS ($ESI^+$) m/z calc'd. for $C_{16}H_{23}BrN_3O_3^+$ $(M+H)^+$ 384.0917, found 384.0906.

tert-butyl (5-((5-bromobenzo[d]oxazol-2-yl)amino) pentyl)carbamate (11d)

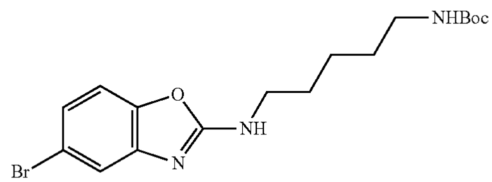 [SMILES: CC(C)(C)OC(=O)NCCCCCNc1nc2cc(Br)ccc2o1]

Synthesized according to General Procedure 13. White solid (64%, 68 mg). $^1$H NMR (500 MHz, Chloroform-d) δ 7.46 (d, J=1.9 Hz, 1H), 7.12 (s, 1H), 7.08 (d, J=8.4 Hz, 1H), 5.40 (s, 1H), 4.58 (s, 1H), 3.47 (q, J=6.6 Hz, 2H), 3.14 (q, J=6.6 Hz, 2H), 1.71 (p, J=7.1 Hz, 2H), 1.54 (p, J=7.0 Hz, 2H), 1.44 (s, 9H), 1.43 (d, J=8.8 Hz, 2H). HRMS ($ESI^+$) m/z calc'd. for $C_{17}H_{25}BrN_3O_3^+$ $(M+H)^+$ 398.1074, found 398.1053.

tert-butyl 3-((5-bromobenzo[d]oxazol-2-yl)amino) azetidine-1-carboxylate (11e)

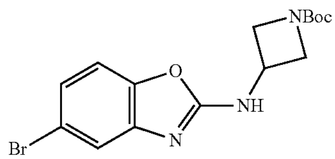 [SMILES: CC(C)(C)OC(=O)N1CC(Nc2nc3cc(Br)ccc3o2)C1]

Synthesized according to General Procedure 13. White solid (66%, 90 mg). $^1$H NMR (500 MHz, Chloroform-d) δ 7.48 (d, J=2.0 Hz, 1H), 7.18 (dd, J=8.4, 1.9 Hz, 1H), 7.13 (d, J=8.4 Hz, 1H), 6.44 (s, 1H), 4.64 (p, J=6.3, 5.7 Hz, 1H), 4.41-4.34 (m, 2H), 3.94 (dd, J=9.5, 5.0 Hz, 2H), 1.46 (s, 9H). HRMS (ESI$^+$) m/z calc'd. for $C_{15}H_{18}BrN_3O_3^+$ (M+H)$^+$ 368.0610, found 368.0587.

tert-butyl (S)-3-((5-bromobenzo[d]oxazol-2-yl) amino)pyrrolidine-1-carboxylate (11f)

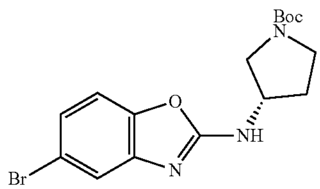 [SMILES: CC(C)(C)OC(=O)N1CC[C@H](Nc2nc3cc(Br)ccc3o2)C1]

Synthesized according to General Procedure 13. White solid (73%, 122 mg). $^1$H NMR (500 MHz, Chloroform-d) δ 7.53-7.45 (m, 1H), 7.21-7.05 (m, 2H), 5.60 (d, J=37.4 Hz, 1H), 4.46 (s, 1H), 3.74 (dd, J=11.6, 5.9 Hz, 1H), 3.58-3.31 (m, 3H), 2.35-2.20 (m, 1H), 2.18-1.96 (m, 1H), 1.47 (s, 9H). HRMS (ESI$^+$) m/z calc'd. for $C_{16}H_{21}BrN_3O_3^+$ (M+H)$^+$ 382.0761, found 382.0763.

tert-butyl (R)-3-((5-bromobenzo[d]oxazol-2-yl) amino)pyrrolidine-1-carboxylate (11g)

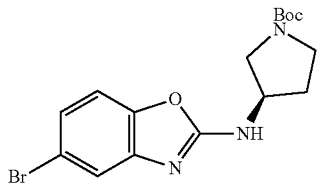 [SMILES: CC(C)(C)OC(=O)N1CC[C@@H](Nc2nc3cc(Br)ccc3o2)C1]

Synthesized according to General Procedure 13. White solid (83%, 175 mg). $^1$H NMR (400 MHz, Chloroform-d) δ 7.50 (d, J=1.8 Hz, 1H), 7.17 (dd, J=8.5, 1.9 Hz, 1H), 7.11 (d, J=8.4 Hz, 1H), 5.04 (s, 1H), 4.46 (s, 1H), 3.74 (dd, J=11.6, 5.9 Hz, 1H), 3.57-3.28 (m, 3H), 2.33-2.23 (m, 1H), 2.04 (s, 1H), 1.47 (s, 9H). HRMS (ESI$^+$) m/z calc'd. for $C_{16}H_{21}BrN_3O_3^+$ (M+H)$^+$ 382.0749, found 382.0763.

tert-butyl (3R,4S)-3-((5-bromobenzo[d]oxazol-2-yl) amino)-4-fluoropyrrolidine-1-carboxylate amine (11h)

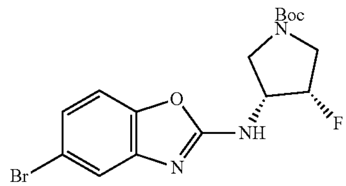 [SMILES: CC(C)(C)OC(=O)N1C[C@H](F)[C@H](Nc2nc3cc(Br)ccc3o2)C1]

Synthesized according to General Procedure 13. Off-white solid (77%, 114 mg). $^1$H NMR (400 MHz, Chloroform-d) δ 7.50 (d, J=2.4 Hz, 1H), 7.22-7.08 (m, 2H), 5.63 (s, 1H), 5.22 (dt, J=54.0, 3.4 Hz, 1H), 4.58 (d, J=27.9 Hz, 1H), 4.11-4.00 (m, 1H), 3.90-3.54 (m, 2H), 3.25 (p, J=9.0, 8.5 Hz, 1H), 1.48 (s, 9H). $^{19}$F NMR (376 MHz, Chloroform-d) δ −195.77-−196.25 (m). HRMS (ESI$^+$) m/z calc'd. for $C_{16}H_{20}BrFN_3O_3^+$ (M+H)$^+$ 400.0672, found 400.0656.

tert-butyl 4-((5-bromobenzo[d]oxazol-2-yl)amino) piperidine-1-carboxylate amine (11i)

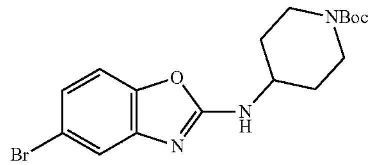 [SMILES: CC(C)(C)OC(=O)N1CCC(Nc2nc3cc(Br)ccc3o2)CC1]

Synthesized according to General Procedure 13. White solid (65%). $^1$H NMR (500 MHz, Chloroform-d) δ 7.47 (t, J=1.7 Hz, 1H), 7.15 (dt, J=8.4, 1.8 Hz, 1H), 7.10 (dd, J=8.5, 1.6 Hz, 1H), 5.14 (d, J=7.8 Hz, 1H), 4.10 (s, 2H), 3.94-3.85 (m, 1H), 2.95 (t, J=12.9 Hz, 2H), 2.17-2.07 (m, 2H), 1.53-1.40 (m, 11H). HRMS (ESI+) m/z calc'd. for $C_{16}H_{21}BrN_3O_3^+$ (M+H)$^+$ 382.0766, found 382.0737.

tert-butyl (S)-(1-(5-bromobenzo[d]oxazol-2-yl)pyrrolidin-3-yl)carbamate (11j)

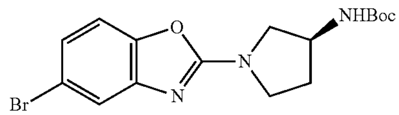 [SMILES: CC(C)(C)OC(=O)N[C@H]1CCN(c2nc3cc(Br)ccc3o2)C1]

Synthesized according to General Procedure 13. White solid (49%, 70 mg). $^1$H NMR (400 MHz, Chloroform-d) δ 7.47 (s, 1H), 7.11 (s, 2H), 4.71 (s, 1H), 4.37 (s, 1H), 3.89 (dd, J=11.0, 6.0 Hz, 1H), 3.78-3.67 (m, 2H), 3.53 (dd, J=11.1, 4.2 Hz, 1H), 2.37-2.24 (m, 1H), 2.07-1.96 (m, 1H), 1.46 (s, 9H). HRMS (ESI+) m/z calc'd. for $C_{16}H_{21}BrN_3O_3^+$ (M+H)$^+$ 382.0766, found 382.0737.

tert-butyl (R)-(1-(5-bromobenzo[d]oxazol-2-yl)pyrrolidin-3-yl)carbamate (11k)

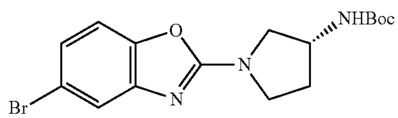 [SMILES: CC(C)(C)OC(=O)N[C@@H]1CCN(c2nc3cc(Br)ccc3o2)C1]

Synthesized according to General Procedure 13. White solid (66%, 72 mg). $^1$H NMR (400 MHz, Chloroform-d) δ 7.48-7.45 (m, 1H), 7.12-7.11 (m, 2H), 4.71 (s, 1H), 4.37 (s, 1H), 3.89 (dd, J=11.0, 6.0 Hz, 1H), 3.78-3.70 (m, 2H), 3.53 (dd, J=11.2, 4.2 Hz, 1H), 2.38-2.23 (m, 1H), 2.07-1.95 (m, 1H), 1.46 (s, 9H). HRMS (ESI$^+$) m/z calc'd. for $C_{16}H_{21}BrN_3O_3^+$ (M+H)$^+$ 382.0766, found 382.0737.

tert-butyl 4-(5-bromobenzo[d]oxazol-2-yl)piperazine-1-carboxylate (11l)

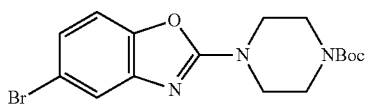 [SMILES: CC(C)(C)OC(=O)N1CCN(c2nc3cc(Br)ccc3o2)CC1]

Synthesized according to General Procedure 13. Off-white solid (71%, 105 mg). $^1$H NMR (500 MHz, Chloroform-d) δ 7.47 (d, J=1.8 Hz, 1H), 7.16-7.09 (m, 2H), 3.67 (t, J=6.6 Hz, 4H), 3.57 (t, J=6.7, 4H), 1.49 (s, 9H). HRMS (ESI+) m/z calc'd. for $C_{16}H_{21}BrN_3O_3^+$ (M+H)$^+$ 382.0766, found 382.0737.

tert-butyl (2-((6-bromobenzo[d]oxazol-2-yl)amino)ethyl)carbamate (11m)

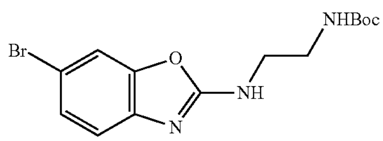 [SMILES: CC(C)(C)OC(=O)NCCNc1nc2ccc(Br)cc2o1]

Synthesized according to General Procedure 13. White solid (87%, 79 mg). $^1$H NMR (500 MHz, Chloroform-d) δ $^1$H NMR (500 MHz, Chloroform-d) δ 7.38 (d, J=1.9 Hz, 1H), 7.30-7.25 (m, 1H), 7.20 (d, J=8.3 Hz, 1H), 5.95 (s, 1H), 5.00 (s, 1H), 3.58 (t, J=5.4 Hz, 2H), 3.44 (q, J=5.9 Hz, 2H), 1.43 (s, 9H). HRMS (ESI$^+$) m/z calc'd. for $C_{14}H_{19}BrN_3O_3^+$ (M+H)$^+$ 356.0604, found 356.0613.

tert-butyl (3-((6-bromobenzo[d]oxazol-2-yl)amino)propyl)carbamate (11n)

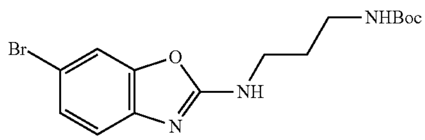 [SMILES: CC(C)(C)OC(=O)NCCCNc1nc2ccc(Br)cc2o1]

Synthesized according to General Procedure 13. White solid (81%, 63 mg). $^1$H NMR (500 MHz, Chloroform-d) δ 7.37 (d, J=1.9 Hz, 1H), 7.28-7.23 (m, 1H), 7.19 (d, J=8.3 Hz, 1H), 6.06 (s, 1H), 4.89 (s, 1H), 3.52 (q, J=6.2 Hz, 2H), 3.27 (q, J=6.3 Hz, 2H), 1.82-1.76 (m, 2H), 1.46 (s, 9H). HRMS (ESI$^+$) m/z calc'd. for $C_{15}H_{21}BrN_3O_3^+$ (M+H)$^+$ 370.0761, found 370.0766.

tert-butyl (S)-3-((6-bromobenzo[d]oxazol-2-yl)amino)pyrrolidine-1-carboxylate (11o)

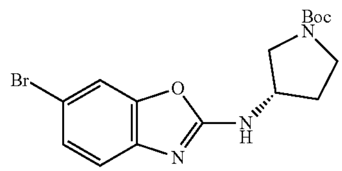 [SMILES: CC(C)(C)OC(=O)N1CC[C@H](Nc2nc3ccc(Br)cc3o2)C1]

Synthesized according to General Procedure 13. White solid (76%, 83 mg). $^1$H NMR (500 MHz, Chloroform-d) δ 7.41 (s, 1H), 7.30 (d, J=8.4 Hz, 1H), 7.23 (d, J=8.3 Hz, 1H), 5.46 (d, J=19.9 Hz, 1H), 4.46 (s, 1H), 3.74 (dd, J=11.6, 5.9 Hz, 1H), 3.59-3.32 (m, 3H), 2.34-2.22 (m, 1H), 2.15-1.98 (m, 1H), 1.47 (s, 9H). HRMS (ESI$^+$) m/z calc'd. for $C_{16}H_{21}N_3O_3^+$ (M+H)$^+$ 382.0761, found 382.0764.

tert-butyl (R)-3-((6-bromobenzo[d]oxazol-2-yl)amino)pyrrolidine-1-carboxylate (11p)

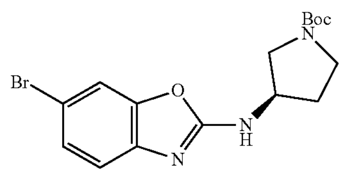 [SMILES: CC(C)(C)OC(=O)N1CC[C@@H](Nc2nc3ccc(Br)cc3o2)C1]

Synthesized according to General Procedure 13. Off-white solid (74%, 112 mg). $^1$H NMR (400 MHz, Chloroform-d) δ 7.40 (s, 1H), 7.31-7.27 (m, 1H), 7.22 (d, J=8.3, 1.7 Hz, 1H), 5.98-5.71 (m, 1H), 4.45 (s, 1H), 3.74 (dd, J=11.6, 5.9 Hz, 1H), 3.61-3.32 (m, 3H), 2.34-2.21 (m, 1H), 2.17-1.96 (m, 1H), 1.47 (s, 9H). HRMS (ESI$^+$) m/z calc'd. for $C_{16}H_{21}N_3O_3^+$ (M+H)$^+$ 382.0761, found 382.0766.

tert-butyl (2-((7-bromobenzo[d]oxazol-2-yl)amino)ethyl)carbamate (11q)

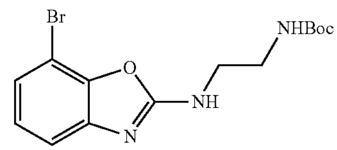 [SMILES: CC(C)(C)OC(=O)NCCNc1nc2cccc(Br)c2o1]

Synthesized according to General Procedure 13. White solid (5300, 70 mg). $^1$H NMR (500 MHz, Chloroform-d) δ 7.28 (s, 1H), 7.16 (d, J=8.0 Hz, 1H), 7.04 (td, J=8.0, 1.7 Hz, 1H), 5.76 (s, 1H), 4.94 (s, 1H), 3.62 (q, J=5.5 Hz, 2H), 3.45 (q, J=5.9 Hz, 2H), 1.44 (s, 9H). HRMS (ESI$^+$) m/z calc'd. for $C_{14}H_{19}BrN_3O_3^+$ (M+H)$^+$ 356.0604, found 356.0607.

tert-butyl (3-((7-bromobenzo[d]oxazol-2-yl)amino) propyl)carbamate (11r)

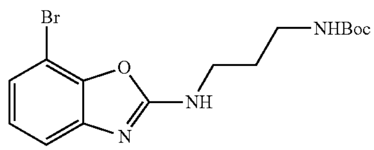 [SMILES: CC(C)(C)OC(=O)NCCCNc1nc2cccc(Br)c2o1]

Synthesized according to General Procedure 13. White solid (68%, 115 mg). $^1H$ NMR (500 MHz, Chloroform-d) δ 7.31 (d, J=8.1, 0.9 Hz, 1H), 7.17 (d, J=7.9, 0.9 Hz, 1H), 6.89 (t, J=8.0 Hz, 1H), 6.13 (s, 1H), 5.09 (s, 1H), 3.59 (q, J=6.4 Hz, 2H), 3.26 (q, J=6.3 Hz, 2H), 1.79 (p, J=6.2 Hz, 2H), 1.46 (s, 9H). HRMS ($ESI^+$) m/z calc'd. for $C_{15}H_{21}BrN_3O_3^+$ $(M+H)^+$ 370.0761, found 370.0762.

tert-butyl (2-((4-bromobenzo[d]oxazol-2-yl)amino) ethyl)carbamate (its)

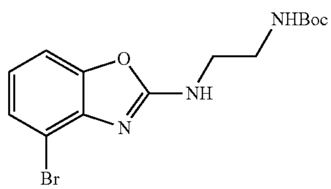 [SMILES: CC(C)(C)OC(=O)NCCNc1nc2c(Br)cccc2o1]

Synthesized according to General Procedure 13. White solid (86%, 141 mg). $^1H$ NMR (500 MHz, Chloroform-d) δ 7.31 (dd, J=8.2, 2.3 Hz, 1H), 7.18 (d, J=8.0 Hz, 1H), 6.94-6.87 (m, 1H), 6.56 (s, 1H), 5.08 (s, 1H), 3.69-3.60 (m, 2H), 3.47-3.40 (m, 2H), 1.41 (s, 9H).

tert-butyl (3-((4-bromobenzo[d]oxazol-2-yl)amino) propyl)carbamate (11t)

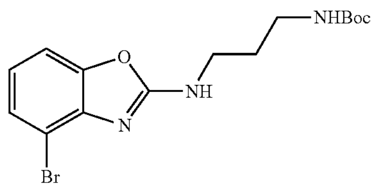 [SMILES: CC(C)(C)OC(=O)NCCCNc1nc2c(Br)cccc2o1]

Synthesized according to General Procedure 13. White solid (68%, 115 mg). $^1H$ NMR (500 MHz, Chloroform-d) δ 7.31 (d, J=8.1, 0.9 Hz, 1H), 7.17 (d, J=7.9, 0.9 Hz, 1H), 6.89 (t, J=8.0 Hz, 1H), 6.13 (s, 1H), 5.09 (s, 1H), 3.59 (q, J=6.4 Hz, 2H), 3.26 (q, J=6.3 Hz, 2H), 1.79 (p, J=6.2 Hz, 2H), 1.46 (s, 9H). HRMS ($ESI^+$) m/z calc'd. for $C_{15}H_{21}BrN_3O_3^+$ $(M+H)^+$ 370.0761, found 370.0762.

di-tert-butyl (((6-bromobenzo[d]oxazol-2-yl) azanediyl)bis(ethane-2,1-diyl))dicarbamate (11u)

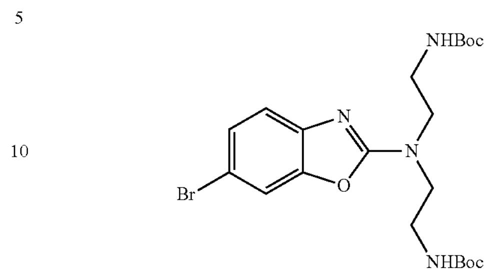

Synthesized according to General Procedure 13. White solid (96%, 186 mg). $^1H$ NMR (400 MHz, $CDCl_3$) δ 7.37 (d, J=1.9 Hz, 1H), 7.29-7.26 (m, 1H), 7.17 (d, J=8.3 Hz, 1H), 5.12 (s, 2H), 3.66 (t, J=6.0 Hz, 5H), 3.42 (q, J=6.1 Hz, 5H), 1.35 (s, 19H). $^{13}C$ NMR (101 MHz, $CDCl_3$) δ 156.3, 149.3, 142.7, 127.3, 117.1, 112.6, 112.4, 79.6, 49.8, 39.4, 28.4. HRMS ($ESI^+$) m/z calc'd. for $C_{21}H_{32}BrN_4O_5$+ (M+H)+ 499.1551, found 499.1601.

tert-butyl (S)-(1-(6-bromobenzo[d]oxazol-2-yl)pyrrolidin-3-yl)carbamate (11v)

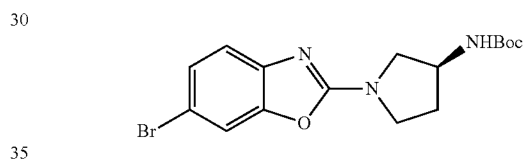

Synthesized according to General Procedure 13. White solid (91%, 134 mg). $^1H$ NMR (400 MHz, $CDCl_3$) δ 7.40 (d, J=1.8 Hz, 1H), 7.29-7.25 (m, 1H), 7.20 (d, J=8.3 Hz, 1H), 4.71 (d, J=7.0 Hz, 1H), 4.37 (s, 1H), 3.88 (dd, J=10.9, 6.0 Hz, 1H), 3.80-3.65 (m, 3H), 3.51 (dd, J=11.0, 4.2 Hz, 1H), 2.30 (m, 1H), 2.01 (m, 1H), 1.45 (s, 11H). $^{13}C$ NMR (101 MHz, $CDCl_3$) δ 160.9, 155.3, 149.6, 142.7, 127.3, 117.2, 112.6, 112.4, 53.4, 50.6, 45.8, 31.9, 28.5. HRMS ($ESI^+$) m/z calc'd. for $C_{16}H_{21}BrN_3O_3$+ (M+H)+ 382.0761, found 382.0764.

tert-butyl (R)-(1-(6-bromobenzo[d]oxazol-2-yl)pyrrolidin-3-yl)carbamate (11w)

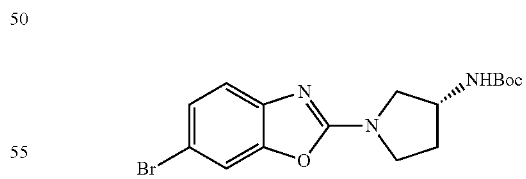

Synthesized according to General Procedure 13. Brown solid (84%, 125 mg). $^1H$ NMR (400 MHz, $CDCl_3$) δ 7.40 (d, J=1.8 Hz, 1H), 7.29-7.26 (m, 1H), 7.20 (d, J=8.3 Hz, 1H), 4.72-4.67 (m, 1H), 4.37 (s, 1H), 3.88 (dd, J=11.0, 6.0 Hz, 1H), 3.75-3.68 (m, 2H), 3.52 (dd, J=11.0, 4.2 Hz, 1H), 2.30 (dtd, J=13.5, 7.7, 5.9 Hz, 1H), 2.07-1.94 (m, 1H), 1.45 (s, 12H). $^{13}C$ NMR (101 MHz, $CDCl_3$) δ 160.9, 155.3, 149.6, 142.7, 127.3, 117.2, 112.6, 112.5, 53.4, 50.7, 45.8, 31.9, 28.5. HRMS ($ESI^+$) m/z calc'd. for $C_{16}H_{21}BrN_3O_3$+ (M+H)+ 382.0761, found 382.0765.

tert-butyl 4-((6-bromobenzo[d]oxazol-2-yl)amino) piperidine-1-carboxylate (11x)

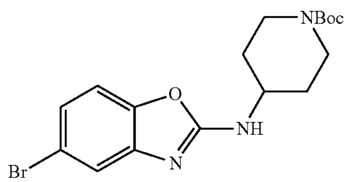 [SMILES: CC(C)(C)OC(=O)N1CCC(Nc2nc3cc(Br)ccc3o2)CC1]

Synthesized according to General Procedure 13. White solid (96%, 155 mg). $^1$H NMR (400 MHz, $CDCl_3$) δ 7.33 (d, J=1.9 Hz, 1H), 7.22 (dt, J=8.4, 1.9 Hz, 1H), 7.13 (dd, J=8.3, 1.8 Hz, 1H), 6.15 (d, J=8.6 Hz, 1H), 4.13-3.97 (m, 2H), 3.84 (h, J=6.7 Hz, 1H), 2.98-2.82 (m, 4H), 2.07 (dd, J=13.4, 3.8 Hz, 3H), 1.42 (d, J=1.5 Hz, 13H), 1.27-1.12 (m, 1H). $^{13}$C NMR (101 MHz, $CDCl_3$) δ 161.4, 154.8, 148.9, 142.2, 127.2, 117.2, 113.1, 112.4, 80.0, 50.7, 42.6, 32.4, 28.5. HRMS (ESI$^+$) m/z calc'd. for $C_{17}H_{23}BrN_3O_3$+ (M+H)+ 396.0917, found 396.0922.

tert-butyl (2-((5-octylbenzo[d]oxazol-2-yl)amino) ethyl)carbamate (12a)

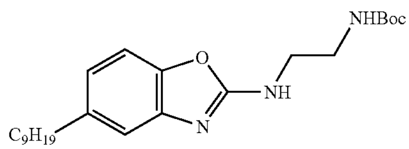

Synthesized according to General Procedure 6. White solid (74%, 58 mg). $^1$H NMR (500 MHz, Chloroform-d) δ 7.17 (s, 1H), 7.12 (d, J=8.1 Hz, 1H), 6.84 (dd, J=8.2, 1.7 Hz, 1H), 5.53 (s, 1H), 4.96 (s, 1H), 3.59 (q, J=5.3 Hz, 2H), 3.43 (q, J=5.9 Hz, 2H), 2.63 (t, J=7.7 Hz, 2H), 1.61 (p, J=7.4 Hz, 2H), 1.43 (s, 9H), 1.33-1.22 (m, 10H), 0.87 (t, J=6.8 Hz, 3H). HRMS (ESI$^+$) m/z calc'd. for $C_{22}H_{36}N_3O_3^+$ (M+H)$^+$ 390.2751, found 390.2749.

tert-butyl (2-((5-nonylbenzo[d]oxazol-2-yl)amino) ethyl)carbamate (12b)

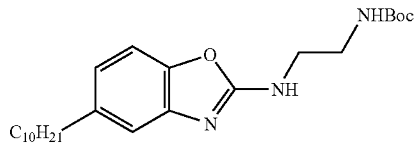

Synthesized according to General Procedure 6. White solid (86%, 70 mg). $^1$H NMR (500 MHz, Chloroform-d) δ 7.17 (d, J=1.7 Hz, 1H), 7.12 (d, J=8.1 Hz, 1H), 6.84 (dd, J=8.1, 1.7 Hz, 1H), 5.59 (s, 1H), 5.00 (s, 1H), 3.59 (q, J=5.2 Hz, 2H), 3.43 (q, J=5.8 Hz, 2H), 2.66-2.60 (m, 2H), 1.60 (dd, J=10.5, 4.7 Hz, 2H), 1.43 (s, 9H), 1.32-1.22 (m, 12H), 0.87 (t, J=6.9 Hz, 3H). HRMS (ESI$^+$) m/z calc'd. for $C_{23}H_{38}N_3O_3^+$ (M+H)$^+$ 404.2908, found 404.2904.

tert-butyl (2-((5-decylbenzo[d]oxazol-2-yl)amino) ethyl)carbamate (12c)

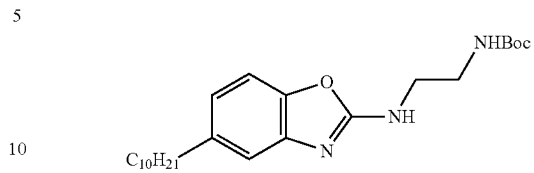

Synthesized according to General Procedure 6. White solid (60%, 56 mg). $^1$H NMR (500 MHz, Chloroform-d) δ 7.15 (d, J=1.7 Hz, 1H), 7.10 (d, J=8.1 Hz, 1H), 6.81 (dd, J=8.1, 1.7 Hz, 1H), 6.22 (d, J=37.0 Hz, 1H), 5.27-5.11 (m, 1H), 3.58 (t, J=5.6 Hz, 2H), 3.42 (q, J=5.9 Hz, 2H), 2.61 (t, J=7.7 Hz, 2H), 1.59 (p, J=7.3 Hz, 2H), 1.40 (s, 9H), 1.26 (d, J=19.9 Hz, 14H), 0.87 (t, J=6.9 Hz, 3H). HRMS (ESI$^+$) m/z calc'd. for $C_{24}H_{40}N_3O_3^+$ (M+H)$^+$ 418.3064, found 418.3078.

tert-butyl (2-((5-undecylbenzo[d]oxazol-2-yl)amino) ethyl)carbamate (12d)

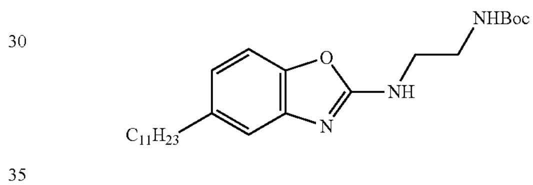

Synthesized according to General Procedure 6. White solid (76%, 66 mg). $^1$H NMR (500 MHz, Chloroform-d) δ 7.17 (d, J=1.7 Hz, 1H), 7.12 (d, J=8.1 Hz, 1H), 6.84 (dd, J=8.2, 1.7 Hz, 1H), 5.60 (s, 1H), 4.97 (s, 1H), 3.58 (s, 2H), 3.43 (d, J=5.8 Hz, 2H), 2.63 (t, J=7.6 Hz, 2H), 1.60 (p, J=7.4 Hz, 2H), 1.43 (s, 9H), 1.31-1.23 (m, 16H), 0.88 (t, J=6.9 Hz, 3H). HRMS (ESI$^+$) m/z calc'd. for $C_{25}H_{42}N_3O_3^+$ (M+H)$^+$ 432.3221, found 432.3221.

tert-butyl (2-((5-dodecylbenzo[d]oxazol-2-yl)amino) ethyl)carbamate diamine (12e)

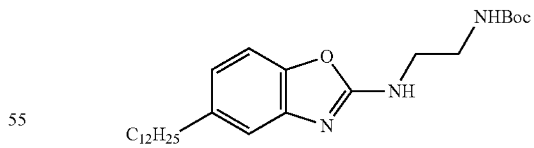

Synthesized according to General Procedure 6. White solid (64%, 58 mg). $^1$H NMR (500 MHz, Chloroform-d) δ 7.19 (s, 1H), 7.14 (d, J=8.1 Hz, 1H), 6.86 (dd, J=8.1, 1.7 Hz, 1H), 5.65 (s, 1H), 5.00 (s, 1H), 3.60 (s, 2H), 3.45 (q, J=5.9 Hz, 2H), 2.65 (t, J=7.6 Hz, 2H), 1.62 (q, J=7.3 Hz, 2H), 1.45 (s, 9H), 1.35-1.23 (m, 18H), 0.90 (t, J=6.8 Hz, 4H). HRMS (ESI$^+$) m/z calc'd. for $C_{26}H_{44}N_3O_3^+$ (M+H)$^+$ 446.3372, found 446.3377.

tert-butyl (3-((5-decylbenzo[d]oxazol-2-yl)amino) propyl)carbamate (12f)

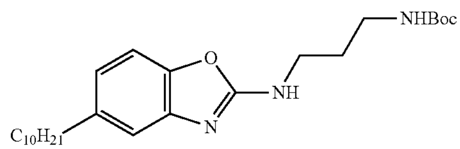

Synthesized according to General Procedure 6. Off-White solid (36%, 99 mg). $^1$H NMR (500 MHz, Chloroform-d) δ 7.42 (s, 1H), 7.32 (d, J=8.3 Hz, 1H), 7.07 (d, J=8.4 Hz, 1H), 4.89 (s, 1H), 3.29-3.16 (m, 2H), 2.93 (t, J=7.3 Hz, 2H), 2.66 (t, J=7.7 Hz, 2H), 2.15-2.00 (m, 2H), 1.92-1.74 (m, 1H), 1.39 (s, 9H), 1.29-1.20 (m, 14H), 0.84 (t, J=6.9 Hz, 3H). HRMS (ESI+) m/z calc'd. for $C_{25}H_{42}N_3O_3^+$ (M+H)$^+$ 432.3221, found 432.3227.

tert-butyl (4-((5-decylbenzo[d]oxazol-2-yl)amino) butyl)carbamate (12g)

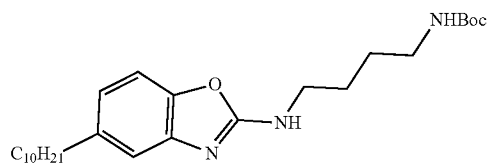

Synthesized according to General Procedure 6. Off-White solid (77%). $^1$H NMR (500 MHz, Chloroform-d) δ 7.15 (s, 1H), 7.11 (d, J=8.1 Hz, 1H), 6.82 (dd, J=8.2, 1.7 Hz, 1H), 5.94 (s, 1H), 4.81 (s, 1H), 3.47 (t, J=7.1 Hz, 2H), 3.16 (q, J=6.8 Hz, 2H), 2.62 (t, J=7.7 Hz, 2H), 1.73-1.66 (m, 2H), 1.63-1.55 (m, 4H), 1.43 (s, 10H), 1.32-1.23 (m, 14H), 0.87 (t, J=6.9 Hz, 3H). HRMS (ESI$^+$) m/z calc'd. for $C_{26}H_{44}N_3O_3^+$ (M+H)$^+$ 446.3377, found 446.3351.

tert-butyl (5-((5-decylbenzo[d]oxazol-2-yl)amino) pentyl)carbamate (12h)

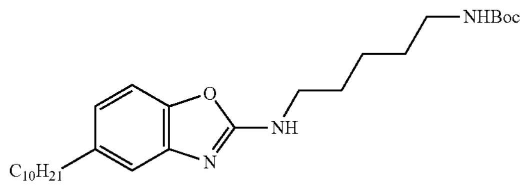

Synthesized according to General Procedure 6. Off-white solid (65%, 51 mg). $^1$H NMR (500 MHz, Chloroform-d) δ 7.17 (d, J=1.7 Hz, 1H), 7.11 (d, J=8.1 Hz, 1H), 6.83 (dd, J=8.1, 1.7 Hz, 1H), 5.00 (s, 1H), 4.55 (s, 1H), 3.47 (q, J=6.6 Hz, 2H), 3.13 (t, J=6.7 Hz, 2H), 2.67-2.58 (m, 2H), 1.70 (p, J=7.2 Hz, 2H), 1.60 (dd, J=10.4, 4.6 Hz, 2H), 1.55-1.49 (m, 2H), 1.44 (s, 10H), 1.42 (d, J=9.1 Hz, 2H), 1.32-1.22 (m, 14H), 0.87 (t, J=6.9 Hz, 3H). HRMS (ESI$^+$) m/z calc'd. for $C_{27}H_{46}N_3O_3^+$ (M+H)$^+$ 460.3534, found 460.3529.

tert-butyl 3-((5-decylbenzo[d]oxazol-2-yl)amino) azetidine-1-carboxylate (12i)

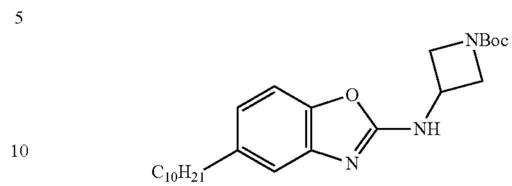

Synthesized according to General Procedure 6. Yellow oil (83%, 87 mg). $^1$H NMR (400 MHz, Chloroform-d) δ 7.19 (d, J=1.6 Hz, 1H), 7.15 (d, J=8.2 Hz, 1H), 6.88 (s, 1H), 5.35 (s, 1H), 4.63 (d, J=5.5 Hz, 1H), 4.42-4.31 (m, 2H), 3.90-3.85 (m, 2H), 2.68-2.59 (m, 2H), 1.45 (d, J=0.7 Hz, 9H), 1.34-1.21 (m, 16H), 0.90-0.82 (m, 3H). $^{13}$C NMR (126 MHz, Chloroform-d) δ 160.7, 156.2, 146.7, 141.9, 139.3, 121.7, 116.4, 108.42, 80.02, 42.7, 36.0, 32.0, 31.9, 29.7, 29.6, 29.6, 29.5, 29.3, 29.2, 28.4, 22.7, 14.1. HRMS (ESI+) m/z calc'd. for $C_{25}H_{39}N_3O_3^+$ (M+H)$^+$ 430.3070, found 430.3100.

tert-butyl (S)-3-((5-decylbenzo[d]oxazol-2-yl) amino)pyrrolidine-1-carboxylate (12j)

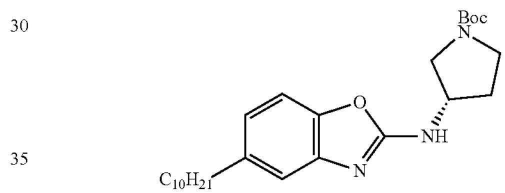

Synthesized according to General Procedure 6. Off-white solid (77%, 76 mg). $^1$H NMR (500 MHz, Chloroform-d) δ 7.20 (s, 1H), 7.13 (d, J=8.0 Hz, 1H), 6.85 (d, J=8.1 Hz, 1H), 6.17 (s, 1H), 4.45 (s, 1H), 3.74 (dd, J=11.5, 6.0 Hz, 1H), 3.58-3.34 (m, 3H), 2.63 (t, J=7.7 Hz, 2H), 2.29-2.23 (m, 1H), 2.14-1.98 (m, 1H), 1.61 (p, J=7.2 Hz, 2H), 1.46 (s, 9H), 1.34-1.20 (m, 14H), 0.88 (t, J=7.0 Hz, 3H). HRMS (ESI+) m/z calc'd. for $C_{26}H_{42}N_3O_3^+$ (M+H)$^+$ 444.3321, found 444.3320.

tert-butyl (R)-3-((5-decylbenzo[d]oxazol-2-yl) amino)pyrrolidine-1-carboxylate (12k)

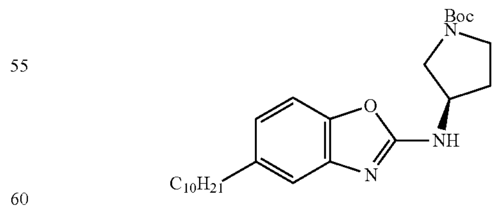

Synthesized according to General Procedure 6. Off-white solid (60%, 122 mg). $^1$H NMR (400 MHz, Chloroform-d) δ 7.19 (d, J=1.7 Hz, 1H), 7.14 (d, J=8.2 Hz, 1H), 6.86 (dd, J=8.2, 1.7 Hz, 1H), 5.29 (s, 1H), 4.47 (s, 1H), 3.74 (dd, J=11.5, 6.0 Hz, 1H), 3.57-3.31 (m, 3H), 2.68-2.60 (m, 2H), 2.34-2.21 (m, 1H), 2.14-1.95 (m, 1H), 1.61 (p, J=7.2 Hz, 2H), 1.47 (s, 10H), 1.33-1.23 (m, 14H), 0.90-0.84 (m, 3H). HRMS (ESI+) m/z calc'd. for $C_{26}H_{42}N_3O_3^+$ (M+H)$^+$ 444.3221, found 444.3229.

tert-butyl (3R,4S)-3-((5-decylbenzo[d]oxazol-2-yl)amino)-4-fluoropyrrolidine-1-carboxylate (12l)

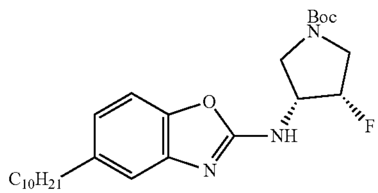

Synthesized according to General Procedure 6. Yellow oil (75%, 98 mg). $^1$H NMR (400 MHz, Chloroform-d) δ 7.22-7.10 (m, 2H), 6.87 (d, J=8.2 Hz, 1H), 6.20 (s, 1H), 5.21 (dt, J=53.9, 3.3 Hz, 1H), 4.58 (d, J=28.5 Hz, 1H), 4.11-3.99 (m, 1H), 3.89-3.52 (m, 2H), 3.34-3.23 (m, 1H), 2.64 (t, J=7.7 Hz, 2H), 1.61 (p, J=7.3 Hz, 2H), 1.47 (s, 9H), 1.32-1.23 (m, 14H), 0.88 (t, J=6.7 Hz, 3H). $^{19}$F NMR (376 MHz, Chloroform-d) δ −196.00-−196.49 (m). HRMS (ESI+) m/z calc'd. for $C_{26}H_{41}FN_3O_3^+$ (M+H)$^+$ 462.3132, found 462.3139.

tert-butyl 4-((5-decylbenzo[d]oxazol-2-yl)amino)piperidine-1-carboxylate (12m)

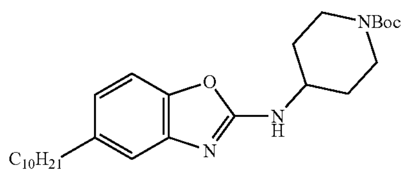

Synthesized according to General Procedure 6. Off-white solid (85%, 95 mg). $^1$H NMR (500 MHz, Chloroform-d) δ 7.22-7.09 (m, 2H), 6.87 (dd, J=8.1, 1.7 Hz, 1H), 4.92 (s, 1H), 4.10 (s, 3H), 3.96-3.88 (m, 1H), 2.97 (t, J=10.2 Hz, 2H), 2.71-2.60 (m, 2H), 2.22-2.12 (m, 2H), 1.62 (h, J=7.1, 6.4 Hz, 2H), 1.51-1.42 (m, 11H), 1.28 (d, J=14.1 Hz, 14H), 0.90 (t, J=6.9 Hz, 3H). HRMS (ESI+) m/z calc'd. for $C_{26}H_{42}N_3O_3^+$ (M+H)$^+$ 444.3226, found 444.3195.

tert-butyl (S)-(1-(5-decylbenzo[d]oxazol-2-yl)pyrrolidin-3-yl)carbamate (12n)

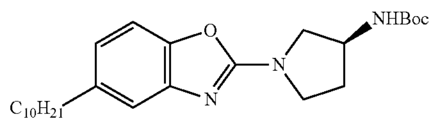

Synthesized according to General Procedure 6. White solid (70%, 53 mg). $^1$H NMR (400 MHz, Chloroform-d) δ 7.18 (d, J=1.6 Hz, 1H), 7.14 (d, J=8.1 Hz, 1H), 6.82 (dd, J=8.1, 1.7 Hz, 1H), 4.72 (s, 1H), 4.37 (s, 1H), 3.88 (dd, J=10.9, 6.0 Hz, 1H), 3.80-3.68 (m, 2H), 3.58-3.47 (m, 1H), 2.63 (t, J=7.6 Hz, 2H), 2.37-2.24 (m, 1H), 2.07-1.95 (m, 1H), 1.61 (t, J=7.4 Hz, 2H), 1.46 (s, 9H), 1.32-1.22 (m, 14H), 0.88 (t, J=6.7 Hz, 3H). HRMS (ESI+) m/z calc'd. for $C_{26}H_{42}N_3O_3^+$ (M+H)$^+$ 444.3226, found 444.3195.

tert-butyl (R)-(1-(5-decylbenzo[d]oxazol-2-yl)pyrrolidin-3-yl)carbamate (12o)

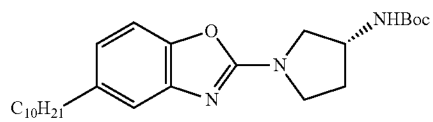

Synthesized according to General Procedure 6. Off-white solid (77%, 64 mg). $^1$H NMR (500 MHz, Chloroform-d) δ 7.19-7.11 (m, 2H), 6.82 (dd, J=8.1, 1.7 Hz, 1H), 4.75 (d, J=7.3 Hz, 1H), 4.37 (s, 1H), 3.87 (dd, J=10.9, 6.0 Hz, 1H), 3.78-3.67 (m, 2H), 3.52 (dd, J=10.9, 4.1 Hz, 1H), 2.66-2.59 (m, 2H), 2.35-2.22 (m, 1H), 2.04-1.80 (m, 2H), 1.60 (p, J=7.1 Hz, 2H), 1.45 (s, 9H), 1.33-1.21 (m, 14H), 0.87 (t, J=6.9 Hz, 3H). HRMS (ESI$^+$) m/z calc'd. for $C_{26}H_{42}N_3O_3^+$ (M+H)$^+$ 444.3226, found 444.3195.

tert-butyl 4-(5-decylbenzo[d]oxazol-2-yl)piperazine-1-carboxylate (12p)

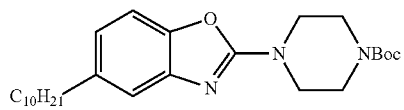

Synthesized according to General Procedure 6. White solid (79%, 84 mg). $^1$H NMR (500 MHz, Chloroform-d) δ 7.18 (s, 1H), 7.15 (d, J=8.1 Hz, 1H), 6.85 (dd, J=8.1, 1.7 Hz, 1H), 3.69-3.62 (m, 4H), 3.58-3.53 (m, 4H), 2.64 (t, J=7.6 Hz, 2H), 1.65-1.56 (m, 2H), 1.49 (s, 9H), 1.34-1.19 (m, 14H), 0.87 (t, J=7.0 Hz, 3H).). HRMS (ESI+) m/z calc'd. for $C_{26}H_{42}N_3O_3^+$ (M+H)$^+$ 444.3221, found 444.3195.

tert-butyl (2-((6-decylbenzo[d]oxazol-2-yl)amino)ethyl)carbamate (12q)

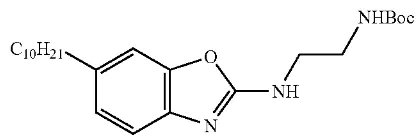

Synthesized according to General Procedure 6. Off-white solid (73%, 73 mg). $^1$H NMR (500 MHz, Chloroform-d) δ 7.24 (d, J=8.0 Hz, 1H), 7.06 (d, J=1.6 Hz, 1H), 6.97 (dd, J=8.0, 1.7 Hz, 1H), 5.53 (s, 1H), 4.97 (s, 1H), 3.43 (d, J=5.9 Hz, 2H), 2.63 (t, J=7.7 Hz, 2H), 1.59 (q, J=7.2 Hz, 1H), 1.43 (s, 9H), 1.33-1.23 (m, 14H), 0.88 (t, J=6.9 Hz, 3H). HRMS (ESI$^+$) m/z calc'd. for $C_{24}H_{39}N_3O_3^+$ (M+H)$^+$ 418.3064, found 418.3059.

tert-butyl (3-((6-decylbenzo[d]oxazol-2-yl)amino) propyl)carbamate (12r)

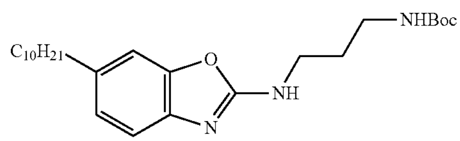

Synthesized according to General Procedure 6. White solid (74%, 54 mg). $^1$H NMR (500 MHz, Chloroform-d) δ 7.24 (d, J=8.0 Hz, 1H), 7.06 (d, J=1.6 Hz, 1H), 6.97 (d, J=7.9, 1H), 5.77 (s, 1H), 4.92 (t, J=6.7 Hz, 1H), 3.52 (q, J=6.1 Hz, 2H), 3.26 (q, J=6.3 Hz, 2H), 2.63 (t, J=7.7 Hz, 2H), 1.79 (p, J=6.3 Hz, 2H), 1.64-1.56 (m, 2H), 1.46 (s, 9H), 1.33-1.20 (m, 14H), 0.88 (t, J=6.9 Hz, 3H). HRMS (ESI$^+$) m/z calc'd. for $C_{25}H_{42}N_3O_3^+$ (M+H)$^+$ 432.3221, found 432.3214.

tert-butyl (S)-3-((6-decylbenzo[d]oxazol-2-yl) amino)pyrrolidine-1-carboxylate (12s)

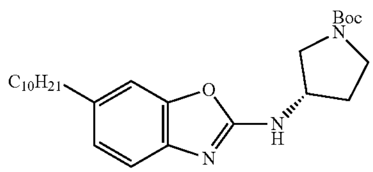

Synthesized according to General Procedure 6. Off-white solid (76%, 83 mg). $^1$H NMR (400 MHz, Chloroform-d) δ 7.25 (d, J=7.9 Hz, 1H), 7.07 (s, 1H), 7.01-6.93 (m, 1H), 6.59 (s, 1H), 4.45 (s, 1H), 3.76 (dd, J=11.4, 6.1 Hz, 1H), 3.63-3.32 (m, 3H), 2.63 (t, J=7.6 Hz, 2H), 2.33-1.97 (m, 2H), 1.60 (p, J=7.3 Hz, 2H), 1.46 (s, 9H), 1.34-1.17 (m, 14H), 0.91-0.83 (m, 3H). HRMS (ESI$^+$) m/z calc'd. for $C_{26}H_{42}N_3O_3^+$ (M+H)$^+$ 444.3221, found 444.3216.

tert-butyl (R)-3-((6-decylbenzo[d]oxazol-2-yl) amino)pyrrolidine-1-carboxylate (12t)

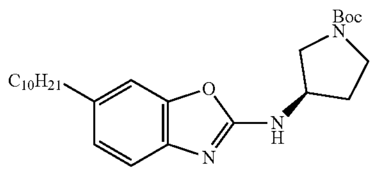

Synthesized according to General Procedure 6. Off-white solid (50%, 63 mg). $^1$H NMR (400 MHz, Chloroform-d) δ 7.21 (d, J=8.0 Hz, 1H), 7.04 (s, 1H), 6.95 (d, J=8.0 Hz, 1H), 6.42 (d, J=23.2 Hz, 1H), 4.42 (s, 1H), 3.73 (dd, J=11.5, 6.1 Hz, 1H), 3.56-3.29 (m, 3H), 2.60 (t, J=7.7 Hz, 2H), 2.30-2.17 (m, 1H), 2.16-1.93 (m, 1H), 1.57 (p, J=7.3 Hz, 2H), 1.43 (s, 9H), 1.30-1.18 (m, 14H), 0.90-0.81 (m, 3H). HRMS (ESI$^+$) m/z calc'd. for $C_{26}H_{42}N_3O_3^+$ (M+H)$^+$ 444.3221, found 444.3217.

tert-butyl (2-((7-decylbenzo[d]oxazol-2-yl)amino) ethyl)carbamate (12u)

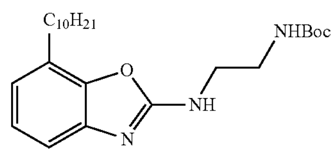

Synthesized according to General Procedure 6. White solid (27%, 22 mg). $^1$H NMR (500 MHz, Chloroform-d) δ 7.21-7.17 (m, 1H), 7.07 (t, J=7.7 Hz, 1H), 6.85-6.83 (m, 1H), 5.89 (s, 1H), 5.10 (s, 1H), 3.59 (s, 2H), 3.47-3.40 (m, 2H), 2.73 (t, J=7.7 Hz, 2H), 1.67 (p, J=7.6 Hz, 2H), 1.43 (s, 9H), 1.35-1.22 (m, 14H), 0.88 (t, J=6.9 Hz, 3H). HRMS (ESI$^+$) m/z calc'd. for $C_{24}H_{40}N_3O_3^+$ (M+H)$^+$ 418.3064, found 418.3064.

tert-butyl (3-((7-decylbenzo[d]oxazol-2-yl)amino) propyl)carbamate (12v)

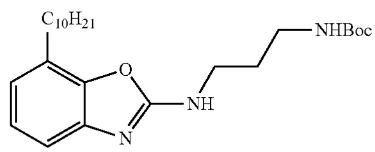

Synthesized according to General Procedure 6. White solid (27%, 23 mg). $^1$H NMR (500 MHz, Chloroform-d) δ 7.21 (dd, J=7.8, 1.2 Hz, 1H), 7.08 (t, J=7.7 Hz, 1H), 6.85 (dd, J=7.6, 1.2 Hz, 1H), 5.92 (s, 1H), 5.02 (t, J=6.5 Hz, 1H), 3.56 (q, J=6.0 Hz, 2H), 3.29 (q, J=6.3 Hz, 2H), 2.75 (t, 2H), 1.85-1.79 (m, 2H), 1.70 (p, J=7.6 Hz, 2H), 1.48 (s, 9H), 1.39-1.26 (m, 14H), 0.90 (t, J=6.9 Hz, 3H). HRMS (ESI$^+$) m/z calc'd. for $C_{25}H_{42}N_3O_3$ (M+H)$^+$ 432.3221, found 432.3218.

tert-butyl (2-((4-decylbenzo[d]oxazol-2-yl)amino) ethyl)carbamate (12w)

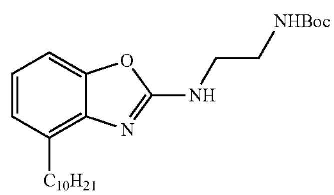

Synthesized according to General Procedure 6. Off-white solid (67%, 107 mg). $^1$H NMR (500 MHz, Chloroform-d) δ 7.09-7.06 (m, 1H), 7.00-6.93 (m, 2H), 5.50 (s, 1H), 5.23 (d, J=6.2 Hz, 1H), 3.60 (q, J=5.5 Hz, 2H), 3.43 (q, J=5.8 Hz, 2H), 2.86-2.78 (m, 2H), 1.70 (p, J=7.5 Hz, 2H), 1.42 (s, 9H), 1.37-1.23 (m, 14H), 0.88 (t, J=6.9 Hz, 3H). HRMS (ESI$^+$) m/z calc'd. for $C_{24}H_{40}N_3O_3^+$ (M+H)$^+$ 418.3064, found 418.3066.

tert-butyl (3-((4-decylbenzo[d]oxazol-2-yl)amino) propyl)carbamate (12x)

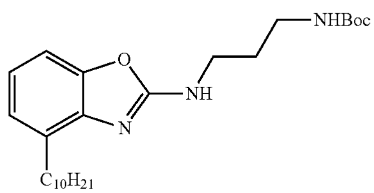

Synthesized according to General Procedure 6. White solid (68%, 115 mg). $^{1}$H NMR (500 MHz, Chloroform-d) δ 7.10-7.04 (m, 1H), 6.99-6.92 (m, 2H), 5.53 (s, 1H), 5.42 (s, 1H), 3.55 (q, J=6.2 Hz, 2H), 3.24 (q, J=6.3 Hz, 2H), 2.84 (t, J=7.7 Hz, 2H), 1.77 (p, J=6.2 Hz, 2H), 1.70 (p, J=7.5 Hz, 3H), 1.46 (s, 9H), 1.35-1.21 (m, 14H), 0.87 (t, J=6.9 Hz, 3H). HRMS (ESI$^{+}$) m/z calc'd. for $C_{25}H_{42}N_3O_3^+$ (M+H)$^+$ 432.3221, found 432.3220.

di-tert-butyl (((6-decylbenzo[d]oxazol-2-yl) azanediyl)bis(ethane-2,1-diyl))dicarbamate (12y)

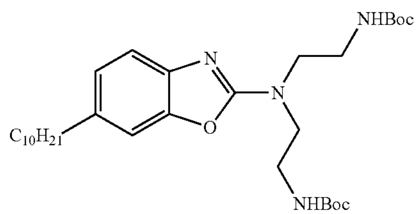

Synthesized according to General Procedure 6. Clear oil (77%, 155 mg). $^{1}$H NMR (400 MHz, $CDCl_3$) δ 7.19 (dd, J=8.1, 2.1 Hz, 1H), 7.03 (s, 1H), 6.94 (d, J=8.0 Hz, 1H), 5.25 (s, 2H), 3.63 (d, J=6.4 Hz, 4H), 3.40 (q, J=6.3 Hz, 4H), 2.61 (t, J=7.7 Hz, 2H), 1.58 (p, J=7.7 Hz, 2H), 1.33 (s, 16H), 1.26 (d, J=16.8 Hz, 13H), 0.85 (t, J=6.5 Hz, 3H). $^{13}$C NMR (101 MHz, $CDCl_3$) δ 162.6, 156.3, 149.0, 140.9, 136.0, 124.3, 115.6, 108.7, 93.7, 79.4, 49.6, 39.5, 36.4, 36.0, 32.2, 32.1, 32.0, 29.7, 29.7, 29.6, 29.4, 29.2, 28.4, 26.4, 22.8, 22.1, 20.7, 14.2. HRMS (ESI$^{+}$) m/z calc'd. for $C_{31}H_{53}N_4O_5$+ (M+H)+ 561.4010, found 561.4012.

tert-butyl (S)-(1-(6-decylbenzo[d]oxazol-2-yl)pyrrolidin-3-yl)carbamate (12z)

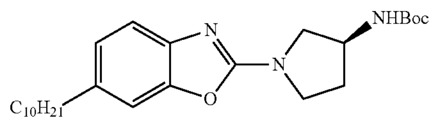

Synthesized according to General Procedure 6. White solid (76%, 118 mg). $^{1}$H NMR (400 MHz, $CDCl_3$) δ 7.25 (d, J=7.9 Hz, 1H), 7.08 (d, J=1.6 Hz, 1H), 6.97 (dd, J=8.0, 1.6 Hz, 1H), 4.71 (s, 1H), 4.36 (s, 1H), 3.87 (dd, J=10.9, 6.0 Hz, 1H), 3.76-3.68 (m, 2H), 3.51 (dd, J=11.1, 4.0 Hz, 1H), 2.66-2.60 (m, 2H), 2.33-2.24 (m, 1H), 2.05-1.94 (m, 1H), 1.66-1.55 (m, 2H), 1.45 (s, 11H), 1.33-1.22 (m, 17H), 0.87 (t, J=6.8 Hz, 3H). $^{13}$C NMR (101 MHz, $CDCl_3$) δ 160.7, 155.3, 149.4, 141.2, 136.0, 124.3, 115.8, 108.7, 53.4, 45.6, 36.1, 32.1, 32.0, 32.0, 29.7, 29.7, 29.5, 29.3, 28.5, 22.8, 14.2.

tert-butyl (R)-(1-(6-decylbenzo[d]oxazol-2-yl)pyrrolidin-3-yl)carbamate (12aa)

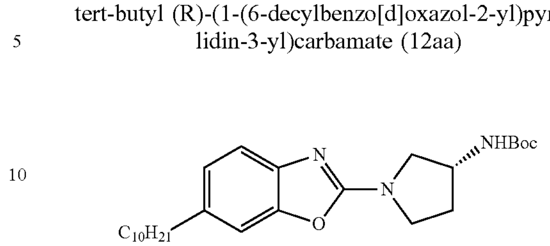

Synthesized according to General Procedure 6. White solid (88%, 127 mg). $^{1}$H NMR (400 MHz, $CDCl_3$) δ 7.25 (d, J=8.2 Hz, 1H), 7.08 (s, 1H), 6.97 (d, J=8.1 Hz, 1H), 4.72 (s, 1H), 4.36 (s, 1H), 3.87 (dd, J=10.9, 6.0 Hz, 1H), 3.76-3.67 (m, 2H), 3.55-3.48 (m, 1H), 2.63 (t, J=7.7 Hz, 2H), 2.28 (dtd, J=13.5, 7.7, 5.9 Hz, 1H), 2.04-1.94 (m, 1H), 1.65-1.55 (m, 2H), 1.45 (s, 10H), 1.33-1.22 (m, 21H), 0.87 (t, J=6.7 Hz, 4H). $^{13}$C NMR (101 MHz, $CDCl_3$) δ 160.6, 155.3, 149.3, 141.1, 136.0, 124.3, 115.8, 108.8, 53.4, 45.6, 36.1, 32.1, 32.0, 32.0, 29.8, 29.7, 29.5, 29.3, 28.5, 22.8, 14.2.

tert-butyl 4-((6-decylbenzo[d]oxazol-2-yl)amino) piperidine-1-carboxylate (12ab)

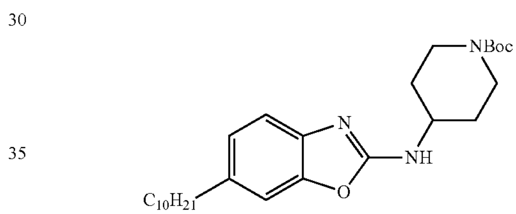

Synthesized according to General Procedure 6. Yellow oil (83%, 102 mg). $^{1}$H NMR (400 MHz, $CDCl_3$) δ 7.22 (d, J=7.9 Hz, 1H), 7.07-7.04 (m, 1H), 6.96 (dd, J=8.0, 1.6 Hz, 1H), 5.67 (s, 1H), 3.88 (s, 1H), 2.93 (t, J=12.4 Hz, 2H), 2.62 (t, J=7.7 Hz, 2H), 2.10 (dd, J=12.8, 3.8 Hz, 3H), 1.59 (h, J=6.5 Hz, 2H), 1.46 (s, 11H), 1.34-1.17 (m, 17H), 0.86 (t, J=6.7 Hz, 3H). $^{13}$C NMR (101 MHz, $CDCl_3$) δ 161.1, 154.8, 148.6, 140.6, 136.4, 136.4, 124.2, 115.7, 108.7, 79.8, 60.5, 50.5, 36.0, 32.5, 32.1, 32.0, 29.7, 29.7, 29.6, 29.4, 29.3, 28.5, 22.8, 14.2. HRMS (ESI$^{+}$) m/z calc'd. for $C_{27}H_{44}N_3O_3^+$ (M+H)+ 458.3383, found 458.3372.

$N^1$-(5-octylbenzo[d]oxazol-2-yl)ethane-1,2-diamine hydrochloride (13a)

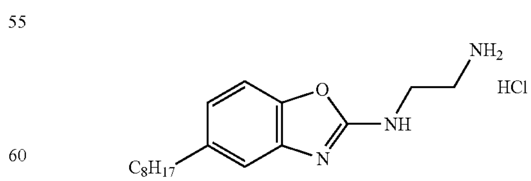

Synthesized according to General Procedure 3. White solid (90%, 42 mg). $^{1}$H NMR (500 MHz, Methanol-$d_4$) δ 7.46 (d, J=8.4 Hz, 1H), 7.28 (s, 1H), 7.19 (dd, J=8.4, 1.7 Hz, 1H), 3.87 (t, J=6.1 Hz, 2H), 3.33-3.30 (m, 2H), 2.72 (t, 2H), 1.67-1.60 (m, 2H), 1.36-1.22 (m, 10H), 0.90-0.85 (m, 3H).

$^{13}C$ NMR (126 MHz, Methanol-$d_4$) δ 160.9, 145.6, 143.3, 132.5, 125.9, 113.7, 111.5, 41.6, 39.6, 36.7, 33.0, 33.0, 30.5, 30.4, 30.2, 23.7, 14.4. HRMS (ESI$^+$) m/z calc'd. for $C_{17}H_{28}N_3O^+$ (M+H)$^+$ 290.2227, found 290.2229.

N$^1$-(5-nonylbenzo[d]oxazol-2-yl)ethane-1,2-diamine hydrochloride (13b)

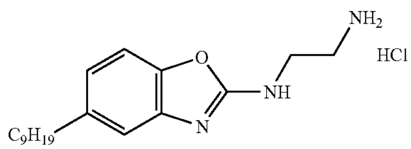

Synthesized according to General Procedure 3. White solid (60%, 48 mg). $^1H$ NMR (500 MHz, Methanol-$d_4$) δ 7.23 (d, J=8.2 Hz, 1H), 7.14 (s, 1H), 6.94 (dd, J=8.2, 1.7 Hz, 1H), 3.70 (t, J=5.9 Hz, 2H), 3.25 (t, J=5.9 Hz, 2H), 2.67-2.62 (m, 2H), 1.65-1.58 (m, 2H), 1.35-1.21 (m, 12H), 0.89 (t, J=6.9 Hz, 3H). $^{13}C$ NMR (126 MHz, Methanol-$d_4$) δ 163.80, 147.82, 141.8, 140.8, 123.2, 116.2, 109.7, 41.4, 40.3, 36.9, 33.2, 33.1, 30.7, 30.6, 30.4, 30.2, 23.7, 14.4. HRMS (ESI$^+$) m/z calc'd. for $C_{18}H_{30}N_3O^+$ (M+H)$^+$ 304.2383, found 304.2381.

N$^1$-(5-decylbenzo[d]oxazol-2-yl)ethane-1,2-diamine hydrochloride (13c)

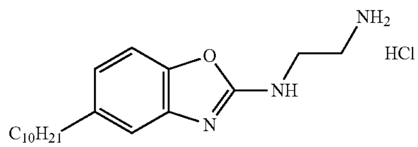

Synthesized according to General Procedure 3. White solid (74%, 35 mg). $^1H$ NMR (500 MHz, Methanol-$d_4$) δ 7.45 (dd, J=8.4, 3.7 Hz, 1H), 7.28 (d, J=1.7 Hz, 1H), 7.18 (dd, J=8.5, 1.7 Hz, 1H), 3.86 (t, J=6.1 Hz, 2H), 3.33-3.30 (m, 3H), 2.74-2.69 (m, 2H), 1.64 (p, J=7.5 Hz, 2H), 1.36-1.23 (m, 14H), 0.88 (t, J=6.9 Hz, 3H). $^{13}C$ NMR (101 MHz, Methanol-$d_4$) δ 160.6, 145.4, 143.4, 131.6, 126.0, 113.5, 111.6, 41.7, 39.5, 36.7, 33.0, 32.9, 30.7, 30.7, 30.6, 30.4, 30.2, 23.7, 14.4. HRMS (ESI$^+$) m/z calc'd. for $C_{19}H_{32}N_3O^+$ (M+H)$^+$ 318.2540, found 318.2550.

N$^1$-(5-undecylbenzo[d]oxazol-2-yl)ethane-1,2-diamine hydrochloride (13d)

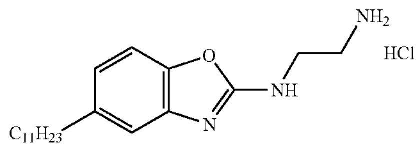

Synthesized according to General Procedure 3. White solid (85%, 42 mg). $^1H$ NMR (500 MHz, Methanol-$d_4$) δ 7.32 (d, J=8.3 Hz, 1H), 7.21 (d, J=1.6 Hz, 1H), 7.04 (dd, J=8.3, 1.7 Hz, 1H), 3.78 (t, J=6.0 Hz, 2H), 3.30 (t, J=6.0 Hz, 2H), 2.73-2.67 (m, 2H), 1.65 (p, J=7.7 Hz, 2H), 1.32 (d, J=25.4 Hz, 16H), 0.91 (t, J=6.9 Hz, 3H). $^{13}C$ NMR (101 MHz, Methanol-$d_4$) δ 161.4, 145.7, 140.1, 137.2, 122.6, 113.9, 108.9, 40.0, 38.7, 35.4, 31.7, 31.6, 29.3, 29.3, 29.3, 29.2, 29.0, 28.8, 22.3, 13.0. HRMS (ESI$^+$) m/z calc'd. for $C_{20}H_{34}N_3O^+$ (M+H)$^+$ 332.2696, found 332.2702.

N$^1$-(5-dodecylbenzo[d]oxazol-2-yl)ethane-1,2-diamine hydrochloride (13e)

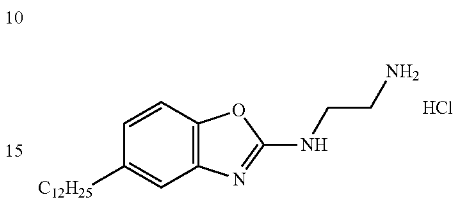

Synthesized according to General Procedure 3. White solid (95%, 43 mg). $^1H$ NMR (500 MHz, Methanol-$d_4$) δ 7.50 (d, J=8.4 Hz, 1H), 7.32 (s, 1H), 7.22 (dd, J=8.5, 1.7 Hz, 1H), 3.91 (t, J=6.1 Hz, 2H), 3.38-3.32 (m, 2H), 2.75 (t, J=7.6 Hz, 2H), 1.66 (q, J=7.3 Hz, 2H), 1.38-1.27 (m, 18H), 0.92 (t, J=6.7 Hz, 3H). $^{13}C$ NMR (126 MHz, Methanol-$d_4$) δ 159.4, 152.5, 144.2, 141.9, 124.5, 112.2, 110.1, 40.2, 38.2, 35.3, 31.7, 31.6, 29.4, 29.3, 29.3, 29.2, 29.1, 28.8, 22.3, 13.0. HRMS (ESI$^+$) m/z calc'd. for $C_{26}H_{44}N_3O_3^+$ (M+H)$^+$ 346.2853, found 346.2855.

N$^1$-(5-bromobenzo[d]oxazol-2-yl)propane-1,3-diamine hydrochloride (13f)

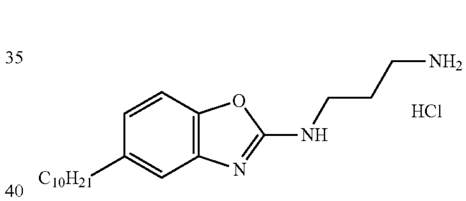

Synthesized according to General Procedure 3. Off-white solid (80%, 39 mg). $^1H$ NMR (500 MHz, Methanol-$d_4$) δ 7.45 (d, J=8.5 Hz, 1H), 7.27 (d, J=1.6 Hz, 1H), 7.18 (dd, J=8.5, 1.7 Hz, 1H), 3.66 (t, J=6.9 Hz, 2H), 3.10 (t, J=7.7 Hz, 2H), 2.75-2.68 (m, 2H), 2.11 (p, J=7.2 Hz, 2H), 1.63 (h, J=6.7, 6.1 Hz, 2H), 1.35-1.24 (m, 13H), 0.91-0.83 (m, 3H). $^{13}C$ NMR (126 MHz, Chloroform-d) δ 162.9, 147.9, 145.9, 134.0, 128.5, 115.8, 114.0, 44.0, 40.6, 39.3, 35.6, 35.5, 33.3, 33.2, 33.1, 33.0, 32.7, 30.3, 26.3, 17.0. HRMS (ESI+) m/z calc'd. for $C_{20}H_{34}N_3O^+$ (M+H)$^+$ 332.2696, found 332.2674.

N$^1$-(5-decylbenzo[d]oxazol-2-yl)butane-1,4-diamine carbamate hydrochloride (13g)

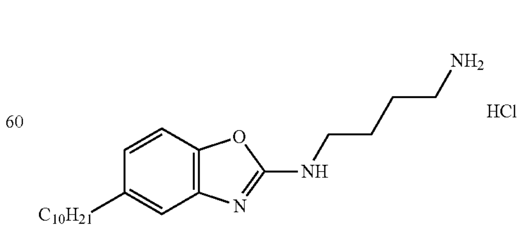

Synthesized according to General Procedure 3. White solid (77%, 89 mg). $^1H$ NMR (500 MHz, Methanol-$d_4$) δ

7.46-7.42 (m, 1H), 7.26 (s, 1H), 7.19 (dt, J=8.3, 1.6 Hz, 1H), 3.61-3.54 (m, 2H), 3.01 (t, J=7.0 Hz, 2H), 2.72 (t, J=7.7 Hz, 2H), 1.87-1.77 (m, 4H), 1.63 (q, J=7.8, 7.2 Hz, 2H), 1.36-1.24 (m, 14H), 0.89 (t, J=6.9 Hz, 3H). $^{13}$C NMR (126 MHz, Methanol-d$_4$) δ 160.1, 145.2, 143.3, 130.9, 126.0, 113.0, 111.6, 43.8, 40.2, 36.7, 33.1, 32.9, 30.7, 30.7, 30.6, 30.4, 30.2, 26.7, 25.7, 23.7, 14.4. HRMS (ESI$^+$) m/z calc'd. for $C_{21}H_{36}N_3O^+$ (M+H)$^+$ 346.2853, found 346.2862.

N$^1$-(5-decylbenzo[d]oxazol-2-yl)pentane-1,5-diamine hydrochloride (13h)

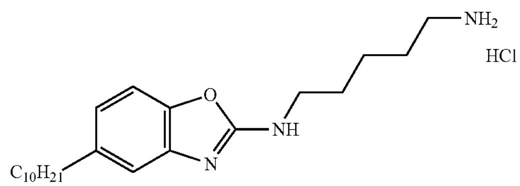

Synthesized according to General Procedure 3. Yellow solid (83%, 40 mg). $^1$H NMR (500 MHz, Methanol-d$_4$) δ 7.44 (d, J=8.4 Hz, 1H), 7.26 (d, J=1.8 Hz, 1H), 7.18 (dd, J=8.5, 1.7 Hz, 1H), 3.56 (t, J=7.2 Hz, 2H), 2.96 (t, J=7.7 Hz, 2H), 2.71 (t, J=7.6 Hz, 2H), 1.84-1.70 (m, 4H), 1.63 (p, J=7.4 Hz, 2H), 1.58-1.49 (m, 2H), 1.34-1.22 (m, 14H), 0.88 (t, J=6.9 Hz, 3H). $^{13}$C NMR (101 MHz, Methanol-d$_4$) δ 160.0, 145.2, 143.2, 131.0, 125.9, 113.0, 111.5, 44.2, 40.5, 36.7, 33.0, 32.9, 30.7, 30.7, 30.5, 30.4, 30.2, 29.1, 28.0, 24.5, 23.7, 14.4. HRMS (ESI+) m/z calc'd. for $C_{22}H_{31}N_3O^+$ (M+H)$^+$ 359.2937, found 359.2927.

N-(azetidin-3-yl)-5-decylbenzo[d]oxazol-2-amine 2,2,2-trifluoroacetate (13i)

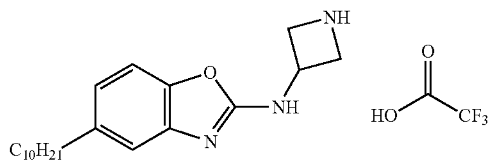

Synthesized according to General Procedure 3. White solid (30%, 31 mg). $^1$H NMR (400 MHz, Methanol-d$_4$) δ 7.23 (d, J=8.2 Hz, 1H), 7.16 (d, J=1.6 Hz, 1H), 6.94 (dd, J=8.2, 1.7 Hz, 1H), 4.83-4.72 (m, 1H), 4.47-4.28 (m, 4H), 2.72-2.62 (m, 2H), 1.64 (p, J=7.3 Hz, 2H), 1.36-1.27 (m, 14H), 0.94-0.87 (m, 2H). $^{13}$C NMR (101 MHz, Methanol-d$_4$) δ 160.9, 146.7, 141.8, 139.0, 121.7, 115.5, 108.1, 52.5, 44.5, 35.4, 31.7, 31.6, 29.3, 29.2, 29.1, 29.0, 28.7, 22.3, 13.0. HRMS (ESI+) m/z calc'd. for $C_{20}H_{32}N_3O^+$ (M+H)$^+$ 330.2545, found 330.2558.

(S)-5-decyl-N-(pyrrolidin-3-yl)benzo[d]oxazol-2-amine hydrochloride (13j)

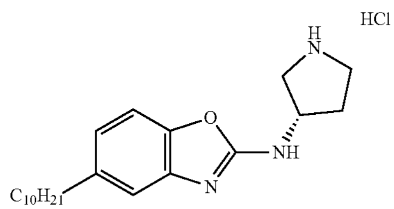

Synthesized according to General Procedure 3. Off-white solid (65%, 50 mg). $^1$H NMR (500 MHz, Methanol-d$_4$) δ 7.40 (d, J=8.3 Hz, 1H), 7.25 (d, J=1.6 Hz, 1H), 7.12 (dd, J=8.4, 1.7 Hz, 1H), 4.63 (tt, J=6.7, 4.4 Hz, 1H), 3.70 (dd, J=12.7, 6.6 Hz, 1H), 3.59-3.45 (m, 3H), 2.70 (t, J=7.6 Hz, 2H), 2.55-2.45 (m, 1H), 2.32-2.22 (m, 1H), 1.68-1.59 (m, 2H), 1.37-1.22 (m, 16H), 0.88 (t, J=7.0 Hz, 3H). $^{13}$C NMR (101 MHz, Methanol-d$_4$) δ 161.8, 147.0, 141.6, 138.4, 124.2, 115.4, 110.3, 53.5, 51.0, 45.6, 36.8, 33.0, 33.0, 31.3, 30.7, 30.7, 30.6, 30.4, 30.2, 23.7, 14.4. HRMS (ESI$^+$) m/z calc'd. for $C_{21}H_{34}N_3O^+$ (M+H)$^+$ 344.2696, found 344.2669.

(R)-5-decyl-N-(pyrrolidin-3-yl)benzo[d]oxazol-2-amine hydrochloride (13k)

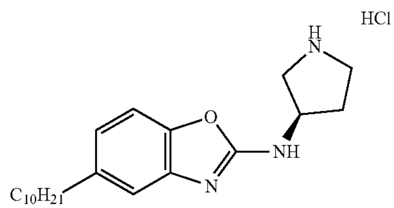

Synthesized according to General Procedure 3. Off-white solid (65%, 30 mg). $^1$H NMR (500 MHz, Methanol-d$_4$) δ 7.51 (d, J=8.5 Hz, 1H), 7.33 (s, 1H), 7.24 (dd, J=8.5, 1.7 Hz, 1H), 4.78-4.69 (m, 1H), 3.79 (dd, J=12.8, 6.8 Hz, 1H), 3.64-3.49 (m, 3H), 2.80-2.71 (m, 2H), 2.62-2.52 (m, 1H), 2.37-2.26 (m, 1H), 1.73-1.64 (m, 2H), 1.38-1.25 (m, 14H), 0.94-0.89 (m, 3H). $^{13}$C NMR (126 MHz, Methanol-d$_4$) δ 160.0, 145.5, 143.4, 131.7, 126.1, 113.5, 111.6, 53.9, 50.7, 45.6, 36.7, 33.1, 33.0, 31.3, 30.7, 30.7, 30.6, 30.5, 30.2, 23.7, 14.4. HRMS (ESI+) m/z calc'd. for $C_{21}H_{34}N_3O^+$ (M+H)$^+$ 344.2696, found 344.2697.

5-decyl-N-((3R,4S)-4-fluoropyrrolidin-3-yl)benzo[d]oxazol-2-amine hydrochloride (13l)

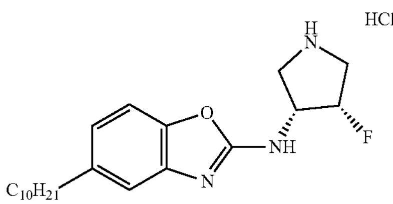

Synthesized according to General Procedure 3. Off-white solid (82%, 69 mg). $^1$H NMR (400 MHz, Methanol-$d_4$) δ 7.47 (dd, J=8.5, 1.3 Hz, 1H), 7.30 (d, J=1.8 Hz, 1H), 7.19 (dd, J=8.4, 1.8 Hz, 1H), 5.51 (dt, J=52.8, 3.0 Hz, 1H), 4.97-4.89 (m, 1H), 4.01-3.92 (m, 1H), 3.89-3.69 (m, 2H), 3.43 (t, J=11.3 Hz, 1H), 2.72 (t, J=7.7 Hz, 2H), 1.68-1.59 (m, 2H), 1.30 (d, J=22.6 Hz, 15H), 0.91-0.83 (m, 3H). $^{19}$F NMR (376 MHz, Methanol-$d_4$) δ −196.27-−196.71 (m). $^{13}$C NMR (126 MHz, Methanol-$d_4$) δ 160.6, 145.7, 143.2, 132.7, 126.0, 113.9, 111.5, 91.5 (d, J=183.1 Hz), 56.2-55.8 (m), 51.3-50.9 (m), 46.1-45.1 (m), 36.7, 33.0, 33.0, 30.7, 30.7, 30.6, 30.4, 30.2, 23.7, 14.4. HRMS (ESI+) m/z calc'd. for $C_{21}H_{33}FN_3O^+$ (M+H)$^+$ 362.2608, found 362.2631.

5-decyl-N-(piperidin-4-yl)benzo[d]oxazol-2-amine hydrochloride (13m)

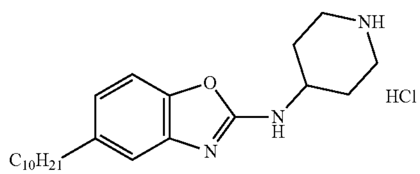

Synthesized according to General Procedure 3. White solid (80%, 45 mg). $^1$H NMR (400 MHz, Methanol-$d_4$) δ 7.38 (d, J=8.4 Hz, 1H), 7.24 (d, J=1.6 Hz, 1H), 7.11 (dd, J=8.4, 1.7 Hz, 1H), 4.08 (tt, J=10.6, 4.0 Hz, 1H), 3.52 (dt, J=12.9, 3.6 Hz, 2H), 3.27-3.15 (m, 2H), 2.74-2.67 (m, 2H), 2.39-2.30 (m, 2H), 2.02-1.88 (m, 2H), 1.64 (p, J=7.1 Hz, 2H), 1.31 (d, J=21.6 Hz, 14H), 0.91-0.86 (m, 3H). $^{13}$C NMR (126 MHz, Methanol-$d_4$) δ 160.7, 146.1, 142.4, 135.0, 125.0, 114.2, 110.9, 49.6, 43.8, 36.8, 33.1, 33.0, 30.7, 30.7, 30.6, 30.5, 30.2, 29.4, 23.7, 14.4. HRMS (ESI+) m/z calc'd. for $C_{21}H_{34}N_3O^+$ (M+H)$^+$ 344.2702, found 344.2679.

(S)-1-(5-decylbenzo[d]oxazol-2-yl)pyrrolidin-3-amine hydrochloride (13n)

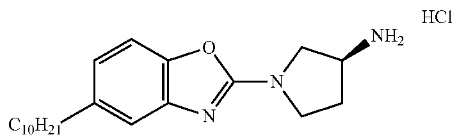

Synthesized according to General Procedure 3. Off-white solid (99%, 38 mg). $^1$H NMR (400 MHz, Methanol-$d_4$) δ 7.51 (d, J=8.5 Hz, 1H), 7.31 (d, J=1.6 Hz, 1H), 7.22 (dd, J=8.5, 1.7 Hz, 1H), 4.28-4.15 (m, 2H), 4.12-3.93 (m, 3H), 2.75 (t, 2H), 2.71-2.60 (m, 1H), 2.44-2.35 (m, 1H), 1.71-1.61 (m, 2H), 1.36-1.27 (m, 14H), 0.94-0.87 (m, 3H). $^{13}$C NMR (101 MHz, Methanol-$d_4$) δ 158.0, 146.1, 143.5, 132.4, 125.9, 113.5, 111.6, 52.7, 51.4, 47.8, 36.7, 33.0, 32.9, 30.7, 30.7, 30.6, 30.4, 30.4, 30.2, 23.7, 14.4. HRMS (ESI+) m/z calc'd. for $C_{21}H_{34}N_3O^+$ (M+H)$^+$ 344.2702, found 344.2679.

(R)-1-(5-decylbenzo[d]oxazol-2-yl)pyrrolidin-3-amine hydrochloride (13o)

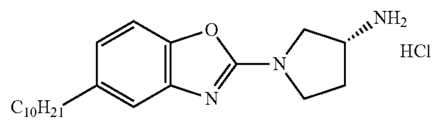

Synthesized according to General Procedure 3. Off-white solid (76%, 35 mg). $^1$H NMR (400 MHz, Methanol-$d_4$) δ 7.50 (dd, J=8.4, 0.5 Hz, 1H), 7.29 (dd, J=1.6, 0.6 Hz, 1H), 7.20 (dd, J=8.5, 1.7 Hz, 1H), 4.26-3.90 (m, 5H), 2.77-2.71 (m, 2H), 2.69-2.59 (m, 1H), 2.43-2.33 (m, 1H), 1.66 (t, J=7.6 Hz, 2H), 1.37-1.24 (m, 14H), 0.92-0.86 (m, 3H). $^{13}$C NMR (126 MHz, Methanol-$d_4$) δ 156.8, 144.8, 141.9, 131.4, 124.4, 112.2, 110.1, 51.3, 50.0, 46.3, 35.3, 31.7, 31.6, 29.3, 29.3, 29.2, 29.1, 28.9, 28.8, 22.3, 13.0. HRMS (ESI+) m/z calc'd. for $C_{21}H_{34}N_3O^+$ (M+H)$^+$ 344.2702, found 344.2679.

5-decyl-2-(piperazin-1-yl)benzo[d]oxazole hydrochloride (13p)

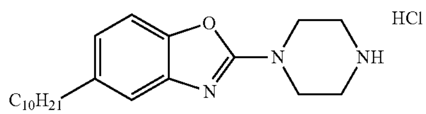

Synthesized according to General Procedure 3. White solid (81%, 55 mg). $^1$H NMR (500 MHz, Methanol-$d_4$) δ 7.30 (d, J=8.2 Hz, 1H), 7.18 (d, J=1.7 Hz, 1H), 6.99 (dd, J=8.2, 1.7 Hz, 1H), 4.01-3.94 (m, 4H), 3.42 (t, J=5.4 Hz, 5H), 2.66 (t, J=7.6 Hz, 2H), 1.62 (t, J=6.7 Hz, 2H), 1.34-1.22 (m, 14H), 0.88 (t, J=6.9 Hz, 3H). $^{13}$C NMR (126 MHz, Methanol-$d_4$) δ 162.3, 148.0, 141.4, 141.2, 123.7, 116.5, 110.1, 43.7, 36.8, 33.1, 33.0, 30.7, 30.7, 30.6, 30.4, 30.2, 23.7, 14.4.

$N^1$-(6-decylbenzo[d]oxazol-2-yl)ethane-1,2-diamine hydrochloride (13q)

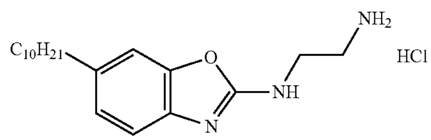

Synthesized according to General Procedure 3. White solid (88%, 51 mg). $^1$H NMR (500 MHz, Methanol-$d_4$) δ 7.42 (d, J=1.5 Hz, 1H), 7.35 (d, J=8.1 Hz, 1H), 7.25 (dd, J=8.1, 1.5 Hz, 1H), 3.87 (t, J=6.1 Hz, 2H), 3.32 (d, J=6.1 Hz, 2H), 2.72 (t, J=7.6 Hz, 2H), 1.63 (dd, J=10.4, 4.7 Hz, 2H), 1.35-1.23 (m, 14H), 0.88 (t, J=7.0 Hz, 3H). $^{13}$C NMR (126 MHz, Methanol-$d_4$) δ 160.7, 147.6, 141.8, 130.2, 127.6, 113.6, 111.6, 41.6, 39.6, 36.8, 33.1, 32.9, 30.7, 30.7, 30.6, 30.5, 30.2, 23.7, 14.4. HRMS (ESI$^+$) m/z calc'd. for $C_{19}H_{32}N_3O^+$ (M+H)$^+$ 318.2540, found 318.2540.

N[1]-(6-decylbenzo[d]oxazol-2-yl)propane-1,3-diamine hydrochloride (13r)

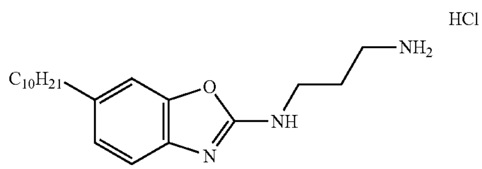

Synthesized according to General Procedure 3. White solid (94%, 40 mg). $^1$H NMR (500 MHz, Methanol-$d_4$) δ 7.42 (d, J=1.4 Hz, 1H), 7.35 (d, J=8.1 Hz, 2H), 7.26 (dd, J=8.1 Hz, 1H), 3.65 (t, J=6.9 Hz, 2H), 3.10 (dd, J=9.0, 6.6 Hz, 2H), 2.72 (t, J=7.7 Hz, 2H), 2.11 (p, J=7.1 Hz, 2H), 1.64 (h, J=7.1 Hz, 2H), 1.35-1.21 (m, 14H), 0.88 (t, J=6.9 Hz, 3H). $^{13}$C NMR (126 MHz, Methanol-$d_4$) δ 158.8, 145.9, 140.5, 127.7, 126.3, 111.7, 110.3, 40.0, 36.7, 35.3, 31.7, 31.5, 29.3, 29.3, 29.2, 29.0, 28.8, 26.4, 22.3, 13.0. HRMS (ESI$^+$) m/z calc'd. for $C_{20}H_{34}N_3O^+$ (M+H)$^+$ 332.2696, found 332.2694.

(S)-6-decyl-N-(pyrrolidin-3-yl)benzo[d]oxazol-2-amine hydrochloride (13s)

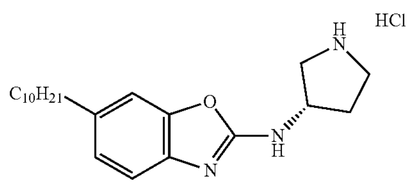

Synthesized according to General Procedure 3. Off-white solid (58%, 41 mg). $^1$H NMR (500 MHz, Methanol-$d_4$) δ 7.37-7.30 (m, 2H), 7.22-7.15 (m, 1H), 4.65-4.55 (m, 1H), 3.73-3.63 (m, 1H), 3.59-3.46 (m, 3H), 2.74-2.68 (m, 2H), 2.55-2.45 (m, 1H), 2.32-2.21 (m, 1H), 1.65 (q, J=7.0 Hz, 2H), 1.38-1.22 (m, 14H), 0.92-0.86 (m, 3H). $^{13}$C NMR (126 MHz, Methanol-$d_4$) δ 160.9, 148.4, 140.7, 133.6, 126.9, 114.6, 111.1, 53.6, 50.9, 45.6, 36.8, 33.1, 33.0, 31.3, 30.7, 30.7, 30.6, 30.4, 30.2, 23.7, 14.4. HRMS (ESI$^+$) m/z calc'd. for $C_{21}H_{34}N_3O^+$ (M+H)$^+$ 344.2696, found 344.2679.

(R)-6-decyl-N-(pyrrolidin-3-yl)benzo[d]oxazol-2-amine hydrochloride (13t)

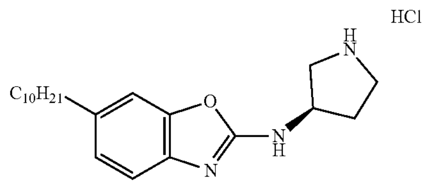

Synthesized according to General Procedure 3. White solid (93%, 50 mg). $^1$H NMR (500 MHz, Methanol-$d_4$) δ 7.38-7.30 (m, 2H), 7.24-7.17 (m, 1H), 4.65-4.57 (m, 1H), 3.72-3.64 (m, 1H), 3.58-3.43 (m, 3H), 2.74-2.68 (m, 2H), 2.56-2.44 (m, 1H), 2.33-2.21 (m, 1H), 1.69-1.58 (m, 2H), 1.37-1.21 (m, 14H), 0.89 (t, J=7.0 Hz, 3H). $^{13}$C NMR (126 MHz, Methanol-$d_4$) δ 160.7, 148.2, 141.0, 132.9, 127.1, 114.4, 111.2, 53.7, 50.9, 45.6, 36.8, 33.1, 33.0, 31.3, 30.7, 30.7, 30.6, 30.5, 30.2, 23.7, 14.4. HRMS (ESI$^+$) m/z calc'd. for $C_{21}H_{34}N_3O^+$ (M+H)$^+$ 344.2696, found 344.2679.

N[1]-(7-decylbenzo[d]oxazol-2-yl)ethane-1,2-diamine hydrochloride (13u)

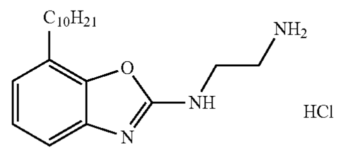

Synthesized according to General Procedure 3. White solid (59%, 11 mg). $^1$H NMR (500 MHz, Methanol-$d_4$) δ 7.37-7.25 (m, 2H), 7.19 (d, J=7.6 Hz, 1H), 3.89 (t, J=6.0 Hz, 2H), 3.27 (s, 2H), 2.84 (t, J=7.7 Hz, 2H), 1.71 (p, J=7.3 Hz, 2H), 1.40-1.18 (m, 14H), 0.86 (t, J=6.8 Hz, 3H). $^{13}$C NMR (126 MHz, Methanol-$d_4$) δ 160.3, 145.7, 131.1, 128.0, 127.6, 126.4, 111.3, 41.7, 39.4, 33.1, 30.8, 30.7, 30.5, 30.4, 30.4, 30.0, 23.7, 14.4. HRMS (ESI$^+$) m/z calc'd. for $C_{19}H_{32}N_3O^+$ (M+H)$^+$ 318.2540, found 318.2542.

N[1]-(7-decylbenzo[d]oxazol-2-yl)propane-1,3-diamine hydrochloride (13v)

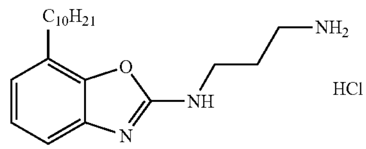

Synthesized according to General Procedure 3. White solid (87%, 17 mg). $^1$H NMR (500 MHz, Methanol-$d_4$) δ 7.32 (t, J=7.8 Hz, 1H), 7.26 (dd, J=7.9, 1.2 Hz, 1H), 7.18 (d, J=7.6 Hz, 1H), 3.64 (t, J=6.9 Hz, 2H), 3.14-3.06 (m, 2H), 2.88-2.80 (m, 2H), 2.16-2.06 (m, 2H), 1.73 (p, J=7.4 Hz, 2H), 1.42-1.21 (m, 14H), 0.89 (t, J=6.9 Hz, 3H). $^{13}$C NMR (126 MHz, Methanol-$d_4$) δ 158.5, 144.1, 129.3, 126.5, 126.1, 125.0, 109.6, 40.1, 36.7, 31.7, 29.4, 29.3, 29.3, 29.1, 29.0, 29.0, 28.6, 26.3, 22.3, 13.0. HRMS (ESI$^+$) m/z calc'd. for $C_{20}H_{34}N_3O^+$ (M+H)$^+$ 332.2696, found 332.2697.

N[1]-(4-decylbenzo[d]oxazol-2-yl)ethane-1,2-diamine hydrochloride (13w)

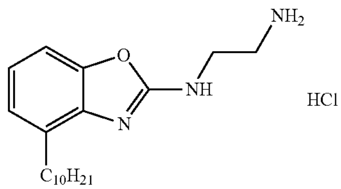

Synthesized according to General Procedure 3. White solid (67%, 104 mg). $^1$H NMR (500 MHz, Methanol-$d_4$) δ 7.41-7.36 (m, 1H), 7.29-7.21 (m, 2H), 3.93 (t, J=6.1 Hz, 2H), 3.33 (t, J=6.0 Hz, 2H), 2.86 (t, J=7.8 Hz, 2H), 1.73-1.64 (m, 2H), 1.45-1.17 (m, 13H), 0.87 (t, J=6.9 Hz, 3H). $^{13}C$ NMR (126 MHz, Methanol-$d_4$) δ 160.8, 147.2, 131.0, 130.3, 127.6, 125.6, 109.3, 41.7, 39.8, 33.1, 31.7, 31.4, 30.7, 30.7, 30.6, 30.5, 30.4, 23.7, 14.4. HRMS ($ESI^+$) m/z calc'd. for $C_{19}H_{32}N_3O^+$ $(M+H)^+$ 318.2540, found 318.2543.

$N^1$-(4-decylbenzo[d]oxazol-2-yl)propane-1,3-diamine hydrochloride (13x)

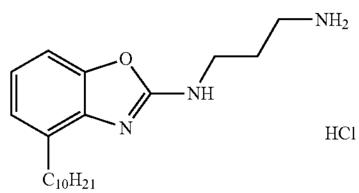

Synthesized according to General Procedure 3. White solid (68%, 115 mg). $^1H$ NMR (500 MHz, Methanol-$d_4$) δ 7.40-7.36 (m, 1H), 7.32-7.22 (m, 2H), 3.73 (t, J=7.0 Hz, 2H), 3.11 (t, J=9.0 Hz, 2H), 2.87 (t, J=7.8 Hz, 2H), 2.16-2.08 (m, 2H), 1.73-1.64 (m, 2H), 1.45-1.12 (m, 14H), 0.88 (t, J=7.0 Hz, 3H). $^{13}C$ NMR (126 MHz, Methanol-$d_4$) δ 158.8, 145.4, 128.5, 128.3, 126.3, 124.5, 107.9, 40.1, 36.7, 31.7, 30.2, 30.0, 29.3, 29.3, 29.2, 29.0, 29.0, 26.5, 22.3, 13.0. HRMS ($ESI^+$) m/z calc'd. for $C_{20}H_{34}N_3O^+$ $(M+H)^+$ 332.2696, found 332.2699.

N1-(2-aminoethyl)-N1-(6-decylbenzo[d]oxazol-2-yl)ethane-1,2-diamine dihydrochloride (13y)

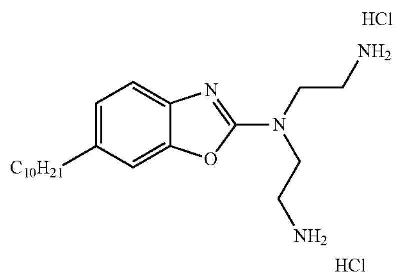

Synthesized according to General Procedure 3. White solid (48%, 57 mg). $^1H$ NMR (400 MHz, $CD_3OD$) δ 7.45 (dd, J=1.5, 0.6 Hz, 1H), 7.41 (dd, J=8.1, 0.5 Hz, 1H), 7.25 (dd, J=8.2, 1.5 Hz, 1H), 4.12 (t, J=6.4 Hz, 4H), 3.42 (t, J=6.4 Hz, 4H), 2.78-2.70 (m, 2H), 1.65 (p, J=7.2 Hz, 2H), 1.31 (d, J=21.3 Hz, 14H), 0.94-0.84 (m, 3H). $^{13}C$ NMR (101 MHz, $CD_3OD$) δ 161.0, 148.4, 141.3, 132.8, 127.5, 114.7, 111.5, 48.2, 38.1, 36.8, 33.0, 32.9, 30.7, 30.7, 30.6, 30.4, 30.2, 23.7, 14.4.

(S)-1-(6-decylbenzo[d]oxazol-2-yl)pyrrolidin-3-amine hydrochloride (13z)

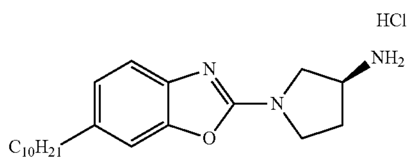

Synthesized according to General Procedure 3. White solid (82%, 77 mg). $^1H$ NMR (400 MHz, $CD_3OD$) δ 7.48 (d, J=1.4 Hz, 1H), 7.42-7.35 (m, 1H), 7.30 (dd, J=8.1, 1.4 Hz, 1H), 4.28-4.17 (m, 2H), 4.12-4.04 (m, 1H), 4.03-3.95 (m, 2H), 2.79-2.71 (m, 2H), 2.71-2.60 (m, 1H), 2.46-2.35 (m, 1H), 1.66 (p, J=7.0 Hz, 2H), 1.38-1.25 (m, 16H), 0.94-0.84 (m, 2H). $^{13}C$ NMR (101 MHz, $CD_3OD$) δ 157.6, 147.8, 142.0, 129.5, 127.8, 113.3, 111.9, 52.8, 51.4, 47.9, 36.7, 33.0, 32.9, 30.7, 30.7, 30.5, 30.4, 30.3, 30.2, 23.7, 14.4. HRMS ($ESI^+$) m/z calc'd. for $C_{21}H_{34}N_3O$+ (M+H)+ 344.2696, found 344.2697.

(R)-1-(6-decylbenzo[d]oxazol-2-yl)pyrrolidin-3-amine hydrochloride (13aa)

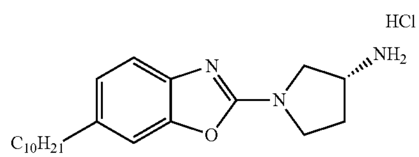

Synthesized according to General Procedure 3. White solid (74%, 75 mg). $^1H$ NMR (500 MHz, $CD_3OD$) δ 7.48 (d, J=1.4 Hz, 1H), 7.39 (d, J=8.1 Hz, 1H), 7.30 (dd, J=8.1, 1.4 Hz, 1H), 4.26-4.16 (m, 2H), 4.11-4.03 (m, 1H), 4.02-3.94 (m, 2H), 2.76-2.72 (m, 2H), 2.70-2.60 (m, 1H), 2.44-2.35 (m, 1H), 1.69-1.62 (m, 2H), 1.38-1.21 (m, 15H), 0.89 (d, J=7.1 Hz, 3H). $^{13}C$ NMR (126 MHz, $CD_3OD$) δ 157.7, 147.9, 141.9, 129.7, 127.8, 113.3, 111.8, 52.7, 51.4, 47.8, 36.8, 33.1, 33.0, 30.8, 30.7, 30.6, 30.5, 30.3, 30.2, 23.8, 14.5. HRMS ($ESI^+$) m/z calc'd. for $C_{26}H_{42}N_3O_3$+ (M+H)+ 344.2696, found 344.2694.

6-decyl-N-(piperidin-4-yl)benzo[d]oxazol-2-amine hydrochloride (13ab)

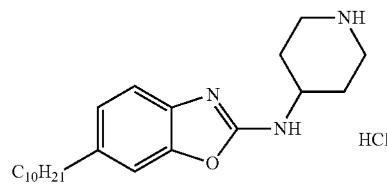

Synthesized according to General Procedure 3. White solid (87%, 76 mg). $^1H$ NMR (400 MHz, $CD_3OD$) δ 7.42 (d, J=1.4 Hz, 1H), 7.37 (d, J=8.1 Hz, 1H), 7.27 (dd, J=8.1, 1.4 Hz, 1H), 4.13 (ddt, J=10.2, 7.7, 3.7 Hz, 1H), 3.58-3.50 (m, 2H), 3.29-3.19 (m, 2H), 2.78-2.69 (m, 2H), 2.41-2.32 (m, 3H), 2.06-1.92 (m, 2H), 1.66 (q, J=7.1 Hz, 2H), 1.37-1.22 (m, 13H), 0.94-0.84 (m, 3H). $^{13}C$ NMR (101 MHz, $CD_3OD$) δ 159.6, 147.3, 141.8, 129.6, 127.6, 113.3, 111.6, 43.8, 36.7, 33.0, 32.9, 30.7, 30.7, 30.5, 30.4, 30.1, 29.3, 23.7, 14.4. HRMS ($ESI^+$) m/z calc'd. for $C_{22}H_{37}N_3O$+ (M+H)+ 358.2853, found 358.2855.

Scheme 4—Example Synthesis for $N^1$-(6-decyl-benzo[d]thiazol-2-yl)ethane-1,2-diamine hydrochloride

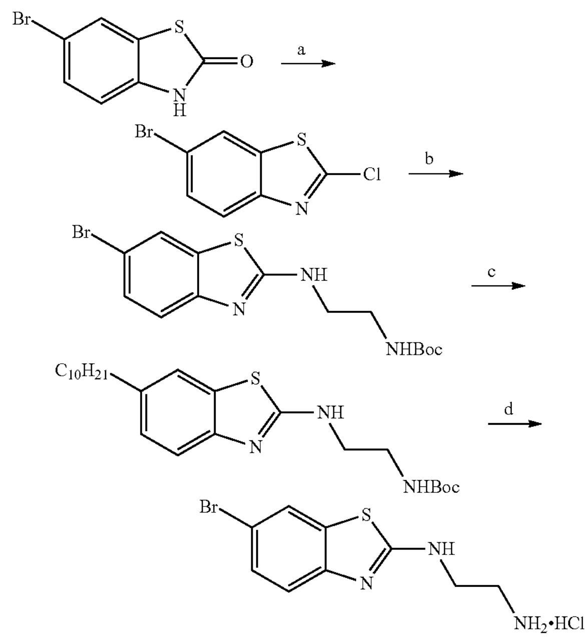

(a) $POCl_3$, neat, 98° C.; (b)N-boc-amine (1.2 equiv), $K_2CO_3$ (2.0 equiv), DMF, 120° C.; (c) (i) 9-BBN (2.2 equiv), 1-decene (2.0 equiv); (ii)aryl bromide (1.0 equiv), Pd(dppf)$Cl_2$*$CH_2Cl_2$ (0.15 equiv), 3M KOH (3.0 equiv), THF, 70° C.; (d) 4 M HCl/Dioxane, DCM, rt.

6-bromo-2-chlorobenzo[d]thiazole (14)

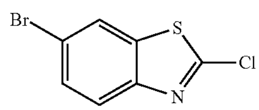 [SMILES: Clc1nc2ccc(Br)cc2s1]

Synthesized according to General Procedure 12. Crude mixture dried in vacuo and carried forward to the next reaction without purification.

tert-butyl (2-((6-bromobenzo[d]thiazol-2-yl)amino) ethyl)carbamate (15a)

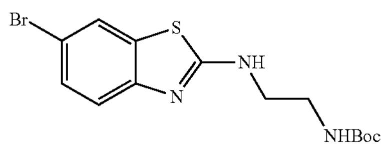 [SMILES: CC(C)(C)OC(=O)NCCNc1nc2ccc(Br)cc2s1]

Synthesized according to General Procedure 13. White solid (60%, 85 mg). $^1$H NMR (500 MHz, Chloroform-d) δ 7.66 (s, 1H), 7.40-7.35 (m, 2H), 6.16 (s, 1H), 5.02 (s, 1H), 3.59 (t, J=5.6 Hz, 2H), 3.43 (q, J=5.8 Hz, 2H), 1.43 (s, 9H). HRMS (ESI+) m/z calc'd. for $C_{14}H_{19}BrN_3O_2S^+$ $(M+H)^+$ 372.0376, found 372.0382.

tert-butyl (3-((6-bromobenzo[d]thiazol-2-yl)amino) propyl)carbamate (15b)

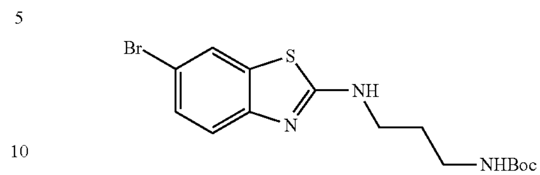

Synthesized according to General Procedure 13. White solid (96%, 37 mg). $^1$H NMR (500 MHz, Chloroform-d) δ 7.66 (s, 1H), 7.38-7.33 (m, 2H), 6.11 (s, 1H), 4.94 (t, J=6.5 Hz, 1H), 3.53 (t, J=6.3 Hz, 2H), 3.25 (q, J=6.3 Hz, 2H), 1.81 (p, J=6.2 Hz, 2H), 1.46 (s, 9H). HRMS (ESI+) m/z calc'd. for $C_{15}H_{21}BrN_3O_2S^+$ $(M+H)^+$ 386.0532, found 386.0540.

tert-butyl (2-((6-decylbenzo[d]thiazol-2-yl)amino) ethyl)carbamate (16a)

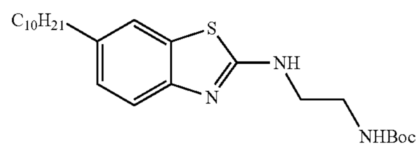

Synthesized according to General Procedure 6. Off-white solid (50%, 50 mg). $^1$H NMR (400 MHz, Chloroform-d) δ 7.43 (d, J=8.2 Hz, 1H), 7.37 (d, J=1.7 Hz, 1H), 7.09 (dd, J=8.3, 1.8 Hz, 1H), 5.82 (s, 1H), 5.04 (s, 1H), 3.65-3.53 (m, 2H), 3.43 (q, J=5.8 Hz, 2H), 2.66-2.59 (m, 2H), 1.61 (p, J=7.2 Hz, 2H), 1.43 (s, 9H), 1.34-1.20 (m, 14H), 0.91-0.85 (m, 3H). HRMS (ESI+) m/z calc'd. for $C_{24}H_{40}N_3O_2S^+$ $(M+H)^+$ 434.2836, found 434.2842.

tert-butyl (3-((6-decylbenzo[d]thiazol-2-yl)amino) propyl)carbamate (16b)

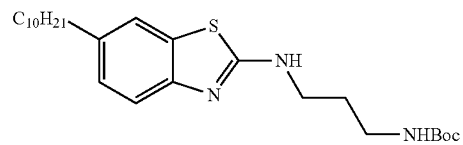

Synthesized according to General Procedure 6. White solid (68%, 76 mg). $^1$H NMR (500 MHz, Chloroform-d) δ 7.44 (d, J=8.1 Hz, 1H), 7.37 (d, J=1.7 Hz, 1H), 7.09 (d, J=8.3, 1.8 Hz, 1H), 5.96 (s, 1H), 5.03 (s, 1H), 3.51 (t, J=6.2 Hz, 2H), 3.25 (q, J=6.3 Hz, 2H), 2.62 (t, J=7.7 Hz, 2H), 1.81 (p, J=6.3 Hz, 2H), 1.65-1.56 (m, 2H), 1.46 (s, 9H), 1.33-1.19 (m, 14H), 0.88 (t, J=6.8 Hz, 3H). HRMS (ESI+) m/z calc'd. for $C_{25}H_{42}BrN_3O_2S^+$ $(M+H)^+$ 488.2992, found 488.2995.

N[1]-(6-decylbenzo[d]thiazol-2-yl)ethane-1,2-diamine hydrochloride (17a)

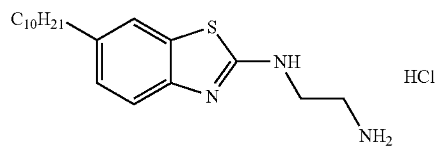

Synthesized according to General Procedure 3. White solid (96%, 37 mg). $^1H$ NMR (500 MHz, Methanol-$d_4$) δ 7.69 (d, J=1.7 Hz, 1H), 7.57-7.53 (m, 1H), 7.39 (dd, J=8.4, 1.7 Hz, 1H), 3.97-3.89 (m, 2H), 3.38 (t, J=6.1 Hz, 2H), 2.74 (t, J=7.7 Hz, 2H), 1.71-1.62 (m, 2H), 1.39-1.24 (m, 14H), 0.91 (t, J=6.9 Hz, 3H). $^{13}C$ NMR (126 MHz, Methanol-$d_4$) δ 170.3, 142.2, 138.2, 129.8, 125.1, 123.3, 115.5, 44.6, 39.0, 36.6, 33.1, 32.8, 30.7, 30.6, 30.4, 30.2, 23.7, 14.4. HRMS (ESI+) m/z calc'd. for $C_{19}H_{32}N_3S^+$ $(M+H)^+$ 334.2311, found 334.2319.

N[1]-(6-decylbenzo[d]thiazol-2-yl)propane-1,3-diamine hydrochloride (17b)

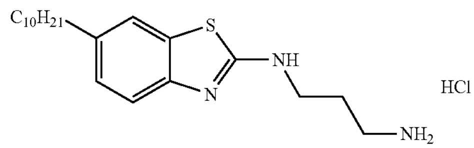

Synthesized according to General Procedure 3. White solid (91%, 54 mg). $^1H$ NMR (500 MHz, Methanol-$d_4$) δ 7.65 (s, 1H), 7.51 (d, J=8.4 Hz, 1H), 7.35 (dd, J=8.4, 1.6 Hz, 1H), 3.70 (t, J=7.0 Hz, 2H), 3.12 (t, J=9.1 Hz, 2H), 2.70 (t, J=8.7 Hz, 2H), 2.15 (p, J=7.2 Hz, 2H), 1.70-1.57 (m, 2H), 1.36-1.20 (m, 14H), 0.88 (t, J=6.9 Hz, 3H).

Scheme 5—Example Synthesis for N-(4-decylphenyl)piperazine-1-carboxamide hydrochloride

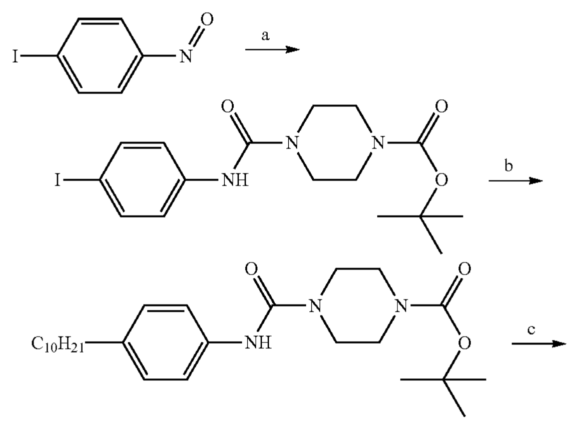

-continued

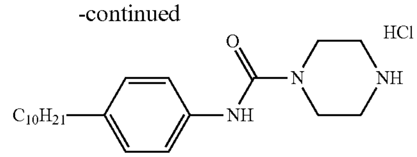

(a) mono-N-Boc-diamine (1.05 equiv), DCM, 0-25° C., 18 h; (b) (i) 9-BBN (1.5 equiv), 1-decene (1.1 equiv), THF, 70° C., 2 h, (ii) aryl iodide (1.0 equiv), $Pd(dppf)Cl_2*CH_2Cl_2$ (0.05 equiv), 3M KOH (3.0 equiv), THF, 70° C., 4 h; (c) 4M HCl/Dioxane (10 equiv), DCM, 25° C., 2 h.

tert-butyl (1-((4-iodophenyl)carbamoyl)piperidin-4-yl)carbamate (18a)

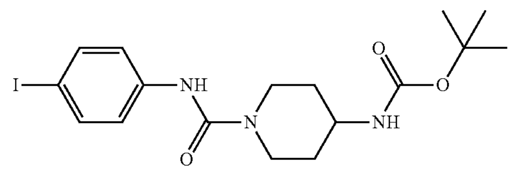 [SMILES: CC(C)(C)OC(=O)NC1CCN(C(=O)Nc2ccc(I)cc2)CC1]

Synthesized according to procedure 14. White solid (95%, 345 mg). $^1H$ NMR (400 MHz, Methanol-$d_4$) δ 7.57 (d, J=8.8 Hz, 2H), 7.19 (d, J=8.8 Hz, 2H), 4.13-4.04 (m, 2H), 3.62-3.52 (m, 1H), 3.08-2.95 (m, 2H), 1.99-1.85 (m, 2H), 1.54-1.36 (m, 11H).

tert-butyl (3-(3-(4-iodophenyl)ureido)propyl)carbamate (18b)

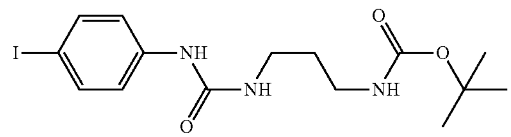 [SMILES: CC(C)(C)OC(=O)NCCCNC(=O)Nc1ccc(I)cc1]

Synthesized according to procedure 14. White solid (92%, 316 mg). $^1H$ NMR (400 MHz, Methanol-$d_4$) δ 7.55 (d, J=8.8 Hz, 2H), 7.19 (d, J=8.8 Hz, 2H), 3.23 (t, J=6.7 Hz, 2H), 3.16-3.08 (m, 2H), 1.66 (p, J=6.7 Hz, 2H), 1.45 (s, 9H). $^{13}C$ NMR (101 MHz, $cd_3od$) δ 158.62, 157.93, 141.04, 138.70, 121.94, 85.14, 79.94, 38.61, 38.00, 31.52, 28.77.

tert-butyl 4-(3-(4-iodophenyl)ureido)piperidine-1-carboxylate (18c)

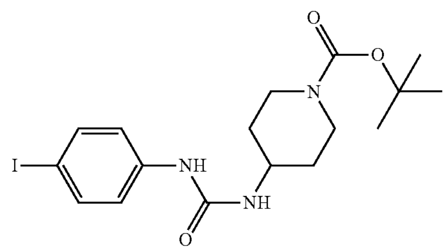 [SMILES: CC(C)(C)OC(=O)N1CCC(NC(=O)Nc2ccc(I)cc2)CC1]

Synthesized according to procedure 14. White solid (96%, 347 mg). $^1$H NMR (400 MHz, Chloroform-d) δ 7.67 (s, 1H), 7.49 (d, J=8.7 Hz, 2H), 7.04 (d, J=8.7 Hz, 2H), 5.60 (d, J=7.6 Hz, 1H), 3.99-3.85 (m, 2H), 3.82-3.69 (m, 1H), 2.89-2.77 (m, 2H), 1.90-1.78 (m, 2H), 1.45 (s, 9H), 1.22-1.07 (m, 2H). $^{13}$C NMR (101 MHz, $cdcl_3$) δ 155.22, 155.09, 139.03, 137.94, 121.28, 85.55, 80.34, 46.95, 42.42, 32.64, 28.60.

tert-butyl (1-((4-decylphenyl)carbamoyl)piperidin-4-yl)carbamate (19a)

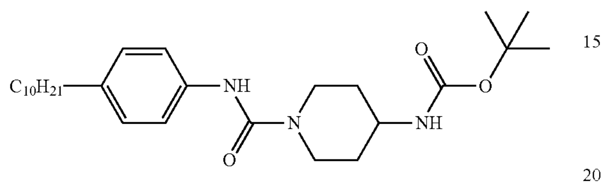

Synthesized according to procedure 7. White solid (53%, 190 mg). $^1$H NMR (400 MHz, Methanol-$d_4$) δ 7.23 (d, J=8.4 Hz, 2H), 7.09 (d, J=8.4 Hz, 2H), 4.14-4.06 (m, 2H), 3.62-3.53 (m, 1H), 3.06-2.96 (m, 2H), 2.57 (t, J=7.6 Hz, 2H), 1.96-1.87 (m, 2H), 1.60 (p, J=7.5 Hz, 2H), 1.47 (s, 9H), 1.38-1.25 (m, 16H), 0.91 (d, J=6.8 Hz, 3H).

tert-butyl (3-(3-(4-decylphenyl)ureido)propyl)carbamate (19b)

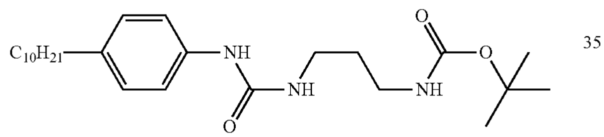

Synthesized according to procedure 7. White solid (68%, 224 mg). $^1$H NMR (400 MHz, Chloroform-d) δ 7.36 (s, 1H), 7.18 (d, J=8.0 Hz, 2H), 7.04 (d, J=8.2 Hz, 2H), 5.80 (t, J=7.6 Hz, 1H), 5.13 (t, J=6.2 Hz, 1H), 3.21 (q, J=6.2 Hz, 2H), 3.12 (q, J=6.4 Hz, 2H), 2.51 (t, J=7.8 Hz, 2H), 1.62-1.50 (m, 4H), 1.41 (s, 9H), 1.33-1.20 (m, 14H), 0.87 (t, J=6.8 Hz, 3H). $^{13}$C NMR (101 MHz, $cdcl_3$) δ 156.95, 156.69, 138.00, 136.57, 129.00, 120.69, 79.36, 37.44, 36.82, 35.40, 32.00, 31.69, 30.82, 29.74, 29.73, 29.63, 29.45, 29.44, 28.52, 22.78, 14.21.

tert-butyl 4-(3-(4-decylphenyl)ureido)piperidine-1-carboxylate (19c)

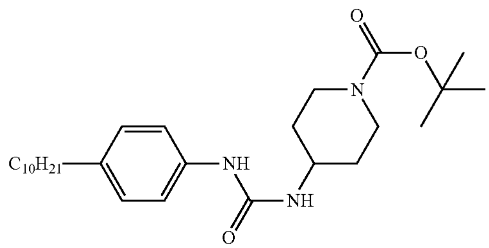

Synthesized according to procedure 7. White solid (82%, 295 mg). $^1$H NMR (400 MHz, Chloroform-d) δ 7.48 (s, 1H), 7.15 (d, J=8.1 Hz, 2H), 7.03 (d, J=8.2 Hz, 2H), 5.58 (d, J=7.8 Hz, 1H), 4.01-3.82 (m, 2H), 3.81-3.67 (m, 1H), 2.88-2.72 (m, 2H), 2.50 (t, J=7.8 Hz, 2H), 1.91-1.77 (m, 2H), 1.53 (p, J=7.6 Hz, 2H), 1.44 (s, 9H), 1.33-1.09 (m, 16H), 0.87 (t, J=6.7 Hz, 3H). $^{13}$C NMR (101 MHz, $cdcl_3$) δ 155.87, 154.91, 137.94, 136.53, 128.99, 120.26, 79.91, 46.95, 42.51, 35.37, 32.68, 31.98, 31.70, 29.71, 29.70, 29.60, 29.43, 29.41, 28.53, 22.76, 14.20.

4-amino-N-(4-decylphenyl)piperidine-1-carboxamide hydrochloride (20a)

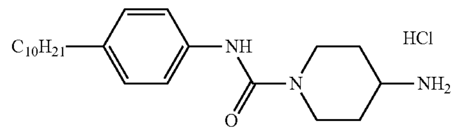

Synthesized according to procedure 3. White solid (86%, 140 mg). $^1$H NMR (400 MHz, Methanol-$d_4$) δ 7.23 (d, J=8.4 Hz, 2H), 7.09 (d, J=8.5 Hz, 2H), 4.29-4.22 (m, 2H), 3.41-3.34 (m, 1H), 3.02-2.92 (m, 2H), 2.56 (t, J=7.6 Hz, 2H), 2.09-2.00 (m, 2H), 1.64-1.51 (m, 4H), 1.36-1.23 (m, 14H), 0.90 (t, J=6.7 Hz, 3H). $^{13}$C NMR (101 MHz, $cd_3od$) δ 157.87, 139.18, 138.23, 129.53, 122.53, 49.78, 43.64, 36.26, 33.06, 32.82, 31.08, 30.74, 30.72, 30.61, 30.46, 30.26, 23.73, 14.44.

1-(3-aminopropyl)-3-(4-decylphenyl)urea hydrochloride (20b)

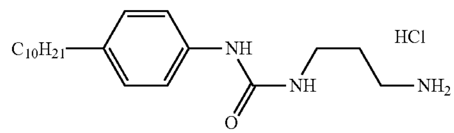

Synthesized according to procedure 3. White solid (84%, 160 mg). $^1$H NMR (400 MHz, Methanol-$d_4$) δ 7.28 (d, J=8.5 Hz, 2H), 7.09 (d, J=8.5 Hz, 2H), 3.37-3.30 (m, 2H), 3.02 (t, J=7.1 Hz, 2H), 2.56 (t, J=7.6 Hz, 2H), 1.88 (p, J=6.9 Hz, 2H), 1.60 (p, J=7.5 Hz, 2H), 1.38-1.25 (m, 14H), 0.92 (t, J=6.7 Hz, 3H). $^{13}$C NMR (101 MHz, $cd_3od$) δ 159.13, 138.52, 138.19, 129.69, 120.75, 38.14, 37.13, 36.22, 33.05, 32.81, 30.73, 30.71, 30.60, 30.44, 30.26, 29.54, 23.72, 14.44. HRMS: (ESI) [M+H]+ calc. for $C_{20}H_{36}N_3O$, 334.2853, observed, 334.2866.

1-(4-decylphenyl)-3-(piperidin-4-yl)urea hydrochloride (20c)

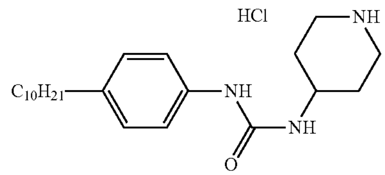

Synthesized according to procedure 3. White solid (82%, 71 mg). $^{1}$H NMR (400 MHz, Methanol-$d_4$) δ 7.25 (d, J=8.4 Hz, 2H), 7.06 (d, J=8.4 Hz, 2H), 3.90-3.80 (m, 1H), 3.45-3.36 (m, 2H), 3.16-3.06 (m, 2H), 2.53 (t, J=7.6 Hz, 2H), 2.19-2.09 (m, 2H), 1.81-1.68 (m, 2H), 1.57 (p, J=7.2 Hz, 2H), 1.37-1.22 (m, 14H), 0.89 (t, J=6.7 Hz, 3H). $^{13}$C NMR (101 MHz, $cd_3od$) δ 157.55, 138.34, 138.17, 129.66, 120.49, 45.62, 43.99, 36.22, 33.05, 32.80, 30.73, 30.71, 30.60, 30.44, 30.27, 30.14, 23.72, 14.46.

Scheme 6—Example Synthesis for 2-aminoethyl (4-decylphenyl)carbamate hydrochloride

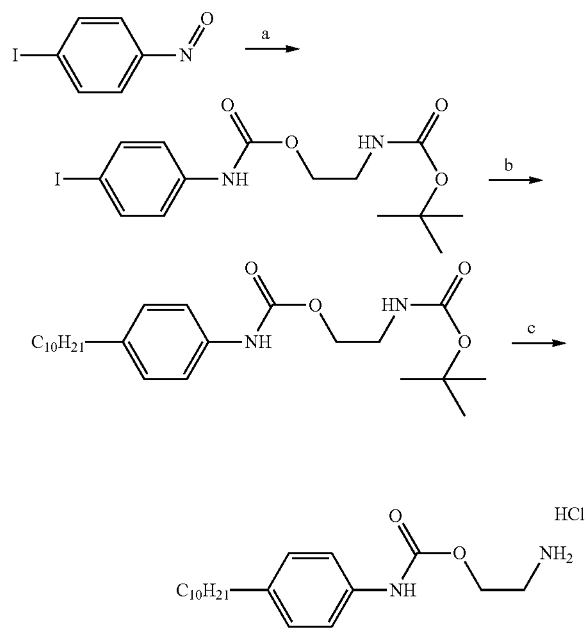

(a) N-Boc amino-alcohol (1.05 equiv), DCM, 0-25° C., 18 h; (b) (i) 9-BBN (1.5 equiv), 1-decene (1.1 equiv), THF, 70° C., 2 h, (ii) aryl iodide (1.0 equiv), Pd(dppf)$Cl_2$*$CH_2Cl_2$ (0.05 equiv), 3M KOH (3.0 equiv), THF, 70° C., 4 h; (c) 4M HCl/Dioxane (10 equiv), DCM, 25° C., 2 h.

2-((tert-butoxycarbonyl)amino)ethyl (4-iodophenyl) carbamate (21a)

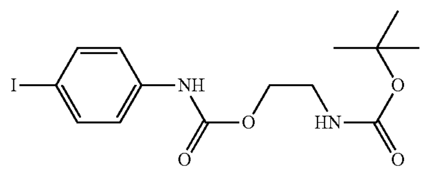 [SMILES: CC(C)(C)OC(=O)NCCOC(=O)Nc1ccc(I)cc1]

Synthesized according to procedure 15. White solid (67%, 223 mg). $^{1}$H NMR (400 MHz, Methanol-$d_4$) δ 7.60 (d, J=8.8 Hz, 2H), 7.27 (d, J=8.3 Hz, 2H), 4.17 (t, J=5.6 Hz, 2H), 3.36 (t, J=5.6 Hz, 2H), 1.45 (s, 9H). $^{13}$C NMR (101 MHz, $cd_3od$) δ 158.43, 155.43, 140.20, 138.80, 121.66, 86.15, 80.22, 64.81, 40.75, 28.73.

tert-butyl (S)-3-(((4-iodophenyl)carbamoyl)oxy) pyrrolidine-1-carboxylate (21b)

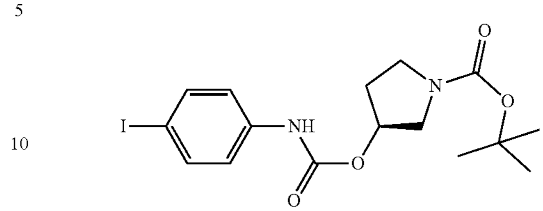

Synthesized according to procedure 15. White solid (47%, 247 mg). $^{1}$H NMR (400 MHz, Chloroform-d) δ 8.19 (d, J=130.7 Hz, 1H), 7.56 (d, J=8.4 Hz, 2H), 7.33-7.24 (m, 2H), 5.36-5.29 (m, 1H), 3.63-3.45 (m, 3H), 3.44-3.30 (m, 1H), 2.12-2.02 (m, 2H), 1.48 (d, J=7.9 Hz, 9H). $^{13}$C NMR (101 MHz, Chloroform-d) δ 154.58 (d, J=16.9 Hz), 152.91 (d, J=6.8 Hz), 138.25 (d, J=18.6 Hz), 137.74 (d, J=4.2 Hz), 120.58, 86.02 (d, J=13.7 Hz), 79.83, 74.11 (d, J=106.5 Hz), 51.76 (d, J=67.0 Hz), 43.85 (d, J=28.8 Hz), 31.44 (d, J=100.1 Hz), 28.52 (d, J=3.1 Hz).

tert-butyl (R)-3-(((4-iodophenyl)carbamoyl)oxy) pyrrolidine-1-carboxylate (21c)

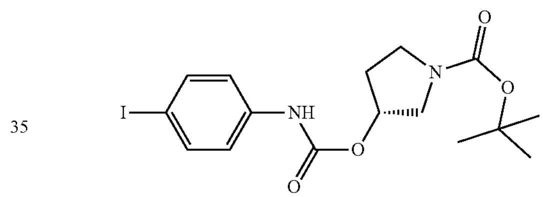

Synthesized according to procedure 15. White solid (40%, 210 mg). $^{1}$H NMR (400 MHz, Chloroform-d) δ 7.91-7.49 (m, 3H), 7.29-7.19 (m, 2H), 5.33-5.26 (m, 1H), 3.61-3.31 (m, 4H), 2.13-2.00 (m, 2H), 1.46 (d, J=5.9 Hz, 9H). $^{13}$C NMR (101 MHz, Chloroform-d) δ 154.66 (d, J=13.9 Hz), 152.88, 138.12 (d, J=16.9 Hz), 137.92 (d, J=3.2 Hz), 120.63, 86.20, 79.89, 74.35 (d, J=104.1 Hz), 51.87 (d, J=63.9 Hz), 43.94 (d, J=29.5 Hz), 31.52 (d, J=97.9 Hz), 28.61.

2-((tert-butoxycarbonyl)amino)ethyl (4-decylphenyl) carbamate (22a)

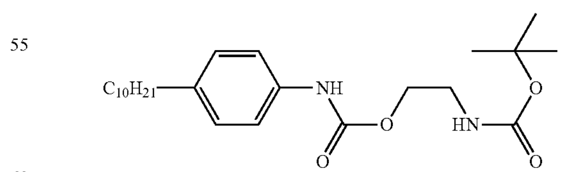

Synthesized according to procedure 7. Yellow solid (96%, 225 mg). $^{1}$H NMR (400 MHz, Chloroform-d) δ 7.28 (d, J=7.4 Hz, 2H), 7.09 (d, J=8.2 Hz, 2H), 7.04 (s, 1H), 5.04-4.93 (m, 1H), 4.20 (t, J=5.3 Hz, 2H), 3.41 (q, J=5.6 Hz, 2H), 2.53 (t, J=7.9 Hz, 2H), 1.55 (p, J=7.1 Hz, 2H), 1.44 (s, 9H), 1.32-1.21 (m, 14H), 0.87 (t, J=6.8 Hz, 3H).

tert-butyl (S)-3-(((4-decylphenyl)carbamoyl)oxy) pyrrolidine-1-carboxylate (22b)

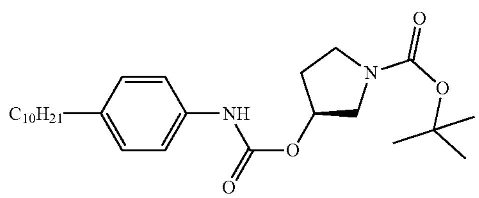

Synthesized according to procedure 7. White solid (79%, 201 mg). $^1$H NMR (400 MHz, Chloroform-d) δ 7.30 (d, J=7.9 Hz, 2H), 7.17-6.95 (m, 3H), 5.29 (s, 1H), 3.61-3.35 (m, 4H), 2.54 (t, J=7.7 Hz, 2H), 2.12-2.06 (m, 2H), 1.55 (p, J=7.3 Hz, 2H), 1.46 (s, 9H), 1.33-1.20 (m, 14H), 0.87 (t, J=6.7 Hz, 3H). $^{13}$C NMR (101 MHz, $cdcl_3$) δ 154.59, 153.13, 138.37, 135.44, 128.99, 118.84, 79.68, 74.24, 51.92, 43.95, 35.37, 32.00, 31.65, 31.01, 29.72, 29.70, 29.61, 29.43, 29.34, 28.60, 22.78, 14.21.

tert-butyl (R)-3-(((4-decylphenyl)carbamoyl)oxy) pyrrolidine-1-carboxylate (22c)

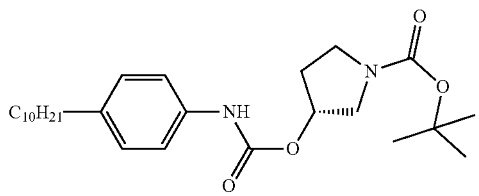

Synthesized according to procedure 7. White solid (92%, 200 mg). $^1$H NMR (400 MHz, Chloroform-d) δ 7.29 (d, J=7.9 Hz, 2H), 7.13-6.87 (m, 3H), 5.30 (s, 1H), 3.60-3.35 (m, 4H), 2.54 (t, J=7.7 Hz, 2H), 2.12-2.06 (m, 2H), 1.55 (p, J=7.3 Hz, 2H), 1.46 (s, 9H), 1.34-1.22 (m, 14H), 0.87 (t, J=6.8 Hz, 3H). $^{13}$C NMR (101 MHz, $cdcl_3$) δ 154.59, 153.09, 138.40, 135.48, 129.02, 118.84, 79.69, 74.21, 51.94, 43.98, 35.38, 32.01, 31.65, 31.01, 29.73, 29.71, 29.62, 29.44, 29.35, 28.61, 22.79, 14.22.

2-aminoethyl (4-decylphenyl)carbamate hydrochloride (23a)

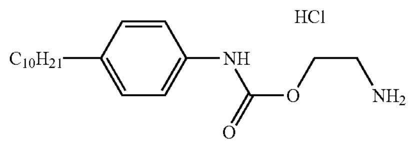

Synthesized according to procedure 3. White solid (78%, 33 mg). $^1$H NMR (400 MHz, Methanol-$d_4$) δ 7.36 (d, J=8.1 Hz, 2H), 7.11 (d, J=8.5 Hz, 2H), 4.42-4.34 (m, 2H), 3.30-3.26 (m, 2H), 2.57 (t, J=7.6 Hz, 2H), 1.59 (p, J=7.5 Hz, 2H), 1.41-1.23 (m, 14H), 0.91 (t, J=6.8 Hz, 3H). $^{13}$C NMR (101 MHz, $cd_3od$) δ 155.21, 139.20, 137.32, 129.75, 120.06, 62.19, 40.43, 36.23, 33.06, 32.77, 30.72, 30.70, 30.59, 30.45, 30.26, 23.73, 14.44.

(S)-pyrrolidin-3-yl (4-decylphenyl)carbamate hydrochloride (23b)

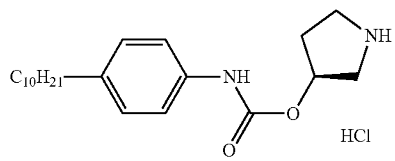

Synthesized according to procedure 3. White solid (81%, 52 mg). $^1$H NMR (400 MHz, Methanol-$d_4$) δ 7.35 (d, J=8.0 Hz, 2H), 7.11 (d, J=8.4 Hz, 2H), 5.43-5.38 (m, 1H), 3.59-3.41 (m, 4H), 2.62-2.52 (m, 2H), 2.35-2.26 (m, 2H), 1.59 (p, J=7.4 Hz, 2H), 1.37-1.23 (m, 14H), 0.96-0.87 (m, 3H). $^{13}$C NMR (101 MHz, $cd_3od$) δ 154.57, 139.15, 137.28, 129.75, 119.98, 74.45, 52.13, 45.35, 36.23, 33.05, 32.76, 31.92, 30.72, 30.70, 30.58, 30.44, 30.26, 23.72, 14.45.

(R)-pyrrolidin-3-yl (4-decylphenyl)carbamate hydrochloride (23c)

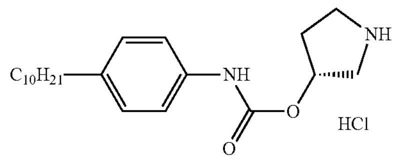

Synthesized according to procedure 3. White solid (82%, 53 mg). $^1$H NMR (400 MHz, Methanol-$d_4$) δ 7.34 (d, J=8.0 Hz, 1H), 7.11 (d, J=8.5 Hz, 1H), 5.43-5.38 (m, OH), 3.57-3.42 (m, 2H), 2.57 (t, J=7.6 Hz, 1H), 2.34-2.28 (m, 1H), 1.59 (p, J=7.4 Hz, 1H), 1.36-1.24 (m, 7H), 0.91 (t, J=6.8 Hz, 1H). $^{13}$C NMR (101 MHz, $cd_3od$) δ 154.59, 139.18, 137.28, 129.76, 119.99, 74.46, 52.16, 45.37, 36.23, 33.06, 32.76, 31.91, 30.72, 30.70, 30.58, 30.44, 30.26, 23.72, 14.44.

Scheme 7—Example Synthesis for (4-decylphenyl)(piperazin-1-yl)methanone hydrochloride

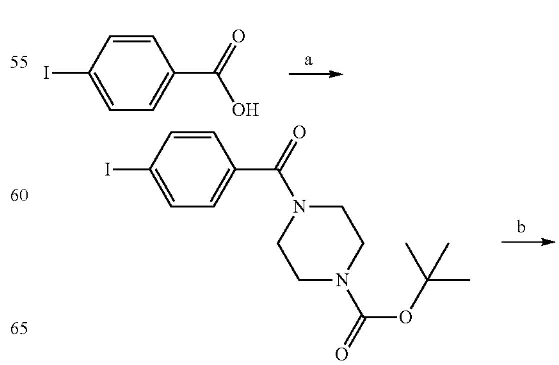

-continued

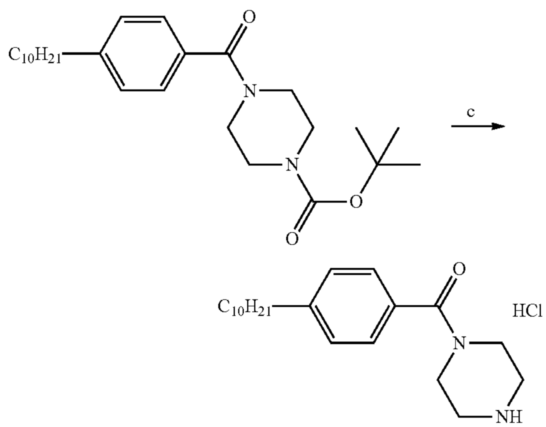

(a) 4-iodobenzoic acid (1.1 equiv), HCTU (1.1 equiv), DIEA (1.8 equiv), mono-N-Boc-protected diamine (1.0 equiv), DCM, rt, 18 h; (b) (i) 9-BBN (1.5 equiv), 1-decene (1.1 equiv), THF, 70° C., 2 h, (ii) aryl iodide (1.0 equiv), $Pd(dppf)Cl_2*CH_2Cl_2$ (0.05 equiv), 3M KOH (3.0 equiv), THF, 70° C., 4 h; (c) 4M HCl/Dioxane (10 equiv), DCM, rt, 2 h.

tert-butyl (S)-3-(4-iodobenzamido)pyrrolidine-1-carboxylate (24a)

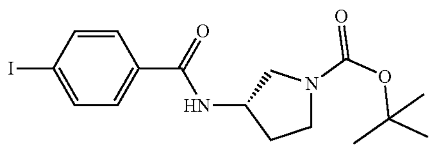 [SMILES: CC(C)(C)OC(=O)N1CC[C@H](NC(=O)c2ccc(I)cc2)C1]

Synthesized according to procedure 2. White solid (99%, 838 mg). $^1$H NMR (400 MHz, Chloroform-d) δ 7.60 (d, J=8.4 Hz, 2H), 7.41 (d, J=8.0 Hz, 2H), 7.35-7.15 (m, 1H), 4.54-4.41 (m, 1H), 3.65-3.46 (m, 1H), 3.42-3.12 (m, 3H), 2.15-2.01 (m, 1H), 1.94-1.77 (m, 1H), 1.35 (s, 9H).

tert-butyl (R)-3-(4-iodobenzamido)pyrrolidine-1-carboxylate (24b)

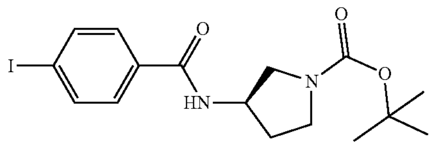 [SMILES: CC(C)(C)OC(=O)N1CC[C@@H](NC(=O)c2ccc(I)cc2)C1]

Synthesized according to procedure 2. Clear oil (95%, 480 mg). $^1$H NMR (400 MHz, Chloroform-d) δ 7.68 (d, J=8.1 Hz, 2H), 7.46 (d, J=8.0 Hz, 2H), 7.16-6.74 (m, 1H), 4.61-4.48 (m, 1H), 3.72-3.52 (m, 1H), 3.50-3.06 (m, 3H), 2.22-2.08 (m, 1H), 2.00-1.82 (m, 1H), 1.41 (s, 9H). $^{13}$C NMR (101 MHz, cdcl$_3$) δ 166.92, 154.54, 137.64, 133.58, 128.82, 98.59, 79.70, 51.00, 49.66, 44.07, 31.21, 28.54.

tert-butyl 4-(4-iodobenzoyl)piperazine-1-carboxylate (24c)

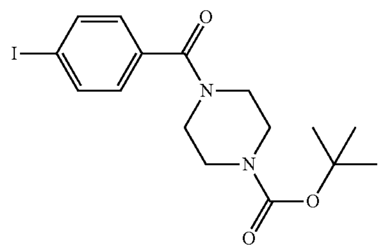 [SMILES: CC(C)(C)OC(=O)N1CCN(C(=O)c2ccc(I)cc2)CC1]

Synthesized according to procedure 2. White solid (93%, 780 mg). $^1$H NMR (400 MHz, Methanol-d$_4$) δ 7.84 (d, J=8.4 Hz, 2H), 7.21 (d, J=8.4 Hz, 2H), 3.79-3.35 (m, 8H), 1.47 (s, 9H). $^{13}$C NMR (101 MHz, cd$_3$od) δ 171.74, 156.17, 139.05, 136.03, 129.96, 97.06, 81.67, 44.50, 43.12, 28.60. $^{13}$C NMR (101 MHz, cd$_3$od) δ 171.74, 156.17, 139.05, 136.03, 129.96, 97.06, 81.67, 44.50, 43.12, 28.60.

tert-butyl (3-(4-decylbenzamido)propyl)carbamate (24d)

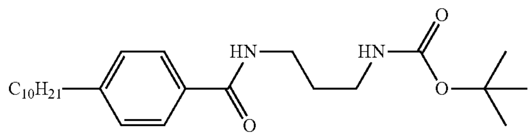

Synthesized according to General Procedure 11. Tan solid (82%, 260 mg). $^1$H NMR (400 MHz, $CDCl_3$) δ 7.75 (d, J=7.8 Hz, 2H), 7.22 (d, J=8.2 Hz, 2H), 7.17 (s, 1H), 5.01 (d, J=7.2 Hz, 1H), 3.49 (q, J=6.2 Hz, 2H), 3.23 (q, J=6.3 Hz, 2H), 2.63 (d, J=7.7 Hz, 2H), 1.74-1.65 (m, 2H), 1.60 (p, J=7.4 Hz, 2H), 1.44 (s, 9H), 1.35-1.20 (m, 14H), 0.86 (t, J=7.0 Hz, 3H). $^{13}$C NMR (101 MHz, $CDCl_3$) δ 167.7, 157.0, 146.8, 132.0, 128.7, 127.1, 79.6, 37.1, 36.1, 36.0, 32.0, 31.4, 30.4, 29.7, 29.7, 29.6, 29.5, 29.4, 28.5, 22.8, 14.3. HRMS: (ESI) [M+H]+ calc. for $C_{25}H_{43}N_2O_3$, 419.3268, observed, 419.3258.

tert-butyl (2-(4-decylbenzamido)ethyl)carbamate (24e)

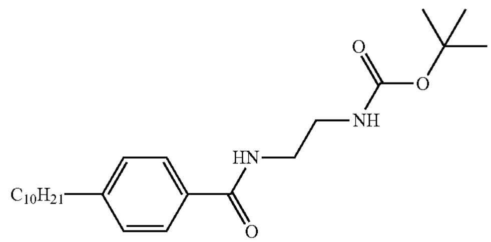

Synthesized according to General Procedure 11. Tan solid (73%, 225 mg). $^1$H NMR (400 MHz, $CDCl_3$) δ 7.72 (d, J=8.3 Hz, 2H), 7.21 (d, J=8.3 Hz, 2H), 7.10 (s, 1H), 5.04 (t, J=5.3 Hz, 1H), 3.59-3.50 (m, 2H), 3.44-3.35 (m, 2H), 2.62 (t, J=7.7 Hz, 2H), 1.60 (p, J=7.2 Hz, 2H), 1.42 (s, 9H), 1.34-1.19 (m, 14H), 0.87 (d, J=6.8 Hz, 3H). $^{13}$C NMR (101 MHz, $CDCl_3$) δ 168.0, 157.5, 146.9, 131.6, 128.6, 127.1, 80.0, 42.0, 40.2, 36.0, 32.0, 31.4, 29.7, 29.7, 29.6, 29.5, 29.4, 28.5, 22.8, 14.3. HRMS: (ESI) [M+H]+ calc. for $C_{24}H_{41}N_2O_3$, 405.3112, observed, 405.3108.

tert-butyl (S)-3-(4-decylbenzamido)pyrrolidine-1-carboxylate (25a)

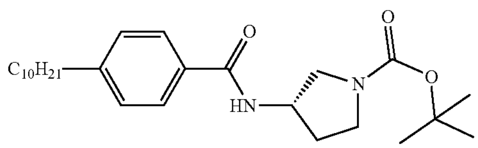

Synthesized according to procedure 7. White solid (80%, 691 mg). $^1$H NMR (400 MHz, Chloroform-d) δ 7.64 (d, J=8.0 Hz, 2H), 7.13 (d, J=8.0 Hz, 2H), 6.77-6.67 (m, 1H), 4.56 (h, J=6.1 Hz, 1H), 3.69-3.55 (m, 1H), 3.49-3.15 (m, 3H), 2.56 (t, J=7.7 Hz, 2H), 2.18-2.06 (m, 1H), 1.98-1.79 (m, 1H), 1.54 (p, J=7.1 Hz, 2H), 1.39 (s, 9H), 1.29-1.15 (m, 14H), 0.82 (t, J=6.7 Hz, 3H). $^{13}$C NMR (101 MHz, $cdcl_3$) δ 167.50, 154.46, 146.89, 131.46, 128.42, 127.05, 79.45, 51.02, 49.64, 43.81, 35.75, 31.82, 31.16, 31.10, 29.53, 29.51, 29.39, 29.25, 29.16, 28.42, 22.61, 14.05.

tert-butyl (R)-3-(4-decylbenzamido)pyrrolidine-1-carboxylate (25b)

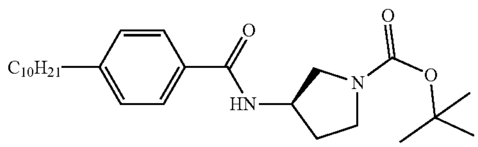

Synthesized according to procedure 7. White solid (98%, 490 mg). $^1$H NMR (400 MHz, Chloroform-d) δ 7.65 (d, J=8.1 Hz, 2H), 7.16 (d, J=8.0 Hz, 2H), 6.67 (d, J=7.0 Hz, 1H), 4.58 (h, J=6.0 Hz, 1H), 3.72-3.59 (m, 1H), 3.51-3.16 (m, 3H), 2.58 (t, J=7.7 Hz, 2H), 2.27-2.09 (m, 1H), 1.96-1.85 (m, 1H), 1.57 (p, J=7.8, 7.3 Hz, 2H), 1.41 (s, 9H), 1.29-1.12 (m, 14H), 0.84 (t, J=6.7 Hz, 3H). $^{13}$C NMR (101 MHz, $cdcl_3$) δ 167.57, 154.56, 147.01, 131.55, 128.53, 127.12, 79.56, 51.21, 49.39, 43.96, 35.84, 31.91, 31.63, 31.25, 29.62, 29.60, 29.49, 29.34, 29.25, 28.51, 22.70, 14.14.

tert-butyl 4-(4-decylbenzoyl)piperazine-1-carboxylate (25c)

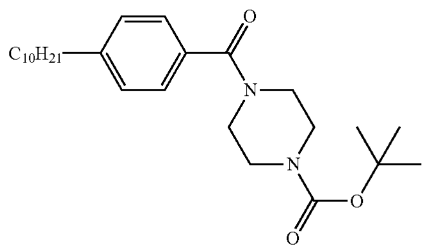

Synthesized according to procedure 7. White solid (92%, 740 mg). $^1$H NMR (400 MHz, Chloroform-d) δ 7.30 (d, J=7.8 Hz, 2H), 7.20 (d, J=7.8 Hz, 2H), 3.81-3.29 (m, 8H), 2.61 (t, J=7.7 Hz, 2H), 1.60 (p, J=7.1 Hz, 2H), 1.46 (s, 9H), 1.35-1.20 (m, 14H), 0.87 (t, J=6.7 Hz, 3H). $^{13}$C NMR (101 MHz, $cdcl_3$) δ 170.97, 154.70, 145.28, 132.75, 128.66, 127.28, 80.42, 43.73, 42.28, 35.94, 32.01, 31.40, 29.73, 29.69, 29.59, 29.44, 29.37, 28.49, 22.80, 14.24.

(S)-4-decyl-N-(pyrrolidin-3-yl)benzamide hydrochloride (26a)

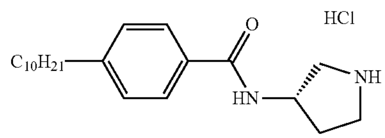

Synthesized according to procedure 3. White solid (77%, 99 mg). $^1$H NMR (400 MHz, Methanol-$d_4$) δ 7.77 (d, J=1.9 Hz, 2H), 7.26 (d, J=8.2 Hz, 2H), 4.65-4.54 (m, 1H), 3.62-3.50 (m, 2H), 3.41-3.33 (m, 2H), 2.64 (t, J=7.6 Hz, 2H), 2.44-2.32 (m, 1H), 2.22-2.13 (m, 1H), 1.61 (p, J=7.4 Hz, 2H), 1.36-1.18 (m, 14H), 0.87 (t, J=6.8 Hz, 3H). $^{13}$C NMR (101 MHz, $cd_3od$) δ 170.48, 148.70, 132.27, 129.60, 128.59, 51.16, 50.84, 45.84, 36.73, 33.04, 32.38, 30.93, 30.69, 30.68, 30.54, 30.43, 30.26, 23.71, 14.44. HRMS: (ESI) [M+H]+ calc. for $C_{21}H_{35}N_2O$, 331.2744, observed, 331.2731.

(R)-4-decyl-N-(pyrrolidin-3-yl)benzamide hydrochloride (26b)

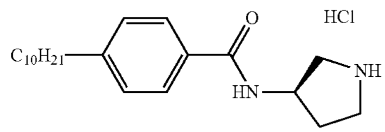

Synthesized according to procedure 3. White solid (79%, 101 mg). $^1$H NMR (400 MHz, Methanol-$d_4$) δ 7.80 (d, J=8.3 Hz, 2H), 7.28 (d, J=8.1 Hz, 2H), 4.69-4.59 (m, 1H), 3.64-3.53 (m, 2H), 3.44-3.35 (m, 2H), 2.66 (t, J=7.7 Hz, 2H), 2.46-2.35 (m, 1H), 2.27-2.15 (m, 1H), 1.63 (p, J=7.0 Hz, 2H), 1.36-1.23 (m, 14H), 0.89 (t, J=6.8 Hz, 3H). $^{13}$C NMR (101 MHz, $cd_3od$) δ 170.44, 148.68, 132.26, 129.59, 128.59, 51.14, 50.83, 45.83, 36.73, 33.04, 32.38, 30.94, 30.68, 30.67, 30.54, 30.43, 30.26, 23.71, 14.44. HRMS: (ESI) [M+H]+ calc. for $C_{21}H_{35}N_2O$, 331.2744, observed, 331.2731.

(4-decylphenyl)(piperazin-1-yl)methanone hydrochloride (26c)

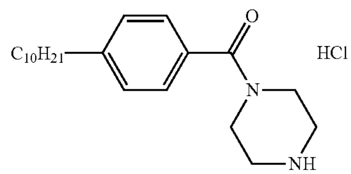

Synthesized according to procedure 3. White solid (74%, 95 mg). $^1$H NMR (400 MHz, Methanol-d4) δ 7.42 (d, J=8.1 Hz, 2H), 7.33 (d, J=7.9 Hz, 2H), 4.00-3.80 (m, 4H), 3.36-3.26 (m, 4H), 2.68 (t, J=7.7 Hz, 2H), 1.65 (p, J=7.1 Hz, 2H), 1.39-1.25 (m, 14H), 0.91 (t, J=6.7 Hz, 3H). $^{13}$C NMR (101 MHz, cd$_3$od) δ 172.92, 147.31, 132.74, 129.87, 128.46, 44.42, 36.75, 33.06, 32.51, 30.71, 30.71, 30.58, 30.45, 30.31, 23.73, 14.44. HRMS: (ESI) [M+H]+ calc. for $C_{21}H_{35}N_2O$, 331.2744, observed, 331.2731.

N-(3-aminopropyl)-4-decylbenzamide hydrochloride (26d)

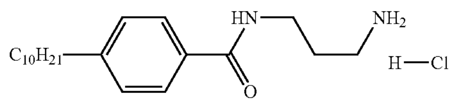

Synthesized according to General Procedure 3. White solid (77%, 164 mg). $^1$H NMR (400 MHz, $CD_3OD$) δ 7.77 (d, J=8.5 Hz, 2H), 7.29 (d, J=8.6 Hz, 2H), 3.50 (t, J=6.5 Hz, 2H), 2.99 (t, J=7.3 Hz, 2H), 2.67 (t, J=7.7 Hz (2, H), 1.96 (p, J=7.0 Hz, 2H), 1.63 (p, J=6.3 Hz, 2H), 1.38-1.21 (m, 14H), 0.89 (t, J=6.8 Hz, 3H). $^{13}$C NMR (101 MHz, $CD_3OD$) δ 170.9, 148.6, 132.4, 129.7, 128.4, 38.3, 37.3, 36.7, 33.1, 32.4, 30.7, 30.6, 30.5, 30.3, 29.0, 23.7, 14.5. HRMS: (ESI) [M+H]+ calc. for $C_{20}H_{35}N_2O$, 319.2744, observed, 319.2736.

N-(2-aminoethyl)-4-decylbenzamide hydrochloride (26e)

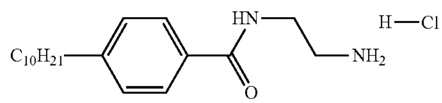

Synthesized according to General Procedure 3. White solid (66%, 120 mg). $^1$H NMR (400 MHz, $CD_3OD$) δ 7.80 (d, J=8.3 Hz, 2H), 7.30 (d, J=8.3 Hz, 2H), 3.66 (t, J=5.9 Hz, 2H), 3.17 (t, J=5.9 Hz, 2H), 2.67 (t, J=7.6 Hz, 2H), 1.63 (p, J=6.7 Hz, 2H), 1.40-1.20 (m, 14H), 0.89 (t, J=6.8 Hz, 3H). $^{13}$C NMR (101 MHz, $CD_3OD$) δ 171.2, 148.7, 132.2, 129.6, 128.6, 41.1, 38.7, 36.7, 33.1, 32.4, 30.7, 30.7, 30.6, 30.5, 30.3, 23.7, 14.5. HRMS: (ESI) [M+H]+ calc. for $C_{19}H_{33}N_2O$, 305.2587, observed, 305.2584.

Scheme 6—Example Synthesis for 3-(6-decyl-1H-benzo[d]imidazol-2-yl)propan-1-amine hydrochloride

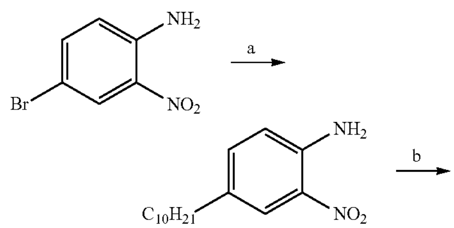

-continued

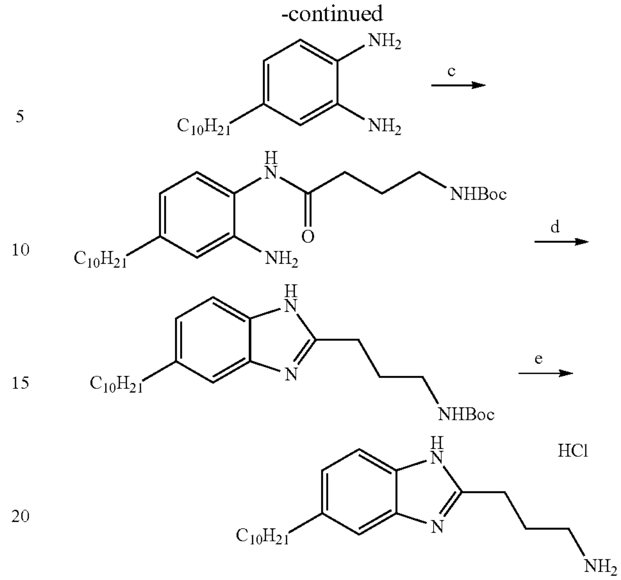

(a) (i) 9-BBN (2.2 equiv), 1-decene (2.0 equiv) THF, 70° C., (ii) Pd(dppf)$Cl_2$*$CH_2Cl_2$ (0.075 equiv), 3M KOH (3.0 equiv), THF, 70° C.; (b) $SnCl_2$ (5.0 equiv), HCl (10 equiv), EtOH, 80° C.; (c) N-Boc amino acid (1.3 equiv), DIEA (4.0 equiv), HCTU (1.0 equiv), DMF, 0-25° C.; (d) 13.7 M AcOH (70 equiv), neat, 65° C.; (e) 4M HCl/Dioxane (10 equiv), DCM, rt.

4-decyl-2-nitroaniline (27)

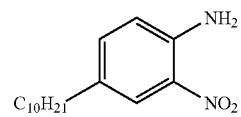

Synthesized according to General Procedure 6. Orange solid (36%, 560 mg). $^1$H NMR (400 MHz, Chloroform-d) δ 7.91 (d, J=2.1 Hz, 1H), 7.20 (dd, J=8.5, 2.1 Hz, 1H), 6.73 (d, J=8.5 Hz, 1H), 5.92 (s, 2H), 2.58-2.46 (m, 2H), 1.56 (q, J=7.3, 6.5 Hz, 4H), 1.32-1.21 (m, 14H), 0.99-0.81 (m, 3H).

4-decylbenzene-1,2-diamine (28)

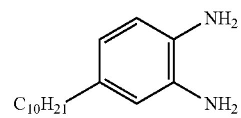

Synthesized according to General Procedure 16. Brown solid (54%, 24 mg). $^1$H NMR (500 MHz, Chloroform-d) δ 6.63 (d, J=7.6 Hz, 1H), 6.55-6.51 (m, 2H), 3.32 (s, 4H), 2.48-2.42 (m, 2H), 1.54 (p, J=7.3 Hz, 2H), 1.30-1.21 (m, 14H), 0.88 (t, J=6.9 Hz, 3H).

tert-butyl (4-((2-amino-4-decylphenyl)amino)-4-oxobutyl)carbamate (29)

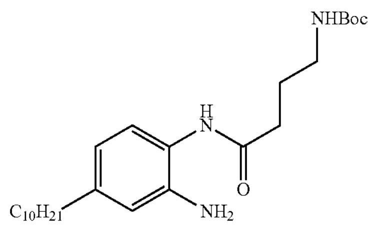

Synthesized according to General Procedure 1. Reaction carried forward crude with no further purification.

tert-butyl (3-(6-decyl-1H-benzo[d]imidazol-2-yl) propyl)carbamate (30)

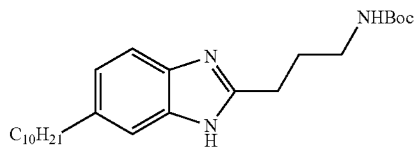

Synthesized according to General Procedure 17. Clear oil (73%, 46 mg). $^{1}$H NMR (400 MHz, $CDCl_3$) δ 7.46 (d, J=8.2 Hz, 1H), 7.35 (s, 1H), 7.03 (d, J=8.2 Hz, 1H), 5.07 (t, J=6.6 Hz, 1H), 3.21 (q, J=6.3 Hz, 2H), 2.92 (t, J=6.6 Hz, 2H), 2.69 (t, J=7.8 Hz, 2H), 1.96-1.87 (m, 2H), 1.63 (q, J=7.4 Hz, 2H), 1.45 (s, 9H), 1.35-1.20 (m, 16H), 0.87 (t, J=6.7 Hz, 3H). $^{13}$C NMR (101 MHz, $CDCl_3$) δ 157.4, 154.4, 137.2, 123.0, 79.9, 39.1, 38.7, 36.3, 32.3, 32.0, 29.7, 29.7, 29.5, 29.4, 28.5, 25.7, 22.8, 14.2. HRMS ($ESI^+$) m/z calc'd. for $C_{25}H_{42}N_3O_2^+$ (M+H)+ 416.3277, found 416.3256.

3-(6-decyl-1H-benzo[d]imidazol-2-yl)propan-1-amine hydrochloride (31)

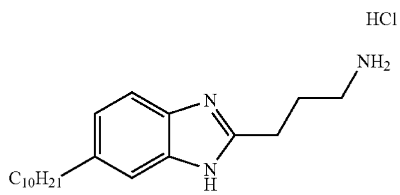

Synthesized according to General Procedure 6. White solid (90%, 35 mg). $^{1}$H NMR (400 MHz, $CD_3OD$) δ 7.67 (dd, J=8.5, 0.7 Hz, 1H), 7.56 (dt, J=1.5, 0.7 Hz, 1H), 7.44 (dd, J=8.5, 1.5 Hz, 1H), 3.17-3.08 (m, 2H), 2.86-2.77 (m, 2H), 2.35-2.23 (m, 2H), 1.68 (q, J=7.2 Hz, 2H), 1.37-1.26 (m, 15H), 0.93-0.86 (m, 3H). $^{13}$C NMR (101 MHz, $CD_3OD$) δ 153.4, 143.2, 132.8, 130.8, 128.3, 114.4, 113.8, 39.7, 36.9, 33.0, 32.9, 30.7, 30.7, 30.6, 30.4, 30.2, 25.9, 24.9, 23.7, 14.4. HRMS ($ESI^+$) m/z calc'd. for $C_{20}H_{34}N_3$+ (M+H)+ 316.2747, found 316.2757.

tert-butyl 4-(4-iodobenzamido)piperidine-1-carboxylate

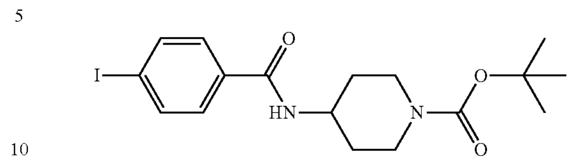

Synthesized according to procedure 2. Purified via column chromatography (40% ethyl acetate/hexanes). White solid (92%, 799 mg). $^{1}$H NMR (400 MHz, Chloroform-d) δ 7.82 (d, J=8.6 Hz, 2H), 7.56 (d, J=8.6 Hz, 2H), 4.16-3.95 (m, 3H), 2.97-2.85 (m, 2H), 2.01-1.84 (m, 2H), 1.46 (s, 11H). $^{13}$C NMR (101 MHz, Chloroform-d) δ 168.79, 156.42, 138.83, 135.32, 130.09, 99.09, 81.14, 48.83, 43.97, 32.54, 28.67.

tert-butyl (S)-3-(3-(4-iodophenyl)ureido)pyrrolidine-1-carboxylate

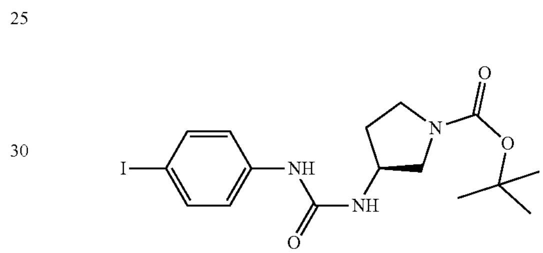

Synthesized according to procedure 14. Purified via column chromatography (50-70% ethyl acetate/hexanes). White solid (95%, 670 mg). $^{1}$H NMR (400 MHz, Chloroform-d) δ 7.88 (d, J=35.1 Hz, 1H), 7.47 (d, J=8.9 Hz, 2H), 7.08 (d, J=8.7 Hz, 2H), 6.07 (dd, J=38.0, 7.0 Hz, 1H), 4.38-4.27 (m, 1H), 3.50 (dd, J=11.5, 5.6 Hz, 1H), 3.46-3.26 (m, 2H), 3.15 (dd, J=11.5, 2.2 Hz, 1H), 2.12-1.95 (m, 1H), 1.94-1.73 (m, 1H), 1.45 (d, J=12.5 Hz, 9H). $^{13}$C NMR (101 MHz, Chloroform-d) δ 155.32, 155.23, 139.16, 137.75, 120.76, 85.01, 80.38 (d, J=8.4 Hz), 52.08 (d, J=68.3 Hz), 49.49 (d, J=69.0 Hz), 44.00 (d, J=18.7 Hz), 31.80 (d, J=107.6 Hz), 28.60.

tert-butyl 4-((4-iodophenyl)carbamoyl)piperazine-1-carboxylate

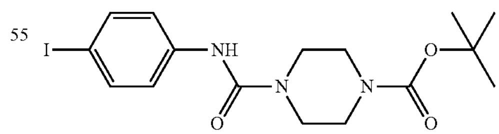

Synthesized according to procedure 14. Purified via column chromatography (40-50% ethyl acetate/hexanes). White solid (97%, 512 mg). $^{1}$H NMR (400 MHz, Chloroform-d) δ 7.47 (d, J=8.7 Hz, 2H), 7.17 (s, 1H), 7.07 (d, J=8.8 Hz, 2H), 3.43-3.32 (m, 8H), 1.44 (s, 9H). $^{13}$C NMR (101 MHz, Chloroform-d) δ 155.01, 154.62, 138.96, 137.57, 122.34, 86.16, 80.44, 43.78, 42.92, 28.43.

tert-butyl 4-(4-decylbenzamido)piperidine-1-carboxylate

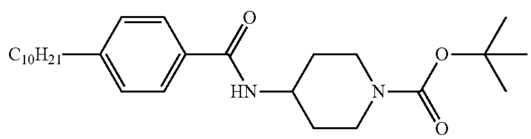

Synthesized according to procedure 6. Purified via column chromatography (30% ethyl acetate/hexanes). White solid (87%, 721 mg). $^1$H NMR (400 MHz, Chloroform-d) δ 7.65 (d, J=8.2 Hz, 2H), 7.13 (d, J=8.2 Hz, 2H), 6.59 (d, J=7.9 Hz, 1H), 4.11-3.97 (m, 3H), 2.79 (t, J=12.8 Hz, 2H), 2.57 (t, J=7.7 Hz, 2H), 1.94-1.86 (m, 2H), 1.54 (p, J=7.0 Hz, 2H), 1.40 (s, 11H), 1.29-1.13 (m, 14H), 0.83 (t, J=6.9 Hz, 3H). $^{13}$C NMR (101 MHz, Chloroform-d) δ 166.89, 154.64, 146.68, 131.90, 128.41, 127.05, 79.53, 47.13, 42.75, 35.76, 32.02, 31.85, 31.22, 29.56, 29.54, 29.42, 29.28, 29.19, 28.39, 22.64, 14.09.

tert-butyl (S)-3-(3-(4-decylphenyl)ureido)pyrrolidine-1-carboxylate

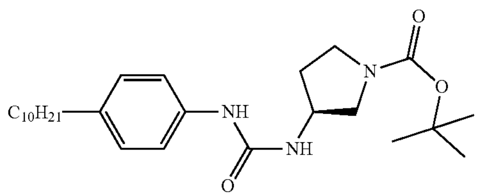

Synthesized according to procedure 6. Purified via column chromatography (30-40% ethyl acetate/hexanes). Off-white solid (73%, 505 mg). $^1$H NMR (400 MHz, Chloroform-d) δ 7.63 (d, J=24.8 Hz, 1H), 7.20 (d, J=6.3 Hz, 2H), 7.03 (d, J=8.5 Hz, 2H), 5.98 (dd, J=38.9, 7.1 Hz, 1H), 4.41-4.29 (m, 1H), 3.53 (dd, J=11.4, 5.8 Hz, 1H), 3.46-3.29 (m, 2H), 3.16 (dd, J=11.2, 3.6 Hz, 1H), 2.50 (t, J=7.7 Hz, 2H), 2.12-1.95 (m, 1H), 1.93-1.70 (m, 1H), 1.60-1.43 (m, 11H), 1.35-1.17 (m, 14H), 0.87 (t, J=6.9 Hz, 3H). $^{13}$C NMR (101 MHz, Chloroform-d) δ 155.96, 155.16, 137.51, 136.76, 128.91, 119.58, 80.09 (d, J=8.8 Hz), 52.07 (d, J=81.3 Hz), 49.60 (d, J=70.2 Hz), 44.09 (d, J=23.3 Hz), 35.35, 31.98, 31.84 (d, J=120.6 Hz), 31.69, 29.71, 29.70, 29.61, 29.41, 29.39, 28.62, 22.76, 14.19.

tert-butyl 4-((4-decylphenyl)carbamoyl)piperazine-1-carboxylate

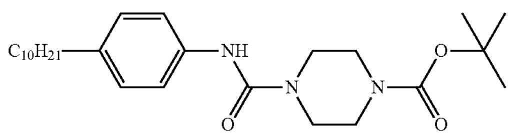

Synthesized according to procedure 6. Purified via column chromatography (60-70% ethyl acetate/hexanes). Brown solid (22%, 122 mg). $^1$H NMR (400 MHz, Chloroform-d) δ 7.22 (d, J=8.5 Hz, 2H), 7.08 (d, J=8.5 Hz, 2H), 6.48 (s, 1H), 3.49-3.41 (m, 8H), 2.53 (t, J=7.7 Hz, 2H), 1.56 (p, J=7.6 Hz, 2H), 1.47 (s, 9H), 1.33-1.22 (m, 14H), 0.87 (t, J=6.8 Hz, 3H). $^{13}$C NMR (101 MHz, Chloroform-d) δ 155.41, 154.76, 138.23, 136.40, 128.89, 120.47, 80.40, 43.98, 43.00, 35.40, 32.01, 31.66, 29.74, 29.72, 29.63, 29.44, 29.38, 28.50, 22.79, 14.23.

tert-butyl (R)-3-(4-decyl-N-methylbenzamido)pyrrolidine-1-carboxylate

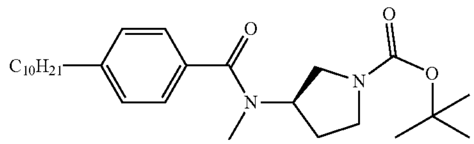

To a round bottom flask SM (0.20 g, 0.62 mmol), anhydrous THE (10 mL) was added under argon. The solution was then cooled to −78° C. To the cold solution, n-butyl lithium (0.39 mL, 0.62 mmol) was added drop wise and allowed to stir at −78° C. for 10 min. To this solution, iodomethane (0.038 mL, 0.62 mmol) was added drop wise at −78° C. The solution was then allowed to warm to room temperature and then refluxed for 24 h. Purified via column chromatography (40-60% ethyl acetate/hexanes). Clear oil (67%, 103 mg). $^1$H NMR (400 MHz, Chloroform-d) δ 7.29 (d, J=8.1 Hz, 2H), 7.20 (d, J=8.2 Hz, 2H), 5.27-4.35 (m, 1H), 3.68-3.46 (m, 2H), 3.42-3.17 (m, 2H), 2.94 (s, 3H), 2.62 (t, J=7.5 Hz, 2H), 2.12-1.98 (m, 2H), 1.60 (p, J=7.6 Hz, 2H), 1.44 (s, 9H), 1.37-1.19 (m, 14H), 0.87 (t, J=6.8 Hz, 3H). $^{13}$C NMR (101 MHz, Chloroform-d) δ 172.48, 154.45, 145.04, 133.65, 128.66, 126.93, 79.79, 46.99 (d, J=41.6 Hz), 44.43 (d, J=37.4 Hz), 35.92, 32.00, 31.38, 29.71, 29.68, 29.58, 29.42, 29.37, 28.58, 28.14 (d, J=53.4 Hz), 22.78, 14.22.

tert-butyl (R)-3-(4-decylphenylthioamido)pyrrolidine-1-carboxylate

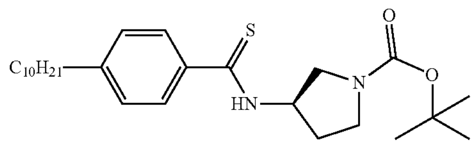

Synthesized according to procedure 6. Purified via column chromatography (40% ethyl acetate/hexanes). Yellow oil (69%, 151 mg). $^1$H NMR (400 MHz, Chloroform-d) δ 7.86 (d, J=38.3 Hz, 1H), 7.63 (d, J=8.3 Hz, 2H), 7.15 (d, J=8.2 Hz, 2H), 5.17-5.03 (m, 1H), 3.80-3.63 (m, 1H), 3.53-3.30 (m, 3H), 2.60 (t, J=7.7 Hz, 2H), 2.29 (h, J=7.2 Hz, 1H), 2.19-2.00 (m, 1H), 1.58 (p, J=7.2 Hz, 2H), 1.43 (s, 9H), 1.34-1.20 (m, 14H), 0.86 (t, J=6.8 Hz, 3H). $^{13}$C NMR (101 MHz, Chloroform-d) δ 199.35, 154.55, 146.89, 139.05, 128.52, 126.88, 79.89, 55.66 (d, J=59.1 Hz), 50.76 (d, J=54.2 Hz), 44.11 (d, J=24.4 Hz), 35.78, 31.94, 31.29, 30.68 (d, J=76.7 Hz), 29.66, 29.63, 29.53, 29.37, 29.27, 28.52, 22.74, 14.18.

4-decyl-N-(piperidin-4-yl)benzamide hydrochloride (39)

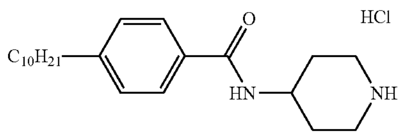

Synthesized according to procedure 3. Purified via trituration with ethyl acetate and diethyl ether. White solid (84%, 72 mg). $^1$H NMR (400 MHz, Methanol-$d_4$) δ 8.44 (d, J=7.4 Hz, 1H), 7.77 (d, J=8.1 Hz, 2H), 7.27 (d, J=8.4 Hz, 2H), 4.24-4.11 (m, 1H), 3.48 (dt, J=14.1, 4.2 Hz, 2H), 3.15 (td, J=12.8, 3.1 Hz, 2H), 2.65 (t, J=7.7 Hz, 2H), 2.23-2.12 (m, 2H), 2.00-1.85 (m, 2H), 1.61 (p, J=7.4 Hz, 2H), 1.37-1.20 (m, 14H), 0.89 (t, J=6.8 Hz, 3H). $^{13}$C NMR (101 MHz, Methanol-$d_4$) δ 169.86 (d, J=7.6 Hz), 148.35, 132.77 (d, J=3.8 Hz), 129.53, 128.52, 46.28 (d, J=10.7 Hz), 44.35, 36.72, 33.03, 32.39, 30.68, 30.67, 30.53, 30.42, 30.27, 29.46 (d, J=2.7 Hz), 23.71, 14.46.

(S)-1-(4-decylphenyl)-3-(pyrrolidin-3-yl)urea hydrochloride (34)

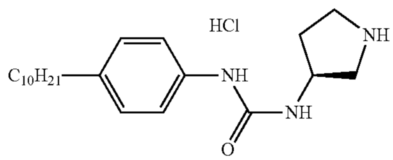

Synthesized according to procedure 3. Purified via trituration with ethyl acetate and diethyl ether. White solid (77%, 66 mg). $^1$H NMR (400 MHz, Methanol-$d_4$) δ 7.27 (d, J=8.5 Hz, 2H), 7.08 (d, J=8.6 Hz, 2H), 4.44-4.33 (m, 1H), 3.57-3.45 (m, 2H), 3.40-3.28 (m, 2H), 2.55 (t, J=7.6 Hz, 2H), 2.36 (ddt, J=13.9, 8.3, 7.0 Hz, 1H), 2.14-1.99 (m, 1H), 1.59 (p, J=7.5 Hz, 2H), 1.36-1.26 (m, 14H), 0.91 (t, J=6.8 Hz, 3H). $^{13}$C NMR (101 MHz, Methanol-$d_4$) δ 157.95, 138.63, 137.98, 129.71, 120.65, 51.84, 50.81, 45.63, 36.23, 33.06, 32.80, 31.37, 30.73, 30.71, 30.60, 30.44, 30.26, 23.72, 14.44.

N-(4-decylphenyl)piperazine-1-carboxamide hydrochloride (35)

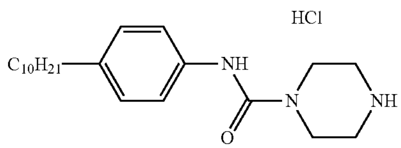

Synthesized according to procedure 3. Purified via trituration with ethyl acetate and diethyl ether. White solid (63%, 27 mg). $^1$H NMR (400 MHz, Methanol-$d_4$) δ 7.26 (d, J=8.6 Hz, 2H), 7.10 (d, J=8.8 Hz, 2H), 3.78 (t, J=5.5 Hz, 4H), 3.28 (t, J=5.3 Hz, 4H), 2.56 (t, J=7.6 Hz, 2H), 1.59 (p, J=7.5 Hz, 2H), 1.36-1.23 (m, 14H), 0.90 (t, J=7.0 Hz, 3H). $^{13}$C NMR (101 MHz, Methanol-$d_4$) δ 157.61, 139.47, 137.92, 129.61, 122.43, 44.49, 42.39, 36.26, 33.06, 32.80, 30.74, 30.71, 30.60, 30.45, 30.26, 23.73, 14.43.

(R)-4-decyl-N-methyl-N-(pyrrolidin-3-yl)benzamide hydrochloride (32)

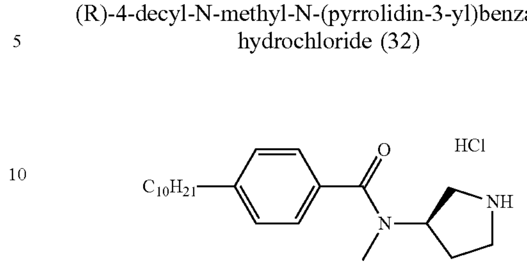

Synthesized according to procedure 3. Purified via column chromatography (10% methanol/dichloromethane). White solid (46%, 41 mg). $^1$H NMR (400 MHz, Methanol-$d_4$) δ 7.38 (d, J=8.1 Hz, 2H), 7.30 (d, J=8.2 Hz, 2H), 4.68 (p, J=7.5 Hz, 1H), 3.73-3.45 (m, 3H), 3.30-3.20 (m, 1H), 3.04 (s, 3H), 2.66 (t, J=7.7 Hz, 2H), 2.52-2.23 (m, 2H), 1.63 (p, J=7.6 Hz, 2H), 1.38-1.21 (m, 14H), 0.90 (t, J=6.9 Hz, 3H). $^{13}$C NMR (101 MHz, Methanol-$d_4$) δ 174.72, 146.90, 134.41, 129.72, 128.22, 58.31, 46.74, 36.73, 33.04, 32.49, 30.70, 30.69, 30.56, 30.43, 30.29, 28.53, 23.72, 14.43.

(R)-4-decyl-N-(pyrrolidin-3-yl)benzothioamide hydrochloride (33)

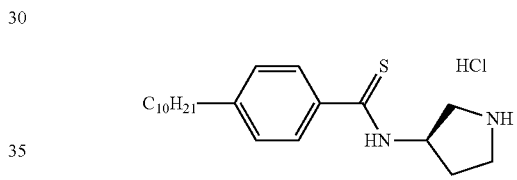

Synthesized according to procedure 3. Purified via trituration with ethyl acetate and diethyl ether. Yellow solid (94%, 122 mg). $^1$H NMR (400 MHz, Methanol-$d_4$) δ 7.77 (d, J=8.2 Hz, 2H), 7.23 (d, J=8.3 Hz, 2H), 5.22 (tt, J=7.2, 4.9 Hz, 1H), 3.77 (dd, J=12.5, 7.1 Hz, 1H), 3.63-3.39 (m, 3H), 2.66 (t, J=7.6 Hz, 2H), 2.50 (dq, J=13.7, 7.5 Hz, 1H), 2.40-2.27 (m, 1H), 1.64 (p, J=7.1 Hz, 2H), 1.39-1.22 (m, 14H), 0.91 (t, J=6.9 Hz, 3H). $^{13}$C NMR (101 MHz, Methanol-$d_4$) δ 201.81, 147.79, 140.13, 129.16, 128.60, 56.24, 50.63, 45.88, 36.63, 33.04, 32.40, 30.71, 30.69, 30.56, 30.44, 30.27, 30.26, 23.72, 14.46.

tert-butyl (R)-3-(((5-bromobenzo[d]oxazol-2-yl)amino)methyl)pyrrolidine-1-carboxylate

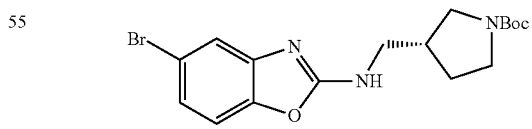

Synthesized according to General Procedure 13. White solid (71%, 108 mg). $^1$H NMR (400 MHz, Chloroform-d) δ 7.45 (s, 1H), 7.19-7.04 (m, 2H), 5.95 (d, J=63.8 Hz, 1H), 3.63-3.30 (m, 5H), 3.23-3.05 (m, 1H), 2.62 (p, J=7.3 Hz, 1H), 2.12-2.00 (m, 1H), 1.70 (q, J=10.4 Hz, 1H), 1.46 (s, 9H). HRMS (ESI$^+$) m/z calc'd. for $C_{18}H_{25}BrN_3O_3^+$ (M+H)$^+$ 396.0917, found 396.0919.

tert-butyl (S)-3-(((5-bromobenzo[d]oxazol-2-yl) amino)methyl)pyrrolidine-1-carboxylate

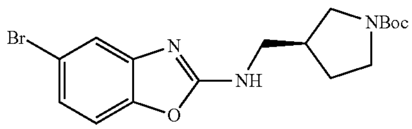 [SMILES: CC(C)(C)OC(=O)N1CC[C@@H](CNc2nc3cc(Br)ccc3o2)C1]

Synthesized according to General Procedure 13. White solid (75%, 113 mg). $^1$H NMR (500 MHz, Chloroform-d) δ 7.45 (s, 1H), 7.17-7.07 (m, 2H), 5.75 (d, J=78.7 Hz, 1H), 3.63-3.27 (m, 5H), 3.21-3.06 (m, 1H), 2.62 (q, J=7.1 Hz, 1H), 2.14-1.99 (m, 1H), 1.78-1.64 (m, 1H), 1.46 (s, 9H). HRMS (ESI$^+$) m/z calc'd. for $C_{18}H_{25}BrN_3O_3^+$ (M+H)$^+$ 396.0917, found 396.0913.

tert-butyl 4-(((5-bromobenzo[d]oxazol-2-yl)amino) methyl)piperidine-1-carboxylate

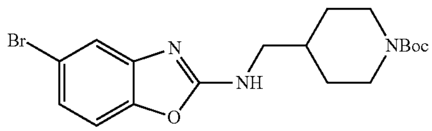 [SMILES: CC(C)(C)OC(=O)N1CCC(CNc2nc3cc(Br)ccc3o2)CC1]

Synthesized according to General Procedure 13. White solid (72%, 116 mg). $^1$H NMR (400 MHz, Chloroform-d) δ 7.45 (t, J=1.8 Hz, 1H), 7.14 (dt, J=8.4, 1.9 Hz, 1H), 7.09 (dd, J=8.4, 1.6 Hz, 1H), 5.67 (s, 1H), 4.13 (s, 3H), 3.45-3.32 (m, 2H), 2.71 (t, J=12.9 Hz, 2H), 1.88-1.71 (m, 4H), 1.46 (s, 9H). HRMS (ESI$^+$) m/z calc'd. for $C_{18}H_{25}BrN_3O_3^+$ (M+H)$^+$ 410.1074, found 410.1076.

tert-butyl (R)-3-(((5-decylbenzo[d]oxazol-2-yl) amino)methyl)pyrrolidine-1-carboxylate

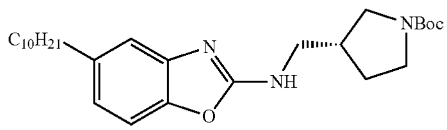

Synthesized according to General Procedure 6. Yellow oil (69%, 72 mg). $^1$H NMR (400 MHz, Chloroform-d) δ 7.16-7.06 (m, 2H), 6.82 (d, J=8.1 Hz, 1H), 6.44 (s, 1H), 3.65-3.38 (m, 4H), 3.39-3.25 (m, 1H), 3.24-3.04 (m, 1H), 2.63 (t, J=7.7 Hz, 2H), 2.09-1.96 (m, 1H), 1.81-1.55 (m, 3H), 1.45 (s, 9H), 1.35-1.20 (m, 14H), 0.88 (t, J=6.7 Hz, 3H). HRMS (ESI$^+$) m/z calc'd. for $C_{27}H_{44}N_3O_3^+$ (M+H)$^+$ 458.3377, found 458.3371.

tert-butyl (S)-3-(((5-decylbenzo[d]oxazol-2-yl) amino)methyl)pyrrolidine-1-carboxylate

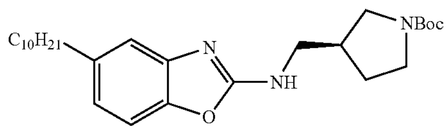

Synthesized according to General Procedure 6. Yellow oil (67%, 79 mg). $^1$H NMR (400 MHz, Chloroform-d) δ 7.19-7.05 (m, 2H), 6.82 (d, J=8.1 Hz, 1H), 6.60 (s, 2H), 3.62-3.39 (m, 4H), 3.39-3.23 (m, 1H), 3.24-3.04 (m, 1H), 2.62 (t, J=7.7 Hz, 3H), 2.10-1.97 (m, 1H), 1.80-1.65 (m, 1H), 1.64-1.56 (m, 2H), 1.45 (s, 9H), 1.33-1.20 (m, 15H), 0.88 (t, J=6.9 Hz, 3H). HRMS (ESI$^+$) m/z calc'd. for $C_{27}H_{44}N_3O_3^+$ (M+H)$^+$ 458.3377, found 458.3381.

tert-butyl 4-(((5-decylbenzo[d]oxazol-2-yl)amino) methyl)piperidine-1-carboxylate

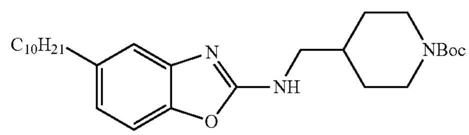

Synthesized according to General Procedure 6. Yellow oil (77%, 88 mg). $^1$H NMR (400 MHz, Chloroform-d) δ 7.15 (d, J=1.6 Hz, 1H), 7.09 (d, J=8.1 Hz, 1H), 6.81 (dd, J=8.1, 1.7 Hz, 1H), 5.76 (s, 1H), 4.10 (s, 2H), 3.33 (d, J=6.7 Hz, 2H), 2.72-2.57 (m, 4H), 1.88-1.70 (m, 3H), 1.58 (p, J=7.4 Hz, 2H), 1.43 (s, 9H), 1.31-1.20 (m, 17H), 0.85 (t, J=6.8 Hz, 3H). HRMS (ESI$^+$) m/z calc'd. for $C_{28}H_{46}N_3O_3^+$ (M+H)$^+$ 472.3534, found 472.3526.

(S)-5-decyl-N-(pyrrolidin-3-ylmethyl)benzo[d]oxazol-2-amine hydrochloride (37)

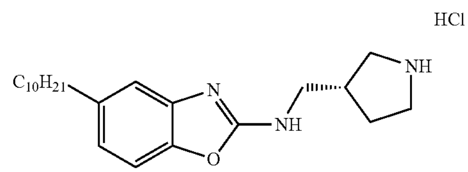

Synthesized according to General Procedure 3. Off-white solid (71%, 44 mg). $^1$H NMR (400 MHz, Methanol-d$_4$) δ 7.44-7.38 (m, 1H), 7.26-7.21 (m, 1H), 7.19-7.12 (m, 1H), 3.66-3.59 (m, 2H), 3.54 (dd, J=11.9, 7.9 Hz, 1H), 3.48-3.39 (m, 1H), 3.36-3.30 (m, 1H), 3.14-3.03 (m, 1H), 2.79 (p, J=7.9 Hz, 1H), 2.70 (t, J=7.6 Hz, 2H), 2.36-2.25 (m, 1H), 1.91-1.77 (m, 1H), 1.63 (t, J=7.5 Hz, 3H), 1.34-1.23 (m, 14H), 0.87 (t, J=6.5 Hz, 3H). $^{13}$C NMR (101 MHz, Methanol-d$_4$) δ 160.6, 145.5, 143.1, 132.0, 125.8, 113.4, 111.4, 49.2, 46.4, 45.9, 38.7, 36.7, 33.0, 32.9, 30.7, 30.7, 30.6, 30.4, 30.2, 29.1, 23.7, 14.4. HRMS (ESI$^+$) m/z calc'd. for $C_{22}H_{36}N_3O^+$ (M+H)$^+$ 358.2853, found 358.2849.

(R)-5-decyl-N-(pyrrolidin-3-ylmethyl)benzo[d]oxazol-2-amine hydrochloride (38)

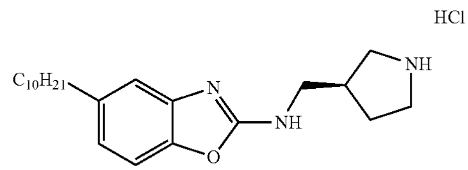

Synthesized according to General Procedure 3. Off-white solid (68%, 46 mg). $^1$H NMR (400 MHz, Methanol-$d_4$) δ 7.43 (dd, J=8.4, 3.3 Hz, 1H), 7.30-7.24 (m, 1H), 7.19-7.13 (m, 1H), 3.67-3.62 (m, 2H), 3.58-3.50 (m, 1H), 3.49-3.40 (m, 1H), 3.37-3.27 (m, 1H), 3.14-3.04 (m, 1H), 2.87-2.74 (m, 1H), 2.71 (t, J=7.7 Hz, 2H), 2.40-2.23 (m, 1H), 1.90-1.76 (m, 1H), 1.62 (q, J=7.2 Hz, 2H), 1.35-1.21 (m, 14H), 0.87 (t, J=6.7 Hz, 3H). $^{13}$C NMR (101 MHz, Methanol-$d_4$) δ 160.6, 145.4, 143.2, 131.9, 125.8, 113.4, 111.4, 49.2, 46.4, 46.0, 38.7, 36.7, 33.0, 32.9, 30.7, 30.7, 30.6, 30.4, 30.2, 29.1, 23.7, 14.4. HRMS (ESI$^+$) m/z calc'd. for $C_{22}H_{36}N_3O^+$ (M+H)$^+$ 358.2853, found 358.2854.

5-decyl-N-(piperidin-4-ylmethyl)benzo[d]oxazol-2-amine (36)

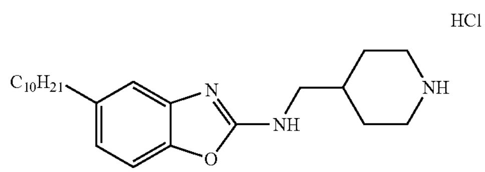

Synthesized according to General Procedure 3. White solid (70%, 53 mg). $^1$H NMR (400 MHz, Methanol-$d_4$) δ 7.46 (d, J=8.4 Hz, 1H), 7.29 (s, 1H), 7.20 (d, J=8.5, 1H), 3.55-3.40 (m, 4H), 3.04 (t, J=13.0, 2.8 Hz, 2H), 2.72 (t, J=7.6 Hz, 2H), 2.18-2.04 (m, 3H), 1.73-1.50 (m, 4H), 1.37-1.22 (m, 14H), 0.88 (t, J=6.6 Hz, 3H). $^{13}$C NMR (101 MHz, Methanol-$d_4$) δ 160.28, 145.21, 143.34, 131.02, 126.02, 113.09, 111.54, 44.73, 36.70, 34.58, 33.04, 32.90, 30.70, 30.7, 30.6, 30.4, 30.2, 27.3, 23.7, 14.4. HRMS (ESI$^+$) m/z calc'd. for $C_{23}H_{38}N_3O^+$ (M+H)$^+$ 372.3009, found 372.3012.

S1P Transporter Assay

Transporter assays are vectorial and therefore require measurement of the transported analyte in different compartments. The S1P transporter SPNS2 only exports S1P, which obviates measuring uptake of S1P into transporter-expressing cells. Thus, transporter activity was determined by quantifying S1P release from whole cells expressing SPNS2. SPNS2 inhibitor potency was assessed using whole cell assays. HeLa cells expressing mouse SPNS2 were used to determine inhibitor potency (IC50). Cells were plated onto 12 well plates and assayed when the cell monolayers became confluent. Cell growth media (RPMI-1640 containing 10% fetal bovine serum) was replaced with 2 mL of serum-free media (RPMI-1640) containing fatty acid free bovine serum albumin (BSA) (0.2% w/v) and supplemented with 4-deoxypyridoxine (DOP) (1 mM), NaF (2 mM), $Na_3VO_4$ (0.2 mM) to inhibit S1P degradation. Test articles (1×10-9-1×10-4 M) were assayed in duplicate or triplicate. After 18 hours, media was collected, an internal recovery standard (0.005 mL of 5×10-7 M deuterated (d7) S1P in methanol) was added, the BSA was precipitated with trichloroacetic acid and the bound S1P extracted with methanol. S1P and S1P-d7 were measured by liquid chromatography mass spectrometry. Inhibitor potency at the human SPNS2 ortholog was determined by an analogous assay using U-937 cells, which endogenously express human SPNS2.

Table 2. In vitro inhibition data against SPNS2 for exemplary compounds, presented here as their pharmaceutical salts, of the disclosure (A≤2 μM, B>2 μM).

| Compound | Structure | $IC_{50}$ |
|---|---|---|
| 2a | 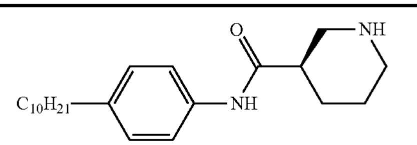 | B |
| 2b | 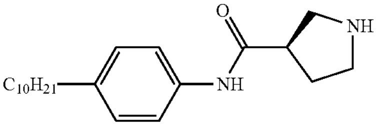 | B |
| 2c | 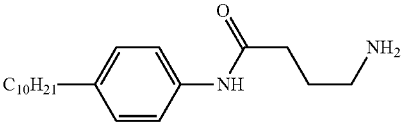 | A |
| 2d | 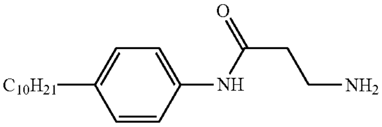 | A |
| 2e | 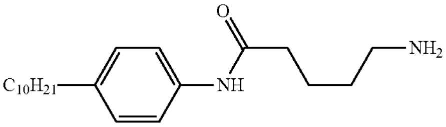 | B |

-continued
| Compound | Structure | $IC_{50}$ |
| --- | --- | --- |
| 2f | 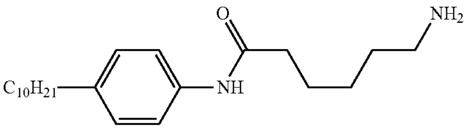 | A |
| 2g | 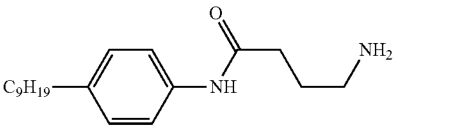 | B |
| 2h | 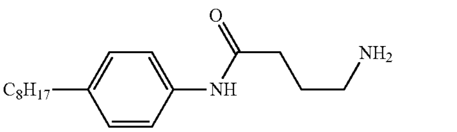 | B |
| 2i | 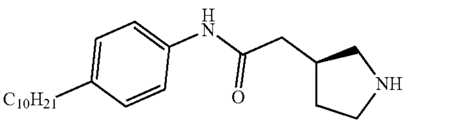 | A |
| 2j | 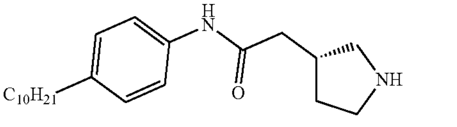 | A |
| 2k | 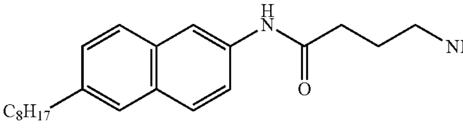 | B |
| 2l | 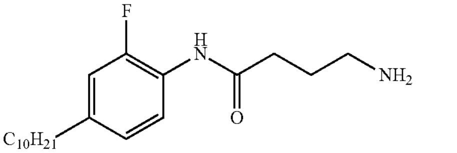 | B |
| 2m | 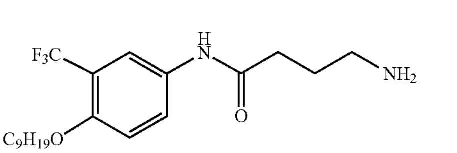 | B |
| 2n | 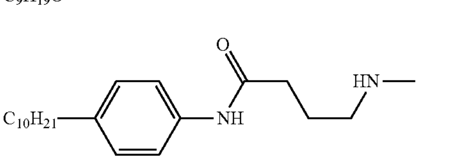 | B |
| 2o | 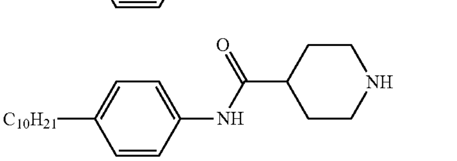 | B |
| 2p | 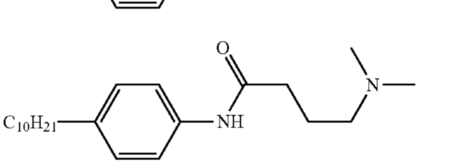 | B |

-continued
| Compound | Structure | $IC_{50}$ |
|---|---|---|
| 4a | 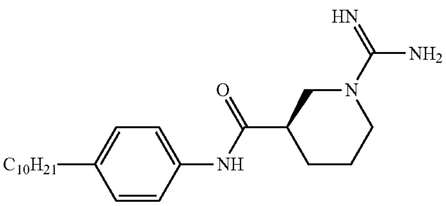 | A |
| 4b | 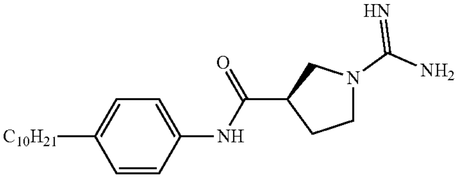 | A |
| 4c | 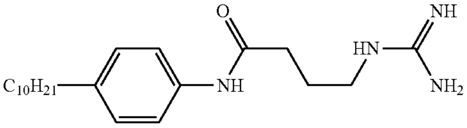 | A |
| 8a | 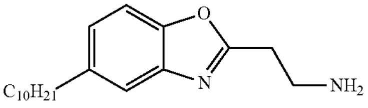 | B |
| 8b | 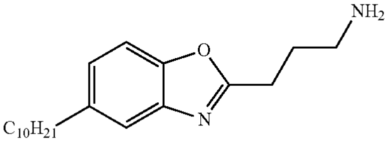 | B |
| 8c | 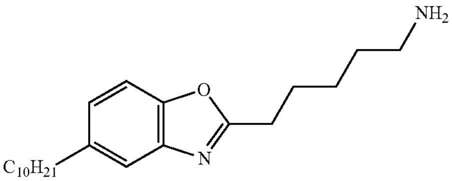 | B |
| 8d | 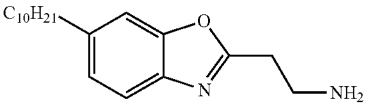 | B |
| 8e | 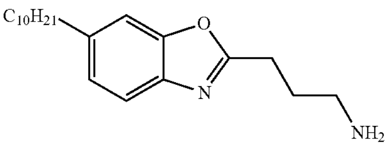 | B |
| 13a | 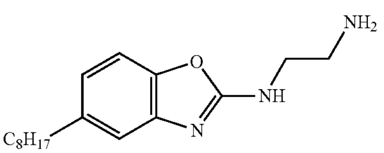 | B |
| 13b | 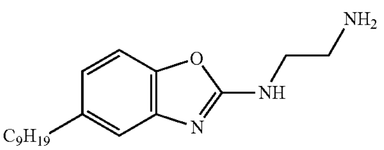 | B |

-continued
| Compound | Structure | $IC_{50}$ |
|---|---|---|
| 13c | 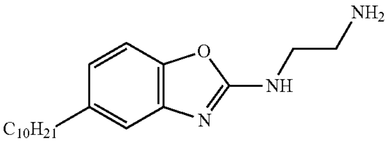 | B |
| 13d | 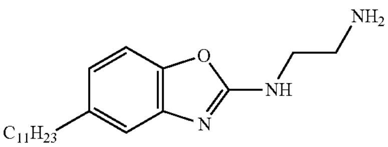 | B |
| 13e | 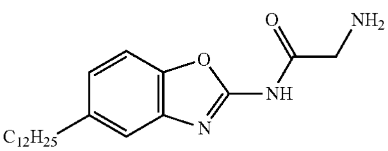 | B |
| 13f | 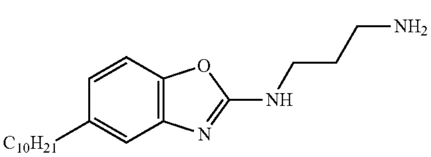 | B |
| 13g | 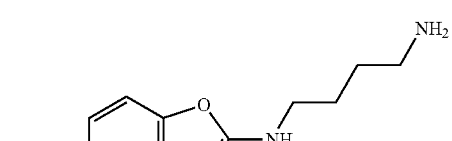 | B |
| 13h | 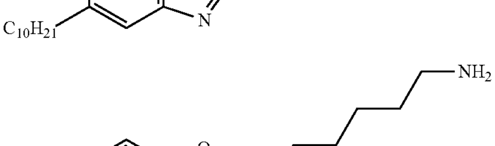 | B |
| 13i | 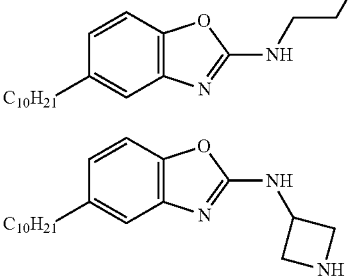 | B |
| 13j | 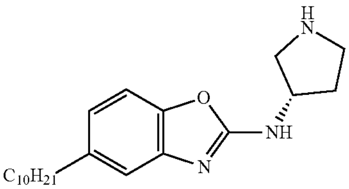 | A |
| 13k | 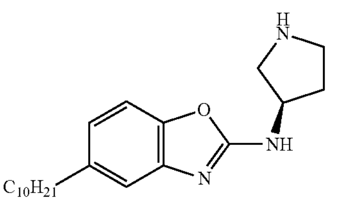 | A |

-continued
| Compound | Structure | $IC_{50}$ |
|---|---|---|
| 13l | 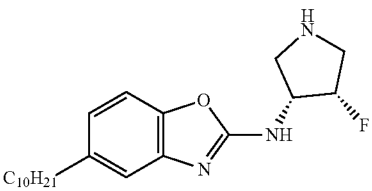 | A |
| 13m | 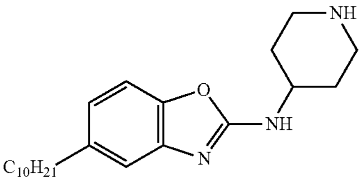 | A |
| 13n | 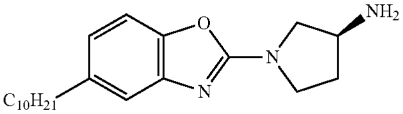 | B |
| 13o | 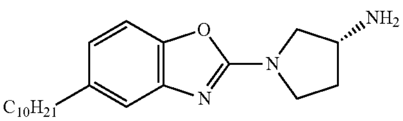 | B |
| 13p | 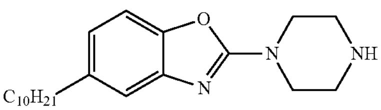 | B |
| 13q | 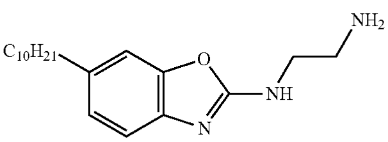 | B |
| 13r | 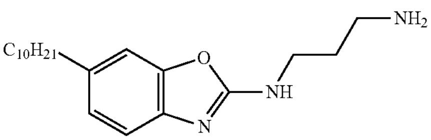 | B |
| 13s | 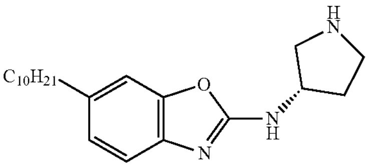 | A |
| 13t | 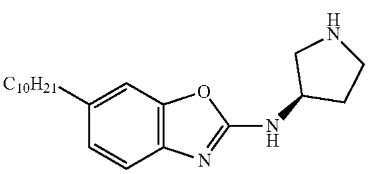 | A |
| 13u | 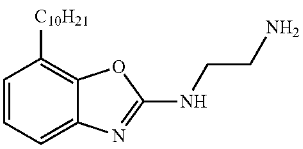 | B |

-continued
| Compound | Structure | $IC_{50}$ |
|---|---|---|
| 13v | 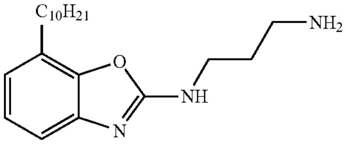 | B |
| 13w | 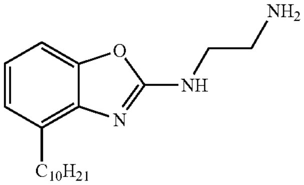 | B |
| 13x | 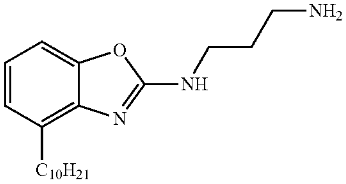 | B |
| 13y | 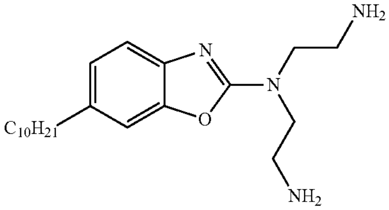 | A |
| 13z | 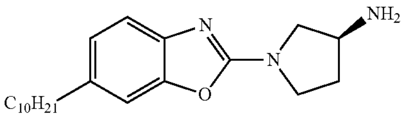 | B |
| 13aa | 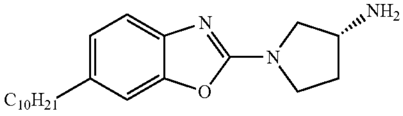 | B |
| 13ab | 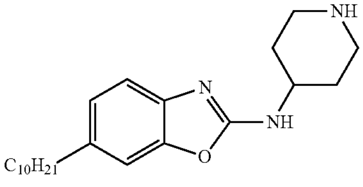 | A |
| 17a | 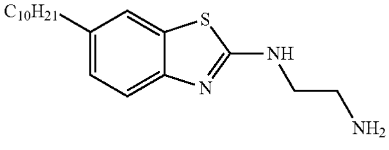 | B |
| 17b | 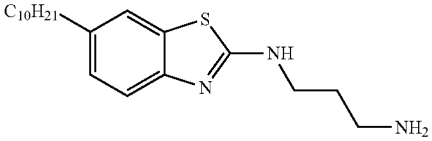 | B |

-continued
| Compound | Structure | IC50 |
| --- | --- | --- |
| 20a | 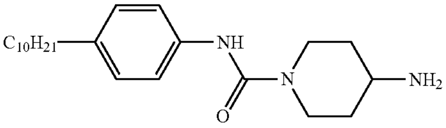 | A |
| 20b | 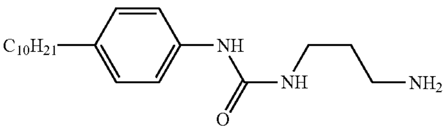 | A |
| 20c | 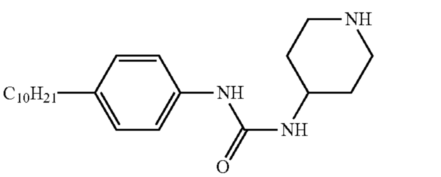 | NA |
| 23a | 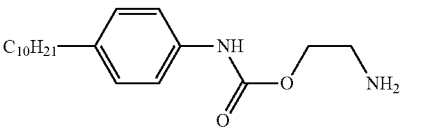 | B |
| 23b | 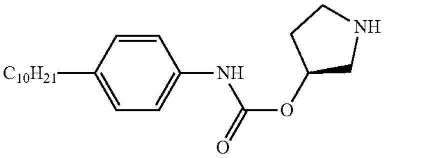 | B |
| 23c | 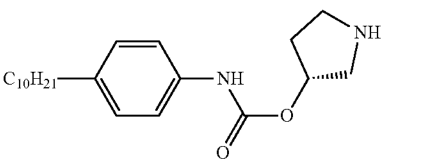 | A |
| 26a | 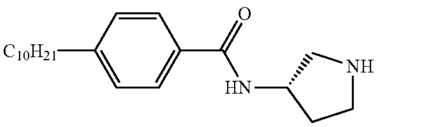 | A |
| 26b | 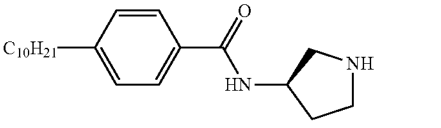 | A |
| 26c | 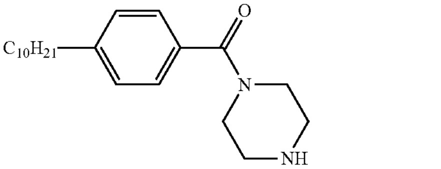 | A |
| 26d | 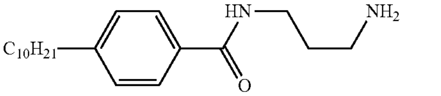 | A |

-continued
| Compound | Structure | $IC_{50}$ |
|---|---|---|
| 26e | 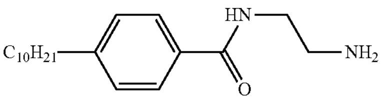 | B |
| 31 | 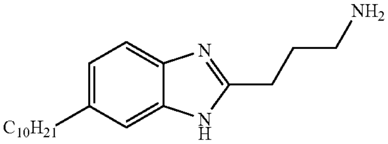 | B |
| 32 | 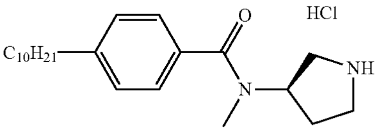 | B |
| 33 | 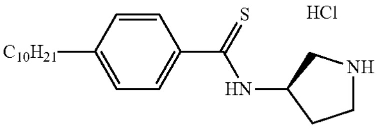 | A |
| 34 | 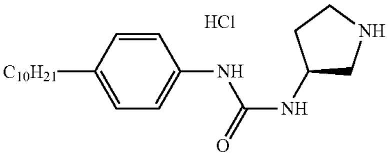 | A |
| 35 | 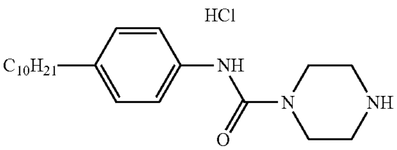 | A |
| 36 | 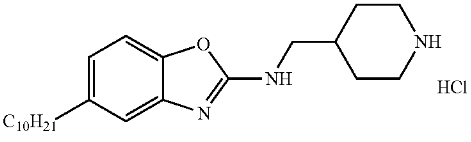 | B |
| 37 | 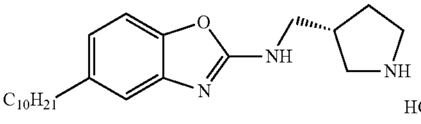 | A |
| 38 | 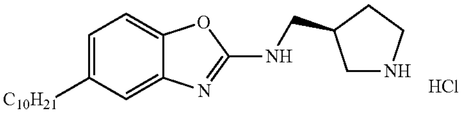 | A |
| 39 | 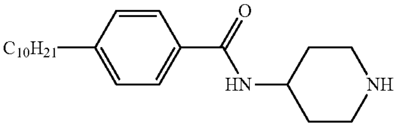 | A |

We claim:

1. A compound according to Formula IA:

(IA)

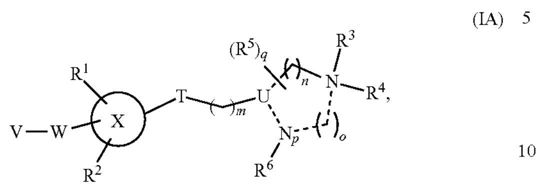

wherein

X is a $C_6$-$C_{10}$-aryl or 5- to 10-membered heteroaryl (wherein 1 to 4 heteroaryl ring members are independently selected from N, O, and S);

$R^1$ and $R^2$ are independently selected from the group consisting of H, $C_1$-$C_6$-alkyl, $C_1$-$C_6$-alkoxy, $C_1$-$C_6$-haloalkoxy, $C_3$-$C_8$-cycloalkyl, $C_1$-$C_6$-haloalkyl, CN, and halo;

W is a bond, O, NH, —NHC(O)—, or —O—(N═)C(R)— (wherein R is H or $C_1$-$C_6$-alkyl);

V is selected from the group consisting of $C_1$-$C_{14}$-alkyl, $C_2$-$C_{12}$-alkenyl, $(C_6$-$C_{10})$aryl, $(C_6$-$C_{10})$heteroaryl, —$C_1$-$C_{10}$-alkyl-$(C_6$-$C_{10})$aryl, —$C_2$-$C_{12}$-alkenyl-$(C_6$-$C_{10})$aryl, —$C_1$-$C_{10}$-alkyl-$(C_3$-$C_8)$cycloalkyl, -(3- to 14-membered heterocycloalkyl) (wherein 1-4 heterocycloalkyl members are independently selected from N, O, and S), —$(C_1$-$C_{10})$alkyl-(3- to 14-membered heterocycloalkyl) (wherein 1-4 heterocycloalkyl members are independently selected from N, O, and S);

T is selected from the group consisting of a bond, —C(O)—, —C(O)$NR^x$—, —C(S)$NR^x$—, —$NR^x$C(O)—, —$NR^x$—, —$NR^x$C(O)$NR^x$—, and —$NR^x$C(O)O—;

$R^x$ in each instance is independently selected from H and $C_1$-$C_6$-alkyl;

m is an integer selected from 0, 1, 2, 3, 4, 5, and 6;

n is an integer selected from 1 and 2, wherein the sum of n and o is greater than 0;

each "---" is a single bond that is optionally present, wherein all "---" are simultaneously present or absent, and wherein when "---" is present, then o is selected from 1, 2, and 3; and p is 0, $(N)_pR^6$ represents a bond, and U is —CH— or N, or p is 1 and U is —CH—; and when "---" is not present, then o is 0 and U is —$CH_2$— or NH;

q is an integer selected from 1, 2, and 3;

$R^3$ is selected from the group consisting of, H, $C_1$-$C_6$-alkyl, and —C(NH)$NH_2$;

$R^4$ is absent when "---" is present, and when "---" is absent, then $R^4$ is H or $C_1$-$C_6$-alkyl;

each $R^5$ is independently selected from the group consisting of H, $C_1$-$C_6$-alkyl, $C_1$-$C_6$-alkoxy, $C_1$-$C_6$-haloalkoxy, $C_3$-$C_8$-cycloalkyl, $C_1$-$C_6$-haloalkyl, CN, $NH_2$, and halo;

$R^6$ is H or $C_1$-$C_6$-alkyl;

wherein each alkyl, alkoxy, alkenyl, alkynyl, aryl, cycloalkyl, heterocycloalkyl, and heteroaryl is optionally substituted with 1-5 substituents independently selected from the group consisting of hydroxy, halo, $C_1$-$C_6$-haloalkoxy, $C_1$-$C_6$-haloalkyl, —$NR'_2$, —NHC(O)($OC_1$-$C_6$-alkyl), —$NO_2$, —CN, oxo, —C(O)OH, —C(O)O($C_1$-$C_6$-alkyl), —$C_1$-$C_6$-alkyl($C_1$-$C_6$-alkoxy), —C(O)$NH_2$, $C_1$-$C_6$-alkyl, —C(O)$C_1$-$C_6$-alkyl, —$OC_1$-$C_6$-alkyl, —Si($C_1$-$C_6$-alkyl$)_3$, —$S(O)_{0-2}$—($C_1$-$C_6$-alkyl), $C_6$-$C_{10}$-aryl, —($C_1$-$C_6$-alkyl)($C_6$-$C_{10}$-aryl), 3- to 14-membered heterocycloalkyl, and —($C_1$-$C_6$-alkyl)-(3- to 14-membered heterocycle) (wherein 1-4 heterocycle members are independently selected from N, O, and S), and —O($C_6$-$C_{14}$-aryl); and wherein each R' is independently selected from the group consisting of $C_1$-$C_6$-alkyl, $C_2$-$C_6$-alkenyl, $C_2$-$C_6$-alkynyl, $C_6$-$C_{10}$-aryl, 3- to 14-membered heterocycloalkyl and —($C_1$-$C_6$-alkyl)-(3- to 14-membered heterocycloalkyl) (wherein 1-4 ring members are independently selected from N, O, and S), and 5- to 10-membered heteroaryl (wherein 1-4 heteroaryl members are independently selected from N, O, and S;

or a pharmaceutically acceptable salt thereof.

2. The compound or pharmaceutically acceptable salt thereof according to claim 1, wherein:

T is a bond;

"---" is absent;

U is —$CH_2$— or —NH; and m is an integer selected from 1, 2, 3, 4, 5, and 6.

3. The compound or pharmaceutically acceptable salt thereof according to claim 1, wherein:

T is —$NR^x$—;

"---" is absent; and

U is —$CH_2$— or —NH.

4. The compound or pharmaceutically acceptable salt thereof according to claim 1, wherein:

T is —$NR^x$C(O)$NR^x$—;

"---" is absent; and

U is —$CH_2$— or —NH.

5. The compound or pharmaceutically acceptable salt thereof according to claim 1, wherein:

"---" is present; and m is 0, 1, 2, or 3.

6. The compound or pharmaceutically acceptable salt thereof according to claim 5, wherein m is 0.

7. The compound or pharmaceutically acceptable salt thereof according to claim 5, wherein p is 0, $(N)_pR^6$ represents a bond, and U is —CH— or N.

8. The compound or pharmaceutically acceptable salt thereof according to claim 5, wherein p is 1 and U is —CH—.

9. The compound or pharmaceutically acceptable salt thereof according to claim 5, wherein T is selected from the group consisting of —C(O)$NR^x$, —$NR^x$C(O)—, —$NR^x$—, —$NR^x$C(O)$NR^x$—, and —$NR^x$C(O)O—.

10. The compound according or pharmaceutically acceptable salt thereof to claim 5, wherein T is a bond.

11. The compound according or pharmaceutically acceptable salt thereof to claim 5, wherein T is —C(O)—.

12. The compound according or pharmaceutically acceptable salt thereof to claim 1, wherein X is $C_6$-$C_{10}$-aryl.

13. The compound according or pharmaceutically acceptable salt thereof to claim 12, wherein X is phenyl.

14. The compound according or pharmaceutically acceptable salt thereof to claim 1, wherein X is a 5- to 10-membered heteroaryl (wherein 1 to 4 heteroaryl ring members are independently selected from N, O, and S).

15. The compound according or pharmaceutically acceptable salt thereof to claim 14, wherein X is selected from the group consisting of benzoxazolyl, benzothiazolyl, and benzimidazolyl.

16. The compound or pharmaceutically acceptable salt thereof according to claim 1, wherein:

X is a 10-membered heteroaryl (wherein 2 heteroaryl ring members are independently selected from N and O);

T is —$NR^x$—;

m is 0; and

"---" is present.

17. The compound or pharmaceutically acceptable salt thereof according to claim 1, wherein the compound is selected from the following table:

| Compound | Structure |
| --- | --- |
| 2a | 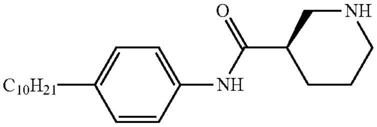 |
| 2b | 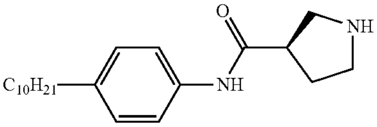 |
| 2c | 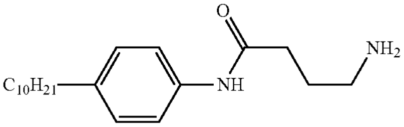 |
| 2d | 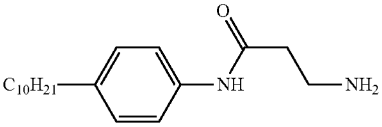 |
| 2e | 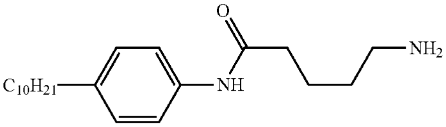 |
| 2f | 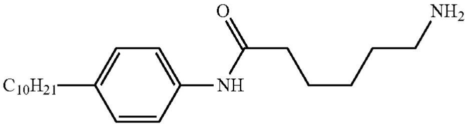 |
| 2g | 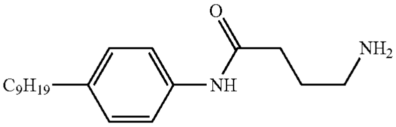 |
| 2h | 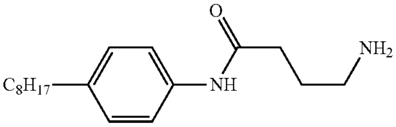 |
| 2i | 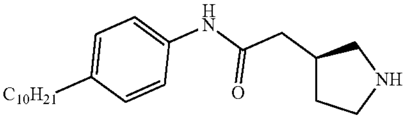 |
| 2j | 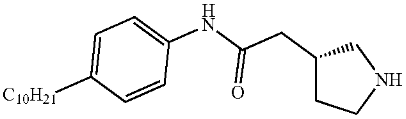 |

-continued
| Compound | Structure |
| --- | --- |
| 2k | 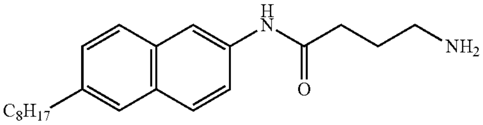 |
| 2l | 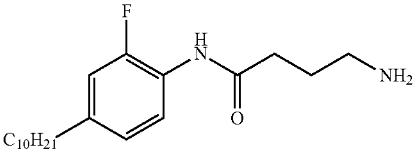 |
| 2m | 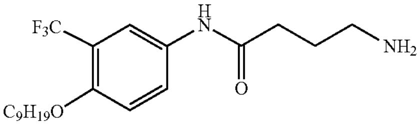 |
| 2n | 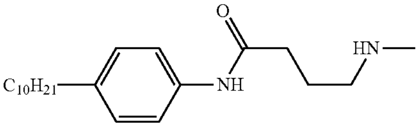 |
| 2o | 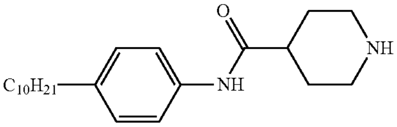 |
| 2p | 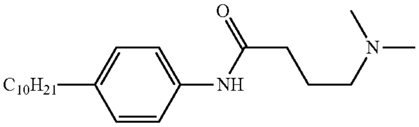 |
| 4a | 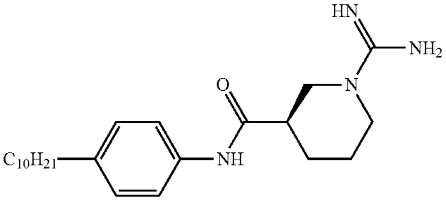 |
| 4b | 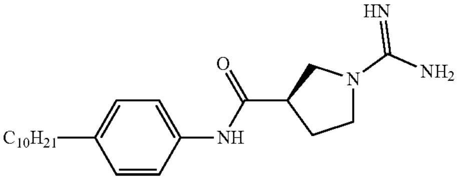 |
| 4c | 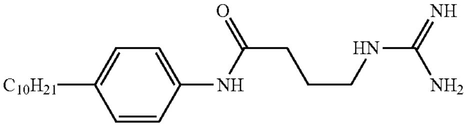 |
| 8a | 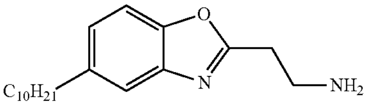 |

-continued
| Compound | Structure |
| --- | --- |
| 8b | 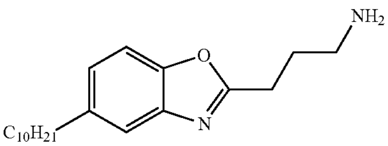 |
| 8c | 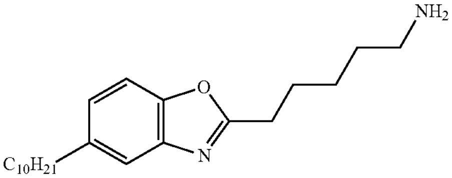 |
| 8d | 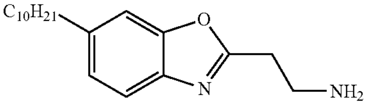 |
| 8e | 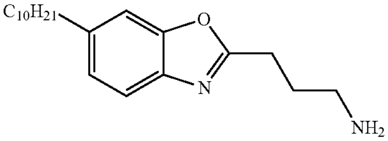 |
| 13a | 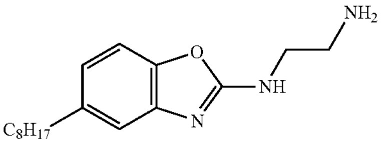 |
| 13b | 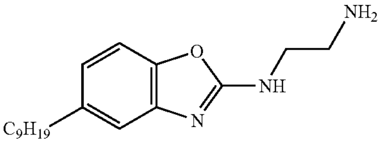 |
| 13c | 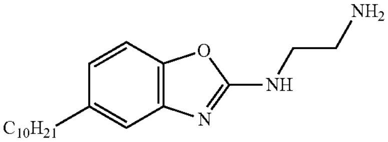 |
| 13d | 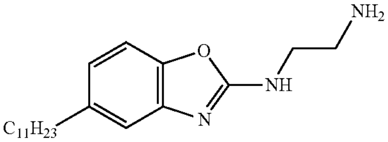 |
| 13e | 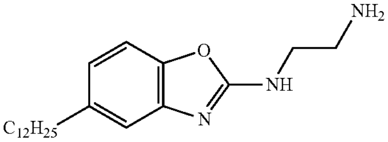 |
| 13f | 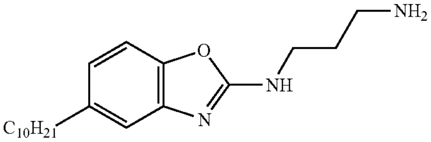 |

-continued
| Compound | Structure |
|---|---|
| 13g | 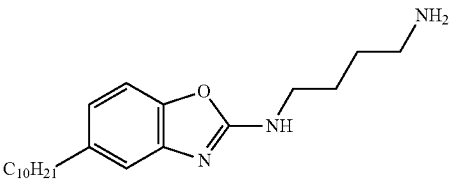 |
| 13h | 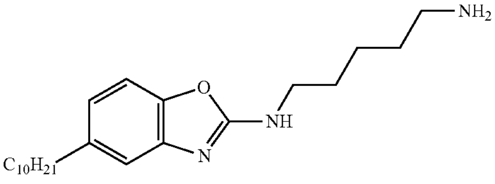 |
| 13 | 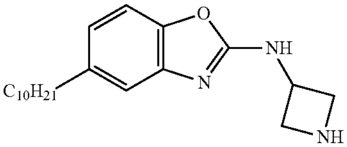 |
| 13j | 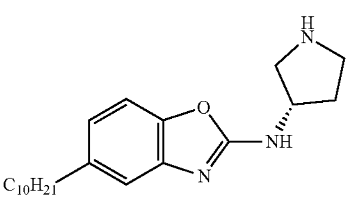 |
| 13k | 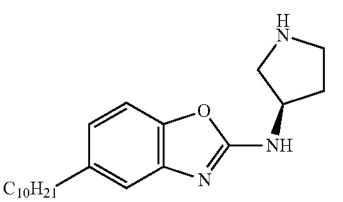 |
| 13l | 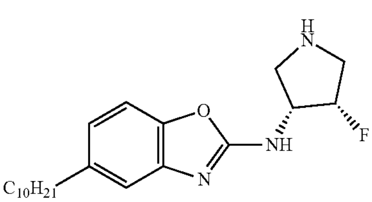 |
| 13m | 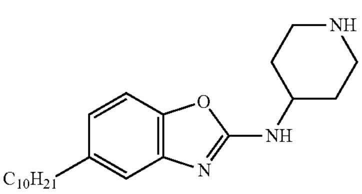 |
| 13n | 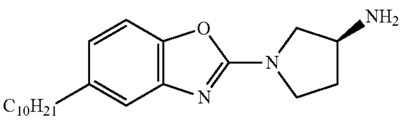 |
| 13o | 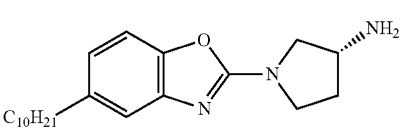 |

-continued
| Compound | Structure |
|---|---|
| 13p | 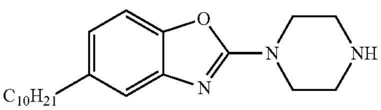 |
| 13q | 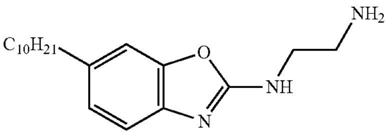 |
| 13r | 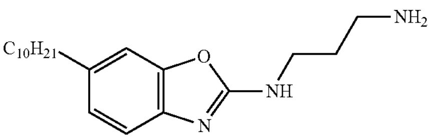 |
| 13s | 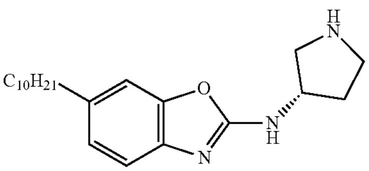 |
| 13t | 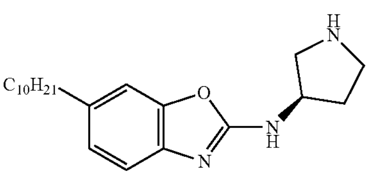 |
| 13u | 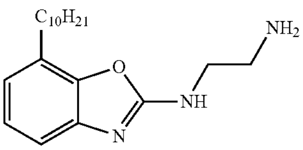 |
| 13v | 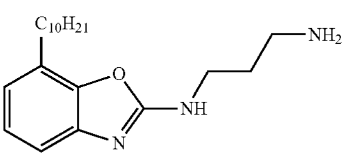 |
| 13w | 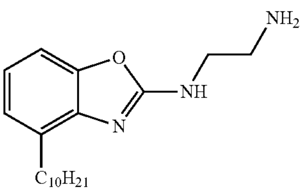 |
| 13x | 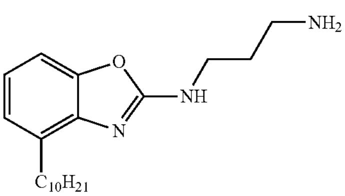 |

-continued
| Compound | Structure |
|---|---|
| 13y | 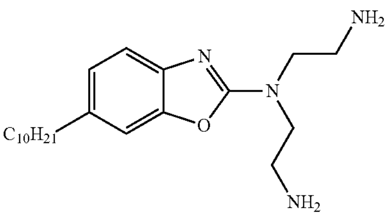 |
| 13z | 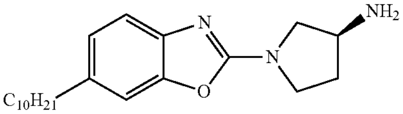 |
| 13aa | 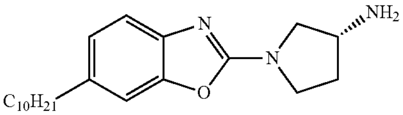 |
| 13ab | 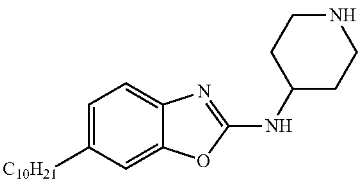 |
| 17a | 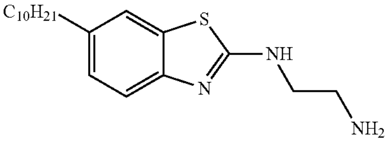 |
| 17b | 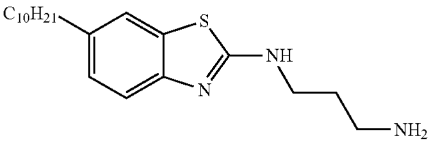 |
| 20a | 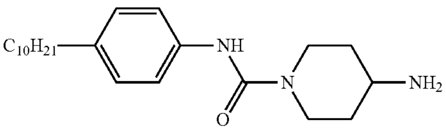 |
| 20b | 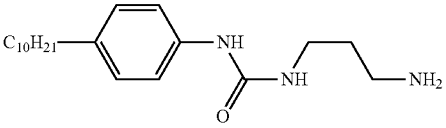 |
| 20c | 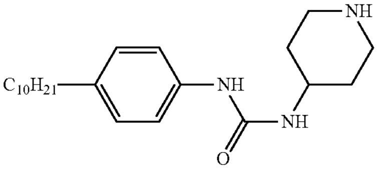 |
| 23a | 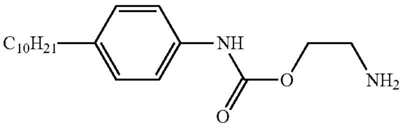 |

-continued
| Compound | Structure |
|---|---|
| 23b | 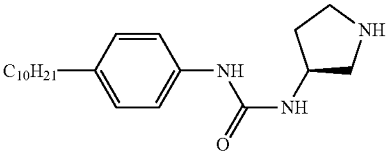 |
| 23c | 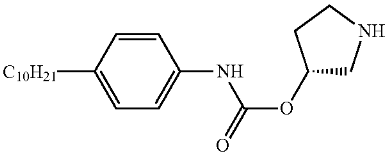 |
| 26a | 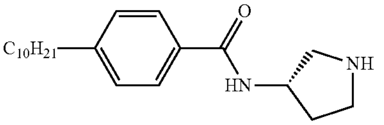 |
| 26b | 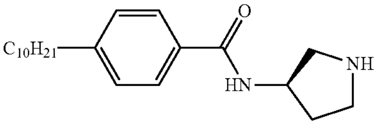 |
| 26c | 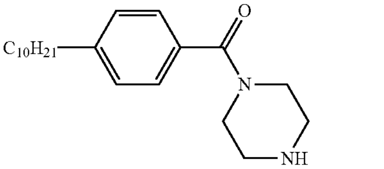 |
| 26d | 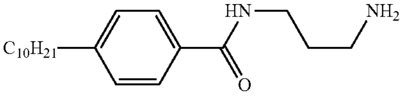 |
| 26e | 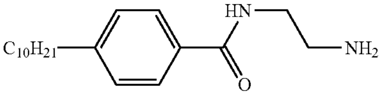 |
| 31 | 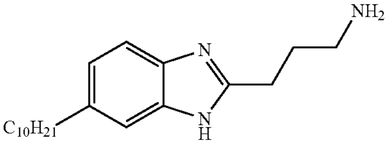 |
| 32 | 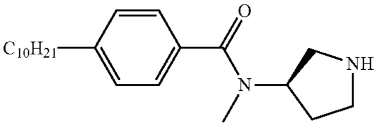 |
| 33 | 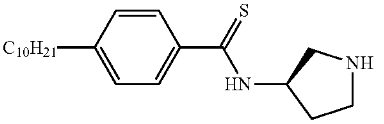 |

-continued
| Compound | Structure |
| --- | --- |
| 34 | 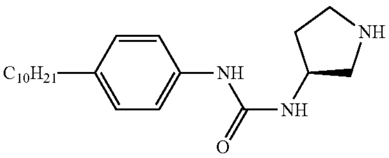 |
| 35 | 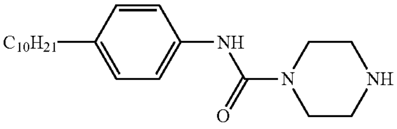 |
| 36 | 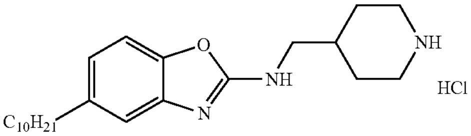 |
| 37 | 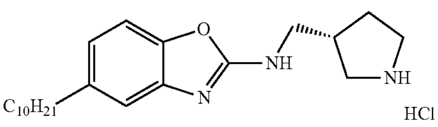 |
| 38 | 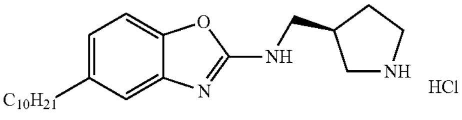 |
| 39 | 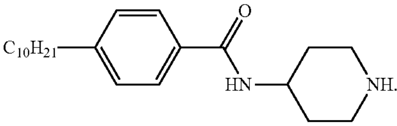 |
18. A pharmaceutical composition comprising a compound or a pharmaceutically acceptable salt thereof according to claim 1.
* * * * *